United States Patent [19]
Shturman et al.

[11] Patent Number: 6,077,282
[45] Date of Patent: *Jun. 20, 2000

[54] ROTATIONAL ATHERECTOMY DEVICE WITH EXCHANGEABLE DRIVE SHAFT CARTRIDGE

[75] Inventors: Leonid Shturman, Minnetonka, Minn.; Georgiy Morov, Moscow, Russian Federation

[73] Assignee: Shturman Cardiology Systems, Inc., Minneapolis, Minn.

[ * ] Notice: This patent is subject to a terminal disclaimer.

[21] Appl. No.: 08/988,493

[22] Filed: Dec. 10, 1997

Related U.S. Application Data

[63] Continuation-in-part of application No. 08/957,942, Oct. 27, 1997.

[51] Int. Cl.[7] ................................................. A61B 17/22
[52] U.S. Cl. ........................... 606/159; 606/180; 606/170
[58] Field of Search ..................... 606/159, 167, 606/170, 180, 171, 169; 604/19, 22

[56] References Cited

U.S. PATENT DOCUMENTS

| | | |
|---|---|---|
| 1,851,146 | 3/1932 | Banker . |
| 3,712,438 | 1/1973 | Roddy et al. . |
| 3,937,222 | 2/1976 | Banko . |
| 4,445,509 | 5/1984 | Auth . |
| 4,679,557 | 7/1987 | Opie et al. . |
| 4,771,774 | 9/1988 | Simpson et al. . |
| 4,857,046 | 8/1989 | Stevens et al. ............................ 604/22 |
| 4,926,986 | 5/1990 | Noel . |
| 4,990,134 | 2/1991 | Auth ........................................ 604/22 |
| 5,217,474 | 6/1993 | Zacca et al. ............................ 606/159 |
| 5,312,427 | 5/1994 | Shturman ................................. 606/159 |
| 5,314,407 | 5/1994 | Auth et al. ................................ 604/22 |
| 5,314,438 | 5/1994 | Shturman ................................. 606/159 |
| 5,356,418 | 10/1994 | Shturman ................................. 606/159 |
| 5,360,432 | 11/1994 | Shturman ................................. 606/159 |
| 5,501,694 | 3/1996 | Ressemann et al. ..................... 606/159 |
| 5,634,933 | 6/1997 | McCombs et al. ...................... 606/180 |
| 5,681,336 | 10/1997 | Clement et al. ......................... 606/159 |
| 5,779,722 | 7/1998 | Shturman et al. ....................... 606/159 |
| 5,833,246 | 11/1998 | Trott . | |
| 5,849,023 | 12/1998 | Mericle .................................. 606/180 |

FOREIGN PATENT DOCUMENTS

| | | |
|---|---|---|
| 0 244 058 | 11/1987 | European Pat. Off. . |
| 0 321 319 | 6/1989 | European Pat. Off. . |
| 761 398 | 9/1933 | France . |
| 1000163 | 10/1996 | Netherlands . |
| 2080454 | 5/1997 | Russian Federation . |
| 1350393 | 11/1987 | U.S.S.R. . |
| WO 94/12132 | 6/1994 | WIPO . |
| WO 96/37153 | 11/1996 | WIPO . |
| WO 97/14470 | 4/1997 | WIPO . |

OTHER PUBLICATIONS

Brochure: "Rotalink—Sizing Up Is a Snap," SCIMED Boston Scientific Corporation, Maple Grove, MN 55311–1566, seven pages, Feb. 1997.

*Primary Examiner*—Glenn K. Dawson
*Attorney, Agent, or Firm*—Fredrikson & Byron, P.A.

[57] ABSTRACT

A rotational atherectomy device having a handle housing and an exchangeable drive shaft cartridge. The handle housing includes a rotatable prime mover carried by a prime mover carriage which is longitudinally movable with respect to the handle housing. The exchangeable drive shaft cartridge includes a cartridge housing, a longitudinally extendable tube, a catheter and a rotatable drive shaft which, near its distal end, has an abrasive tissue removal implement. The cartridge housing may be attached to and detached from the handle housing, the longitudinally extendable tube may be attached to and detached from the prime mover carriage, and the drive shaft together with its tissue removal implement may be attached to and detached from the prime mover, thereby permitting the exchangeable drive shaft cartridge to be selectively attached to and detached from the handle housing.

127 Claims, 98 Drawing Sheets

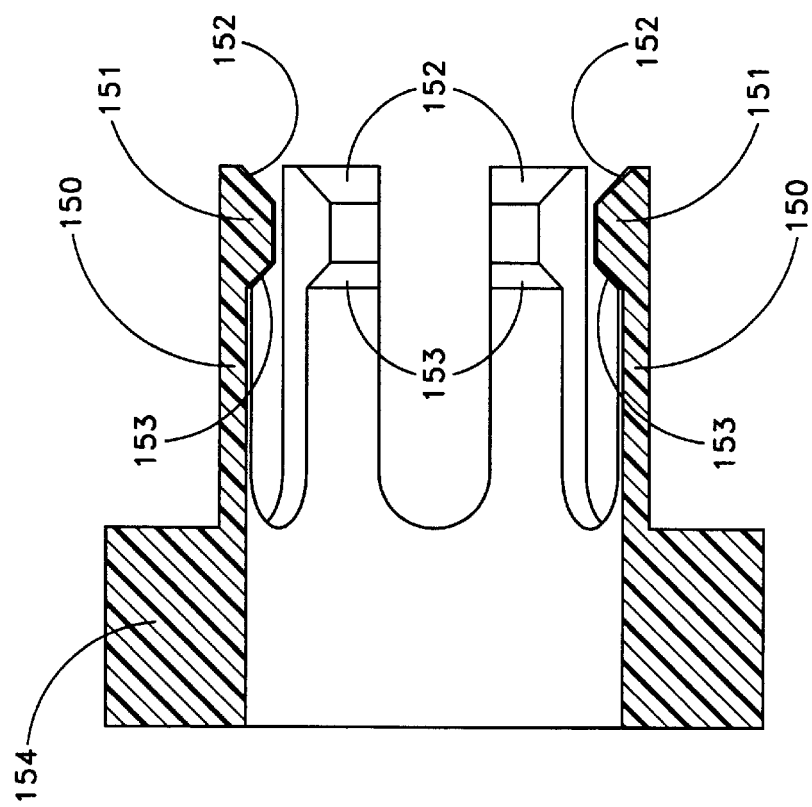
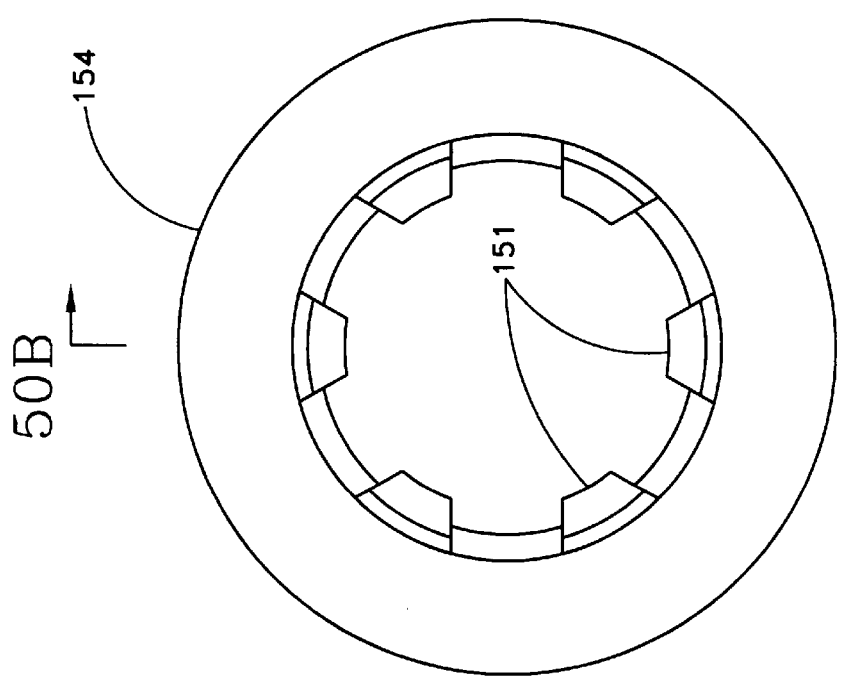

ROTATIONAL ATHERECTOMY DEVICE WITH EXCHANGEABLE DRIVE SHAFT CARTRIDGE

CROSS REFERENCE TO RELATED APPLICATION

This application is a continuation in part of application Ser. No. 08/957,942, filed Oct. 27, 1997.

TECHNICAL FIELD

The invention relates to devices and methods for removing tissue from body passageways, such as removal of atherosclerotic plaque from arteries, utilizing a rotational atherectomy device. In particular, the invention relates to improvements in a rotational atherectomy device having an exchangeable drive shaft cartridge.

BACKGROUND OF THE INVENTION

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterolrich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®. The handle of the Rotablator® device includes a variety of components, including a compressed gas driven turbine, a mechanism for clamping a guide wire extending through the drive shaft, portions of a fiber optic tachometer, and a pump for pumping saline through the drive shaft.

The connection between the drive shaft (with its associated burr) and the turbine in the Rotablator® device is permanent; yet, frequently it is necessary to use more than one size burr during an atherectomy procedure. That is, often a smaller size burr is first used to open a stenosis to a certain diameter, and then one or more larger size burrs are used to open the stenosis further. Such use of multiple burrs of subsequently larger diameter is sometimes referred to as a "step up technique" and is recommended by the manufacturer of the Rotablator® device. In the multiple burr technique it is necessary to use a new Rotablator® device for each such successive size burr. Accordingly, there is a need for an atherectomy system that would permit a physician to use only one handle throughout an entire procedure and to attach to such handle an appropriate drive shaft and tissue removing implement (e.g., a burr) to initiate the procedure and then exchange the drive shaft and the tissue removing implement for a drive shaft having a tissue removing implement of a different size or even a different design.

A subsequent version of the Rotablator® has been introduced with the ability to exchange a flexible distal portion of the drive shaft together with a burr for another distal portion of a drive shaft having a different size burr. Technical details of such a system are contained in international patent application No. WO 96/37153. This system utilizes a flexible drive shaft having a connect/disconnect feature allowing the physician to disconnect the exchangeable distal portion of the flexible drive shaft together with the burr from the flexible proximal portion of the drive shaft which is connected to the turbine of the handle, thus permitting the burr size to be changed without discarding the entire atherectomy unit. Each exchangeable drive shaft portion is disposed within its own exchangeable catheter and catheter housing. The flexible proximal portion of the drive shaft in this system is permanently attached to the turbine and is not exchanged. This system has been commercialized by Boston Scientific under the trademark Rotalink System™. While the Rotalink System™ does permit one to change the burr size, the steps required to actually disconnect the exchangeable portion of the drive shaft and replace it with another exchangeable portion of the drive shaft are quite involved and require relatively intricate manipulation of very small components.

First, a catheter housing must be disconnected from the handle and moved distally away from the handle to expose portions of both the proximal and distal sections of the flexible drive shaft which contain a disconnectable coupling. This coupling is disconnected by sliding a lock tube distally, permitting complementary lock teeth on the proximal and distal portions of the flexible drive shaft to be disengaged from each other. A similar flexible distal drive shaft portion with a different burr may then be connected to the flexible proximal portion of the drive shaft. To accomplish such assembly, the lock tooth on the proximal end of the distal replacement portion of the drive shaft must first be both longitudinally and rotationally aligned with the complementary lock tooth at the distal end of the proximal portion of the drive shaft. Since the flexible drive shaft typically is less than 1mm in diameter, the lock teeth are similarly quite small in size, requiring not insignificant manual dexterity and visual acuity to properly align and interlock the lock teeth. Once the lock teeth have been properly interlocked with each other, the lock tube (also having a very small diameter) is slid proximally to secure the coupling. The catheter housing must then be connected to the handle housing.

While this system does permit one to exchange one size burr (together with a portion of the drive shaft) for a burr of another size, the exchange procedure is not an easy one and must be performed with considerable care. The individual performing the exchange procedure must do so while wearing surgical gloves to protect the individual from the blood of the patient and to maintain the sterility of the elements of the system. Surgical gloves diminish the tactile sensations of the individual performing the exchange procedure and therefore make such exchange procedure even more difficult.

Accordingly, it would be desirable to have an atherectomy device permitting easier attachment and/or exchange of the drive shaft and its tissue removing implement.

SUMMARY OF THE INVENTION

The invention provides a rotational atherectomy device designed to facilitate easy attachment, detachment and exchange of the drive shaft and its tissue removing implement. The rotational atherectomy device includes a handle housing and an exchangeable drive shaft cartridge having a housing which is removably attachable to the handle housing. A rotatable prime mover is carried by a prime mover carriage disposed within the handle housing, the prime mover carriage being longitudinally movable with respect to the handle housing.

The exchangeable drive shaft cartridge includes a longitudinally extendable tube having a distal end portion carried by the cartridge housing and a proximal end portion which is removably attachable to the prime mover carriage for longitudinal movement therewith. The cartridge has an elongated catheter with a proximal end portion which is carried by the cartridge housing, and a rotatable flexible drive shaft having proximal, intermediate and distal portions. The proximal portion of the drive shaft is attached to an elongated shank, the intermediate portion is disposed primarily within the tube and the catheter, and the distal portion extends distally from the catheter and has a tissue removal implement.

A drive shaft attachment mechanism removably attaches the drive shaft to the prime mover. The drive shaft attachment mechanism comprises a prime mover socket carried by the prime mover and the elongated shank carried by the proximal end portion of the drive shaft. The elongated shank is removably insertable into the prime mover socket, at least one of the shank and the socket being radially resilient.

With a rotational atherectomy device of this type, the cartridge housing may be attached to and detached from the handle housing, the longitudinally extendable tube may be attached to and detached from the prime mover carriage, and the drive shaft may be attached to and detached from the prime mover, thereby permitting the exchangeable drive shaft cartridge to be selectively attached to and detached from the handle housing.

Preferably the rotational atherectomy device includes a tube attachment mechanism positioned to removably attach the longitudinally extendable tube to the prime mover carriage, the tube attachment mechanism including a resilient positioning mechanism for moving the prime mover carriage and the shank proximally with respect to the longitudinally extendable tube after the prime mover carriage has been advanced distally and attached to the longitudinally extendable tube and after pressure moving the prime mover carriage distally with respect to the longitudinally extendable tube has been released. The resilient positioning mechanism spaces the shank away from an abutment surface associated with the longitudinally extendable tube to permit free rotation of the shank with respect to the longitudinally extendable tube.

Preferably the rotational atherectomy device of also includes an interlock mechanism—preferably a two stage interlock mechanism—for removably attaching the cartridge housing to the handle housing. The two stage interlock mechanism includes a primary interlocking member carried by either the cartridge housing or the handle housing, and two complementary interlocking members carried by the other of the cartridge housing and the handle housing. The two complementary interlocking members are longitudinally spaced away from each other so that the primary interlocking member may be selectively interlocked with either one of the complementary interlocking members.

BRIEF DESCRIPTION OF THE DRAWINGS

FIG. 9 is a perspective view, FIG. 10 is a broken-away, longitudinal cross-sectional view, and FIG. 11 it a broken-away top view;

FIGS. 50A–51B illustrate the design of two major components of the tube attachment mechanism shown in FIG. 49, FIGS. 50A and 50B being a distal end view and a cross-sectional view, respectively, of the component associated with the prime mover carriage, and FIGS. 51A and 51B being side and proximal end views, respectively, of the component associated with the longitudinally extendable tube;

FIG. 98 being a broken away longitudinal cross-section, and FIG. 99 being a transverse cross-section of FIG. 98 taken along lines 99—99 thereof;

DETAILED DESCRIPTION OF THE INVENTION

Figure 1:
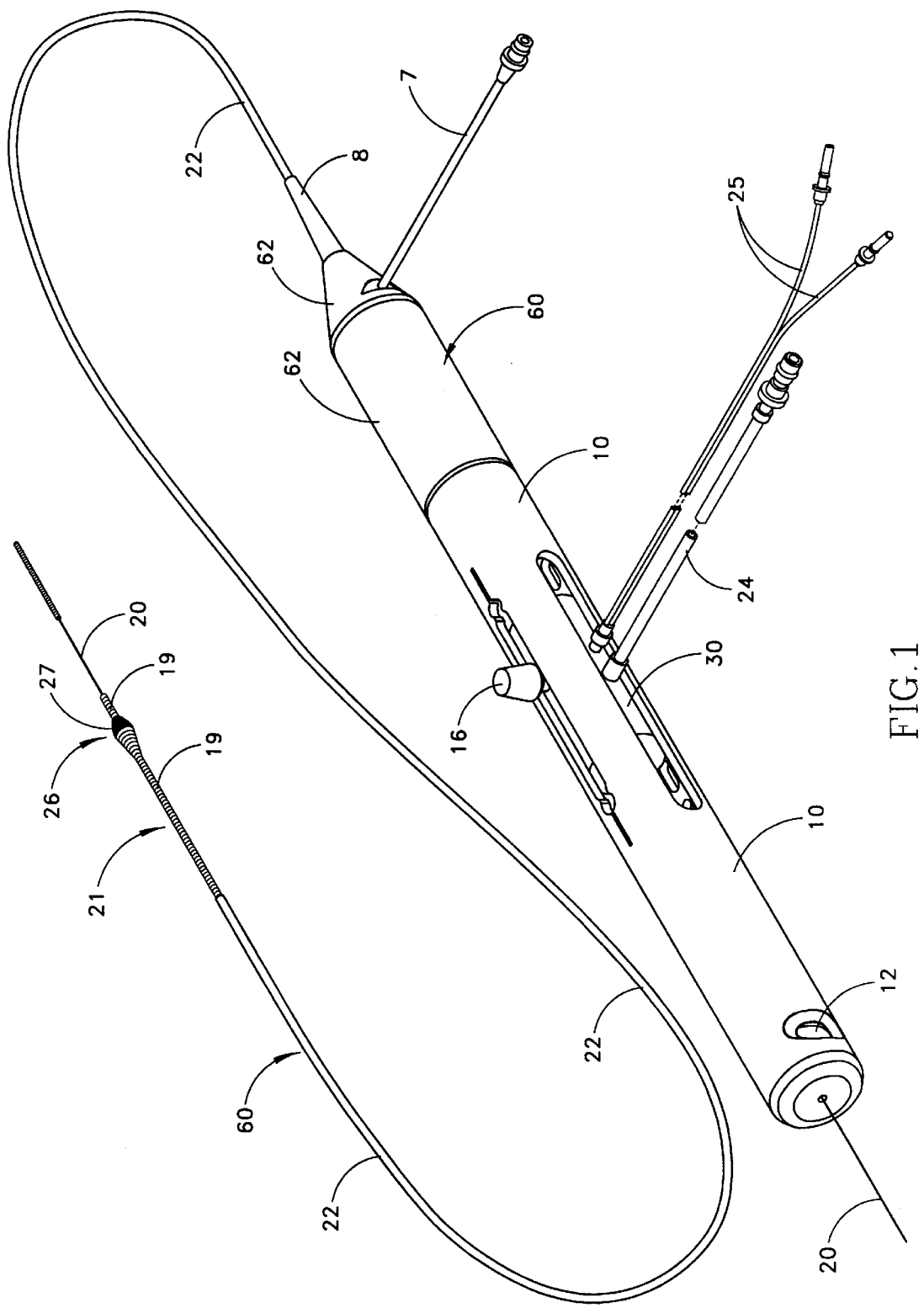
FIG. 1 is a perspective view of one embodiment of a rotational atherectomy device of the present invention showing the assembled atherectomy device of the invention.

FIG. 1 illustrates one embodiment of an atherectomy device of the invention. The device desirably includes a tubular handle housing 10. The handle housing 10 has a proximal portion which carries a guide wire clamp mechanism 12, an intermediate portion which carries a prime mover carriage 30, and a distal portion which is adapted to releasably interlock with an exchangeable drive shaft cartridge 60. Details of a preferred guide wire clamp mechanism used to clamp the guide wire 20 are contained in copending U.S. patent application Ser. No. 08/792,101, filed Jan. 31, 1997, the contents of which are hereby incorporated by reference.

The prime mover carriage 30 can be moved longitudinally within the handle housing 10 through a limited range of motion. A control knob 16 (operatively secured to the prime mover carriage 30) is provided to facilitate advancing and retracting the prime mover carriage 30 with respect to the handle housing 10.

The prime mover carriage 30 carries a prime mover. Preferably the prime mover is a compressed gas driven turbine. The turbine may be powered by, e.g., compressed nitrogen or compressed air. For this purpose a compressed gas supply line 24 may be provided, the supply line 24 being connected to the prime mover carriage 30. A pair of fiber optic cables 25 may also be provided for monitoring the speed of rotation of the turbine (e.g., as described in the Auth '407 patent and implemented in the Rotablator® device).

The exchangeable drive shaft cartridge 60 includes a cartridge housing 62, a longitudinally extendable tube 70 carried by the cartridge housing 62, an elongated catheter 22, and a rotatable flexible drive shaft 21. The longitudinally extendable tube is not seen in FIG. 1, but is discussed below in connection with, e.g., FIGS. 2–3. The elongated catheter 22 is carried by the cartridge housing 62 and is connected to a distal end portion of the longitudinally extendable tube 70. The proximal end portion of the catheter 22 is supported by a strain relief element 8, which is secured to the cartridge housing 62. The flexible drive shaft 21 is rotatable over a guide wire 20 and includes a proximal portion, an intermediate portion, and a distal portion 19. The proximal portion of the drive shaft 21 is removably attachable to the prime mover. The intermediate portion of the drive shaft 21 is disposed primarily within the longitudinally extendable tube 70 and the catheter 22 and therefore is not visible in FIG. 1. The distal portion 19 of the drive shaft 21 extends distally from the catheter 22 and includes a tissue removal implement 26. The tissue removal implement 26 in the illustrated embodiment comprises an enlarged diameter section of the drive shaft 21 which has a generally conical proximal portion and a generally convex distal portion. The convex distal portion is covered with an abrasive material to define an abrasive segment 27 of the drive shaft. (Such a tissue removal implement is described in U.S. patent application Ser. No. 08/679,470, filed Jul. 15, 1996.) It should be understood that any suitable tissue removal implement may be used, including an eccentric tissue removal implement (such as is described in U.S. patent application Ser. No. 08/911,586, filed Aug. 14, 1997) or the diamond-coated burr proposed by Auth in U.S. Pat. No. 4,990,134.

Figure 2:
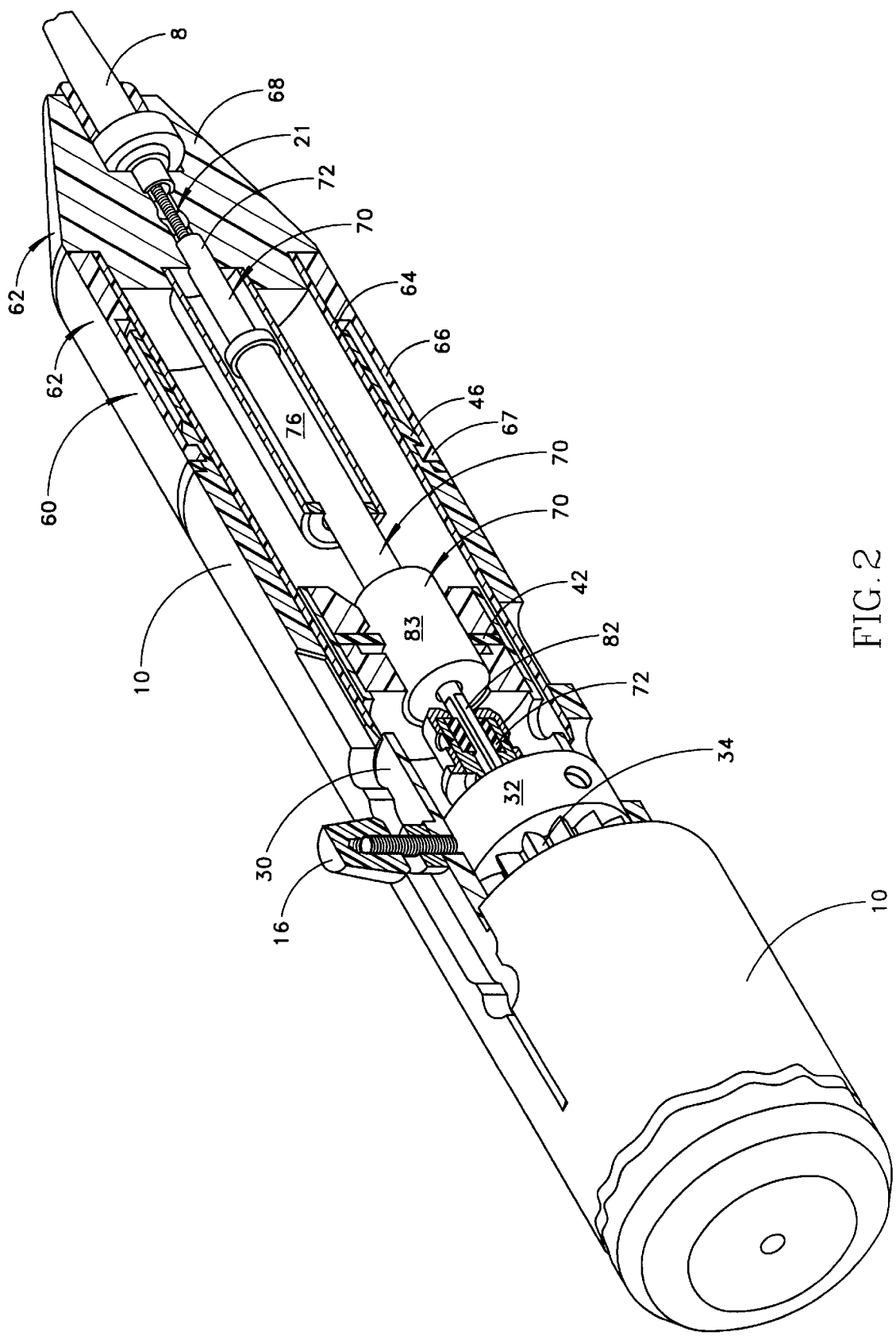
FIG. 2 is an enlarged perspective, partially broken-away view of a portion of the device shown in FIG. 1, illustrating the elements of the exchangeable drive shaft cartridge connected to the handle housing, the prime mover carriage and the prime mover.
Figure 3:
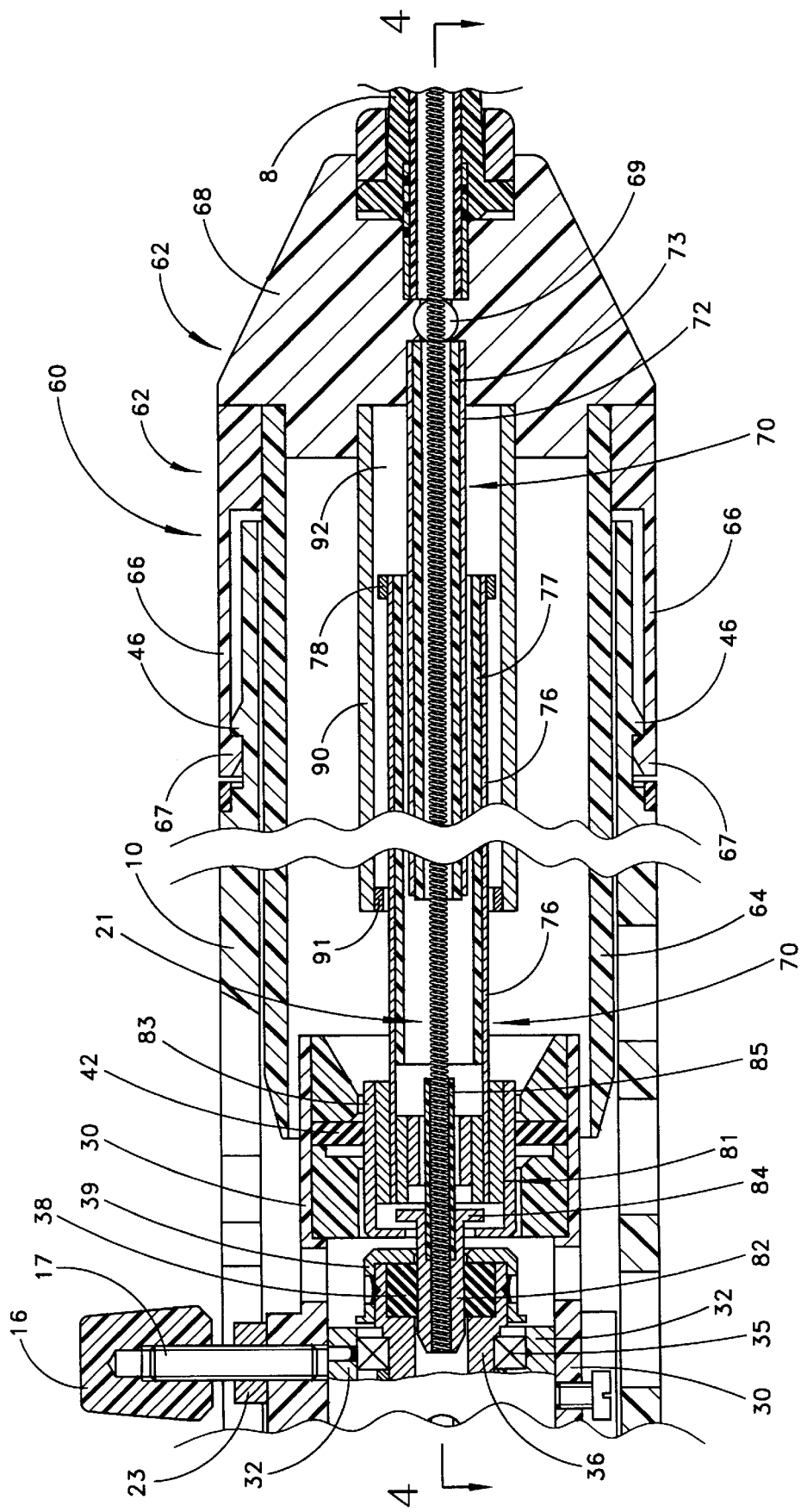
FIG. 3 is a broken away, longitudinal cross-section of the atherectomy device shown in FIG. 2.
Figure 4:
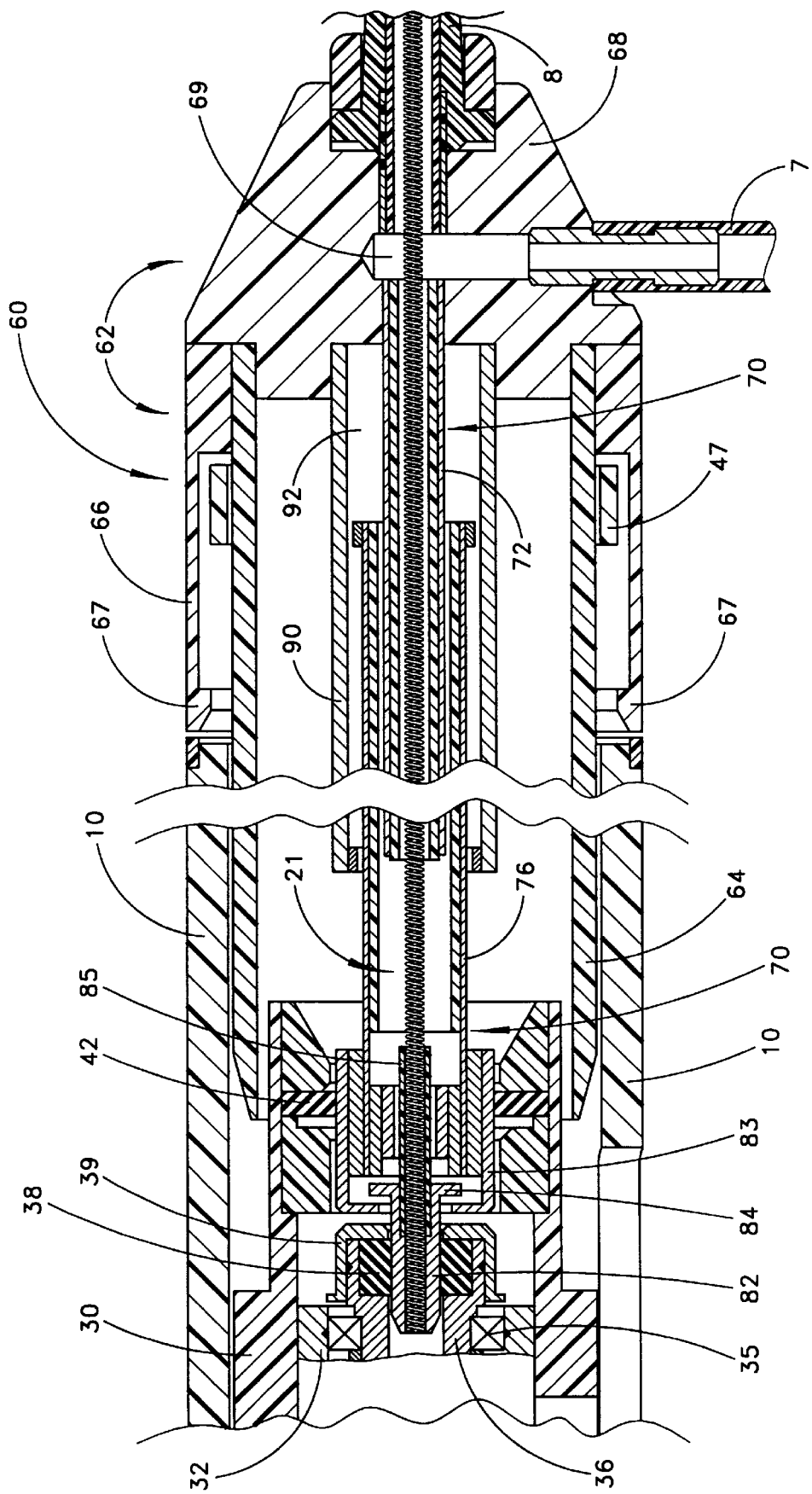
FIG. 4 is a longitudinal cross-sectional view of FIG. 3, taken along lines 4—4 thereof, and illustrating a flexible fluid supply tube attached to the exchangeable drive shaft cartridge.

FIGS. 2–4 illustrate further details regarding the components of the exchangeable drive shaft cartridge 60 and how they are removably attached to the handle housing, the prime mover carriage and the prime mover. A rotatable prime mover (such as a compressed gas driven turbine or similar supply of rotational motion) is removably connectable (as will be described below) to the flexible drive shaft 21. The prime mover can be any device which can rotate the flexible drive shaft 21 at a sufficiently high speed. In the preferred embodiment illustrated in the drawings the prime mover is carried by a prime mover carriage 30 which is disposed within the handle housing 10. The prime mover carriage 30 can be moved longitudinally within the handle housing 10 through a limited range of motion. A control knob 16 (secured to the prime mover carriage 30 by a shaft 17) is provided to facilitate advancing and retracting of the prime mover carriage 30 with respect to the handle housing 10.

In the preferred embodiment shown in the drawings, a compressed gas driven turbine is utilized. The turbine can be constructed in a variety of suitable ways. In the embodiment depicted in the drawings, the turbine includes a turbine wheel 34 carried on a hollow turbine shaft 36 which passes through a turbine housing 32. The hollow turbine shaft 36 is supported by a pair of conventional bearings 35, only one of which is shown in the drawings.

A drive shaft attachment mechanism is provided to removably attach the drive shaft 21 to the prime mover. The drive shaft attachment mechanism comprises a prime mover socket 38 carried by the prime mover, and an elongated shank 82 carried by the proximal end portion of the drive shaft 21. The drive shaft shank 82 is removably insertable into the prime mover socket 38. At least one of the drive shaft shank 82 and the prime mover socket 38 is radially resilient. In the preferred embodiment shown in the drawings, the prime mover socket 38 is resilient. The prime mover socket 38 may be made to be radially resilient in a variety of ways. In the drawings the prime mover socket 38 consists of a resilient collar 38 secured inside a recess in the hollow turbine shaft 36 by a cap 39. A variety of other suitable ways may also be utilized to secure a prime mover socket 38 to the turbine shaft 36.

The inner diameter of the prime mover socket 38 is selected to provide a sufficiently tight interference fit with the drive shaft shank 82 so that, when the drive shaft 21 is attached to the prime mover, the shank 82 and the drive shaft 21 will both rotate and move longitudinally together with the prime mover socket 38 and the prime mover when the prime mover is rotated or moved longitudinally with respect to the handle housing 10.

Figure 40:
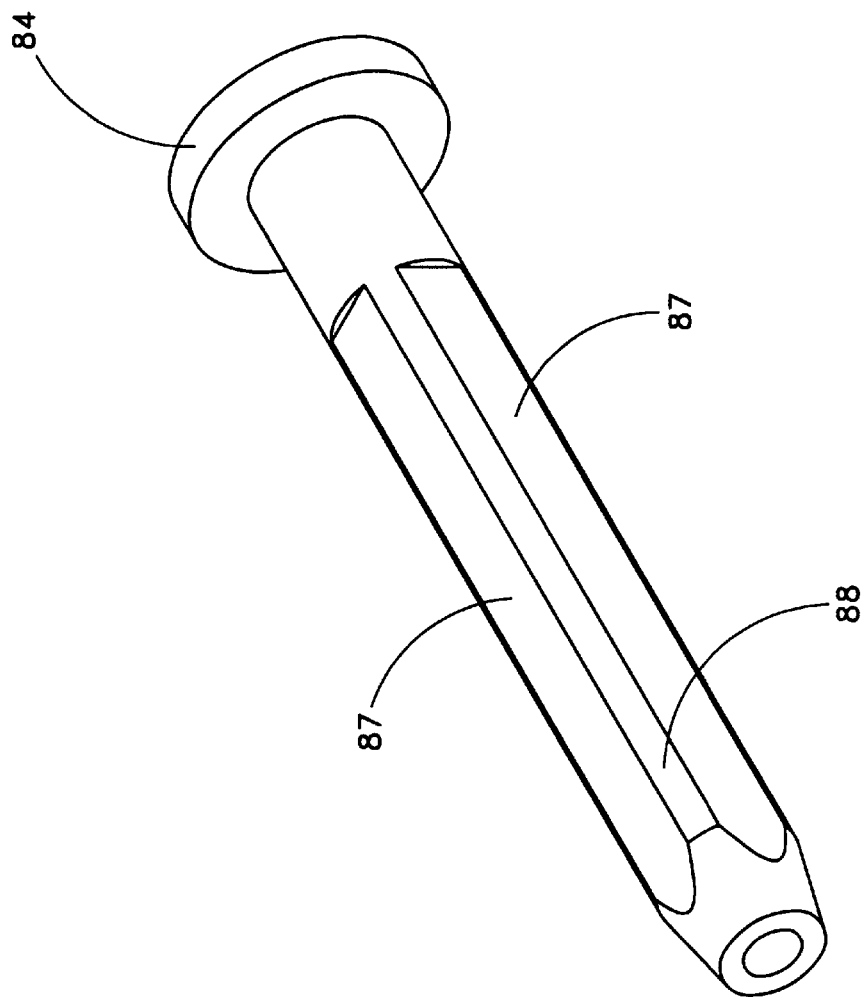
FIG. 40 is an enlarged perspective view of an elongated drive shaft shank.
Figure 41:
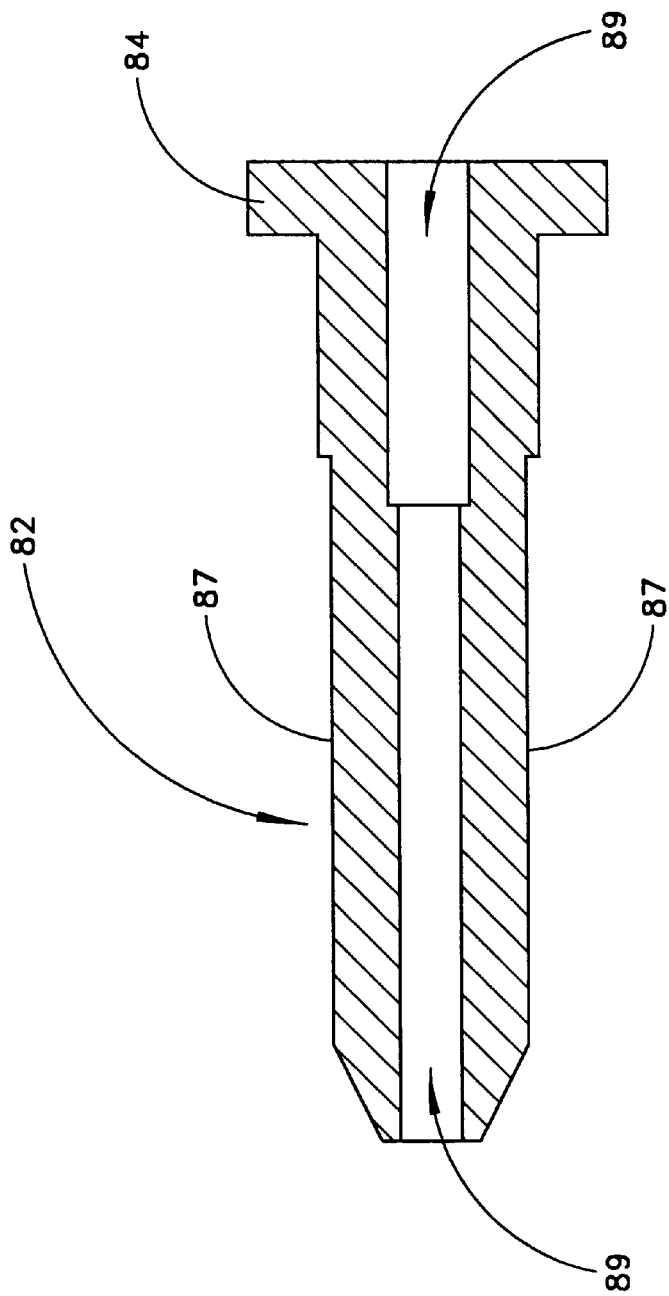
FIG. 41 is a longitudinal cross-sectional view of FIG. 40, taken along lines 41—41 thereof.

The elongated shank 82 (a preferred embodiment of which is shown and described in greater detail in FIGS. 40–41) is secured, either directly or indirectly, to the proximal end portion of the flexible drive shaft 21. Suitable adhesives or other conventional attachment methods may be utilized to attach the shank 82 to the flexible drive shaft 21. Moreover, the proximal end portion of the drive shaft 21 can itself constitute the shank if it is constructed in such a fashion as to be removably insertable into the prime mover socket 38.

The elongated shank 82 preferably includes proximal and distal portions. A substantial length of the proximal portion is removably insertable into the prime mover socket 38, while the distal portion preferably includes a radially outwardly extending flange 84. As is shown in FIGS. 3–4, the flange 84 is positioned between (and spaced away from) proximal and distal abutment surfaces associated with the proximal end portion of the longitudinally extendable tube 70. As is described in more detail below, the flange 84 abuts the distal abutment surface associated with the longitudinally extendable tube 70 when the shank 82 is inserted into the prime mover socket 38. The flange 84 abuts the proximal abutment surface associated with the longitudinally extendable tube 70 when the shank 82 is pulled out of the prime mover socket 38.

The longitudinal lumen of the elongated shank 82 has a slightly larger diameter near its distal end so that a short section of low friction tubing 85 may be received within the lumen of the shank 82 together with the proximal portion of the drive shaft 21. Such low friction tubing 85 may be heat shrunk onto a proximal portion of the drive shaft 21 in order to reduce friction between the drive shaft 21 and the elements of the bushing 81 which forms the distal abutment surface associated with the longitudinally extendable tube 70.

The longitudinally extendable tube 70 has a distal end portion carried by the cartridge housing 62 and a proximal end portion which is removably attachable to the prime mover carriage 30 for longitudinal movement therewith. The longitudinally extendable tube 70 surrounds a length of the flexible drive shaft 21 and facilitates longitudinal movement of the drive shaft 21 (together with the prime mover) with respect to the handle housing 10, the cartridge housing 62 and the catheter 22. The longitudinal extendable tube 70 can be constructed in a variety of ways. In the preferred embodiment shown in the drawings, the longitudinally extendable tube 70 is comprised of two elongated telescopic tubes. One of the tubes is a stationary telescopic tube 72 which is secured to the cartridge housing 62 (preferably to a distal end piece 68). The other tube is a movable telescopic tube 76 which is carried by and is longitudinally movable with respect to the stationary telescopic tube 72. The movable telescopic tube 76 is removably attachable to the prime mover carriage 30 for longitudinal movement therewith. The moveable telescopic tube 76 defines a proximal end portion of the longitudinally extendable tube 70. The stationary telescopic tube 72, or at least a distal length thereof, defines a distal end portion of the longitudinally extendable tube 70.

An additional stationary support tube 90 may be provided. Preferably the stationary support 90 is coaxial with both the stationary 72 and movable 76 telescopic tubes. The support tube 90 is secured to the cartridge housing 62 (preferably to the distal end piece 68).

The movable telescopic tube 72 is slidably received in an elongated annular space 92 defined between the support tube 90 and the stationary telescopic tube 72. The movable telescopic tube 76 is longitudinally moveable within that annular space 92 with respect to both the inner telescopic tube 72 and the support tube 90. Desirably, the inner surfaces of both the stationary 72 and movable 76 telescopic tubes are provided with a low-friction linings 73 and 77, respectively. The lining 73 of the stationary telescopic tube 72 helps minimize friction with the drive shaft 21 as it is rotated and moved proximally and distally around the guide wire. The lining 77 of the movable telescopic tube 76 helps minimize friction between the telescopic tubes as the movable telescopic tube 76 is moved with respect to the stationary telescopic tube 72.

These linings may be made from any suitable material, such as polytetrafluoroethylene tubing. If so desired, the separate linings may be omitted and the tubes 72 and 76 themselves may be made of a low friction material.

To prevent the disassembly of the longitudinally extendable tube 70, proximal movement of the movable telescopic tube 76 is limited by a pair of stops, one stop 78 being carried adjacent the distal end of the movable telescopic tube 76 and the other stop 91 being carried adjacent the proximal end of the support tube 90. To limit friction between the movable telescopic tube 76 and the support tube 90, these stops 78 and 91 may be formed of a low friction material such as polytetrafluoroethylene. If so desired, one or both of these stops 78 and 91 can be formed as an integral part of the movable telescopic tube 76 or the support tube 90. This is particularly advantageous if the movable telescopic tube 76 or the support tube 90 is made from a low friction material.

The atherectomy device also includes a tube attachment mechanism positioned to removably attach the longitudinally extendable tube 70 (i.e., the movable telescopic tube 76) to the prime mover carriage 30. Preferably the tube attachment mechanism includes a resilient positioning mechanism for moving the prime mover carriage 30 and the shank 82 proximally with respect to the longitudinally extendable tube 70 after the prime mover carriage 30 has been advanced distally and attached to the longitudinally extendable tube 70 and after pressure moving the prime mover carriage 30 distally with respect to the longitudinally extendable tube 70 has been released (as is described in greater detail below). The resilient positioning mechanism thus spaces the flange 84 of the shank 82 away from an abutment surface associated with the longitudinally extendable tube 70 (i.e., the movable telescopic tube 76) to permit free rotation of the shank 82 with respect to the longitudinally extendable tube 70.

In the embodiment illustrated in FIGS. 2–4, the resilient positioning mechanism comprises a resilient positioning ring 42 carried by the prime mover carriage 30. The resilient positioning ring 42 includes a radially inner portion and a radially outer portion. The radially outer portion of the positioning ring 42 is secured against longitudinal movement with respect to the prime mover carriage 30. As shown, e.g., in FIGS. 28, 30 and 32, the radially inner portion of the resilient ring 42 is configured with respect to the prime mover carriage 30 so that such inner portion of the ring 42 resiliently deflects proximally when the prime mover carriage 30 and the resilient positioning ring 42 are moved distally over the movable telescopic tube 76. As described in more detail below, the radially inner portion of the resilient ring 42 at least partially returns to its non-deflected configuration, and thereby moves the prime mover carriage 30 and the shank 82 proximally with respect to the movable telescopic tube 76, after pressure urging the prime mover carriage 30 and the resilient positioning ring 42 over the movable telescopic tube 76 has been removed, thus spacing the shank's flange 84 away from the distal abutment surface of the movable telescopic tube 76 and permitting the shank 82 and its flange 84 to rotate freely with respect to the movable telescopic tube 76.

FIG. 4 shows connection of a flexible fluid supply tube 7 to the distal end piece 68 of the cartridge housing 62. One end of the flexible fluid supply tube 7 communicates with an external fluid supply (not shown) while the other end of the tube 7 is attached to the cartridge housing 62 (preferably the distal end piece 68) of the exchangeable drive shaft cartridge 60. The flexible fluid supply tube 7 is in fluid communication with a fluid-receiving recess 69 in the distal end piece 68. From the fluid-receiving recess 69, fluid, supplied from a fluid source external to the exchangeable drive shaft cartridge 60, may flow distally into the lumen of the catheter 22 and proximally into the lumen of the longitudinally extendable tube 70. The lumens of the stationary 64 and movable 66 telescopic tubes and the lumen of the catheter 22 together define the drive shaft lumen within which a majority of the length of the drive shaft 21 is received. Fluid supplied to the drive shaft lumen will help reduce friction between the drive shaft 21 and the walls of the telescopic tubes 72, 76 and the catheter 22.

Desirably, the fluid supply tube 7 is attached to the cartridge housing 62 of the exchangeable drive shaft cartridge 60 distally of the prime mover carriage 30, distally of the drive shaft shank 82 and distally of at least one of the telescopic tubes 72 and 76. Preferably, it is connected to the cartridge housing 62 distally of both of the telescopic tubes 72 and 76 and proximally of the catheter 22, thus positioning it both adjacent a distal end of the longitudinally extendable tube 70 and near the distal end of the cartridge housing 62.

The atherectomy device of the invention also includes an interlock mechanism for removably attaching the cartridge housing 62 to the handle housing 10. Preferably the interlock mechanism is a two stage interlock mechanism including longitudinally spaced proximal and distal stages. In the embodiment shown in FIGS. 1–4, the cartridge housing 62 includes a pair of coaxial, generally cylindrical tubes, 64 and 66, and the handle housing 10 is comprised of a generally cylindrical tube. At least part of the inner cylindrical tube 64 of the cartridge housing 62 is telescopically receivable within the generally tubular handle housing 10. The two stage interlock mechanism depicted in the drawings comprises a primary interlocking member carried by the outer telescopic tube 66 of the cartridge housing 62 and two complementary interlocking members carried by the handle housing 10. The primary interlocking member is comprised of an annular radially inwardly extending shoulder 67 carried by the outer tube 66 of the cartridge housing 62. The annular shoulder 67 is interlockable with a proximal complementary interlocking member carried by the handle housing 10. The proximal complementary interlocking member is comprised of a pair of radially outwardly extending tabs 46 carried by the handle housing 10. Preferably the tabs 46 are circumferentially opposed—i.e., they are located on opposite sides of the tubular handle housing 10. As is described in detail below, the proximal stage of the two-stage interlock mechanism is releasable by compressing the annular shoulder 67 of the cartridge housing 62 to an oval shape and moving the shoulder distally over the tabs 46 of the handle housing 10. To permit this compression, the annular shoulder 67 has an inner diameter which is sufficiently larger than the outer diameter of the inner tube 64 of the cartridge housing 62 so that the annular shoulder 67 may be compressed to an oval shape to be moved over the tabs 46 of the handle housing 10.

Figure 5:
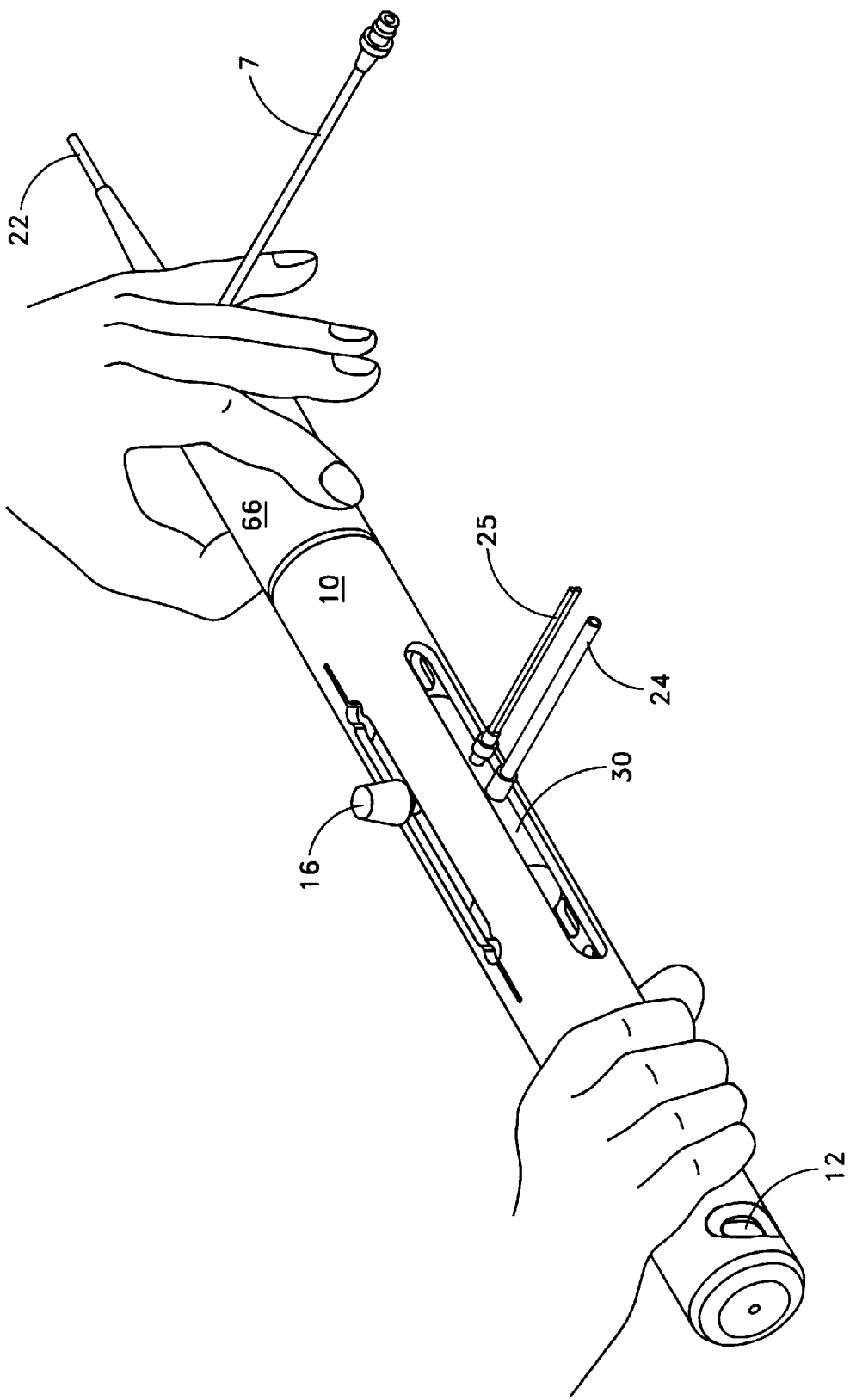
FIGS. 5–7 illustrate the first step in the process of detaching the cartridge housing from the handle housing, FIG. 5 being a perspective view, FIG. 6 being a broken-away, longitudinal cross-sectional view of FIG. 5, and FIG. 7 being a cross-sectional view of FIG. 6, taken along lines 7—7 thereof (for the sake of clarity only the components of the interlock between the cartridge housing and the handle housing are shown in FIG. 7)
Figure 6:
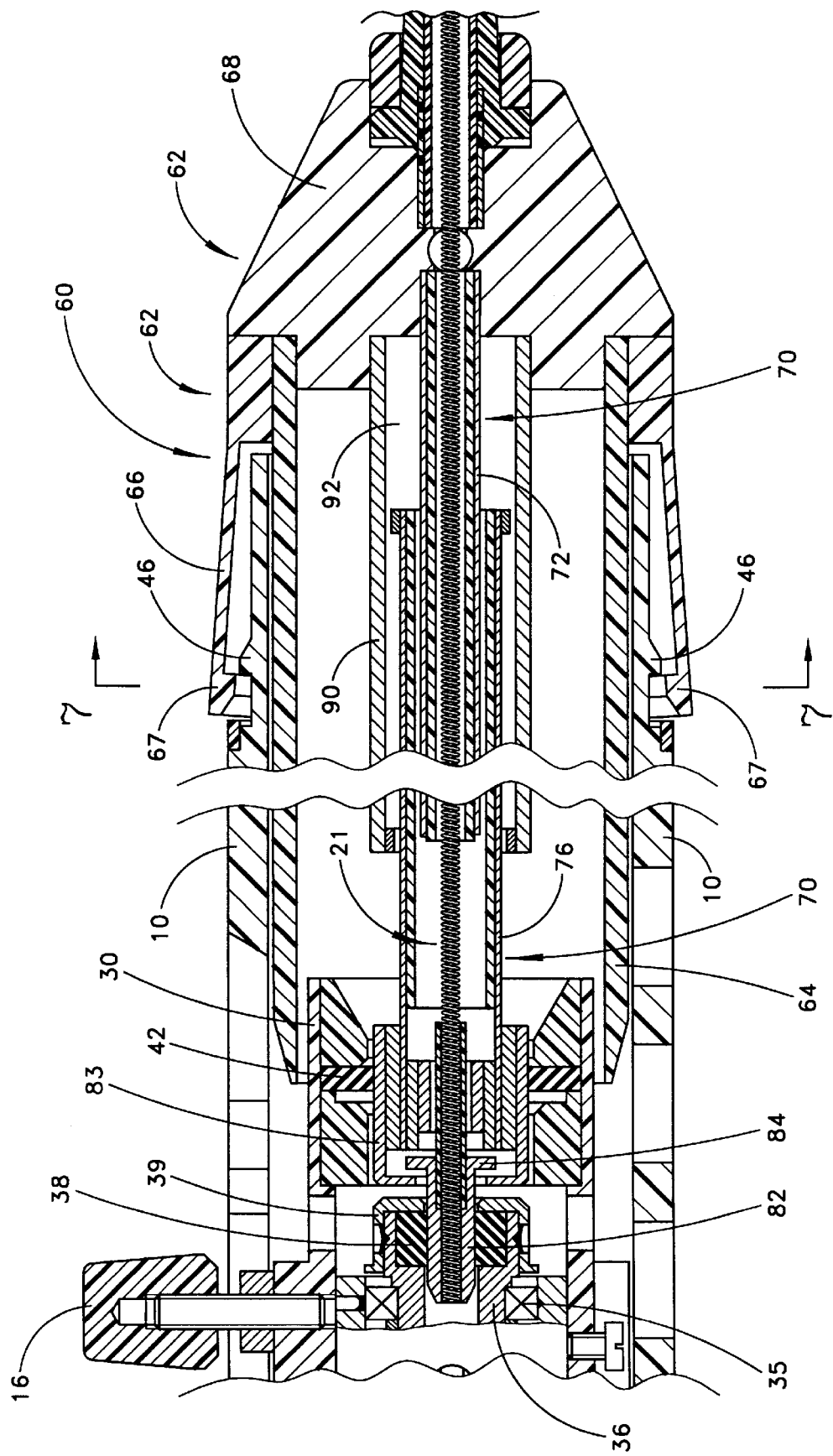
Figure 7:
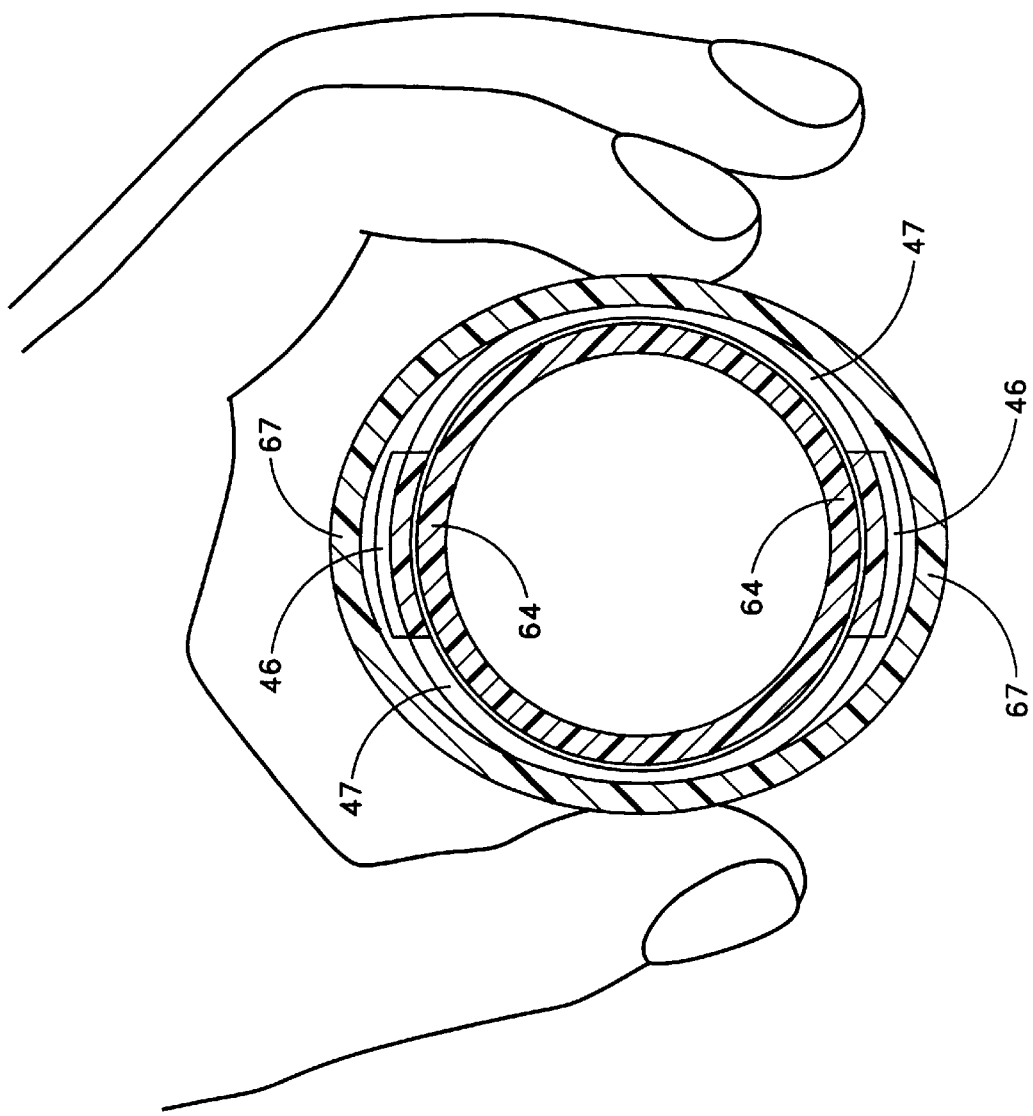

FIGS. 5–16 illustrate the process of detaching the exchangeable drive shaft cartridge from the handle housing 10. In FIG. 5 the user is compressing the outer tube 66 of the cartridge housing 62 between two points located circumferentially between the tabs 46. As a result, and as is shown in FIG. 6–7, the annular shoulder 67 becomes deformed to an oval shape and disengaged from the tabs 46.

Figure 8:
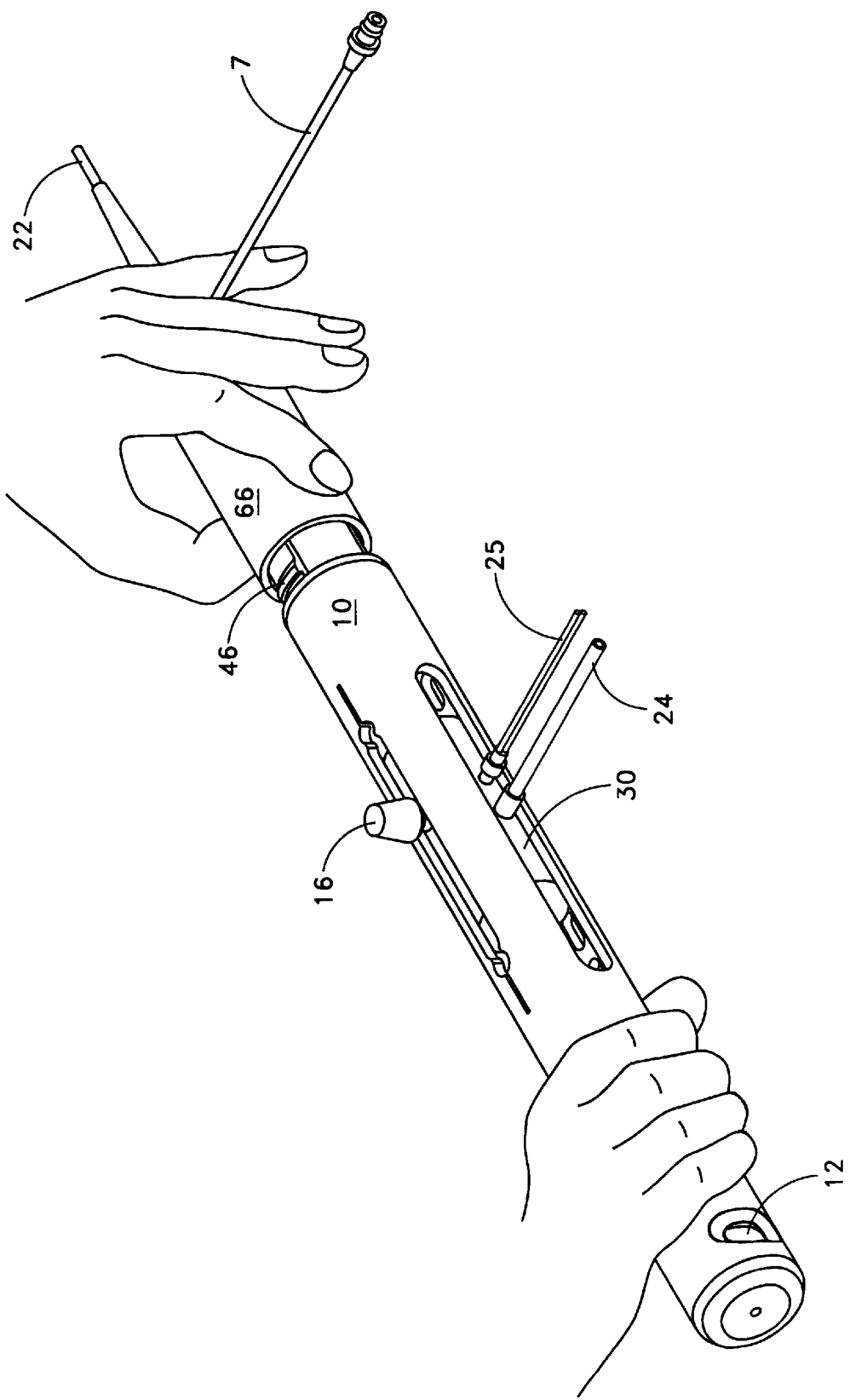
FIG. 8 is a perspective view illustrating the second step in the process of detaching the cartridge housing from the handle housing.
Figure 12:
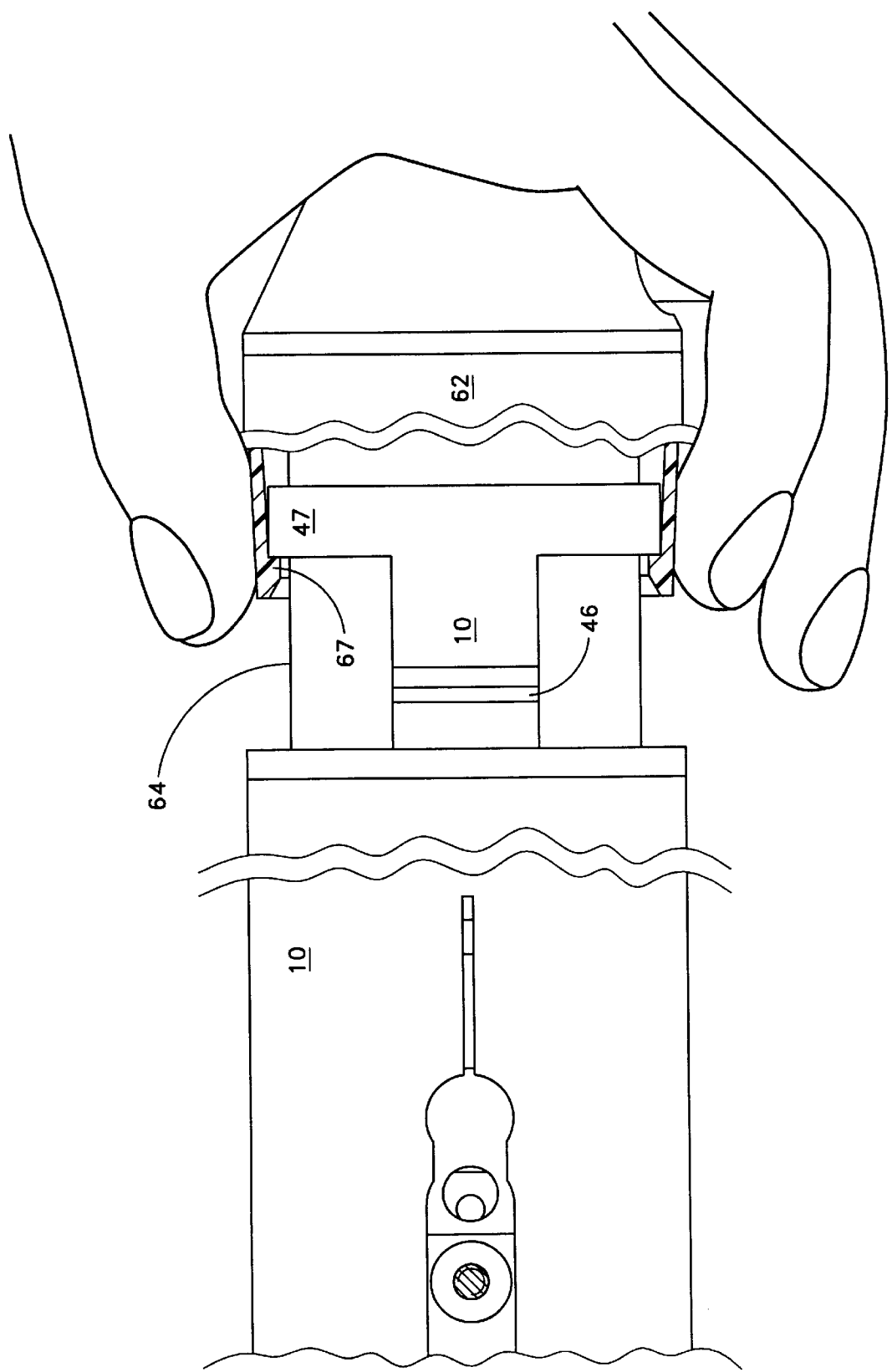
FIG. 12 is a top view, partially broken-away, of the atherectomy device in the position shown in FIG. 8.
Figure 13:
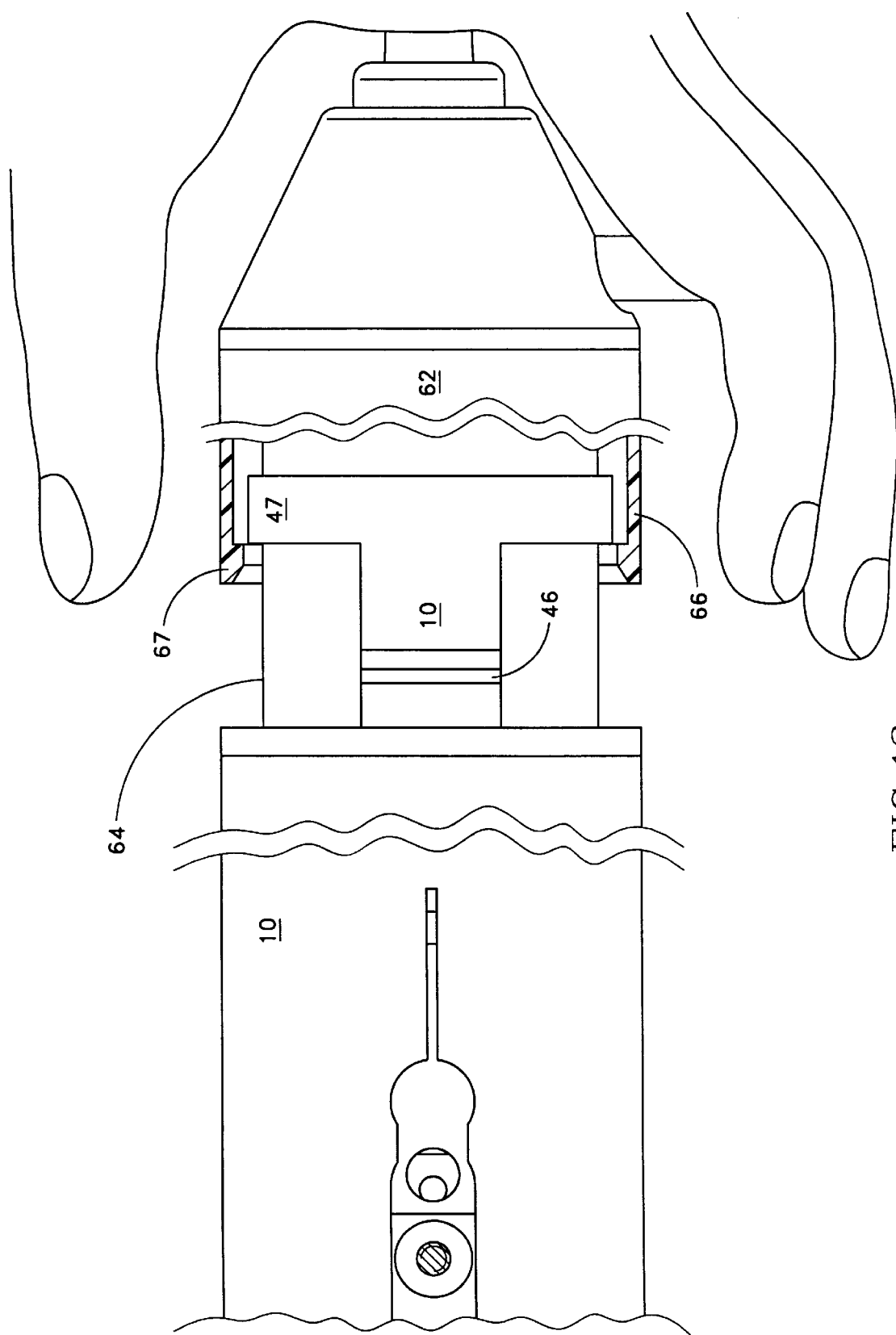
FIG. 13 is a top view, similar to FIG. 12, illustrating the third step in the process of detaching the cartridge housing from the handle housing.

In FIG. 8 the user has moved the compressed shoulder 67 distally over the tabs 46, thereby releasing the first stage of the two stage interlock mechanism. FIGS. 9–13 illustrate the second stage of the two stage interlock mechanism. The handle housing 10 is provided with an annular ring 47 carried distally of the tabs 46. As is shown in FIG. 12, when the user moves the cartridge housing 62 distally while holding the shoulder 67 in the compressed, oval shape, the shoulder 67 engages portions of the annular ring 47, preventing further distal movement of the cartridge housing 62. As is shown in FIG. 13, release of the outer tube 66 of the cartridge housing 62 allows the annular shoulder 67 to return to its original round shape, thereby releasing the annular shoulder 67 of the cartridge housing 62 from engagement with the annular ring 47 of the handle housing 10. As can be seen in these drawings, a pair of windows 48 are provided in the wall of the handle housing 10 circumferentially opposite each other and between the tabs 46 to permit compression of the outer tube 66 of the cartridge housing 62 to release the first stage of the two stage interlock mechanism.

Figure 14:
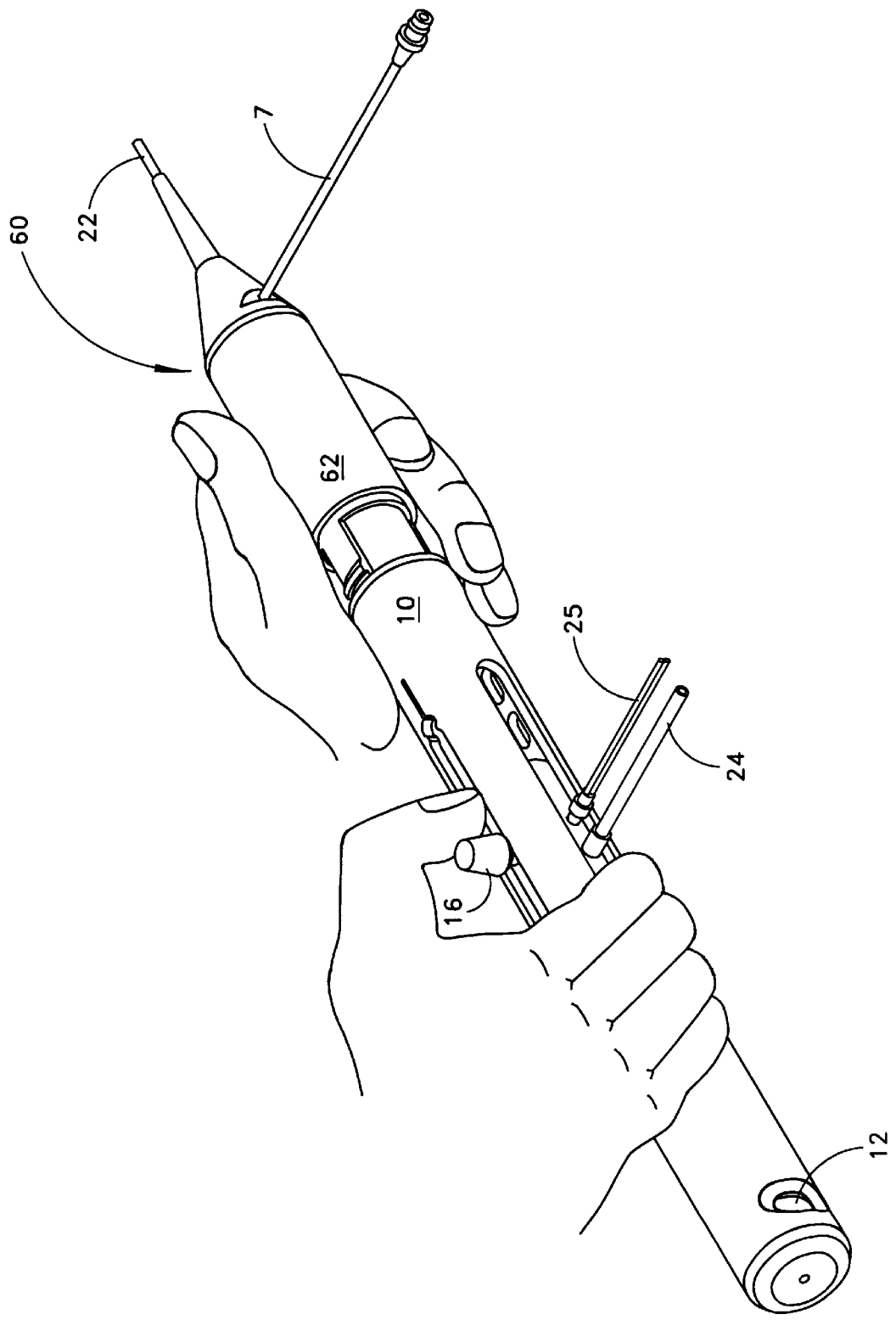
FIG. 14 is a perspective view illustrating a fourth step in the process of detaching the cartridge housing from the handle housing, and the proximal movement of the prime mover carriage to disconnect the flexible drive shaft from the prime mover.

In FIG. 14 the user has moved the drive shaft cartridge 60 slightly distally and is holding, with his left hand, both the cartridge housing 62 and the handle housing 10 to prevent longitudinal movement of the cartridge housing 62 with respect to the handle housing 10. With his right hand the user is pulling proximally on the control knob 16 to move the prime mover carriage 30 proximally to withdraw the drive shaft shank 82 from the prime mover socket 38 and to detach the longitudinally extendable tube 70 (i.e., the movable telescopic tube 76) from the prime mover carriage 30. Preferably the distal complementary interlocking member (i.e., the proximal edge of the annular ring 42, which helps to define the windows 48), is positioned sufficiently distally with respect to the proximal complementary interlocking member (i.e., the radially outwardly extending tabs 46), so that when, in the process of detaching the cartridge housing 62 from the handle housing 10, the primary interlocking member (i.e., the annular shoulder 67 of the outer tube 66 of the cartridge housing 62) interlocks with the distal complementary interlocking member, movement of the prime mover carriage 30 to its proximal limit of movement assures that the drive shaft shank 82 will be withdrawn from the prime mover socket 38 and the longitudinally extendable tube 70 (i.e., the movable telescopic tube 76) will be detached from the prime mover carriage 30.

Figure 15:
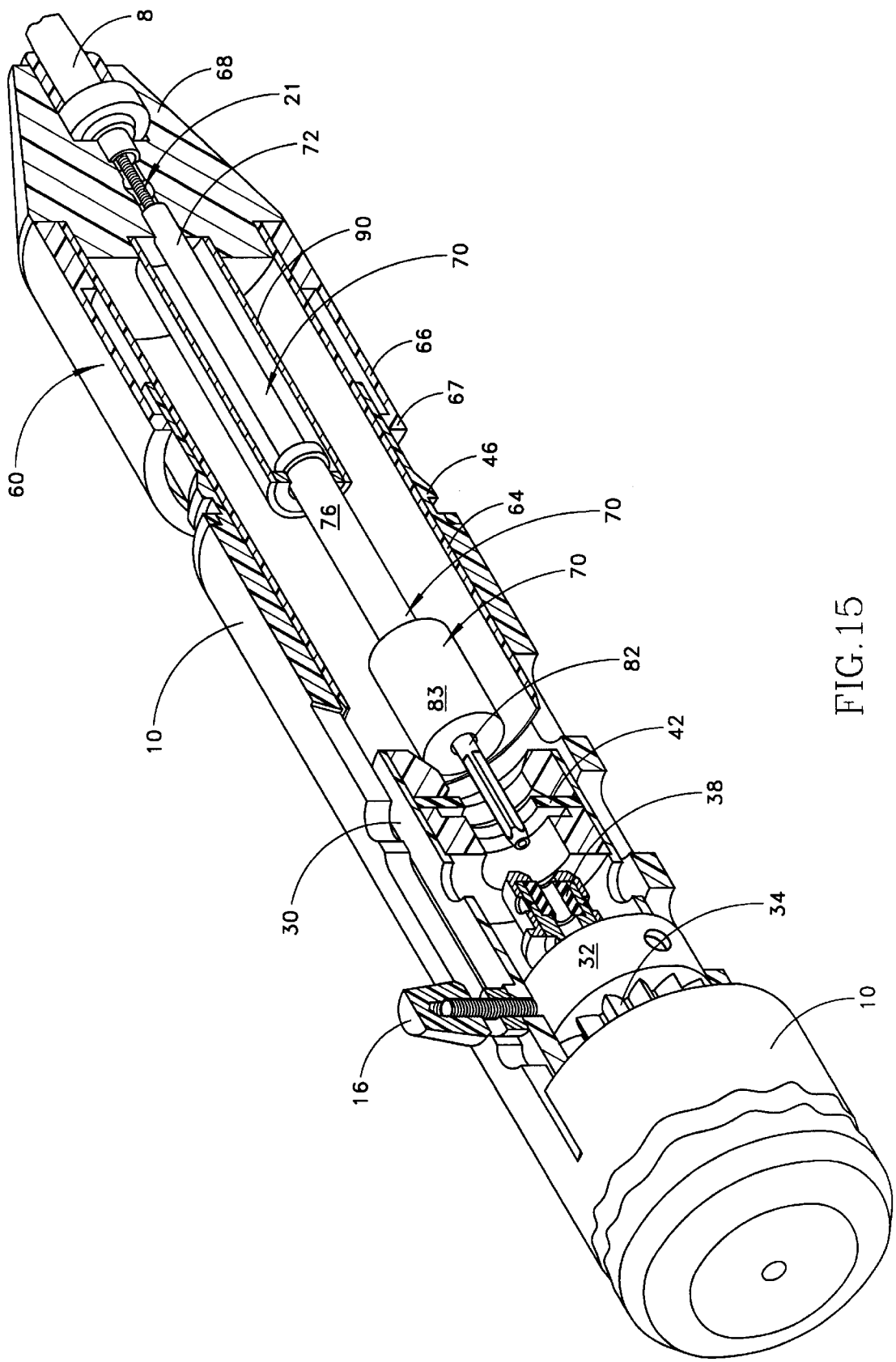
FIG. 15 is a perspective, partially broken-away view similar to FIG. 2 illustrating the elements of the exchangeable drive shaft cartridge not interlocked with the handle housing, the prime mover carriage and the prime mover.

FIG. 15 illustrates the positions of the components of the longitudinally extendable tube 70 of the exchangeable drive shaft cartridge 60 after the drive shaft shank 82 has been withdrawn from the prime mover socket 38 and the longitudinally extendable tube 70 has been detached from the prime mover carriage 30. Note that in this drawing the prime mover carriage 30 is close to but has not yet been moved to its proximal limit of movement, and yet the elongated shank 82 has already been pulled out of the prime mover socket 38 and the longitudinally extendable tube 70 has already been detached from the prime mover carriage 30.

Figure 16:
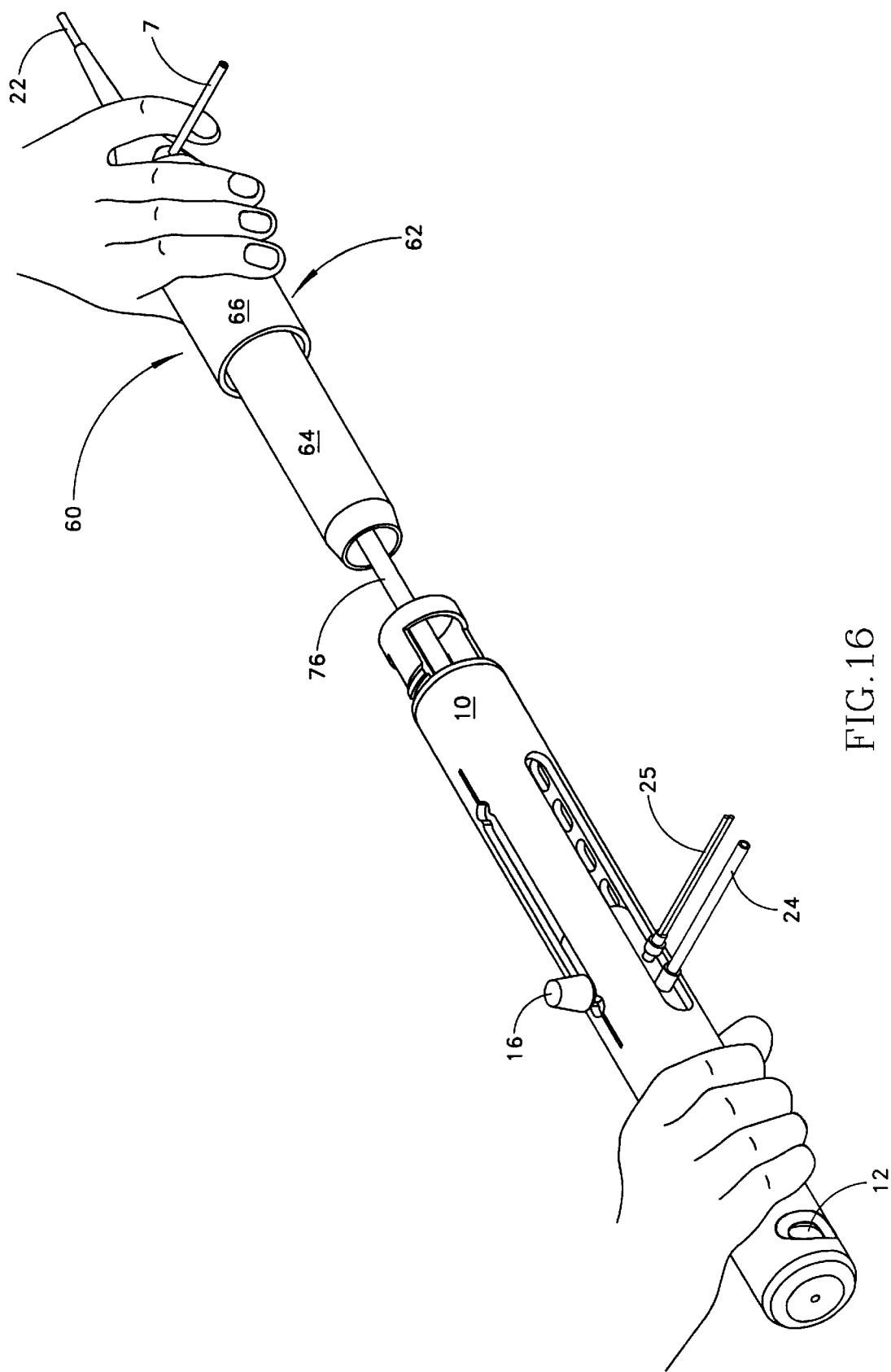
FIG. 16 is perspective view showing the final step in detaching the exchangeable drive shaft cartridge from the handle housing, the cartridge being withdrawn distally from the handle housing.
Figure 17:
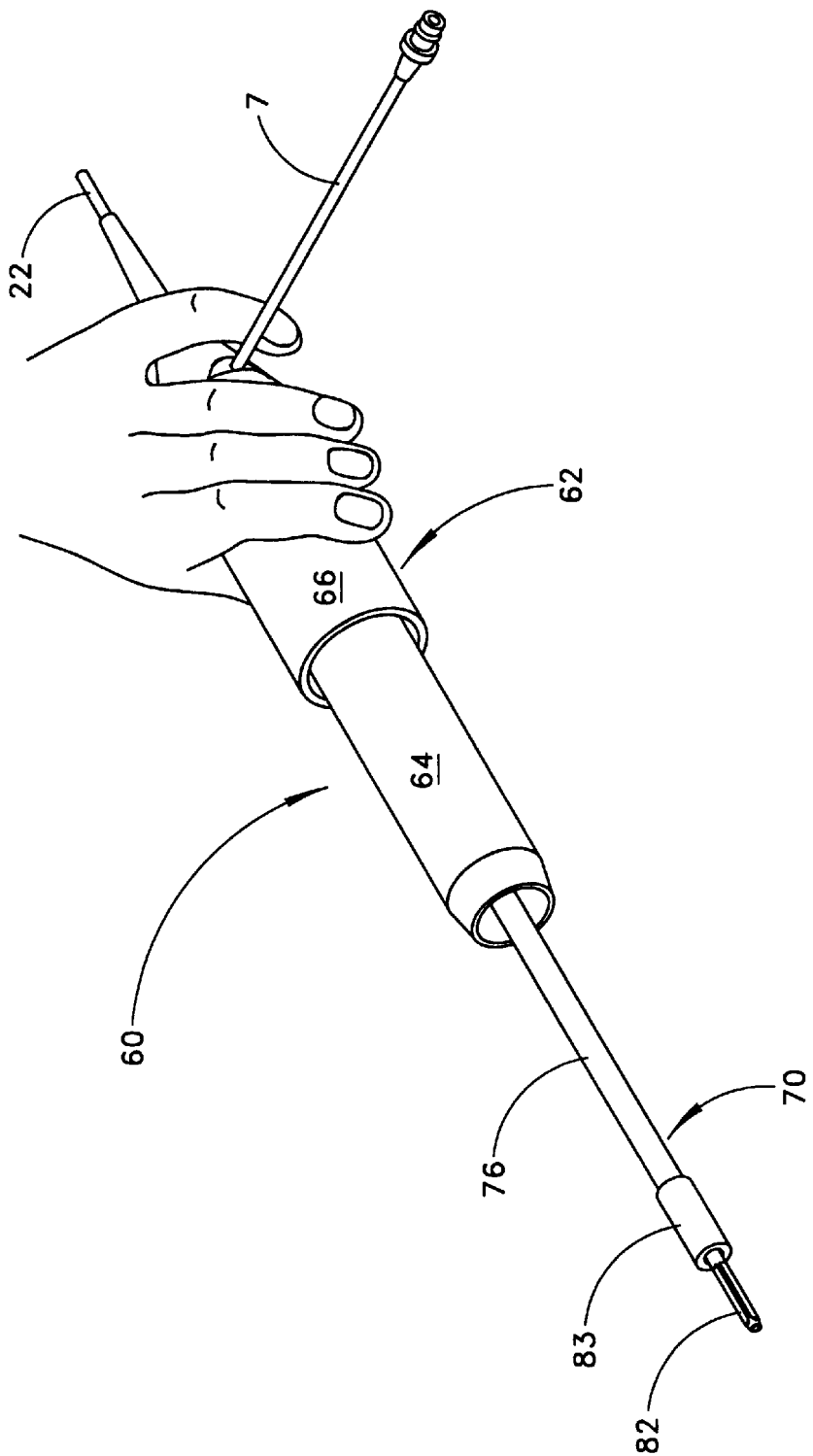
FIG. 17 illustrates the exchangeable drive shaft cartridge immediately after it has been detached from the handle housing.
Figure 18:
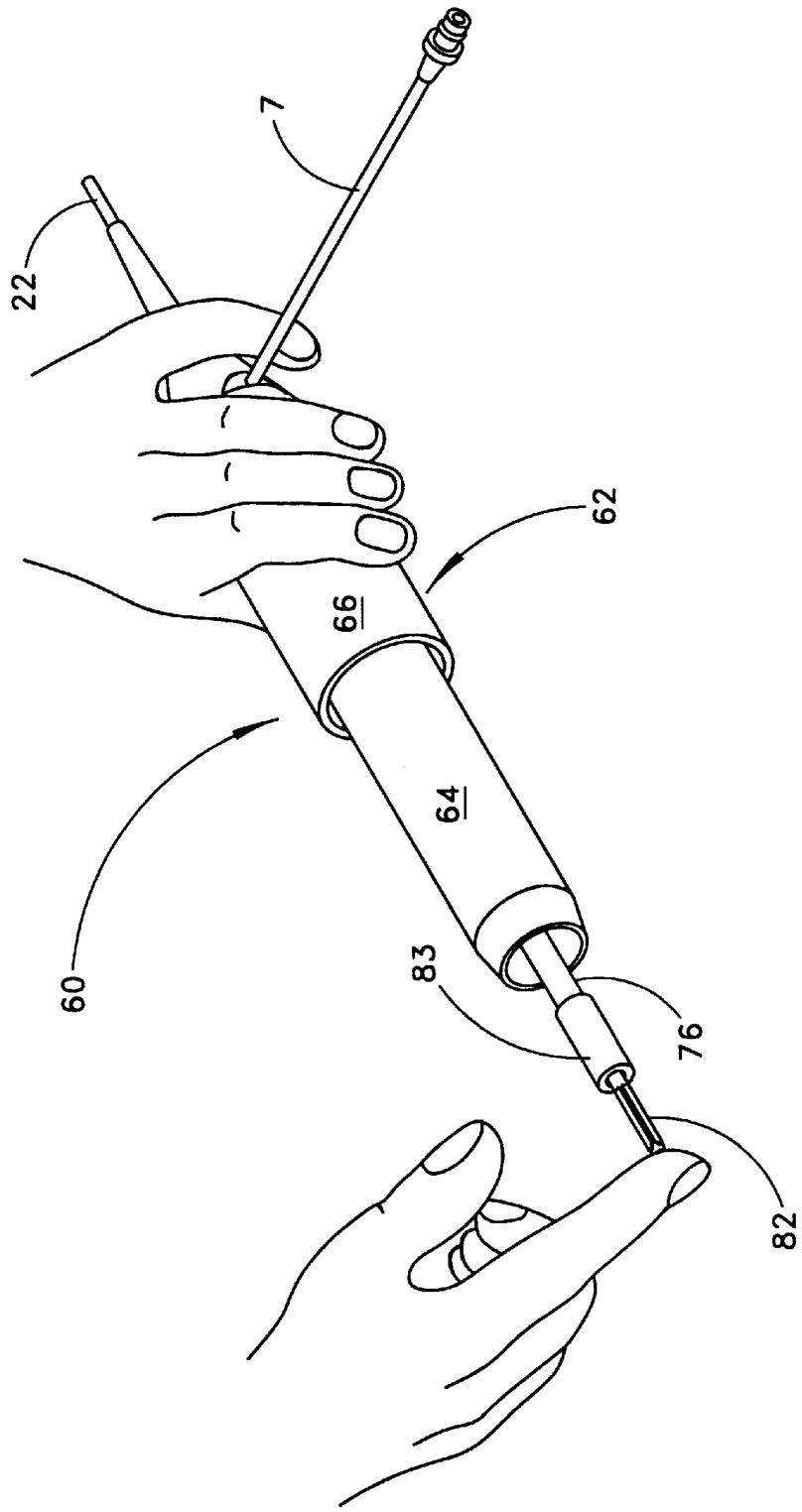
FIG. 18 illustrates how, by pushing distally on the drive shaft shank, one can push the movable telescopic tube inside the cartridge housing.

FIG. 16 shows the final step in detaching the exchangeable drive shaft cartridge 60 from the handle housing 10, the cartridge 60 being withdrawn distally from the handle housing 10. FIG. 17 illustrates the exchangeable drive shaft cartridge 60 immediately after it has been detached from the handle housing 10. Note that the longitudinally extendable tube 70 is in its extended position, extending proximally from the inner tube 64 of the cartridge housing 62. FIG. 18 shows that after removing the exchangeable drive shaft cartridge 60 the user, by pushing distally on the drive shaft shank 82, may push the movable telescopic tube 76 distally so that the longitudinally extendable tube 70 shortens and is substantially confined within the cartridge housing 62.

Figure 19:
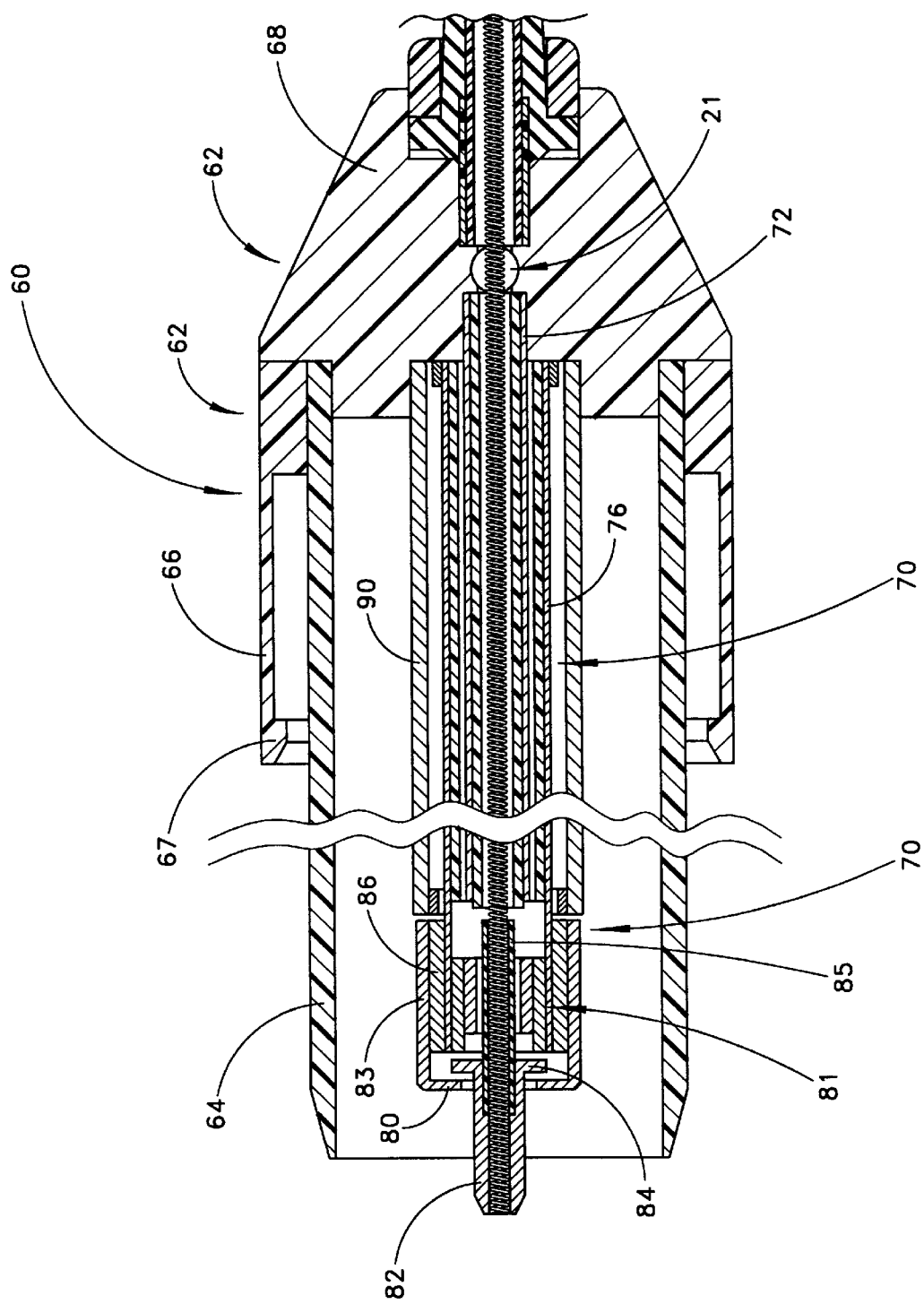
FIG. 19 is a partially broken-away, longitudinal cross-sectional view of the exchangeable drive shaft cartridge.
Figure 20:
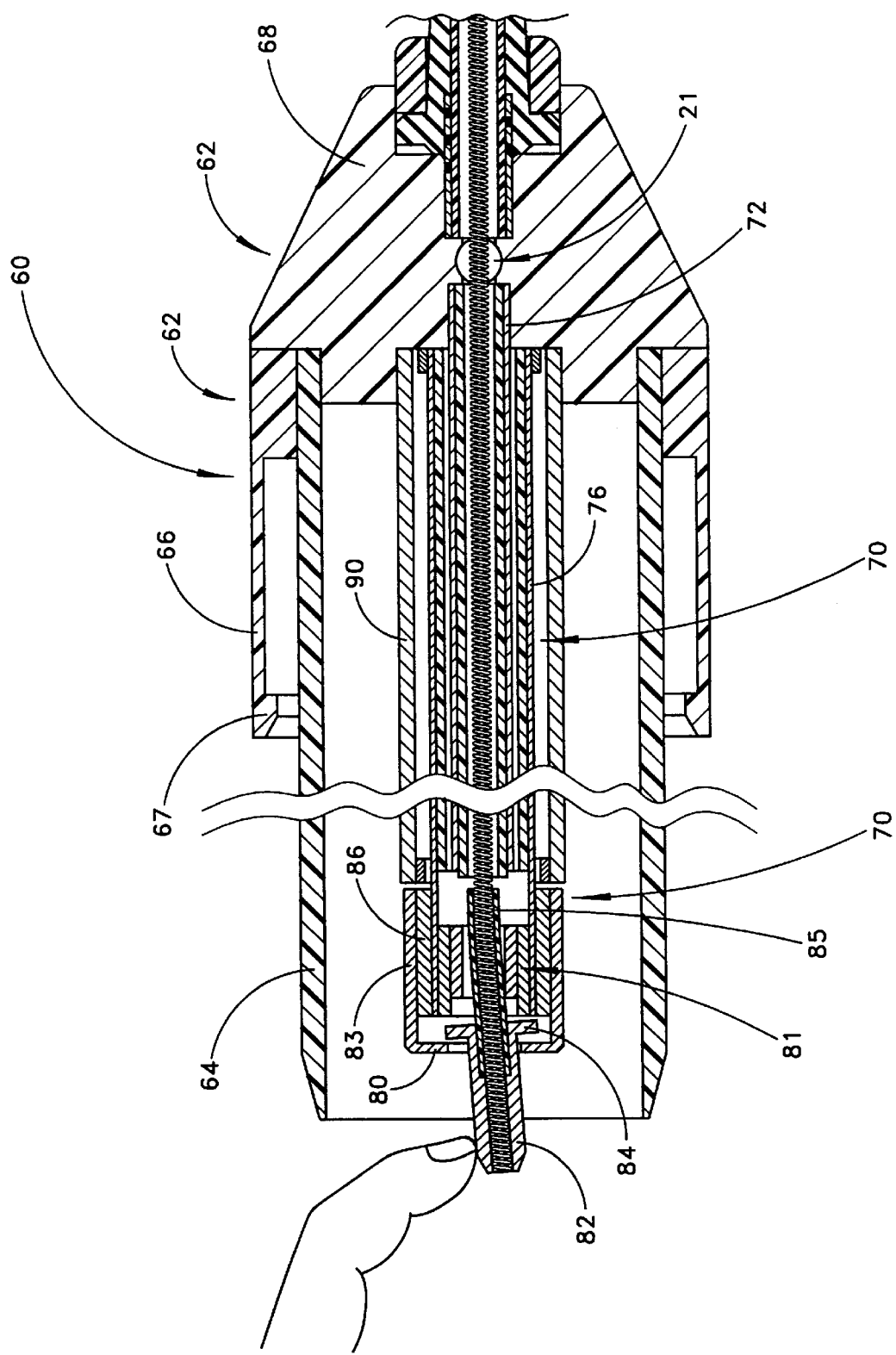
FIG. 20 is a partially broken-away, longitudinal cross-sectional view similar to FIG. 19, illustrating the ability of the shank to be deflected with respect to the rest of the cartridge.

FIG. 19 shows the longitudinally extendable tube 70 in its shortest position. FIG. 20 illustrates important features relating to how the flange 84 of the drive shaft shank 82 is captured within the proximal end portion of the longitudinally extendable tube 70 (i.e., within the proximal end portion of the movable telescopic tube 76). The portion of the drive shaft 21 immediately distal to the flange 84 of the shank 82 is flexible, and the distance between the distal and proximal abutment surfaces located on opposite sides of the flange 84 and associated with the longitudinally extendable tube 70 (i.e., in this case the moveable telescopic tube 76) is such as to permit the shank 82 to be slightly deflected with respect to the axis of the longitudinally extendable tube 70. As described above in connection with FIGS. 3–4, the thin-walled plastic tube 85 which is heat shrunk onto the proximal portion of the drive shaft 21 is also flexible.

Preferably the distal abutment surface associated with the proximal end portion of the movable telescopic tube 76 is a proximal end surface of a bushing 81 having a longitudinal lumen within which the drive shaft 21 is disposed and may freely rotate, the bushing 81 being secured within (and forming a part of) the movable telescopic tube 76. FIGS. 19–20 show that the bushing 81 is positioned distally of the shank 82 and is comprised of two concentric collars, the inner one being shorter than the outer one to facilitate lateral deflection of the elongated shank 82 (and the most proximal portion of the drive shaft 21) with respect to the axis of the longitudinally extendable tube 70 (i.e., the movable telescopic tube 76). As is described in more detail below, the bushing 81 may be made in one piece and have other suitable configurations. The proximal abutment surface associated with the proximal end portion of the movable telescopic tube 76 preferably is a distal surface of a flange 80 carried at the proximal end of an abutment member 83 secured to (and forming a part of) the proximal end portion of the movable telescopic tube 76. In the specific embodiment shown, the abutment member 83 is secured to the movable telescopic tube 76 by a short tubular component 86. As is described in more detail below, the abutment member 83 may have other suitable configurations permitting it to be secured directly to the movable telescopic tube 76.

Desirably, the atherectomy device of the invention is supplied to the user with the handle housing portion of the device packaged separately from the exchangeable drive shaft cartridges. Under such circumstances the user first selects the appropriate exchangeable drive shaft cartridge and then attaches it to the handle housing portion of the device. Frequently it is desirable during an atherectomy procedure to use the same handle housing portion of the device with more than one exchangeable drive shaft cartridge (e.g., to use cartridges having different sizes or designs of tissue removal implements).

FIGS. 21–38 illustrate the process of attaching an exchangeable drive shaft cartridge to the handle housing portion of the atherectomy device. This procedure is the same, regardless of whether it is the first or a subsequent exchangeable drive shaft cartridge used in the procedure.

Figure 21:
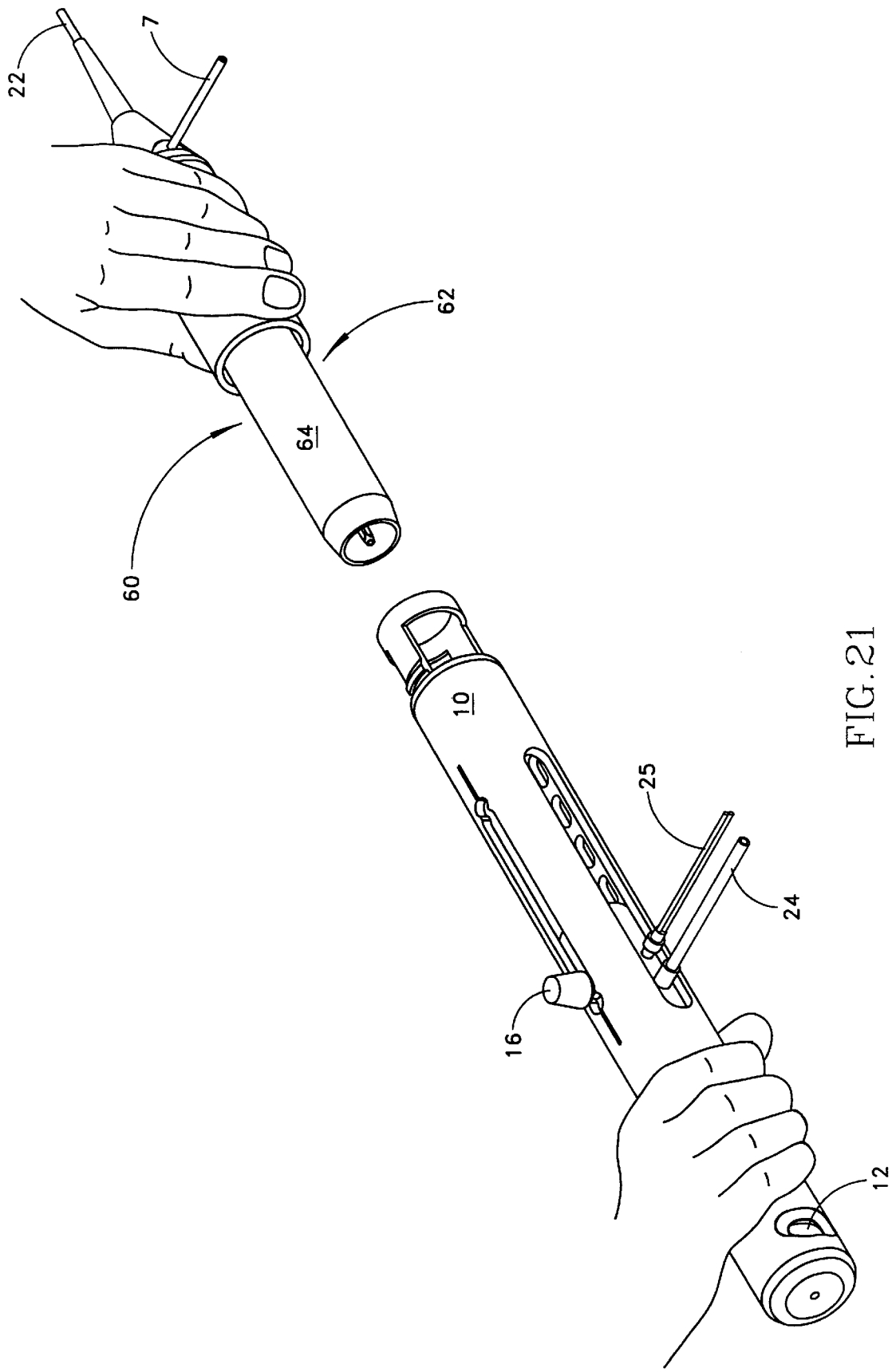
FIGS. 21–24 illustrate the process of attaching the cartridge housing to the handle housing, FIGS. 21–22 being perspective views and FIGS. 23–24 being perspective, partially broken-away views.
Figure 22:
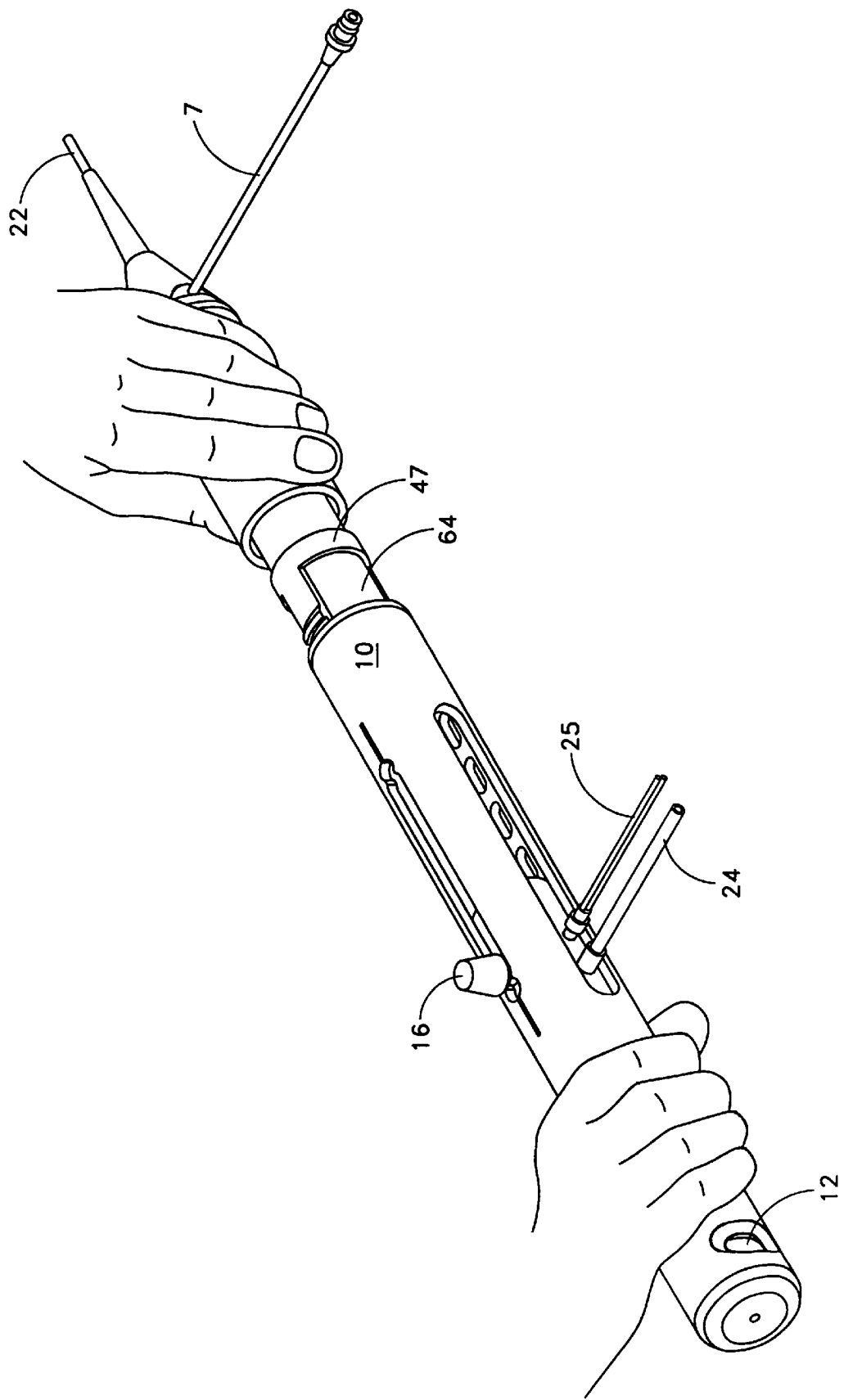
Figure 23:
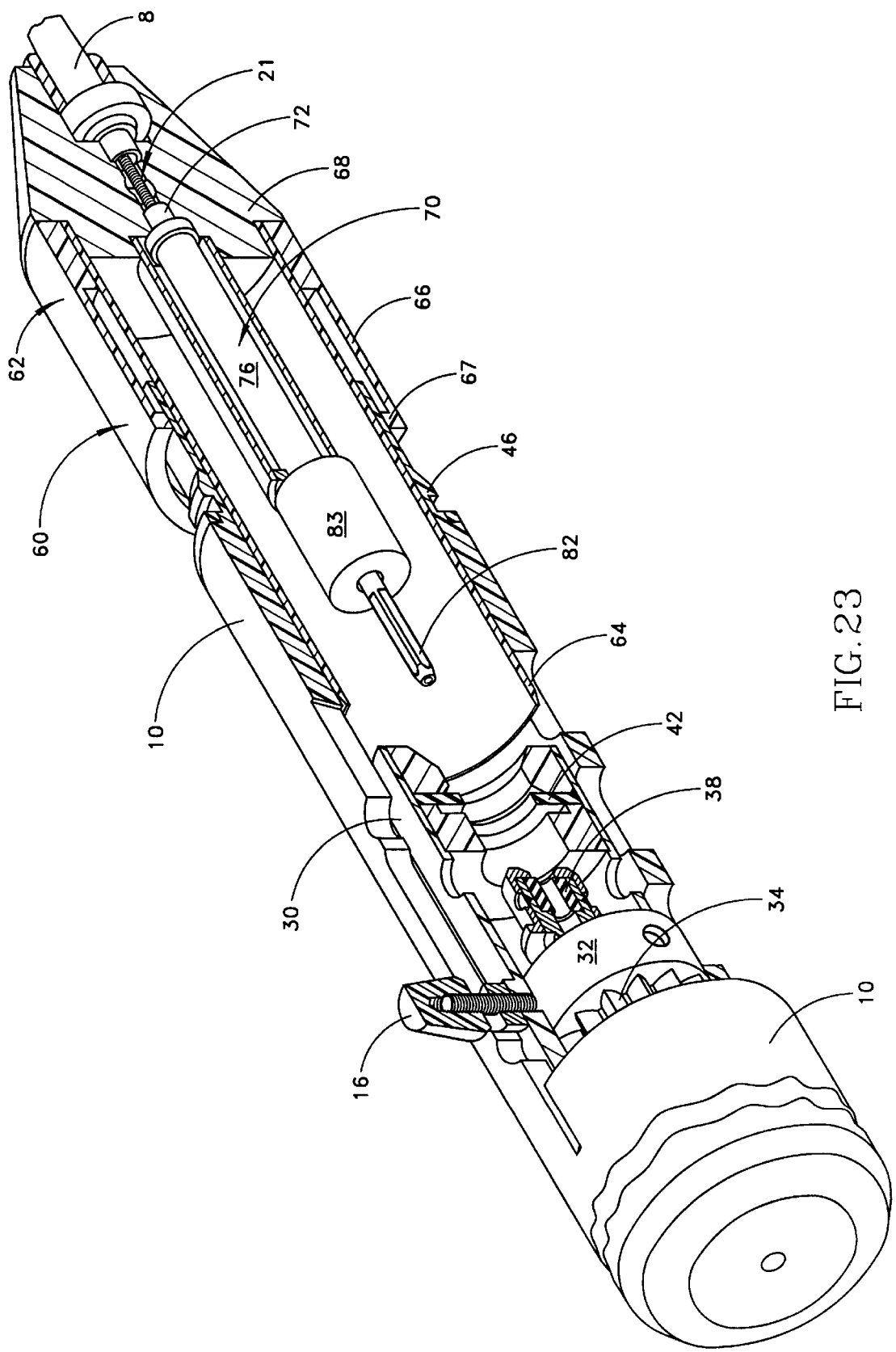
Figure 24:
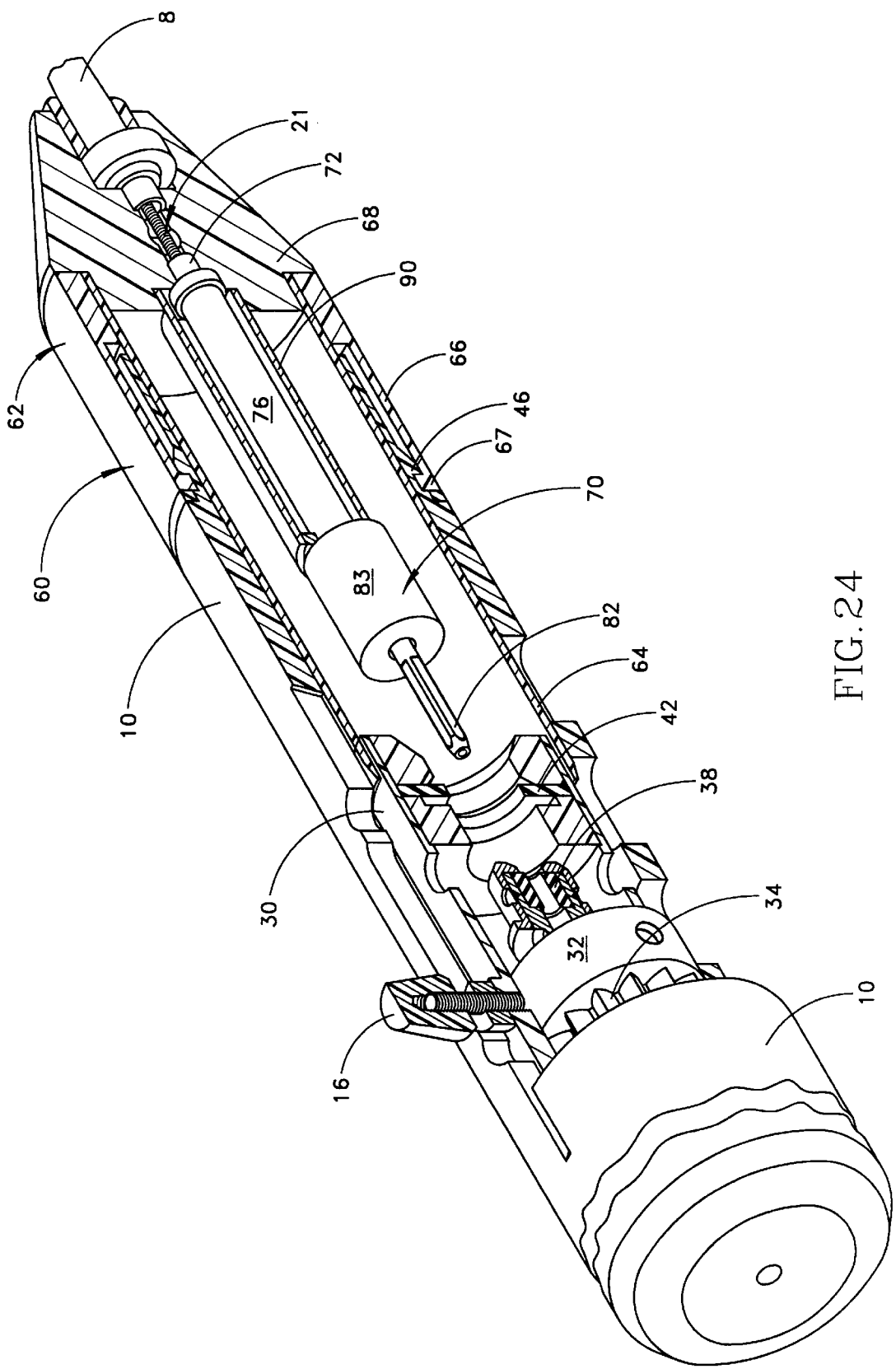

In FIG. 21 the user is preparing to attach an exchangeable drive shaft cartridge 60 to the handle housing portion of the device. In FIGS. 22 the inner tube 64 of the cartridge housing 62 has been partially inserted into the handle housing 10. In FIG. 23 the inner tube 64 has been inserted a little bit further, but still neither the housings (62 and 10) nor any of the other components of the exchangeable drive shaft cartridge 60 and the handle housing 10 have become interlocked with each other. In FIG. 24, the exchangeable drive shaft cartridge 60 has been fully advanced proximally with respect to the handle housing 10 so that the primary interlocking member of the cartridge housing (i.e., the annular shoulder 67 of the outer tube 66 of the cartridge housing 62) has interlocked with the proximal complementary interlocking member of the handle housing 10 (i.e., the radially extending tabs 46).

Figure 25:
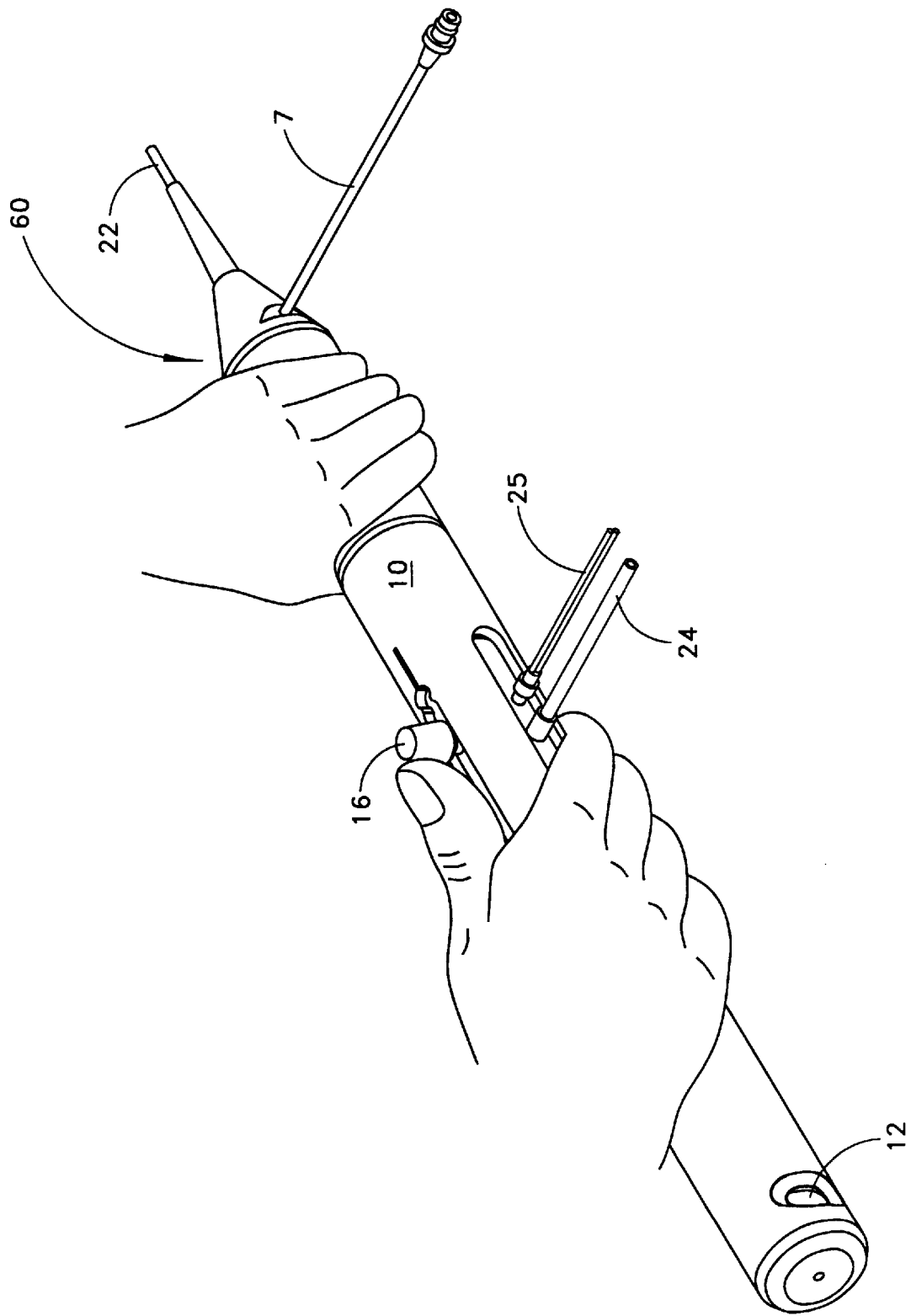
FIGS. 25–35 illustrate the process of attaching the drive shaft shank to the prime mover socket and the longitudinally extendable tube to the prime mover carriage, FIG. 25 being a perspective view, FIG. 26 being a longitudinal cross-sectional view with the shank spaced away from the prime mover socket (and FIG. 27 being a top view), FIG. 28 showing the shank moved closer to the prime mover socket and the longitudinally extendable tube engaging the prime mover carriage (and FIG. 29 being a top view), FIG. 30 showing the shank partially inserted into the prime mover socket (and FIG. 31 being a top view), FIG. 32 showing the shank fully inserted into the prime mover socket (and FIG. 33 being a top view), and FIG. 34 showing the prime mover carriage and the shank moved slightly proximally with respect to the longitudinally extendable tube (and FIG. 35 being a top view)

FIGS. 25–35 illustrate the process of attaching the drive shaft shank 82 to the prime mover socket 38 and the longitudinally extendable tube 70 to the prime mover carriage 30. In FIG. 25 the user is pressing the control knob 16 toward the distal end of its range of movement. As can be seen in this series of drawings, the control knob 16, the control knob shaft 17, the prime mover carriage 30 and the associated components have at least three sets of longitudinal positions with respect to the handle housing 10, as follows:

(1) the "range of working positions" wherein throughout most of the length of the slot 11 the control knob 16, its shaft 17 and the prime mover carriage 30 are permitted to move freely longitudinally with respect to the handle housing 10;

(2) the "range of transitional positions" wherein the control knob 16 and its shaft 17 are moved distally from the range of working positions into a narrowed portion 13 of the slot 11;

(3) the "carriage-restrained position" wherein the control knob 16 and its shaft 17 are advanced to their most distal position in the slot 11. This position is referred to as the carriage-restrained position because in this longitudinal position the prime mover carriage 30 is releasably locked against free movement along the slot 11 in the housing 10.

Again, as shown in FIG. 25, the user advances the control knob 16 (and its shaft 17) from the range of working positions to the carriage-restrained position to move the prime mover socket 38 over the drive shaft shank 82 and to attach the longitudinally extendable tube 70 to the prime mover carriage 30.

Figure 26:
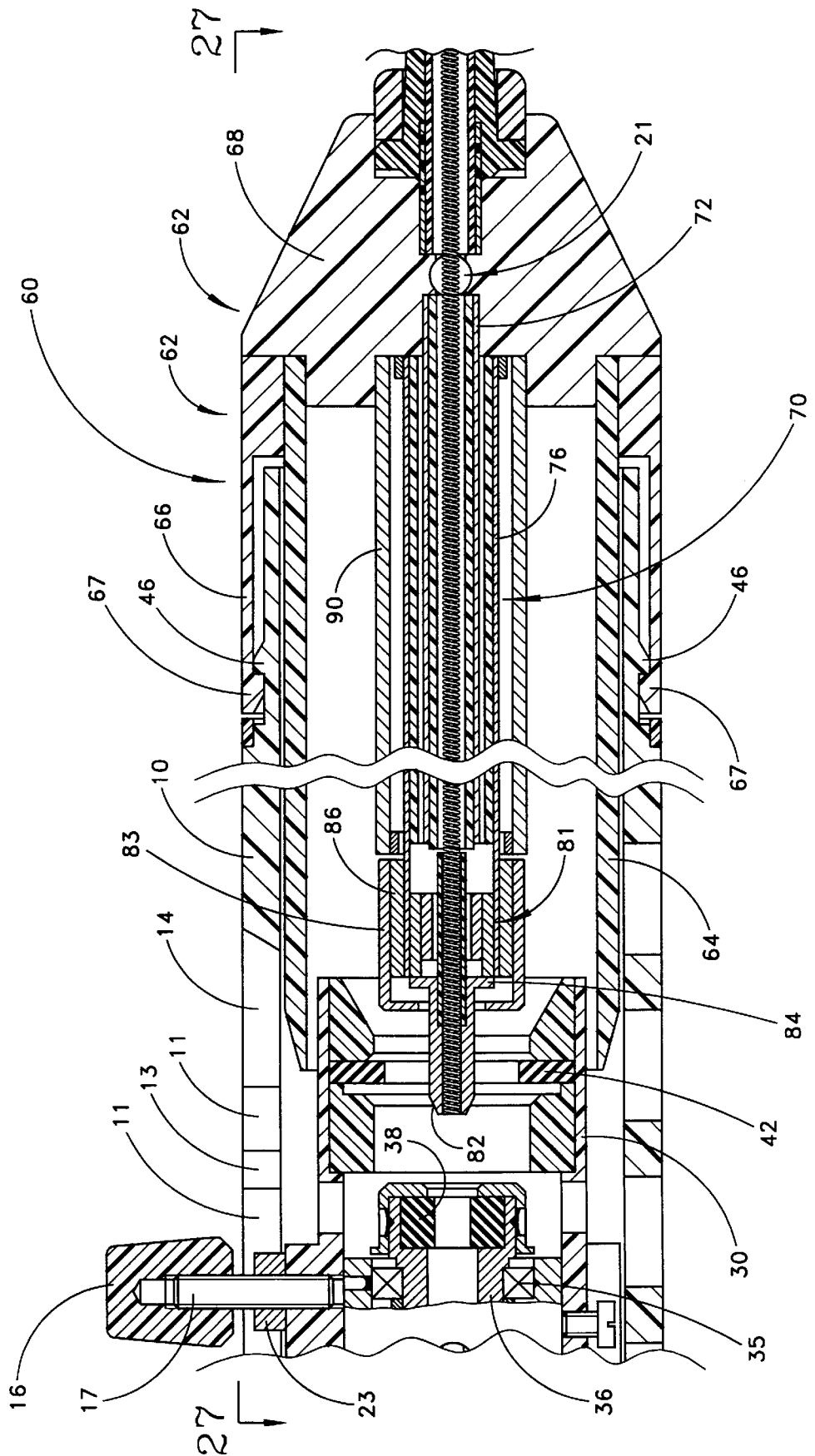
Figure 27:
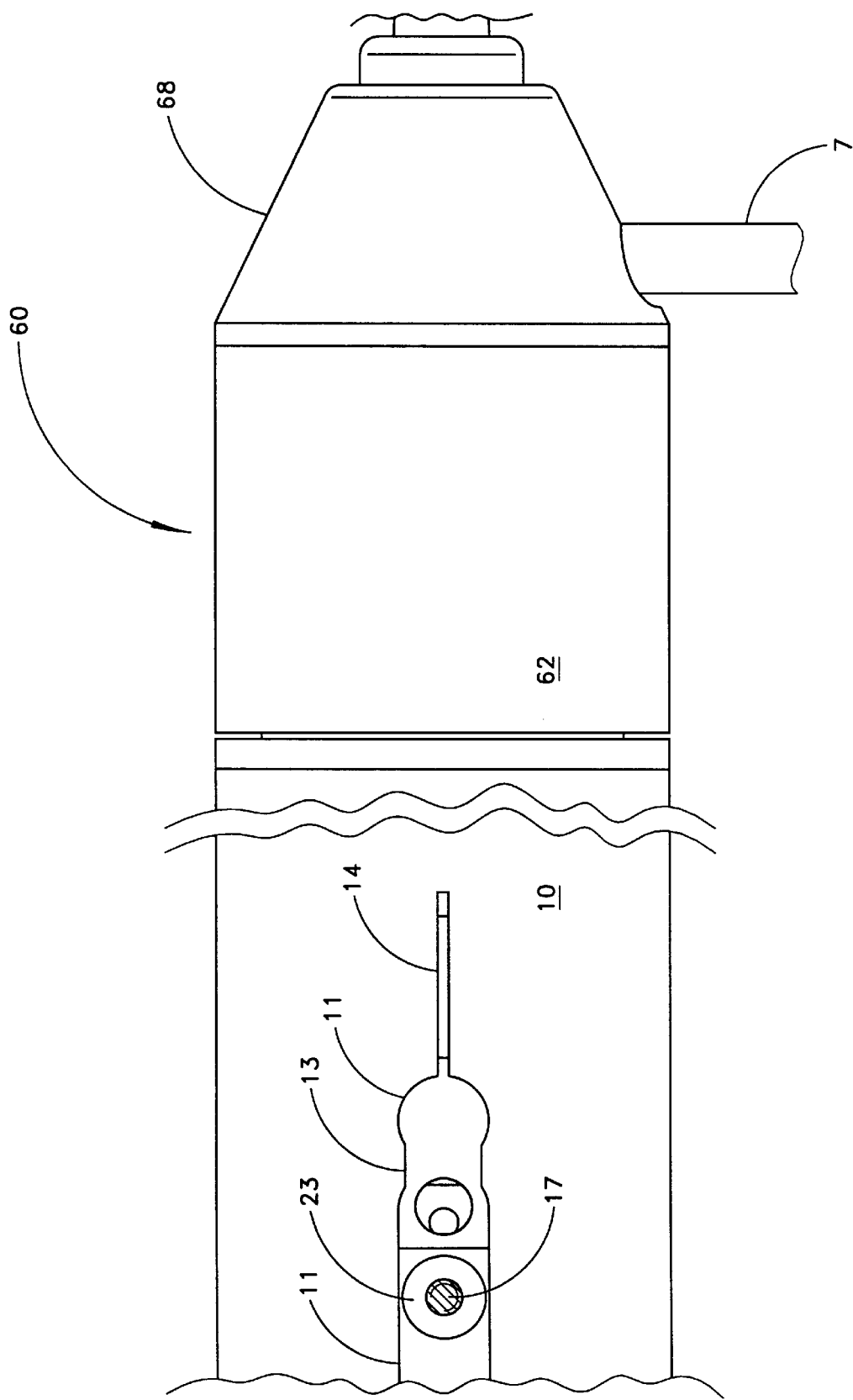
Figure 28:
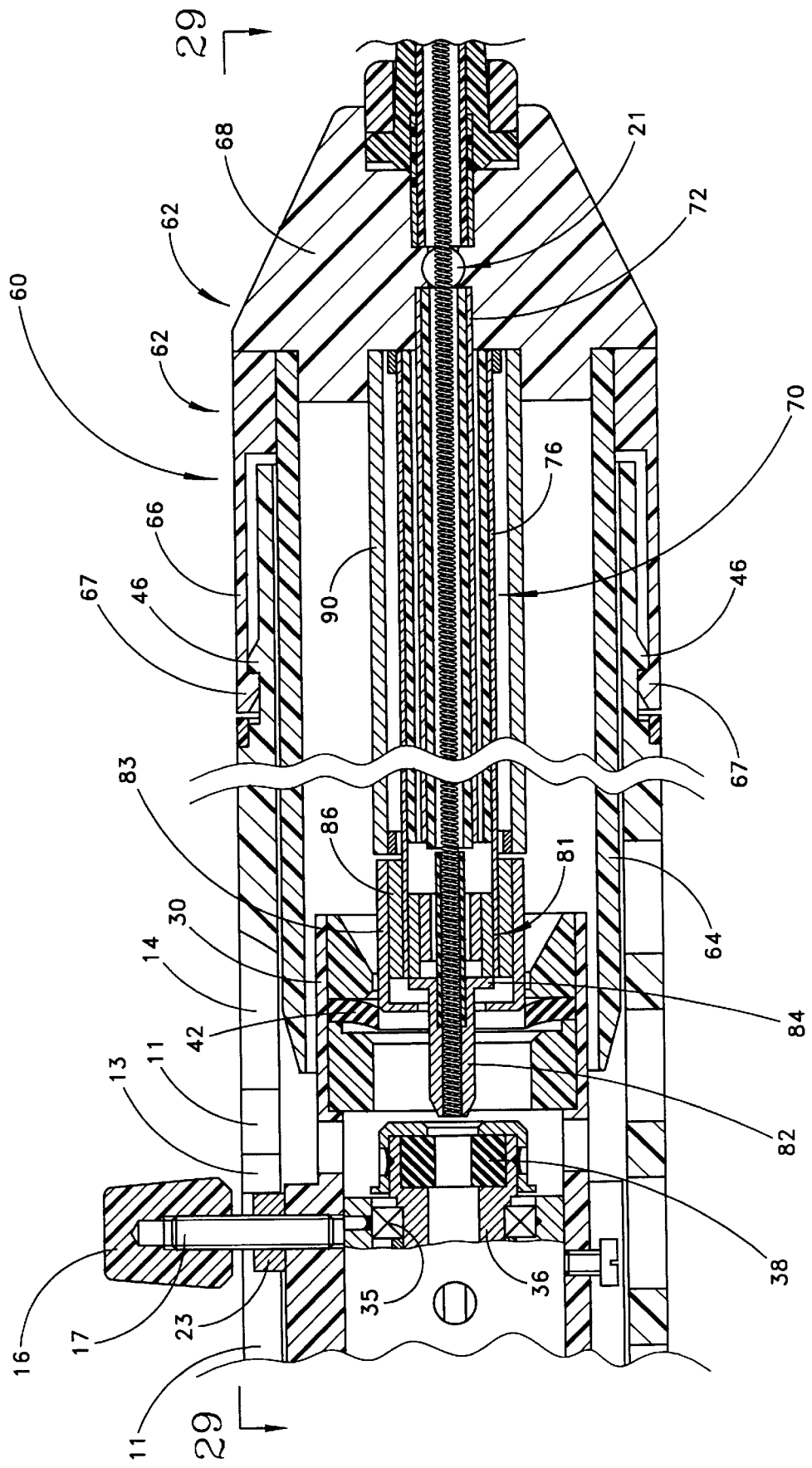
Figure 29:
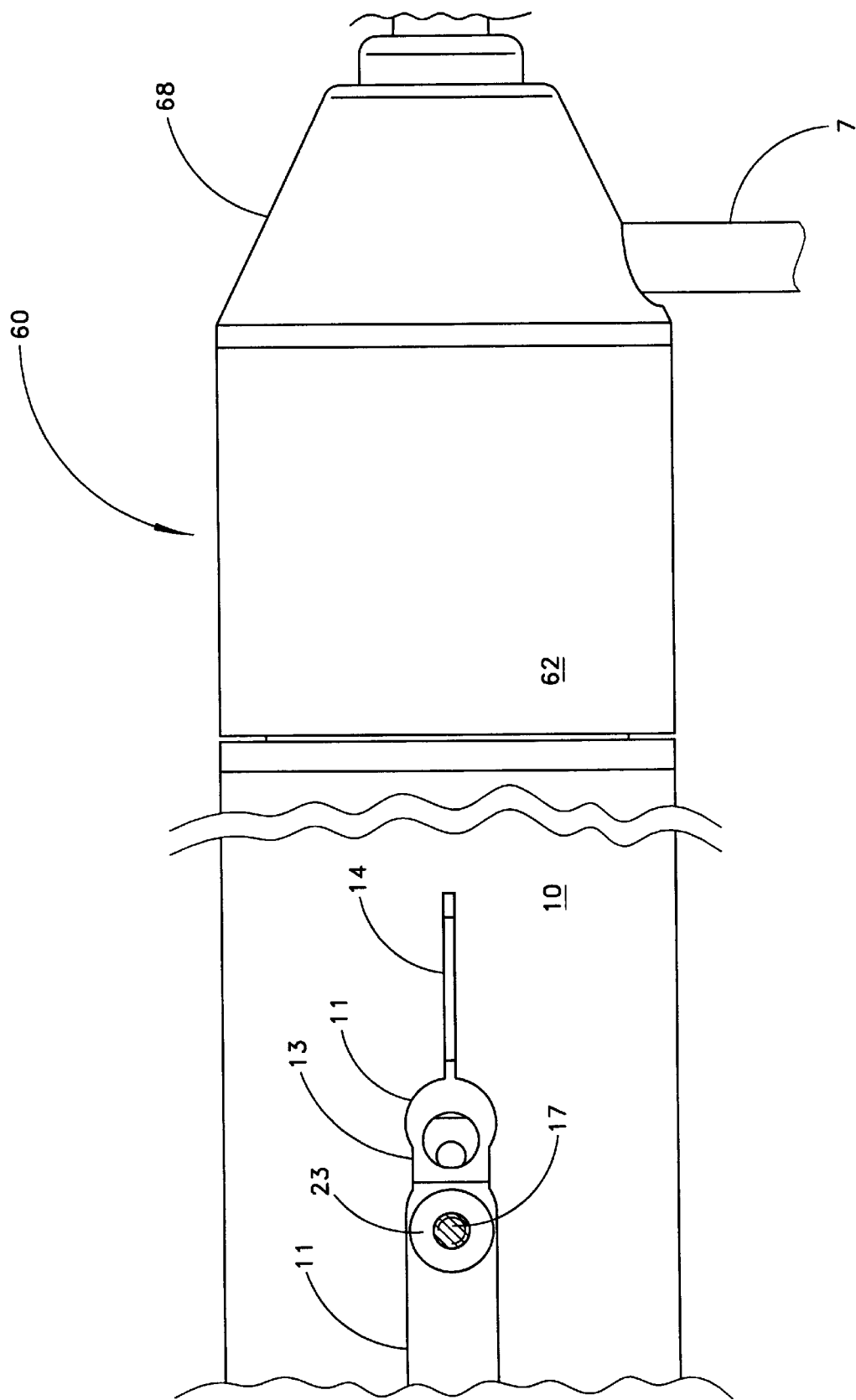

In FIGS. 25–27 the prime mover socket 38 and the drive shaft shank 82 are still spaced a short distance from each other. The proximal end of the longitudinally extendable tube 70 (i.e., the movable telescopic tube 76) and the prime mover carriage 30 are also still spaced a short distance from each other. In FIGS. 28–29 the proximal end of the abutment member 83 has begun to encounter a resilient positioning ring 42. As can be seen in FIG. 28, the proximal end of the abutment member 83 causes the radially inner portion of the resilient positioning ring 42 to deflect proximally. The design and function of the resilient positioning ring 42 is described in more detail below.

Figure 30:
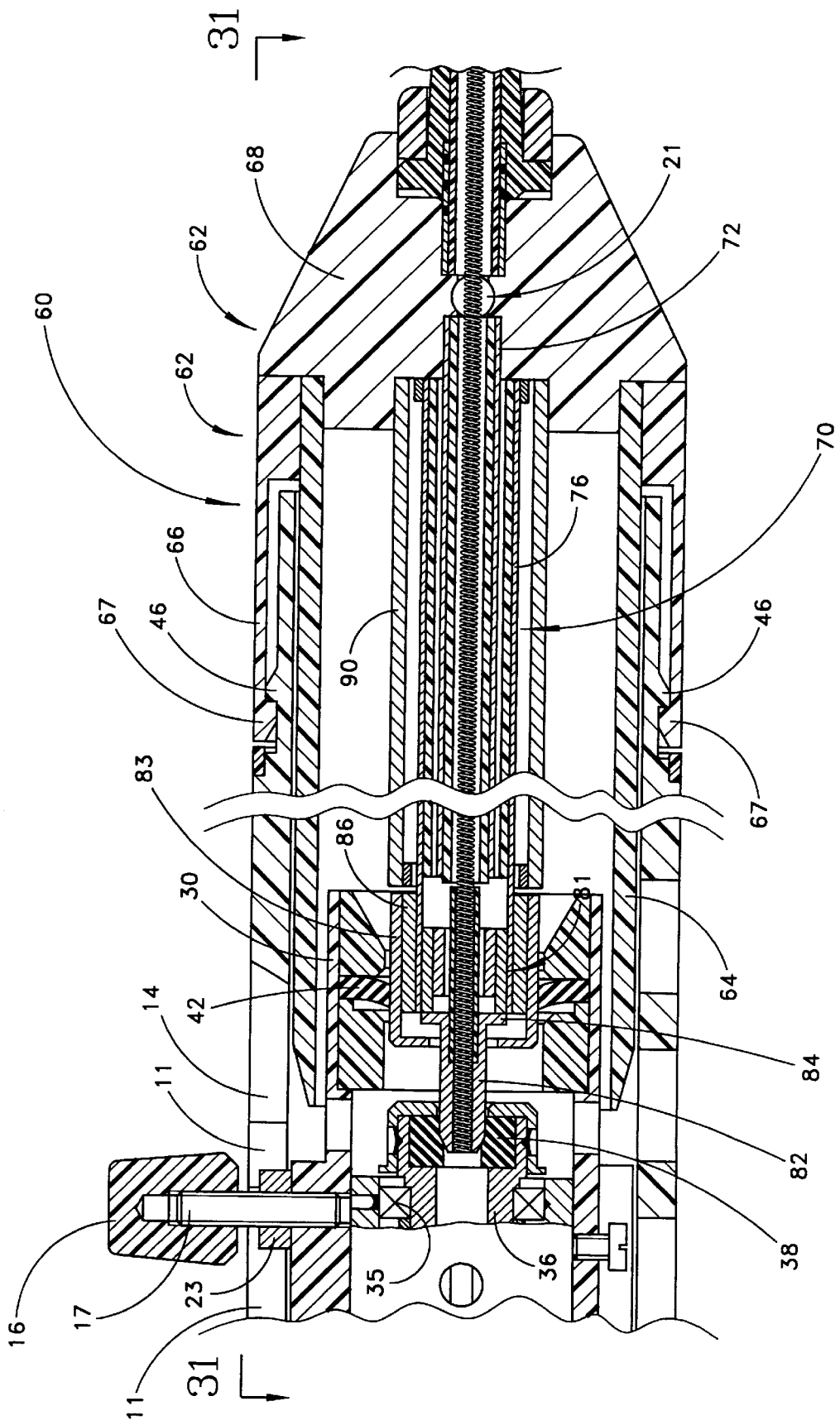
Figure 31:
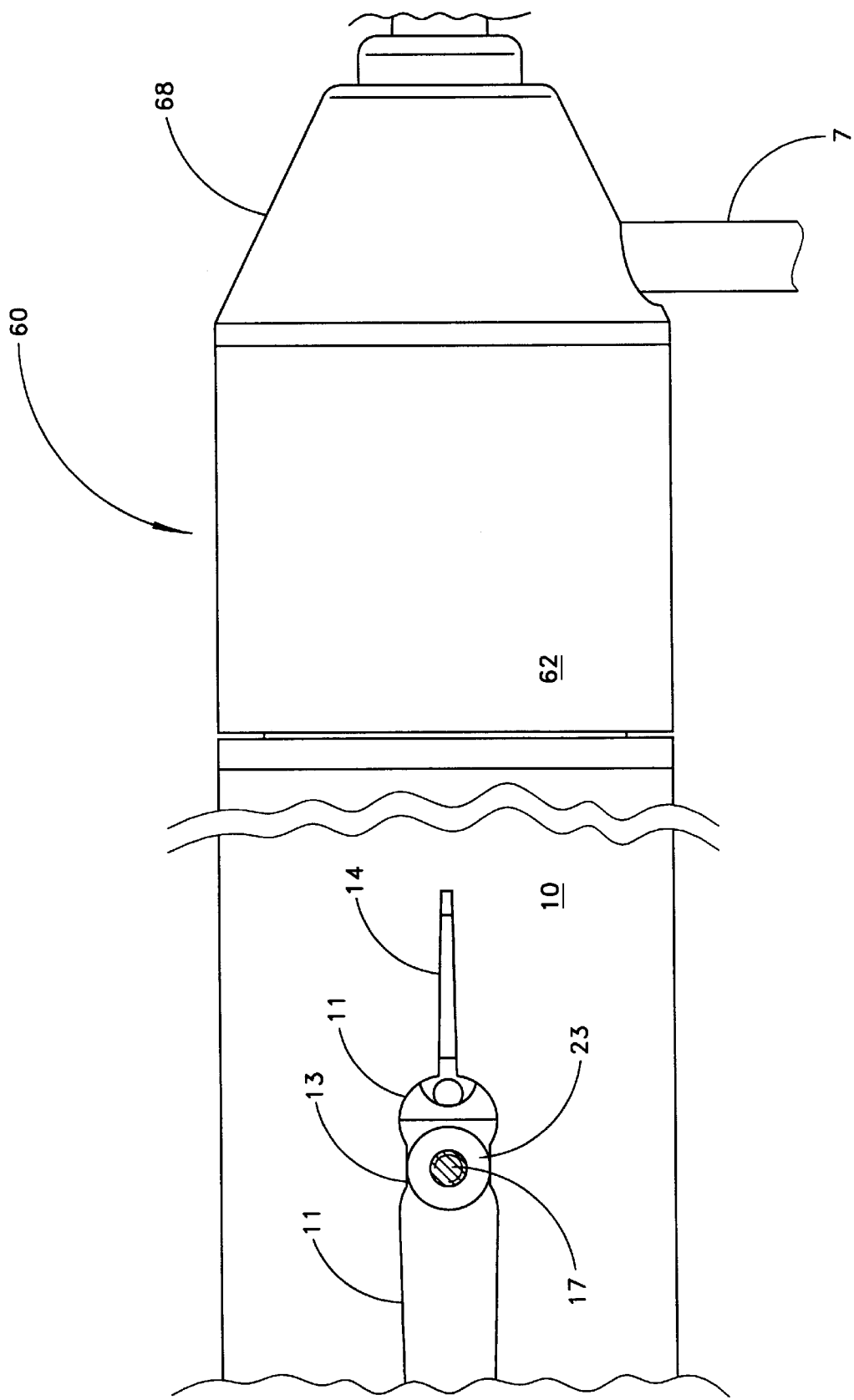

In FIGS. 30–31 the elongated shank 82 has begun to be inserted into the prime mover socket 38, and the control knob 16 and its shaft 17 have entered the range of transitional positions. Notice that the flange 84 of the drive shaft shank 82 abuts the proximal end surface of bushing 81, which defines the distal abutment surface associated with the proximal end portion of the longitudinally extendable tube 70 (i.e. the moveable telescopic tube 76).

Figure 32:
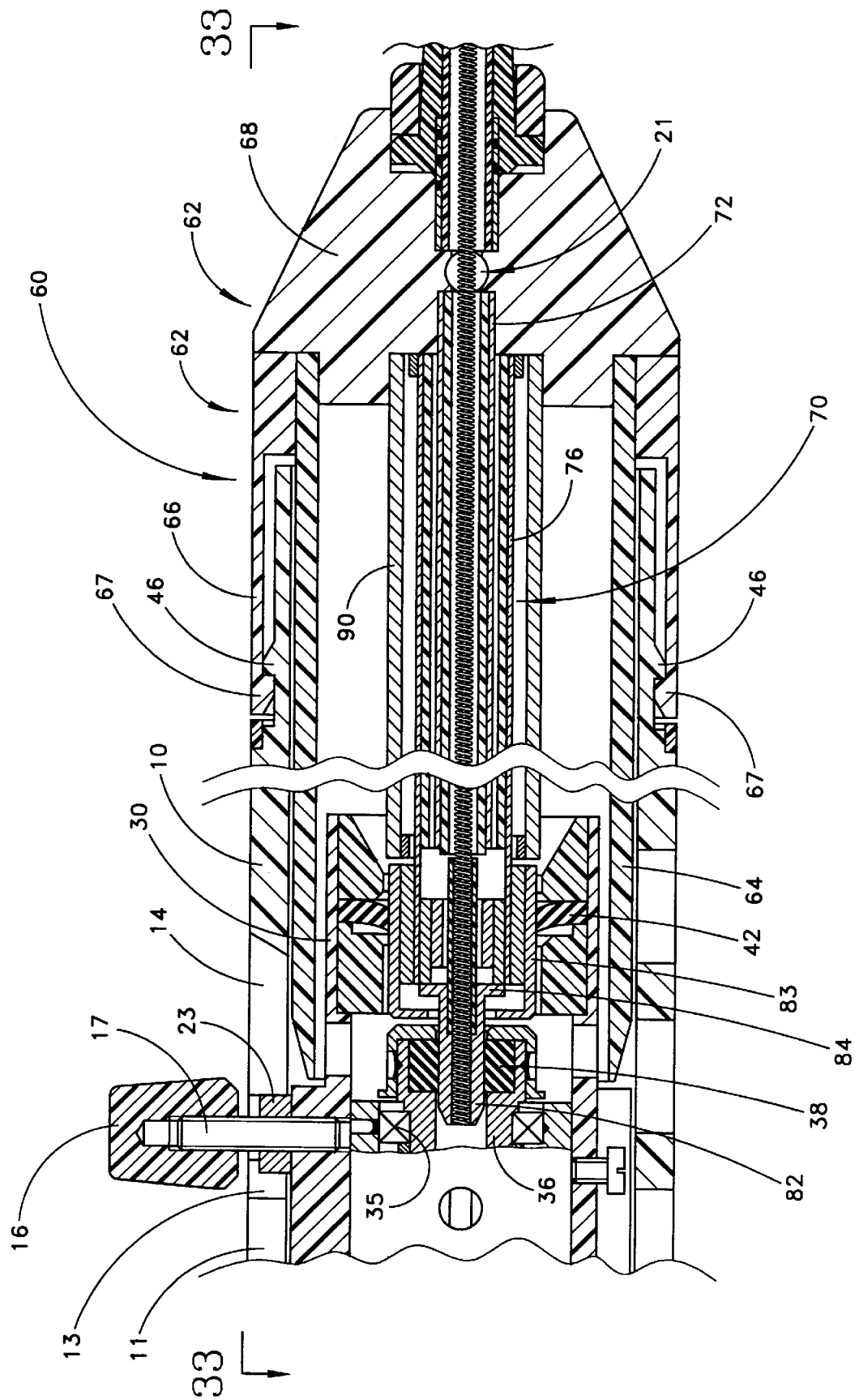
Figure 33:
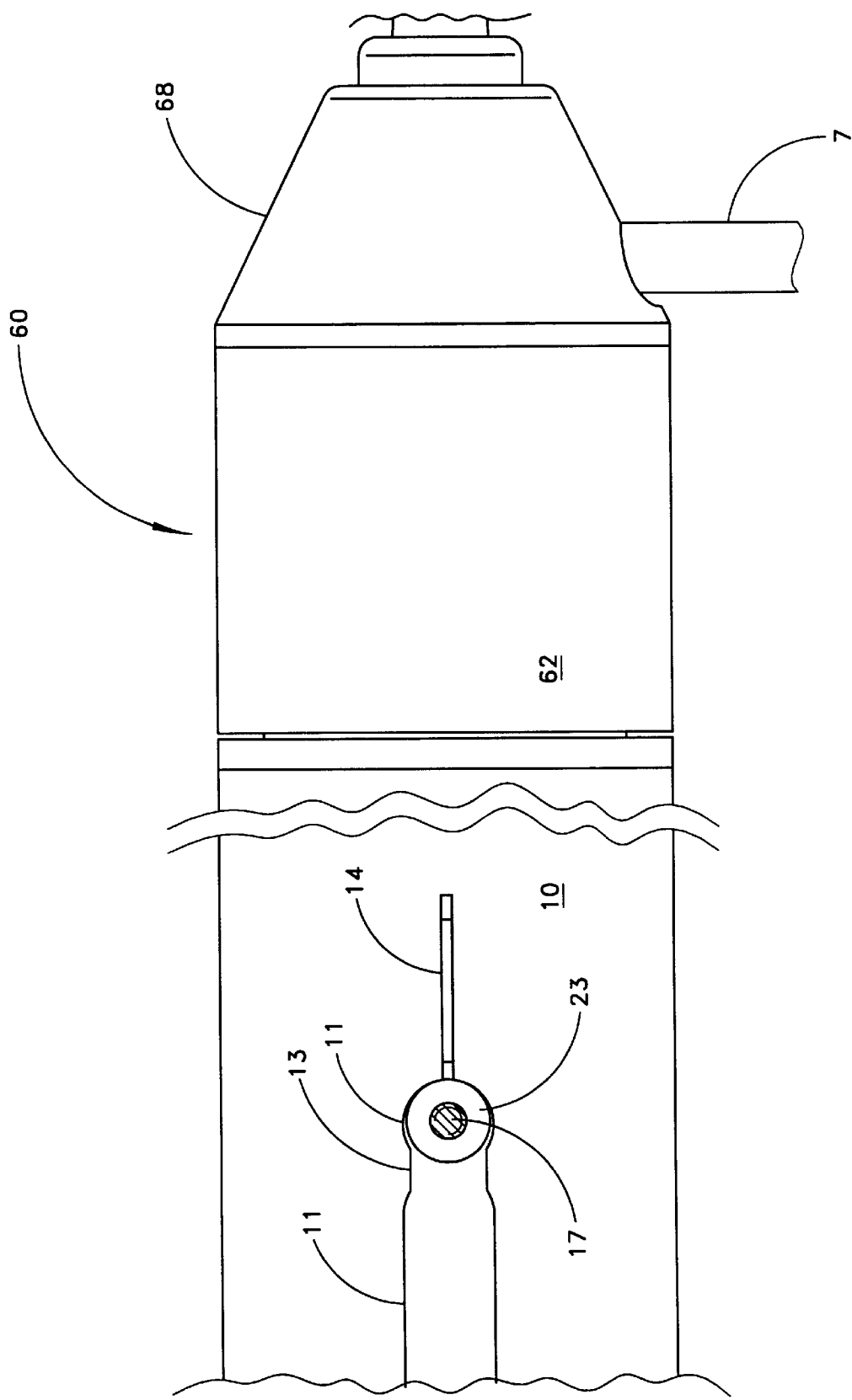

In FIGS. 32–33 the control knob 16 and its shaft 17 have been moved to their most distal position and are in the carriage-restrained position. The elongated shank 82 is fully inserted into the prime mover socket 38, and the proximal end of the longitudinally extendable tube 70 (i.e., the movable telescopic tube 76) is fully inserted into the resilient positioning ring 42. In these figures the user has not yet released the distal pressure on the control knob 16.

Figure 34:
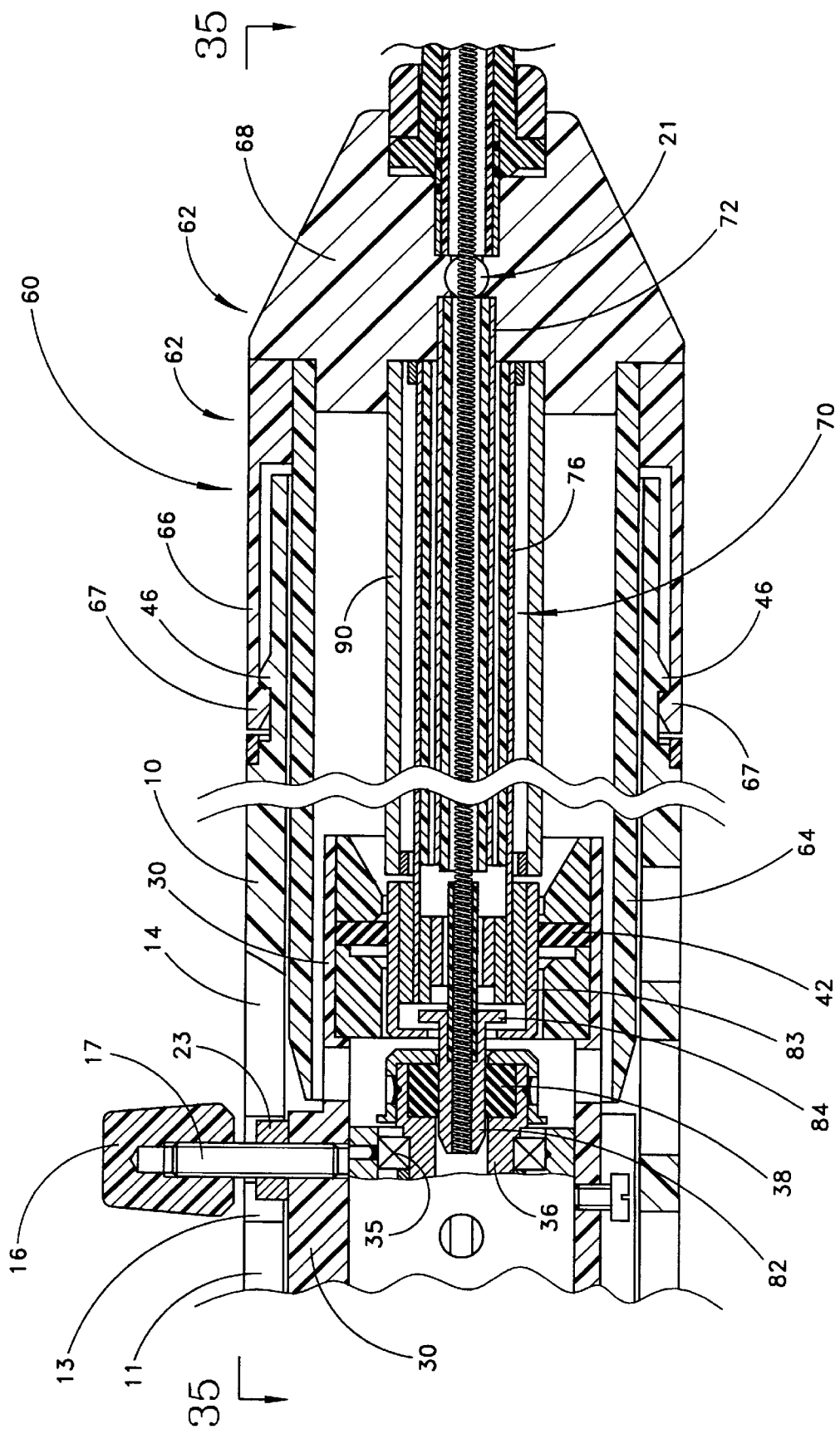
Figure 35:
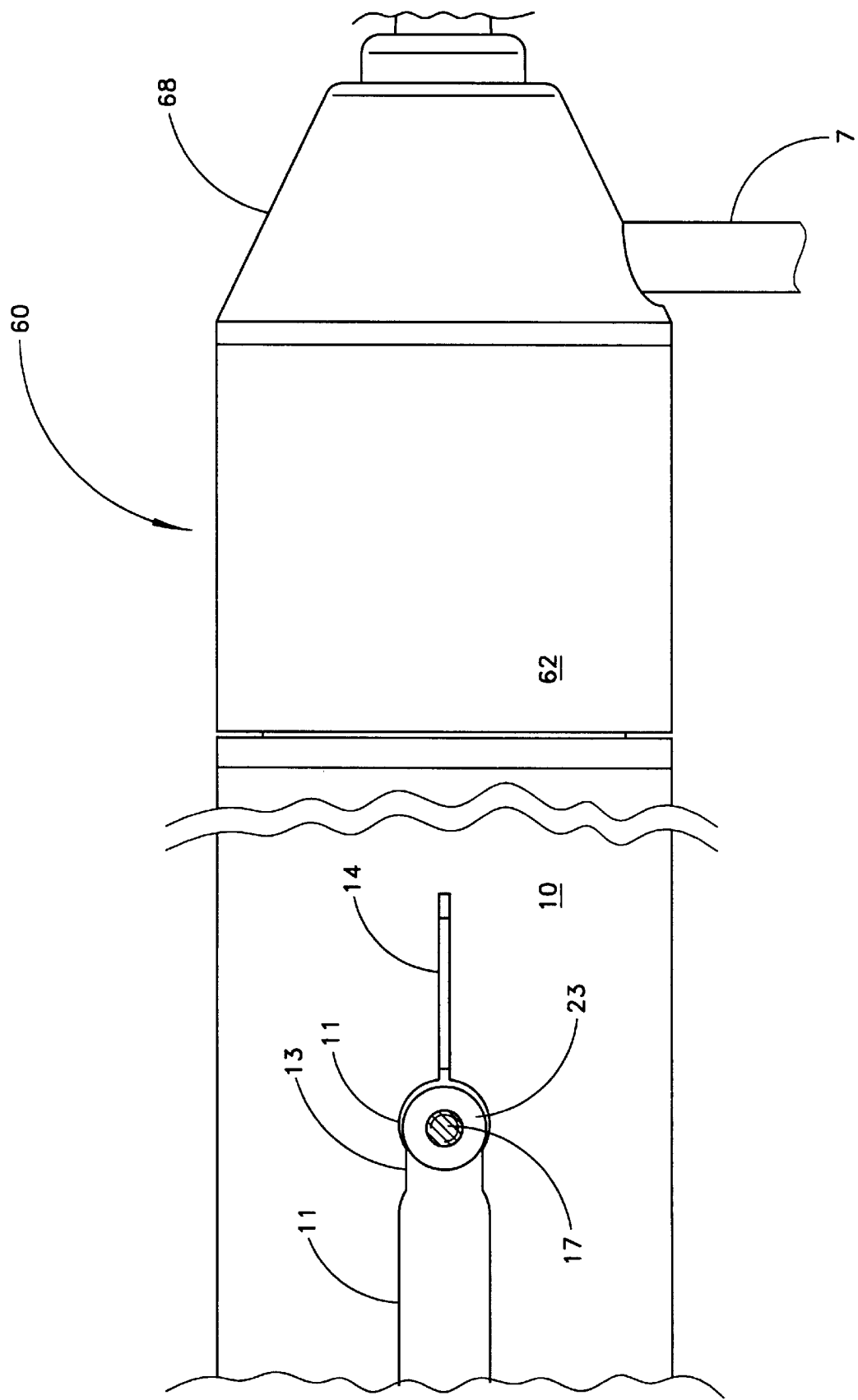

In FIGS. 34–35 the control knob 16 and its shaft 17 are still in the carriage-restrained position, but the user has already released distal pressure on the control knob 16. Notice in FIG. 34 that the radially inner portion of the resilient positioning ring 42 is no longer deflected proximally. When the user released the distal pressure on the control knob 16, the resilient nature of the resilient positioning ring 42 caused the prime mover carriage 30, along with the control knob 16, to move slightly proximally with respect to the longitudinally extendable tube 70 and the handle housing 10. When this slight proximal movement occurs, the shank 82 also moves slightly proximally with respect to the longitudinally extendable tube 70 (i.e., the movable telescopic tube 76). Thus, as can be seen in FIG. 34, the flange 84 of the shank 82 is moved proximally away from the bushing 81 (i.e., the distal abutment surface associated with the proximal end portion of the longitudinally extendable tube 70). In this position the shank 82 is free to rotate together with the prime mover without any frictional engagement with the proximal end of the longitudinally extendable tube 70 (i.e., the movable telescopic tube 76). By comparing FIGS. 33 and 35 one can see the limited range of movement afforded to the control knob 16 and its shaft 17 when the prime mover carriage 30 is in its carriage-restrained position. It should be noted that the function of the resilient positioning ring 42 can be performed by other equivalent structures, some of which are described in more detail below.

Figure 36:
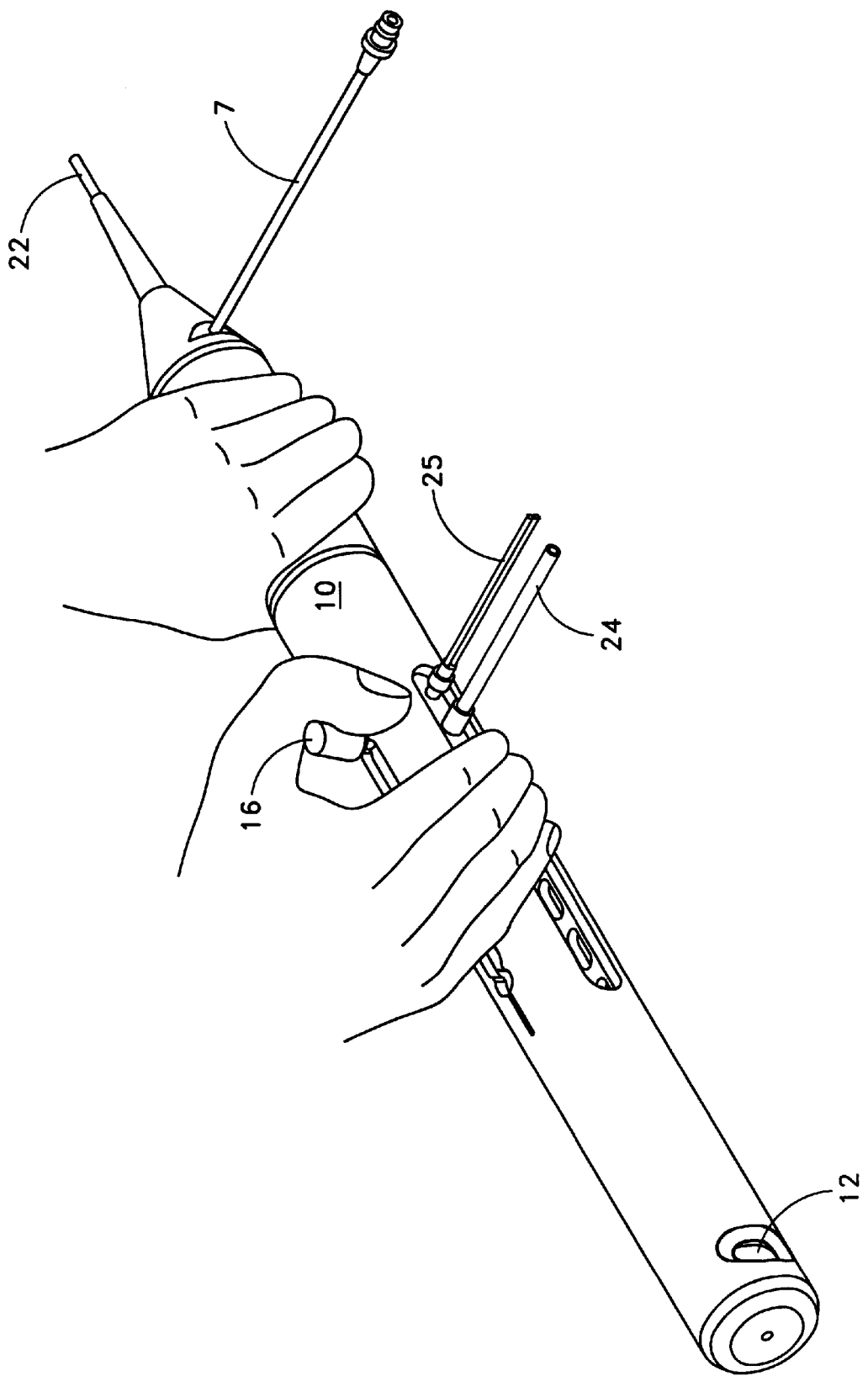
FIG. 36 illustrates the process of moving the prime mover carriage into its range of working positions.
Figure 37:
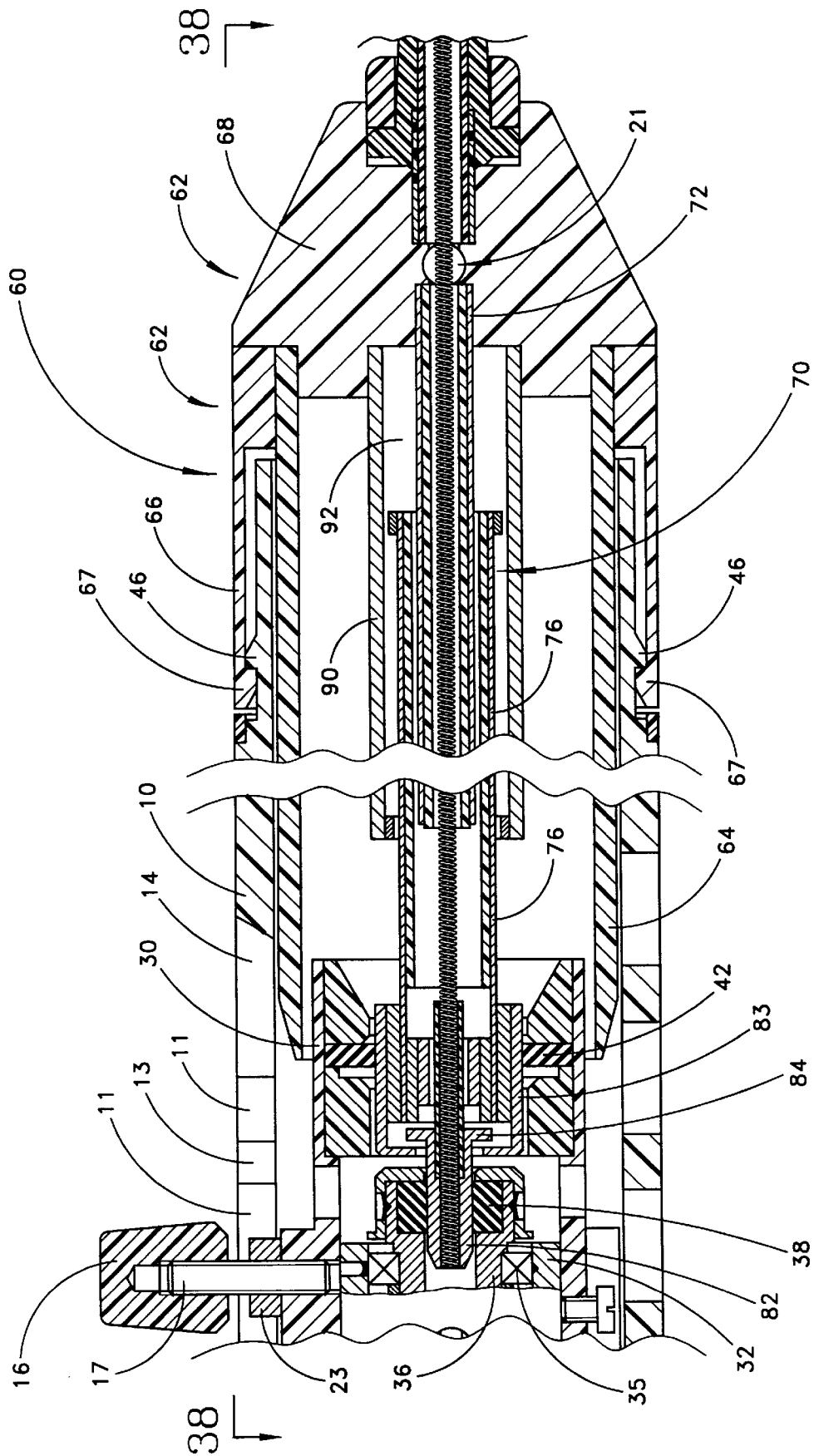
FIG. 37 is a longitudinal cross-sectional view of the assembled atherectomy device of the invention showing the prime mover carriage in its range of working positions.
Figure 38:
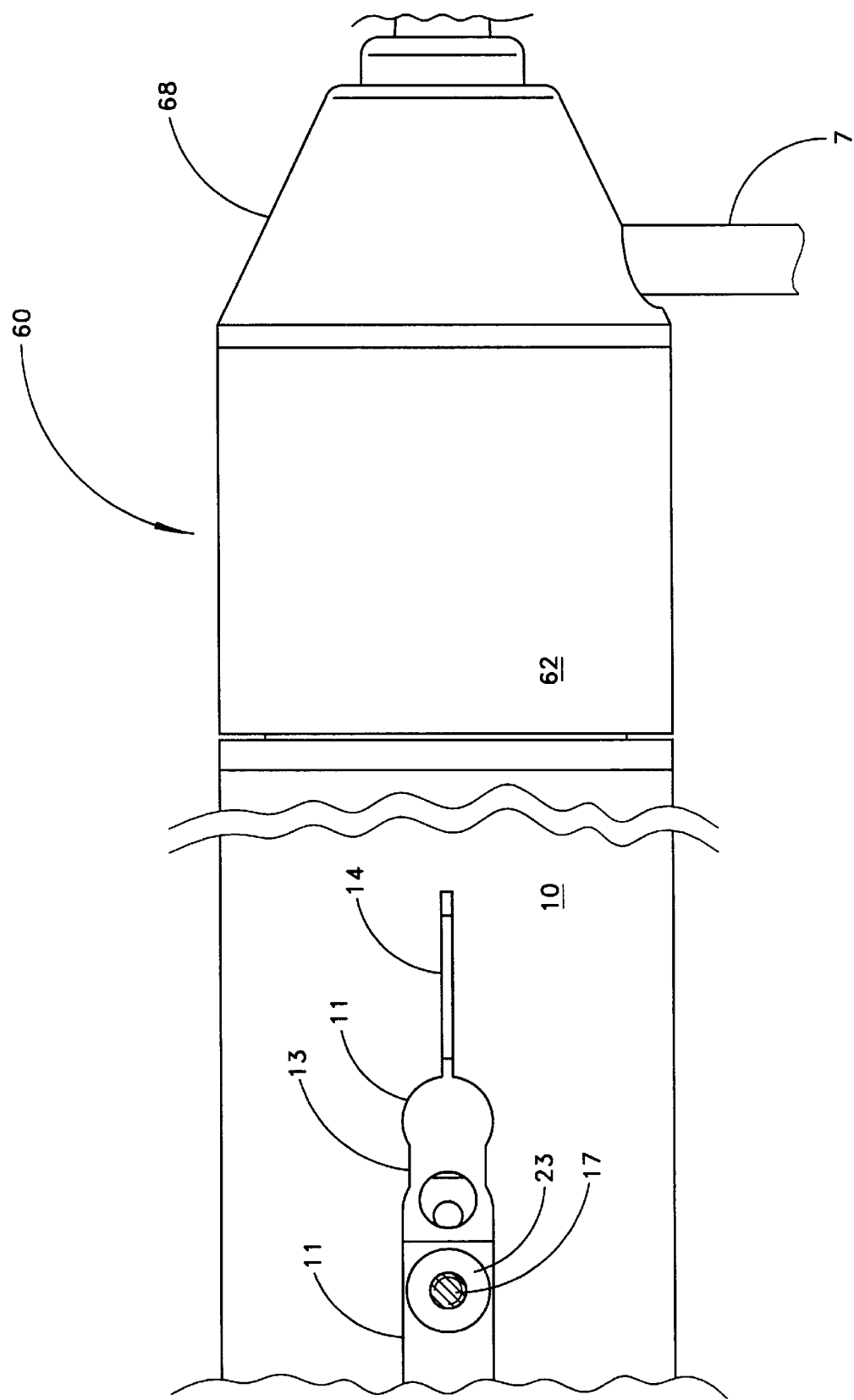
FIG. 38 is a top view of FIG. 37 taken along lines 38—38 thereof.

In FIG. 36 the user is applying proximal force to the control knob 16 to move it from the carriage-restrained position through the range of transitional positions toward the range of working positions. FIGS. 37–38 show the device with the control knob 16 in the range of working positions. The narrowed portion 13 of the slot 11, which defines the range of transitional positions, provides a positive tactile feeling and an audible click when the control knob 16 and its shaft 17 pass through the narrowed portion 13 and either enter the carriage-restrained position or return back to the range of working positions. The narrowed portion 13 thus prevents the user from inadvertently moving the control knob 16 and its shaft 17 into the carriage-restrained position during the atherectomy procedure.

The carriage-restrained position of the prime mover carriage 30 is located within the handle housing 10 such that, when the cartridge housing 60 is attached to the handle housing 10, advancement of the prime mover carriage 30 to its carriage-restrained position assures sufficient distal movement of the prime mover carriage 30 with respect to the drive shaft shank 82 and the moveable telescopic tube 76 so that the elongated shank 82 is inserted into the prime mover socket 38 and the movable telescopic tube 76 is attached to the prime mover carriage 30.

The narrowed portion 13 of the slot 11 can be considered to be an element of a carriage restraining mechanism that inhibits advancement of the prime mover carriage 30 from the range of working positions to the carriage-restrained position. The carriage restraining mechanism can consist of any suitable disengageable mechanical linkage between the prime mover carriage 30 and the handle housing 10. Preferably the disengageable mechanical linkage comprises a detent and a complementary member engageable with the detent. In the preferred embodiment shown in the drawings the elongated slot 11 is defined by opposing walls of the handle housing, and the prime mover carriage 30 includes a control knob shaft 17 extending radially outwardly from the prime mover carriage 30. The detent, thus, is comprised of the narrowed portion 13 in the elongated slot 11, and the complementary member is the control knob shaft 17. Preferably the control knob shaft 17 has a diameter slightly larger than the width of the narrowed portion 13. This may be achieved either by actually making the control knob shaft 17 of a suitable diameter, or by placing about the shaft 17 a collar 23 which has the desired outer diameter.

Preferably the narrowed portion 13 of the elongated slot 11 is constructed so that, when the control knob shaft 17 is urged into the narrowed portion 13, the narrowed portion 13 resiliently widens to permit the shaft 17 to pass therethrough. This can be achieved by providing a relief slot 14 extending distally from a distal end of the elongated slot 11.

Figure 39:
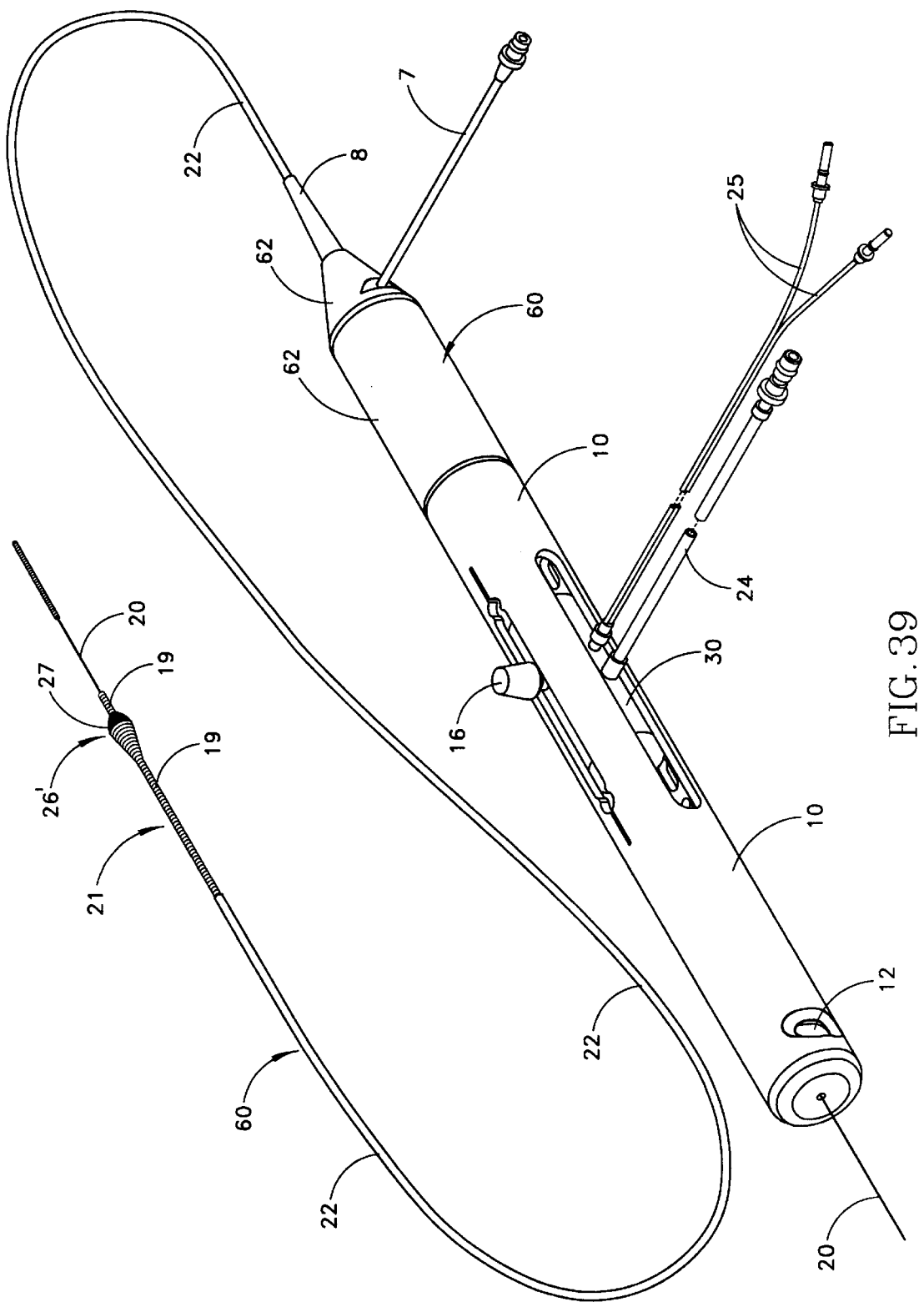
FIG. 39 is a perspective view, similar to FIG. 1, but illustrating the assembled atherectomy device of the invention advanced over the guide wire and shown with an exchangeable drive shaft cartridge having a larger size tissue removal implement.

FIG. 39 shows the assembled atherectomy device of the invention advanced over the guide wire 20. This figure is similar to FIG. 1, except that the exchangeable drive shaft cartridge 60 has a larger diameter tissue removal implement 26'. In actual use, when there is a need to use more than one exchangeable drive shaft cartridge in order to adequately open a stenotic lesion, the guide wire is left across the stenosis in the artery of interest. The atherectomy device is then withdrawn from the patient and the drive shaft cartridge which has been used is exchanged for another exchangeable drive shaft cartridge. The replacement drive shaft cartridge typically has a larger diameter (or a different design) tissue removal implement. The reassembled atherectomy device is then advanced over the guide wire and the larger size (or different design) tissue removal implement is used to continue the atherectomy procedure.

FIGS. 40–41 depict details of the drive shaft shank 82. The elongated shank 82 has a longitudinal lumen 89 which is generally coaxial with the longitudinal axis of the shank. Preferably the lumen has a diameter sufficient to receive a proximal portion of the flexible drive shaft 21 therein so that the elongated shank 82, together with the drive shaft 21, may freely rotate over the guide wire 20. The shank 82 may be secured to the drive shaft 21 by, e.g., a suitable adhesive. The shank 82 includes distal and proximal portions. Desirably at least a portion of the outer periphery of the proximal portion of the shank 82 is non-circular in transverse cross-section. This can be achieved by providing the proximal portion with at least one flat surface 87 substantially parallel to the longitudinal axis of the shank. Preferably the shank 82 has two or more of such flat surfaces 87, and most preferably it has four of such flat surfaces, as is depicted in FIG. 40. These flat surfaces preferably are connected by surfaces 88 which are generally cylindrical in shape. Other suitable non-circular shapes of the proximal portion of the elongated shank 82 may also be employed, such as providing the proximal portion of the shank with longitudinal splines.

Desirably the proximal end of the elongated shank 82 has a frusto-conical shape to facilitate insertion of the shank 82 into the prime mover socket 38. Other shapes of the proximal end of the shank may also be used, including, e.g., generally convex shapes.

As is described above, preferably the distal portion of the elongated shank 82 includes a radially outwardly extending flange 84 which is used to insert and remove the shank 82 from the prime mover socket 38. The elongated shank 82 may also include additional design features useful in securing it to the proximal portion of the drive shaft 21. As described above in connection with, e.g., FIGS. 3–4, and as can be seen by reference to FIG. 41, the shank's longitudinal lumen may have a slightly larger diameter near its distal end in order to receive therein a short section of low friction tubing. Such low friction tubing may be heat shrunk onto a proximal portion of the drive shaft 21 in order to reduce friction between the drive shaft 21 and the bushing 81 secured within the proximal end portion of the movable telescopic tube 76.

Figure 42:
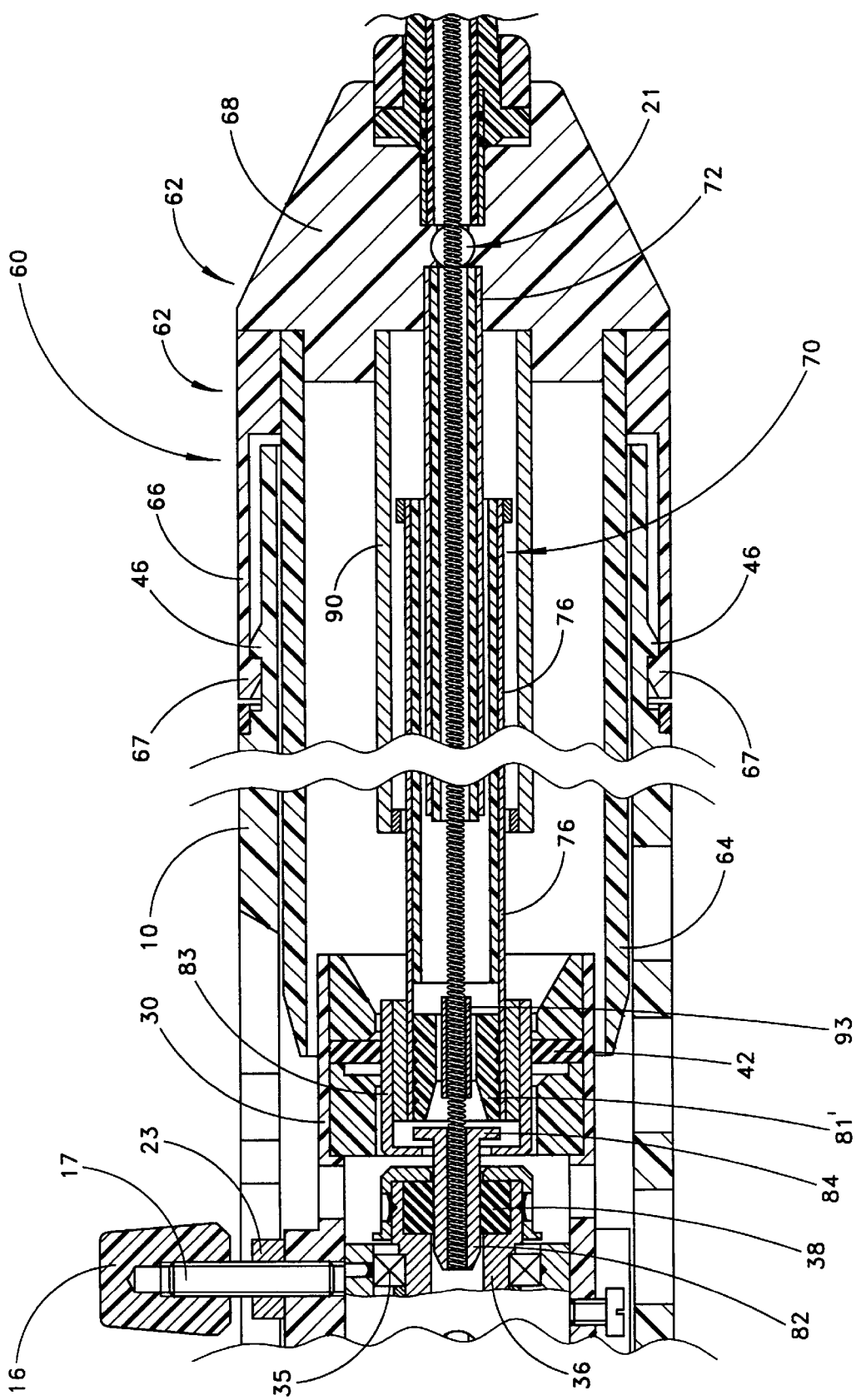
FIGS. 42–44 are longitudinal cross-sectional views, similar to FIG. 38, of modified embodiments of the invention, the modifications being located primarily in the area associated with the proximal end portion of the longitudinally extendable tube.

FIG. 42 depicts an alternate embodiment of the invention wherein the bushing 81' is made of a single piece of a low friction material, such as polytetrafluoroethylene. The bushing 81' has a lumen that is tapered outwardly at its proximal end, permitting the shank 82 and proximal end portion of the drive shaft 21 to deflect slightly laterally (e.g., as is shown in FIG. 20). Making the bushing 81' from a low friction material eliminates the need to heat shrink a section of low friction tubing 85 around a portion of the drive shaft 21 that is rotatable within the bushing 81'. As is shown in FIG. 42 a short section of a metallic tubing 93 (e.g., stainless steel tubing) is secured around that portion of the drive shaft which rotates within the bushing 81.

Figure 43:
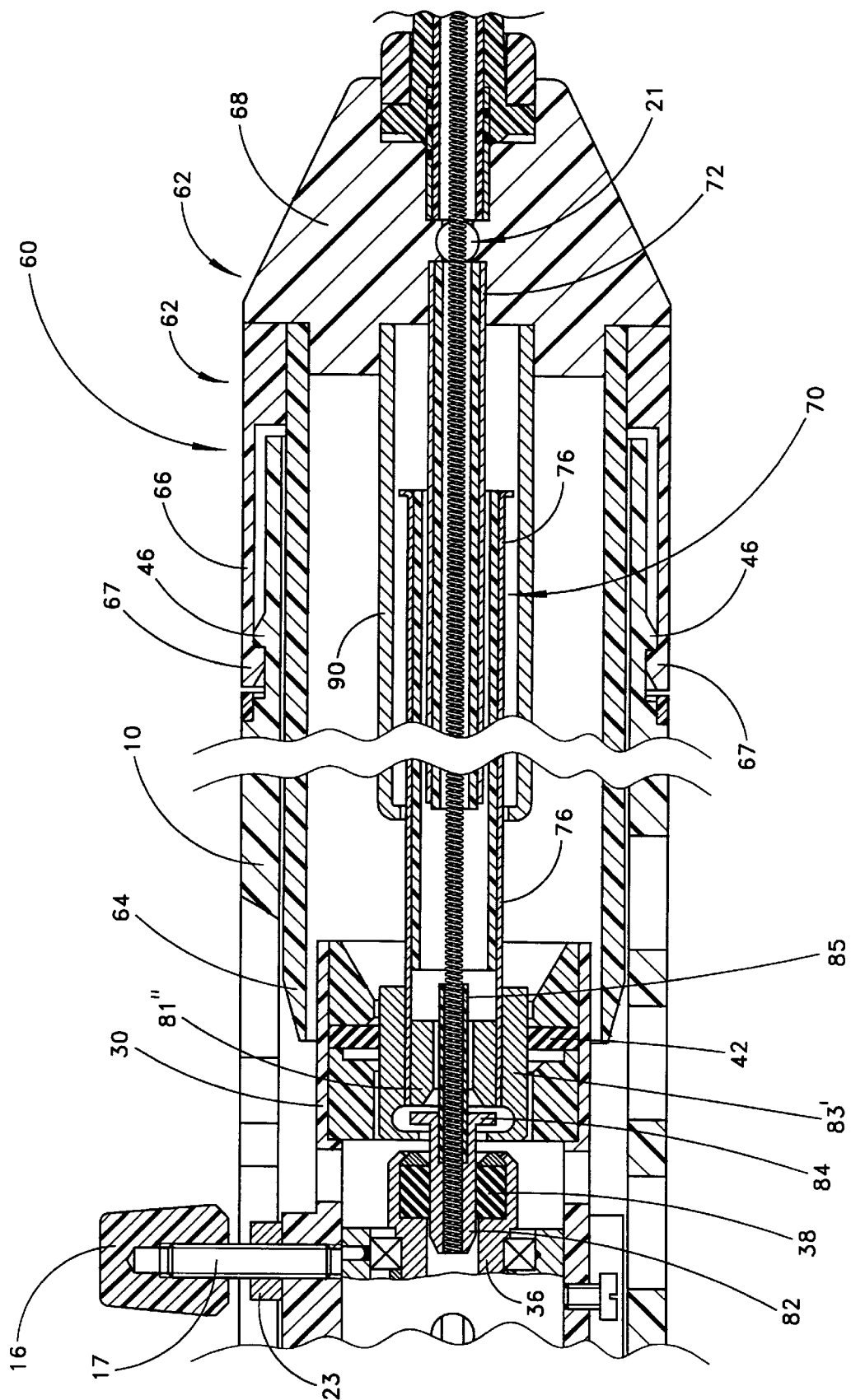

FIG. 43 depicts another alternate embodiment of the invention. In this embodiment, the abutment member 83 and the short tubular component 86 (shown, e.g., in FIG. 19) have been combined into a single piece 83' which functions as the abutment member. It also should be noted that FIG. 43 shows a one piece bushing 81" which is made from a single piece of metallic tubing rather than from a low friction plastic as is shown in FIG. 42. The drive shaft 21 with its short section of heat shrunk tubing 85 is rotatable within such single piece metallic bushing 81". Several other components have also been simplified. The cap 39 securing the prime mover socket 38 in the recess of the turbine shaft 36 has been eliminated by simply crimping the distal end of the turbine shaft around the distal end of the prime mover socket 38 to hold the resilient socket 38 in place. Also, the stops 78 and 91 at the distal end of the movable telescopic tube 76 and the proximal end of the support tube 90 have similarly been replaced by integrally formed flanges.

Figure 44:
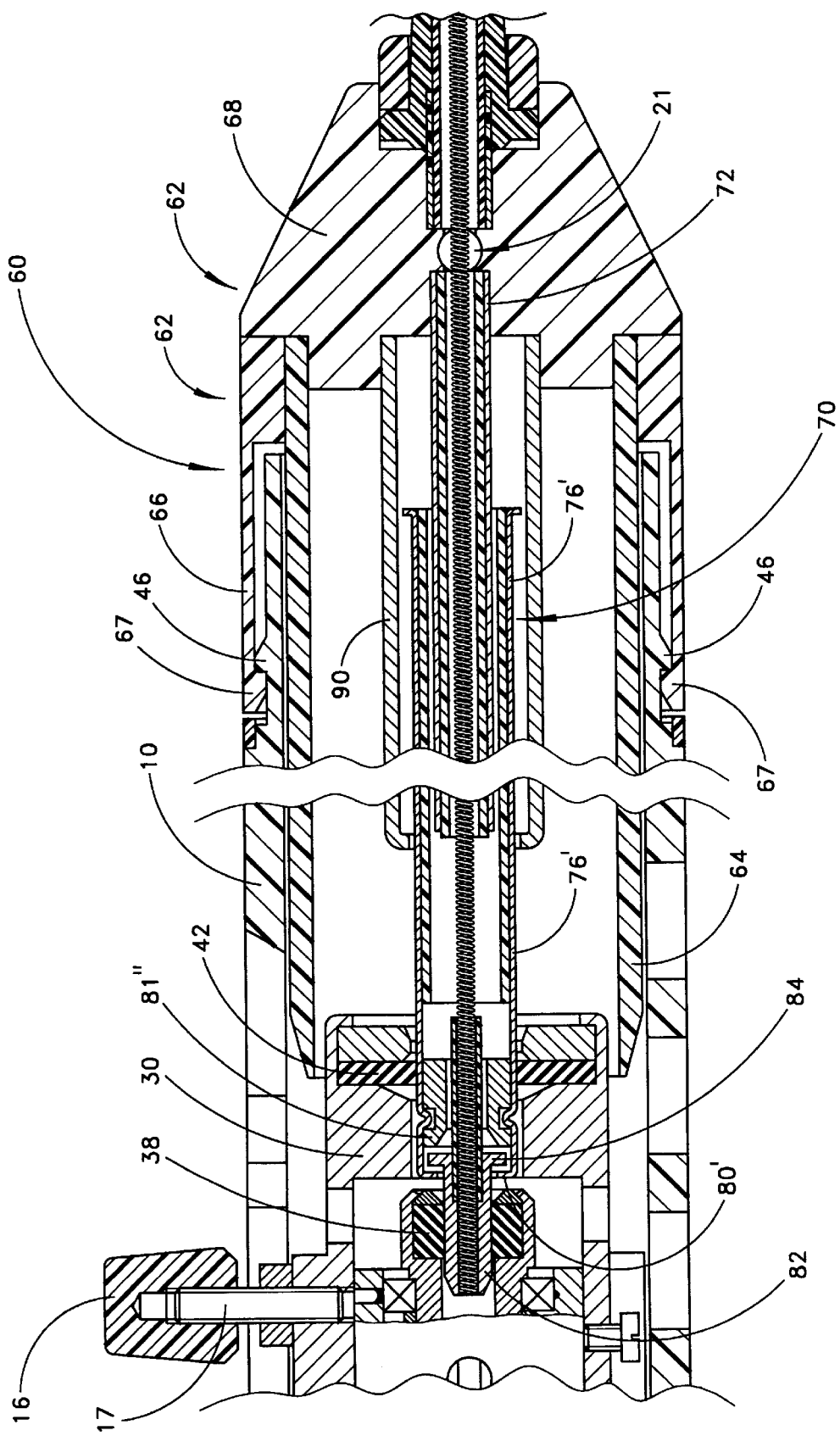

In the embodiment of FIG. 44 the inwardly extending flange 80' is formed integrally with the movable telescopic tube 76'. The single piece metallic bushing 81" is secured within the proximal end portion of the movable telescopic tube 76' by crimping the tube 76' around a complementary annular groove in the outer surface of the bushing 81".

FIGS. 45–71 illustrate alternate embodiments of the tube attachment mechanism employed for attaching the longitudinally extendable tube 70 to the prime mover carriage 30.

Figure 45:
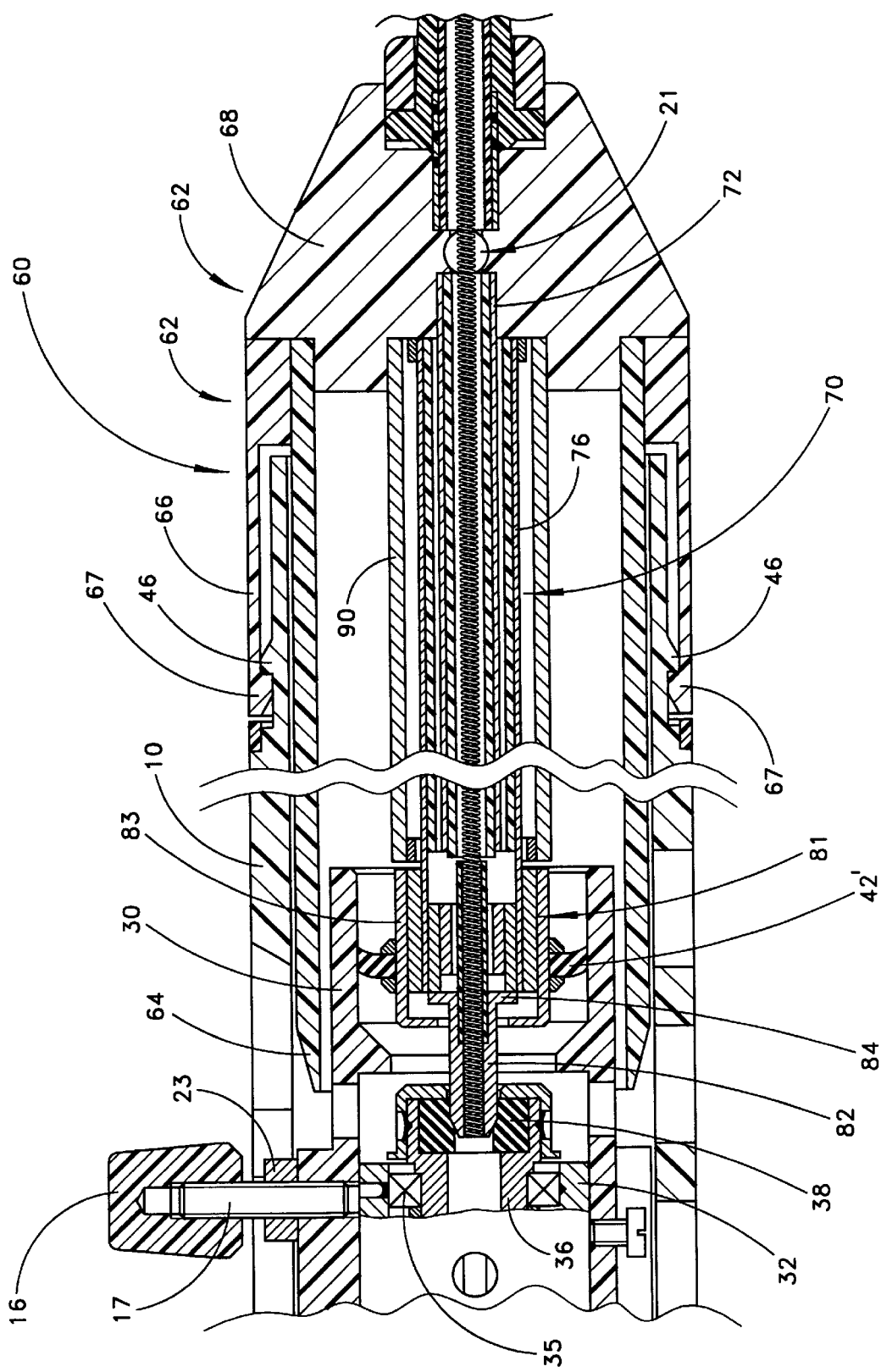
FIGS. 45–48 are longitudinal cross-sectional views, similar to FIG. 38, of modified embodiments of the invention, the modifications being associated with the mechanism for attaching the longitudinally extendable tube to the prime mover carriage.
Figure 46:
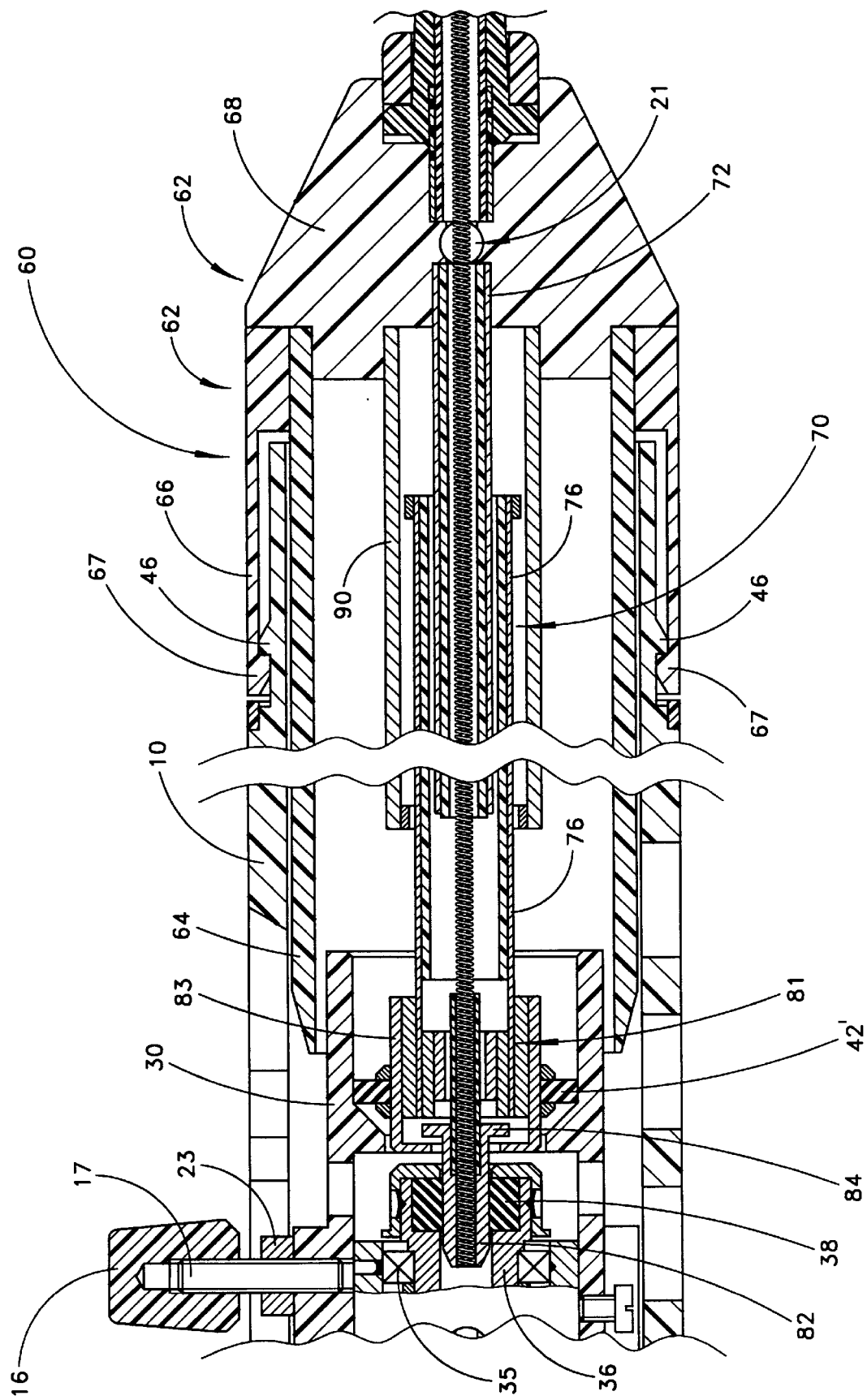
Figure 47:
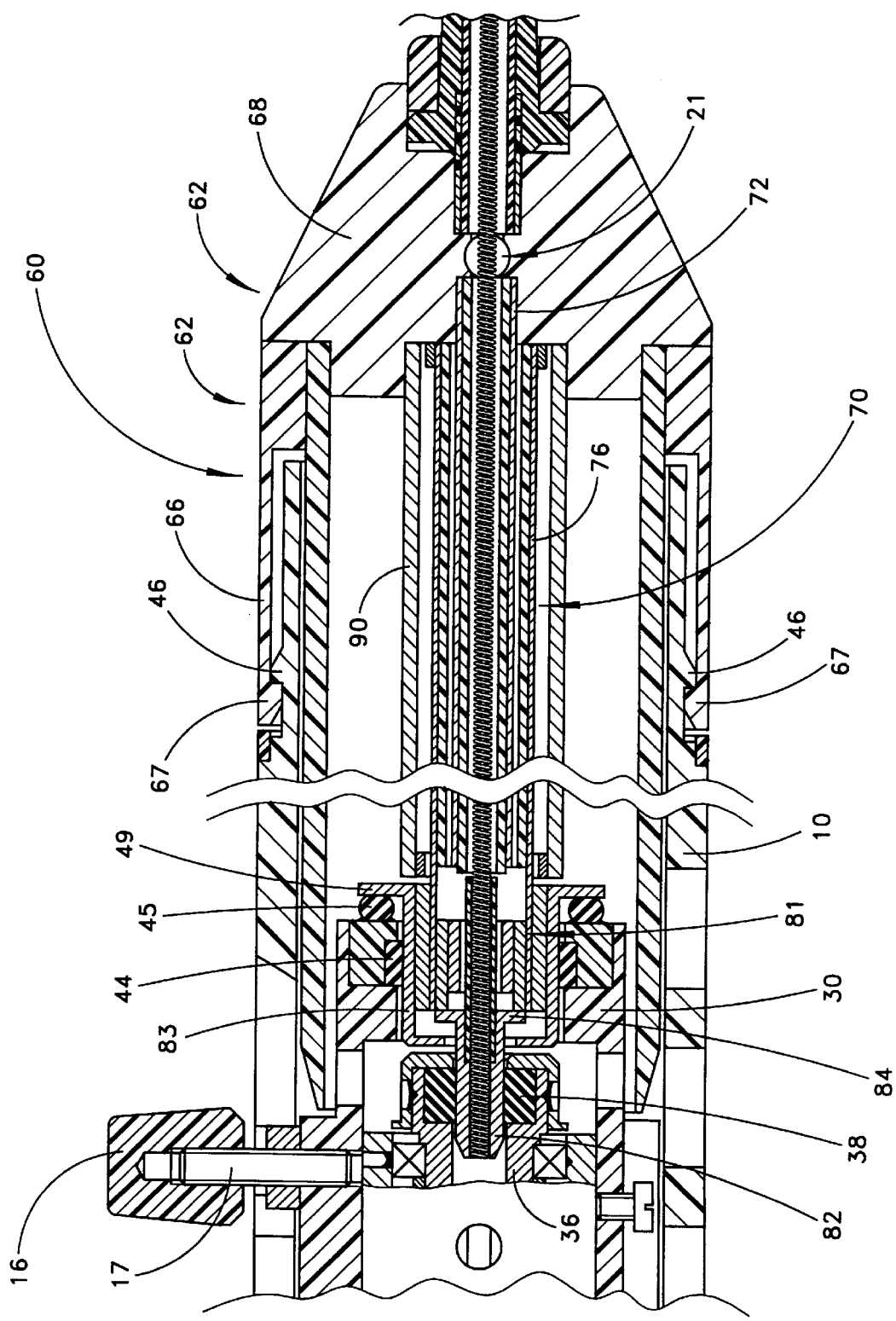
Figure 48:
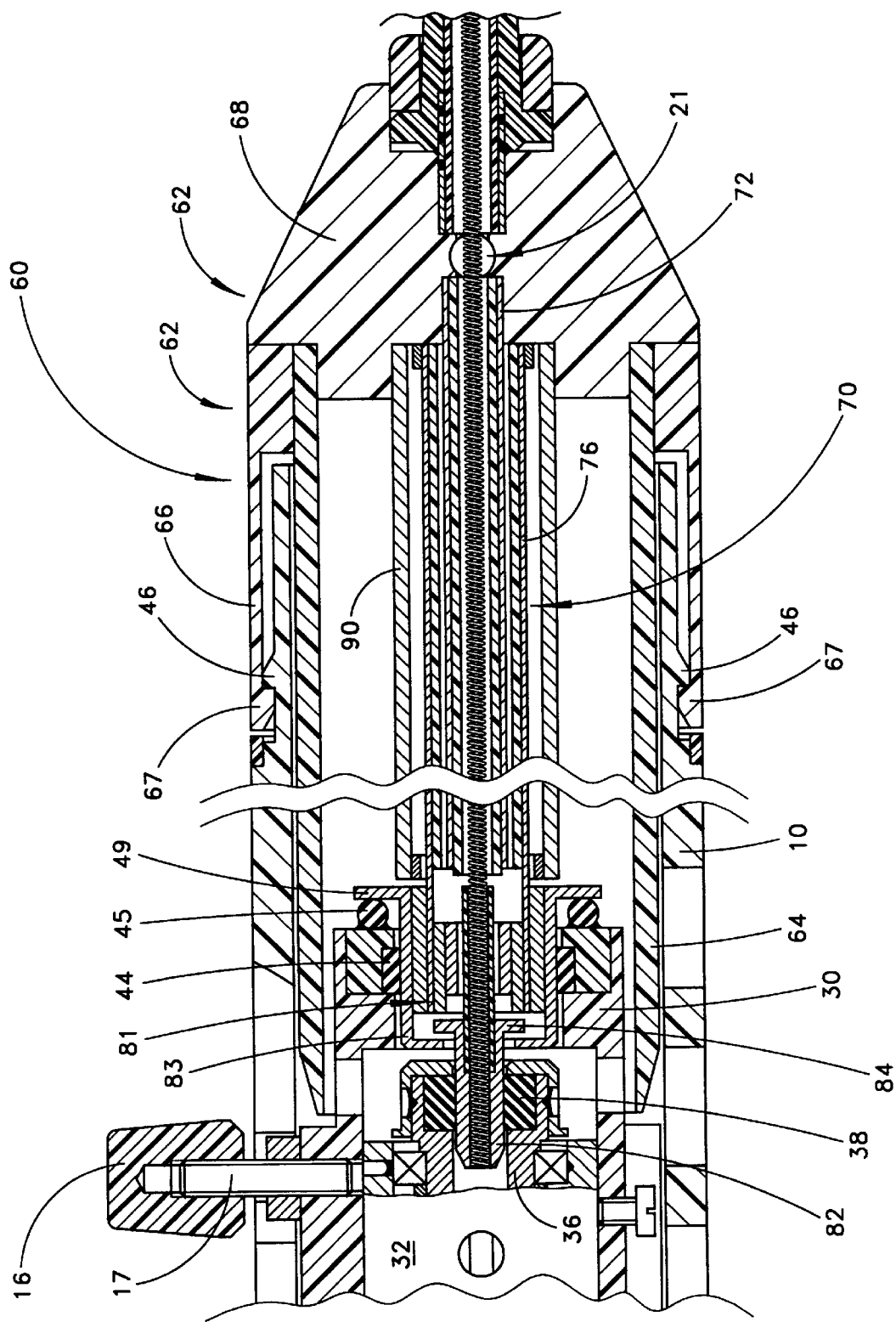

In FIGS. 45–46 the tube attachment mechanism includes a resilient positioning ring 42' carried by the movable telescopic tube 76 (in particular, by the abutment member 83 carried by the proximal end portion of the movable telescopic tube 76) rather than by the prime mover carriage 30 (compare FIGS. 45–46 to FIGS. 32–34). The radially inner portion of the positioning ring 42' is secured against longitudinal movement with respect to the movable telescopic tube 76 by a pair of rings secured to the outer surface of the abutment member 83. The radially outer portion of the resilient ring 42' is configured so that it resiliently deflects distally (see FIG. 45) when the prime mover carriage 30 is moved distally over the resilient positioning ring 42'. The radially outer portion of the resilient ring 42' at least partially returns (and typically completely returns) to its non-deflected configuration, and thereby moves the prime mover carriage 30 and the shank 82 proximally with respect to the movable telescopic tube 76, after pressure urging the prime mover carriage 30 over the resilient positioning ring 42' has been removed (see FIG. 46). This movement of the prime mover carriage 30 and the drive shaft shank 82 thus spaces the shank's flange 84 away from the distal abutment surface associated with the moveable telescopic tube 76 and formed by the proximal end surface of bushing 81. The proximal movement of the prime mover carriage 30 and the drive shaft shank 82 caused by the resilience of the positioning ring 42' permits the drive shaft shank 82 and its flange 84 to rotate freely with respect to the movable telescopic tube 76. FIGS. 47–48 depict another embodiment of a tube attachment mechanism. This embodiment includes two separate elements performing the same function as the resilient positioning ring 42. These two separate elements are comprised of a radially resilient carriage socket 44, attached to the inner surface of the distal portion of the prime mover carriage 30, and a positioning O-ring 45 secured to the distal end of the prime mover carriage 30. The O-ring 45 is resilient so that it compresses (see FIG. 47) when the resilient carriage socket 44 is moved distally over the abutment member 83 to a point where the O-ring 45 encounters the radially outwardly extending flange 49 which is carried at the distal end of the modified abutment member 83. In this position, the drive shaft shank 82 is adequately inserted into the prime mover socket 38. After pressure urging the prime mover carriage 30 distally with respect to the movable telescopic tube 76 has been removed (see FIG. 48) the resilient O-ring 45 returns to its non-deflected configuration, thereby moving the prime mover carriage 30 and the shank 82 proximally with respect to the movable telescopic tube 76. This movement of the prime mover carriage 30 and the drive shaft shank 82 thus spaces the shank's flange 84 away from the distal abutment surface associated with the moveable telescopic tube 76 and formed by the proximal end surface of bushing 81. The radially resilient carriage socket 44 provides sufficient friction against the outer surface of the abutment member 83 to effectively secure the prime mover carriage 30 to the movable telescopic tube 76, while permitting the socket 44 to slide distally when the O-ring 45 is being compressed and proximally when the O-ring 45 regains its shape.

FIGS. 49–51B depict a particularly preferred tube attachment mechanism, including a particularly preferred resilient positioning mechanism, usable in connection with the rotational atherectomy device of the invention. In this embodiment the tube attachment mechanism includes complementary sets of proximal and distal camming surfaces associated with the prime mover carriage 30 and the movable telescopic tube 76 (i.e., the longitudinally extendable tube 70). At least one of each set of camming surfaces is carried by a radially resilient member.

Figure 49:
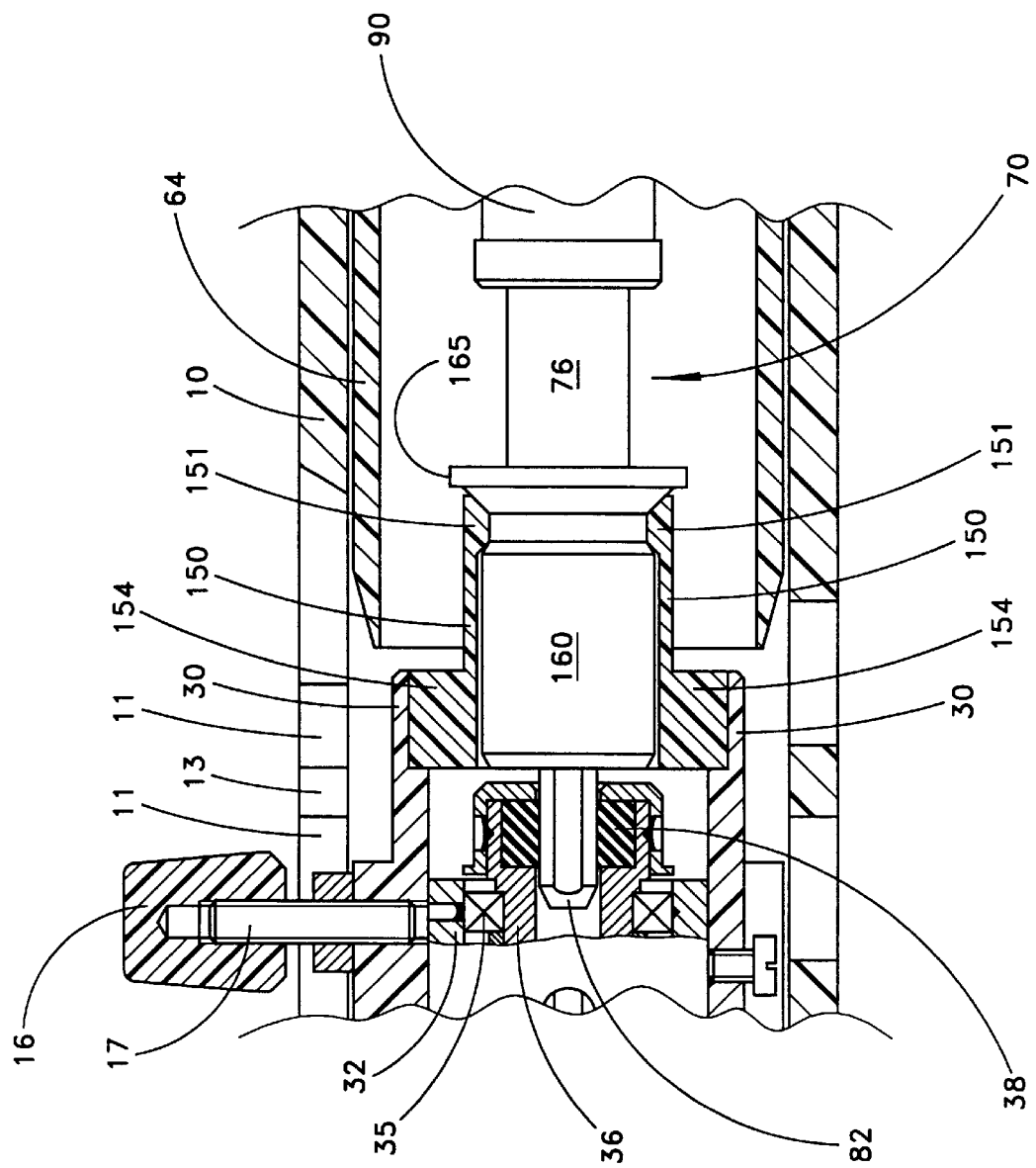
FIG. 49 is a longitudinal cross-sectional, broken away views illustrating the design of a preferred embodiment of a mechanism for attaching the longitudinally extendable tube to the prime mover carriage.
Figure 51B:
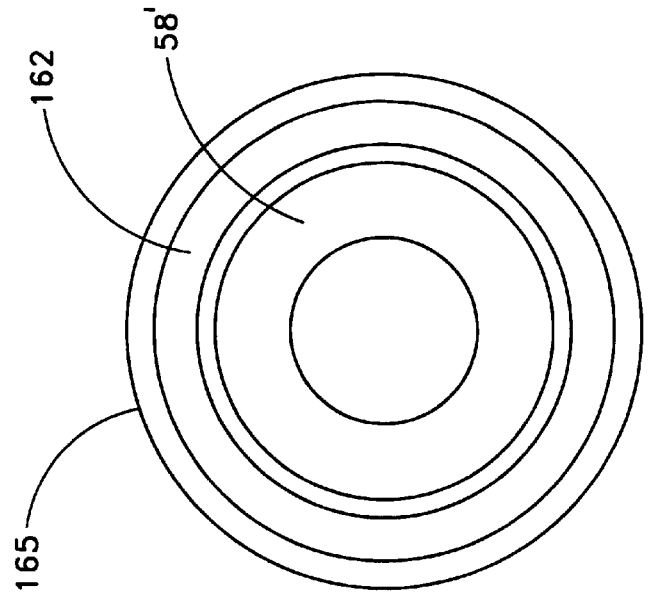
Figure 51A:
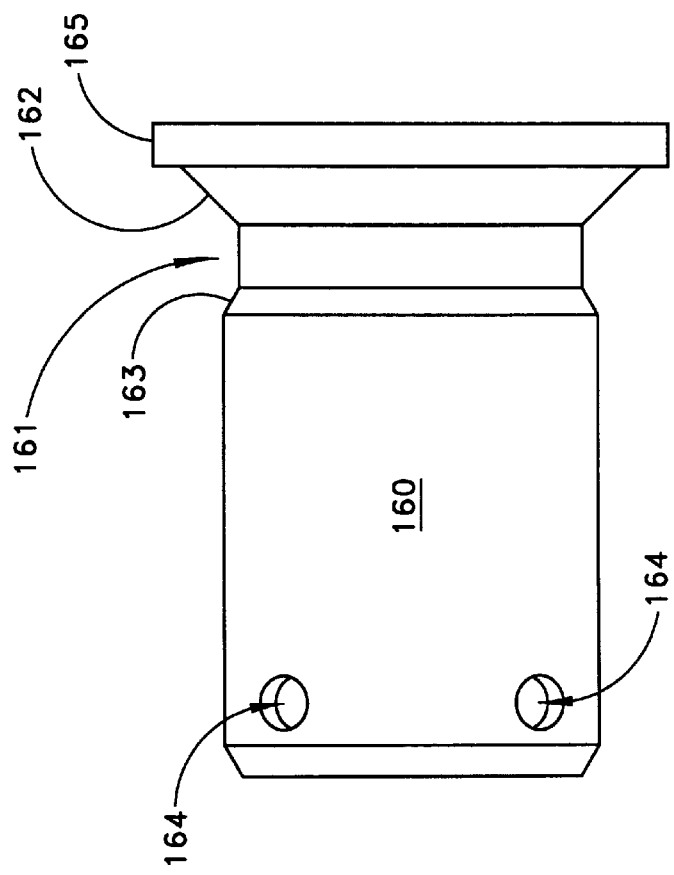

As shown in FIG. 49, in the preferred embodiment the camming surfaces are associated with the radially inwardly extending detent 151 and the complementary annular groove formed in a collar 160 carried by the movable telescopic tube 76 (i.e., the longitudinally extendable tube 70). FIG. 49 also demonstrates that all of the camming surfaces are constructed so that they are stable with respect to one another (i.e., they do not slide longitudinally with respect to one another) when the prime mover carriage of the assembled atherectomy device is moved back and forth along the range of working positions.

The complementary distal camming surfaces are oriented with respect to each other so that, when distal pressure moves the prime mover carriage 30 distally to its most distal position with respect to the movable telescopic tube 76 the distal pressure causes the distal camming surfaces to slide with respect to each other, thereby forcing the radially resilient member and its camming surface to deflect radially outwardly. Then, as soon as distal pressure is removed, the radially resilient member regains its non-deflected configuration, causing the distal camming surface carried by the radially resilient member to slide back to its stable position with respect to the distal camming surface associated with the movable telescopic tube 76 (i.e., collar 160), thereby longitudinally moving the prime mover carriage 30 and the drive shaft shank 82 proximally with respect to the movable telescopic tube 76.

The radially resilient member is sized and positioned to removably attach the movable telescopic tube 76 to the prime mover carriage 30. The complementary proximal camming surfaces are oriented with respect to each other so that, when the prime mover carriage 30 is attached to the movable telescopic tube 76, relative movement of the cartridge housing 62 and the prime mover carriage 30 away from each other will cause the proximal camming surfaces to slide and move longitudinally with respect to each other so that the proximal camming surfaces become disengaged from each other, thereby permitting the prime mover carriage 30 to be detached from the movable telescopic tube 76 (i.e., longitudinally extendable tube 70).

In the preferred embodiment shown FIGS. 49–51B, the radially resilient member is comprised of six distally extending resilient fingers 150 carried by a positioning collar 154 secured to the prime mover carriage 30. Fewer or more fingers 150 could also be employed. For example, applicants have successfully employed a tube attachment mechanism having three such resilient fingers 150. Each resilient finger 150 carries a radially inwardly extending detent 151 which defines the distal 152 and proximal 153 camming surfaces associated with the prime mover carriage 30. Preferably each of the distal camming surfaces 152 is beveled distally outwardly, and each of the proximal camming surfaces 153 is beveled proximally outwardly. Other suitable shapes of detents 151 (including, e.g., a hemisphere) may also be used.

The distal 162 and proximal 163 camming surfaces associated with the movable telescopic tube 76 are shown in FIGS. 49–55 as being defined by a radially inwardly extending annular groove 161 formed in a collar 160 carried by (and forming a part of) the movable telescopic tube 76. Preferably each of the distal camming surfaces 162 is beveled distally outwardly, and each of the proximal camming surfaces 163 is beveled proximally outwardly. Other suitable shapes of camming surfaces and grooves (including, e.g., rounded concave surfaces) may also be used.

Figure 52:
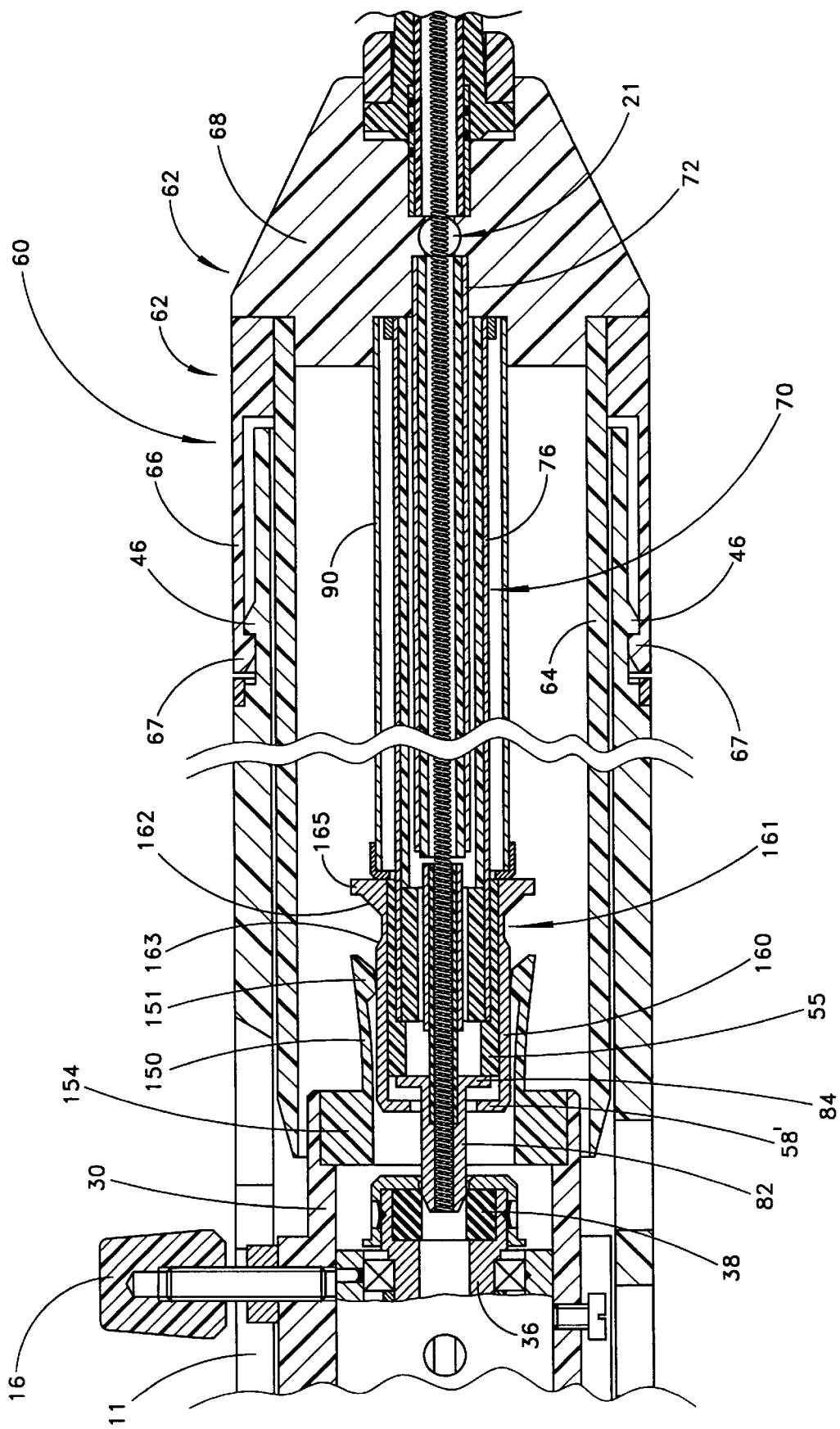
FIGS. 52–55 are longitudinal cross-sectional, broken away views illustrating the use of the preferred embodiment shown in FIGS. 49–51B.

FIGS. 52–55 illustrate the use of the preferred embodiment shown in FIGS. 49–51B. In FIG. 52 the prime mover carriage 30 is being moved distally to insert the shank 82 into the prime mover socket 38. The flange 84 of the shank 82 abuts against the distal abutment member 55, and the resilient fingers 150 are bent radially outwardly, the detents 151 riding on the outer surface of the collar 160.

Figure 53:
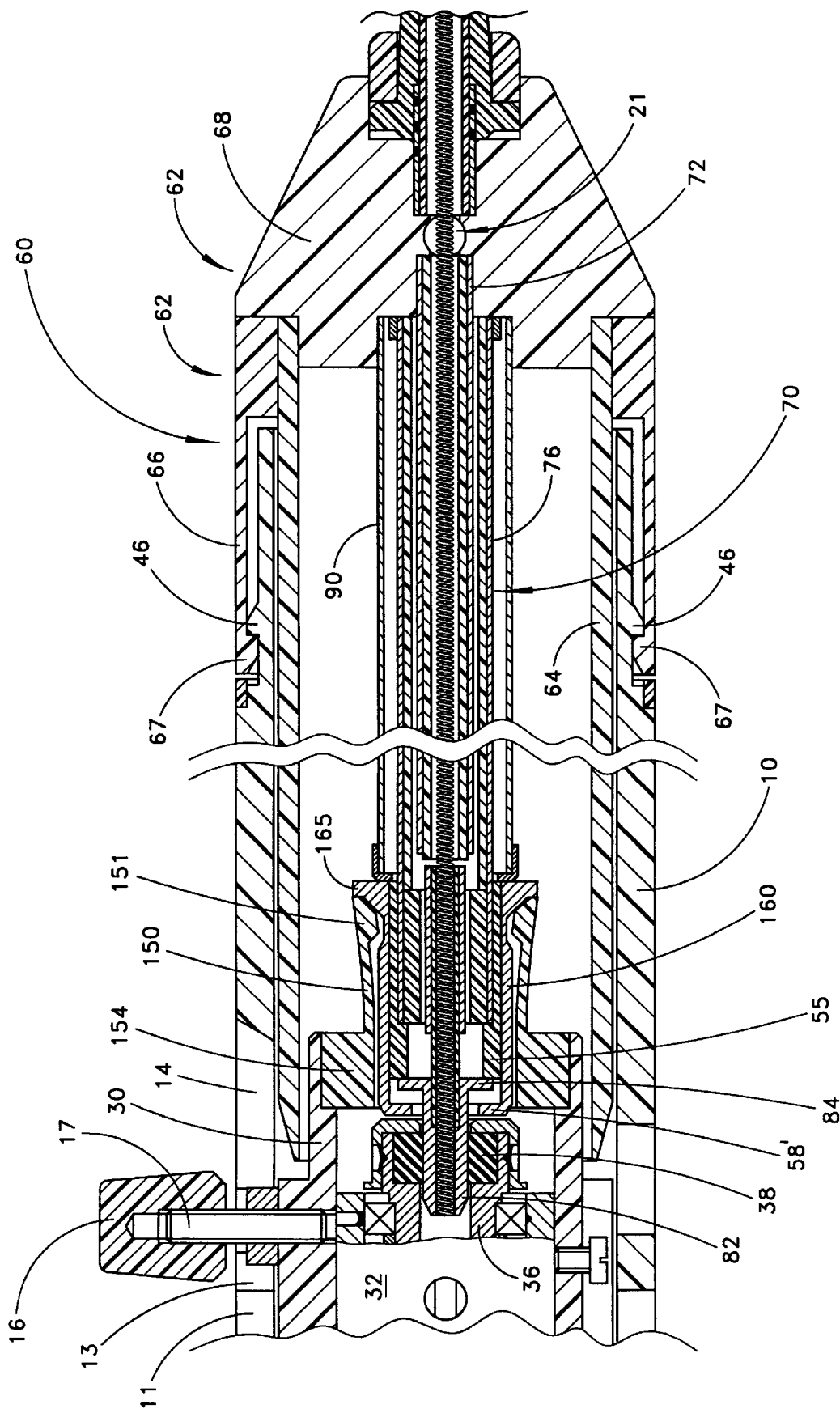
Figure 54:
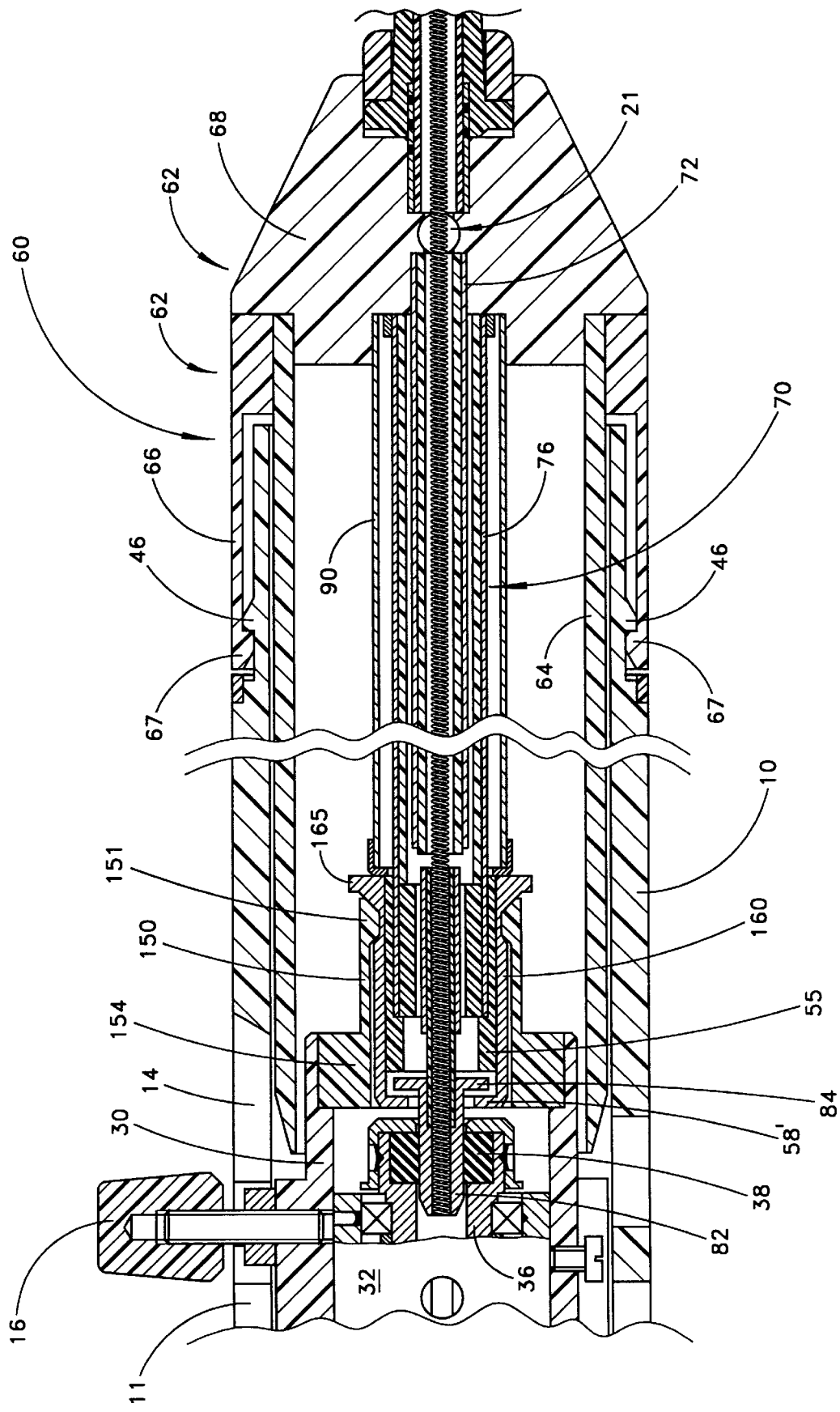

In FIG. 53 the prime mover carriage 30 has been advanced distally to its most distal position with respect to the movable telescopic tube 76. The distal pressure causes the distal camming surfaces 152 carried by the detents 151 to slide with respect to the distal camming surface 162 of the collar 160, thereby forcing the radially resilient fingers 150 to deflect radially outwardly. The collar 160 includes a radially outwardly extending flange 165 which limits the extent of distal movement of the radially resilient fingers 150. The drive shaft shank 82 becomes fully and adequately inserted into the prime mover socket 38 when distal movement of the radially resilient fingers 150 is stopped by the flange 165. In FIG. 54 pressure urging the prime mover carriage 30 distally has been removed. The radially resilient fingers 150, by regaining their non-deflected configuration, have caused the distal camming surfaces 152 carried by the detents 151 to slide back to their stable positions with respect to the distal camming surface associated with the collar 160 (i.e., the movable telescopic tube 76), thereby longitudinally moving the prime mover carriage 30 and the drive shaft shank 82 proximally with respect to the movable telescopic tube 76. In this position the detents 151 are generally centered within the annular groove 161. This movement of the prime mover carriage 30 and the drive shaft shank 82 thus spaces the shank's flange 84 away from the distal abutment member 55 which is secured to (and forms a part of) the moveable telescopic tube 76.

Figure 55:
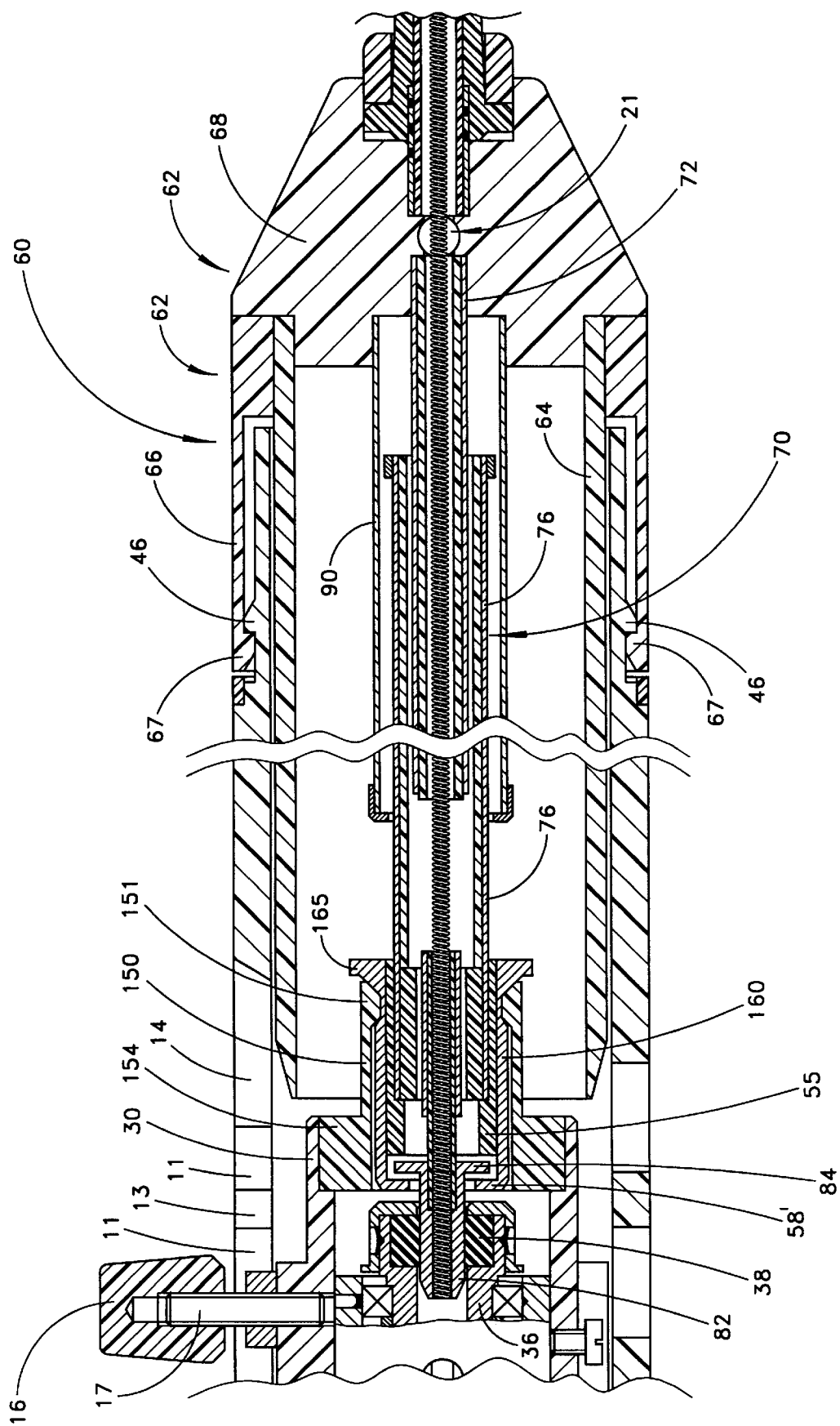

In FIG. 55 the control knob 16 and the prime mover carriage 30 have been withdrawn proximally to the range of working positions. The flange 84 of the drive shaft shank 82 continues to be spaced from both the distal abutment member 55 and the proximal flange 58' which in this embodiment is formed integrally with the collar 160, thereby permitting the flange 84 of the drive shaft shank 82 to rotate freely with respect to the movable telescopic tube 76.

Figure 56:
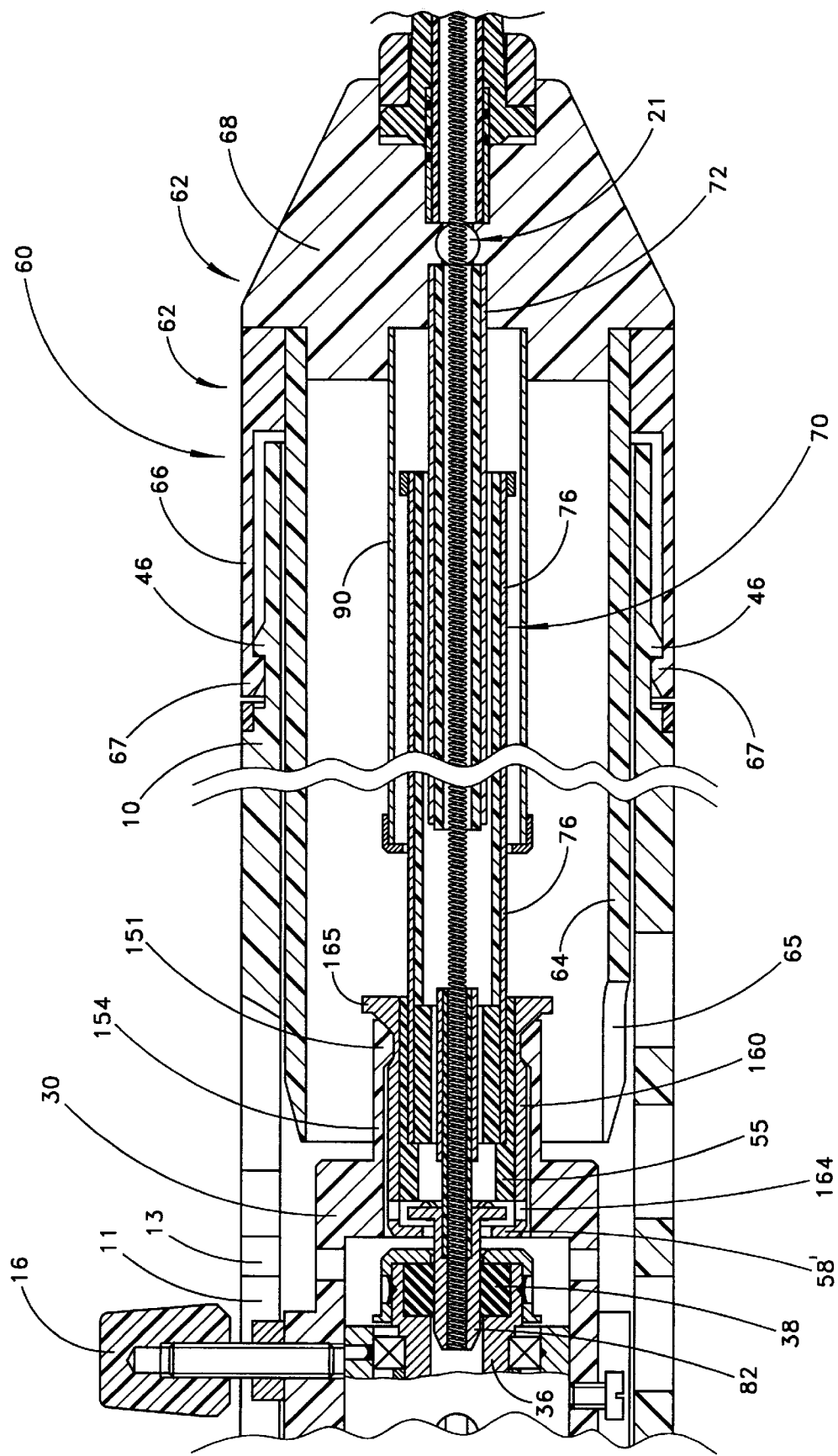
FIG. 56 illustrates one variation of the preferred design of the tube attachment mechanism wherein the component associated with the prime mover carriage is formed integrally with the carriage.

FIG. 56 illustrates one variation of the preferred design shown in FIGS. 49–55. In FIG. 55 distally extending resilient fingers 150 are formed integrally with the prime mover carriage. Also, this drawing illustrates the use of a number of drainage outlets 164 in the collar 160 (also seen in FIG. 51A) and one or more optional drainage slots 65 in the inner tube 64 of the cartridge housing 62. Drainage outlets similar to the drainage outlets 164 preferably are also used in other embodiments of tube attachment mechanisms. Some of such drainage outlets are not shown in many of the drawings for the purposes of clarity in presenting the basic concepts of such tube attachment mechanisms.

Figure 58:
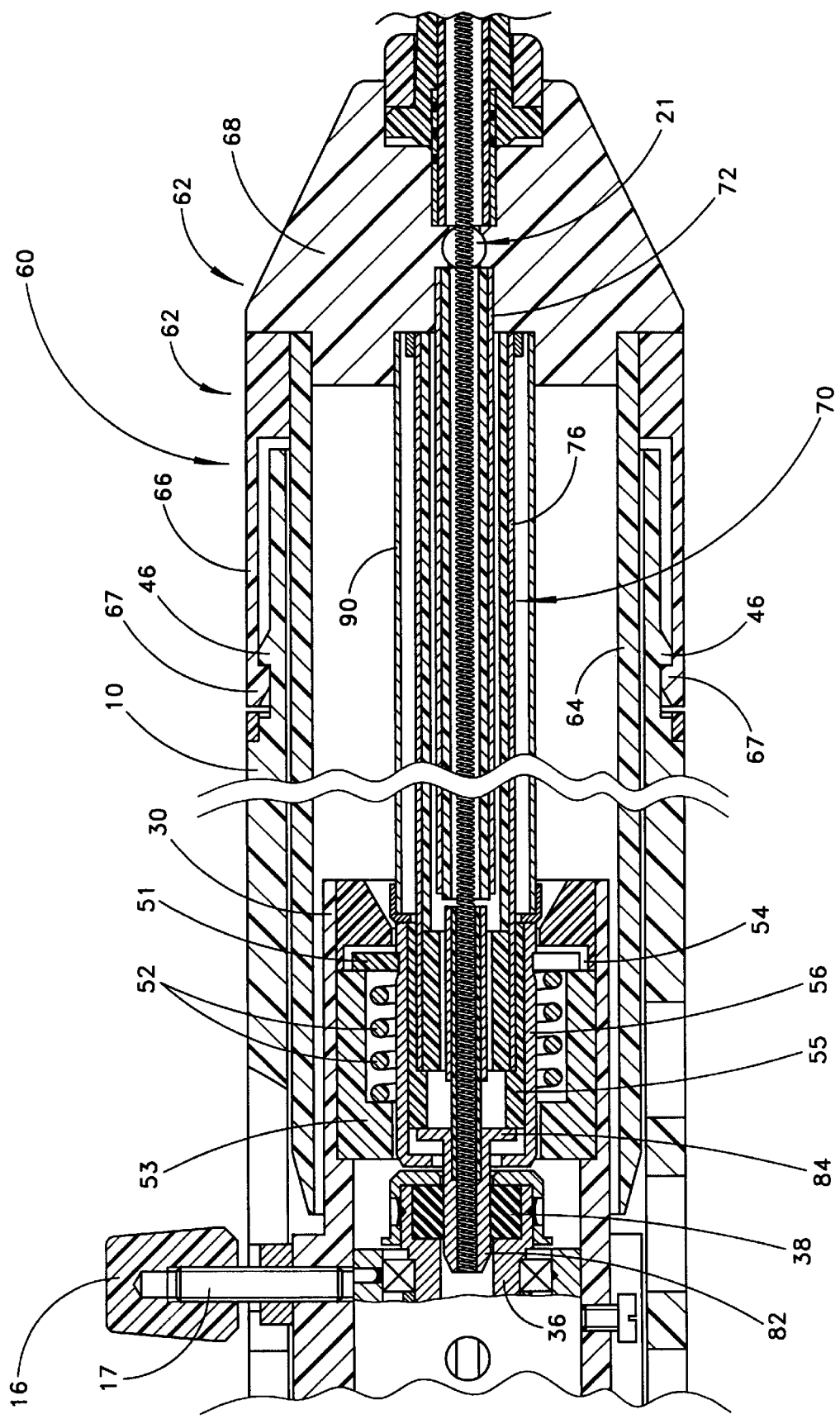
Figure 59:
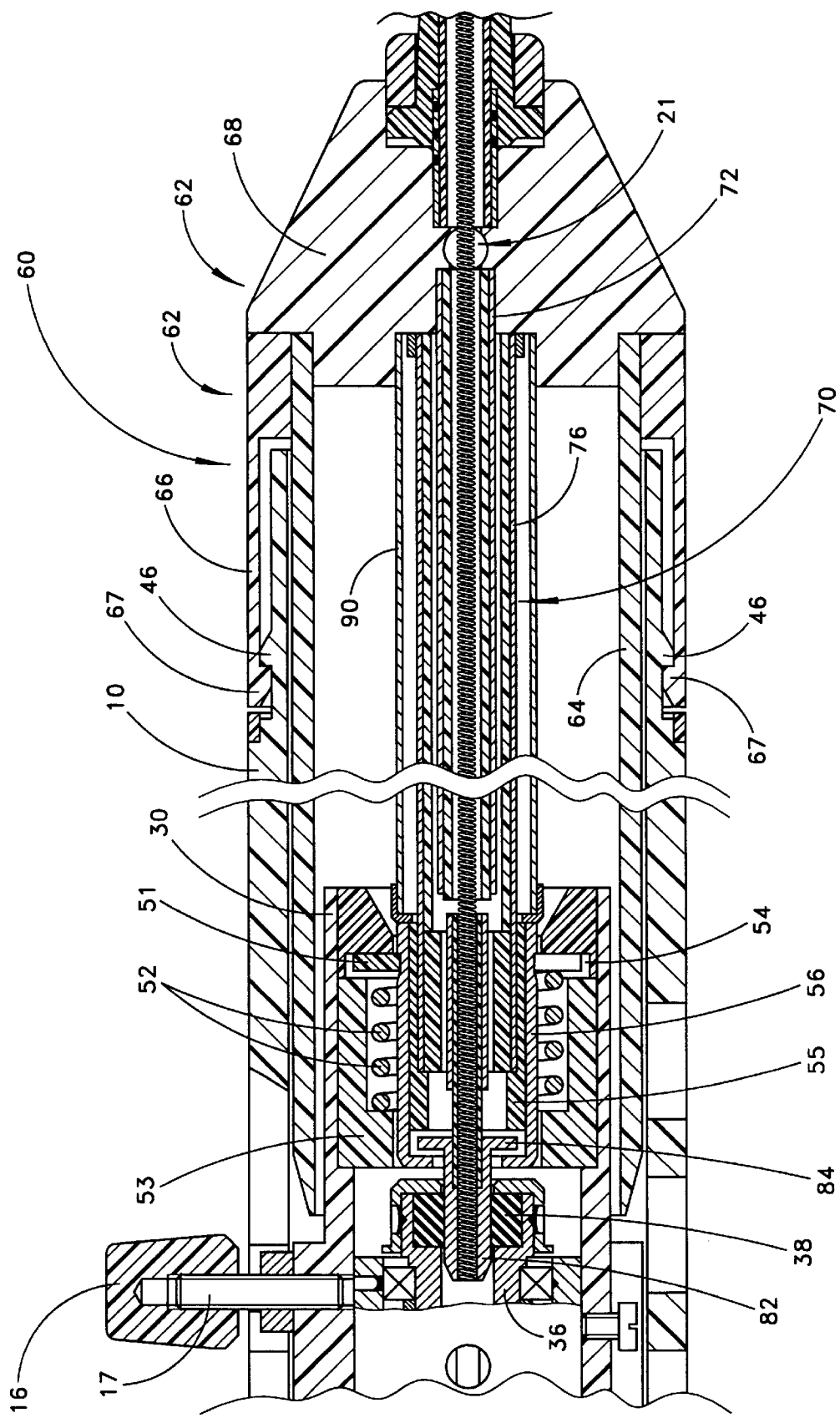
Figure 60:
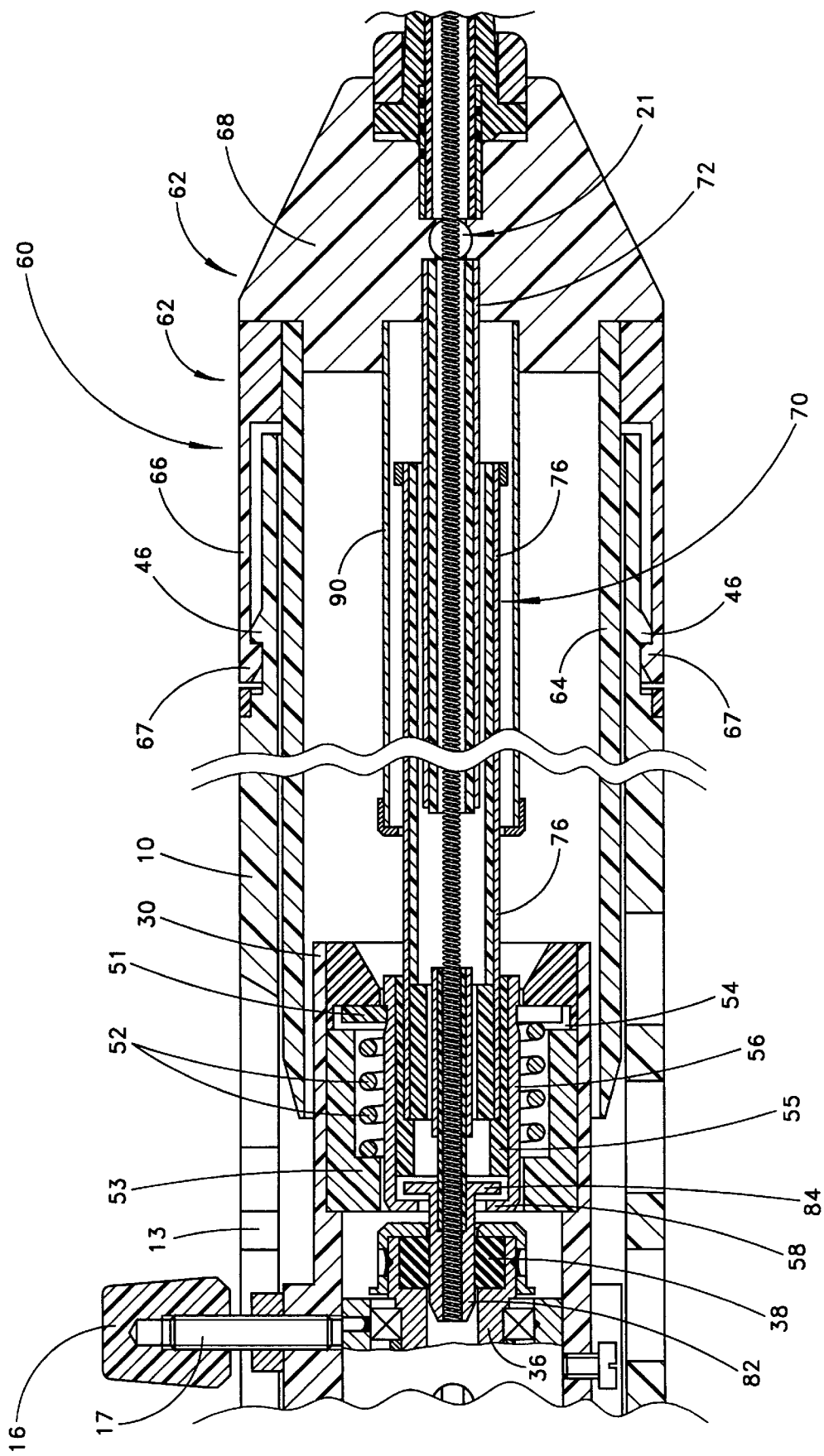
Figure 62:
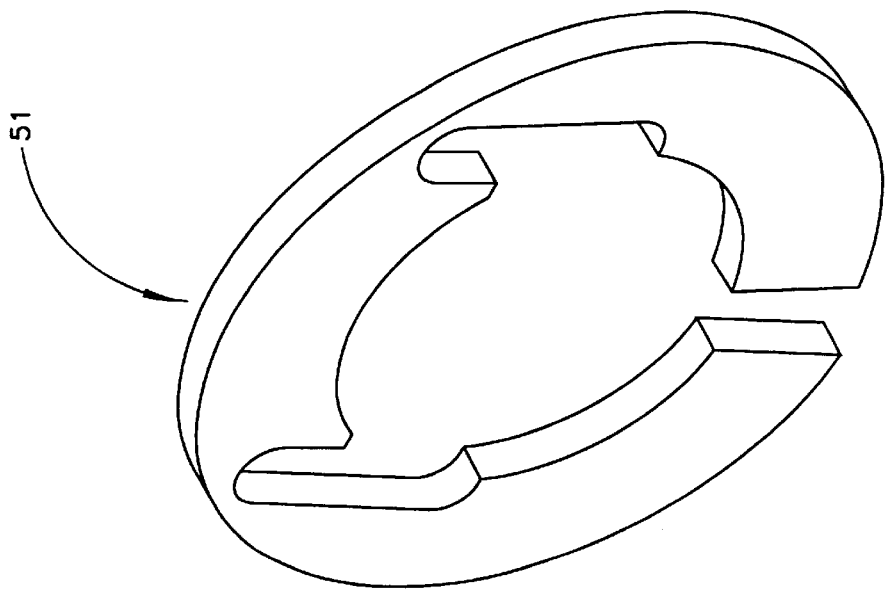
FIGS. 61–62 illustrate the design and function of one of the key components of the tube attachment mechanism shown in FIGS. 57–60.
Figure 61:
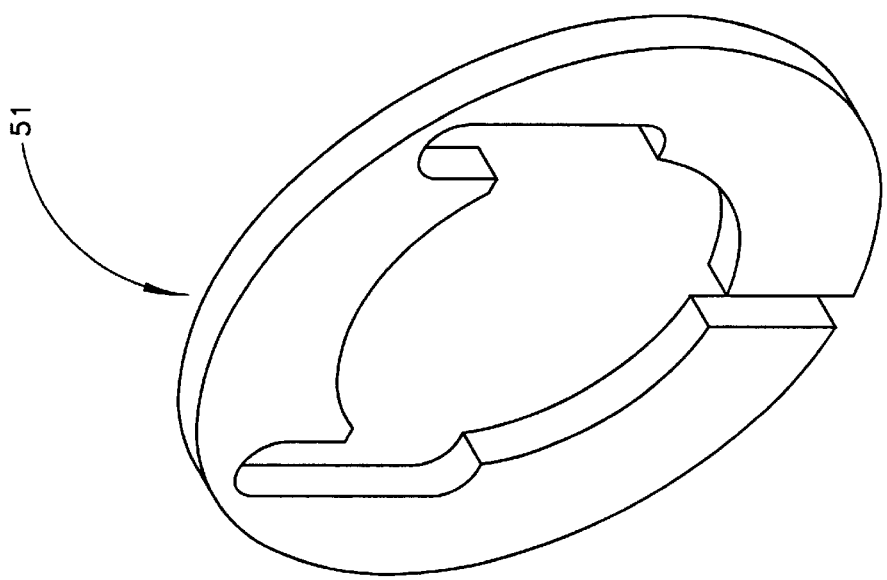

FIGS. 57–62 illustrate yet another embodiment of a tube attachment mechanism. In this embodiment the prime mover carriage 30 includes a circumferentially resilient keeper 51 captured within an annular groove 54 formed in the inner surface of the prime mover carriage 30. (FIG. 61 shows the keeper 51 in its relaxed shape, and FIG. 62 shows the keeper circumferentially expanded, as it would be, e.g., in FIG. 57.) The annular groove 54 in the inner surface of the prime mover carriage 30 has a longitudinal width that is longer than the thickness of the keeper 51. A coil spring 52 is disposed between the annular shoulder 53 of the prime mover carriage 30 and the circumferentially resilient keeper 51. As is shown in FIG. 60, the coil spring 52 urges the keeper 51 distally against the distal wall of the groove 54 when the prime mover carriage 30 of the assembled atherectomy device is moved back and forth within the range of working positions. The outer surface of the proximal abutment member 56 has a shallow annular groove 57, and the circumferentially resilient keeper 51 is interlocked with the shallow groove 57 when the prime mover carriage is attached to the movable telescopic tube 76. The circumferentially resilient keeper 51 and the coil spring 52 function as a resilient positioning mechanism as follows.

Figure 57:
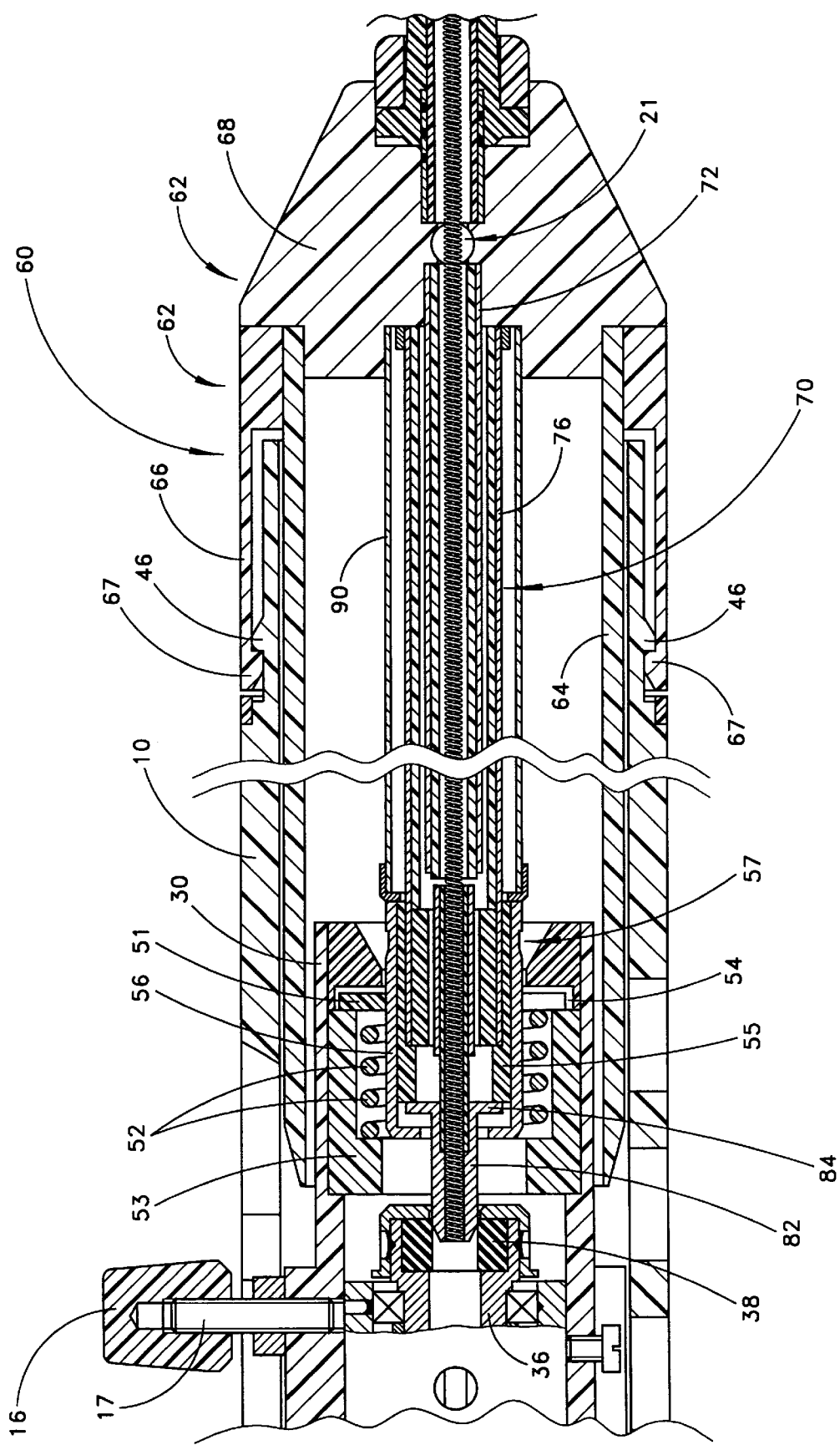
FIGS. 57–60 are longitudinal cross-sectional views illustrating the design and function of another embodiment of a tube attachment mechanism (each figure being in a slightly moved position)

In FIG. 57 the prime mover carriage 30, together with the circumferentially expanded keeper 51, is being moved distally to insert the shank 82 into the prime mover socket 38 and to attach the prime mover carriage 30 to the movable telescopic tube 76. The flange 84 of the shank 82 abuts against the distal abutment member 55. The circumferentially expanded keeper 51 is pressed against the proximal wall of the groove 54 in the prime mover carriage by frictional force which overpowers the spring 52. This frictional force is directed proximally and is a result of friction generated between the inner surface of the keeper 51 and the outer surface of the proximal abutment member 56 when the circumferentially expanded keeper 51 is advanced distally along the abutment member 56.

In FIG. 58 the prime mover carriage 30 has been advanced distally sufficiently that the keeper 51 has engaged the distal wall of the shallow annular groove 57 in the outer surface of the proximal abutment member 56. In this position the drive shaft shank 82 is adequately inserted into the prime mover socket 38. In FIG. 59 pressure urging the prime mover carriage 30 distally has been removed, and the coil spring 52 has pushed the prime mover carriage 30, along with the shank 82, proximally with respect to the movable telescopic tube 76 and the keeper 51. This movement of the prime mover carriage 30 and the drive shaft shank 82 thus spaces the shank's flange 84 away from the distal abutment member 55 which is secured to (and forms a part of) the moveable telescopic tube 76. In FIG. 60 the control knob 16 has been withdrawn proximally to the range of working positions, and the flange 84 of the drive shaft shank 82 has been spaced from both the distal abutment member 55 and the flange 58 of the proximal abutment member 56, thereby permitting the flange 84 of the drive shaft shank 82 to rotate freely with respect to the movable telescopic tube 76.

The distal wall of the shallow annular groove 57 forms approximately a 90° angle with the longitudinal axis of the moveable telescopic tube. The proximal wall of the annular groove 57 preferably forms an angle of less than 90° with the longitudinal axis of the telescopic tube to facilitate removal of the keeper 51 from the groove 57 when the moveable telescopic tube 76 is detached from the prime mover carriage 30.

FIGS. 61–62 depict one embodiment of a keeper 51 usable with this embodiment. The keeper is made to be circumferentially resilient by providing a discontinuity in its ring-like shape and by making some portions radially thin. Other suitable configurations may also be employed. FIG. 61 shows the keeper 51 in its relaxed shape, and FIG. 62 shows the keeper circumferentially expanded, as it would be, e.g., in FIG. 57.

FIGS. 63–69 show one more embodiment of a tube attachment mechanism. In this embodiment the prime mover carriage 30 includes a radially resilient elongated finger 95 urging a ball 96 radially inwardly. The elongated finger 95 may be formed simply by cutting a pair of longitudinal slots in the thin wall of the distal end portion of the prime mover carriage 30. A socket member 97, carried by the prime mover carriage 30, contains an integrally formed longitudinal spring portion 98. The socket member 97, in its distal portion, includes an orifice 102 (see FIG. 69) which captures the ball 96. A distal abutment member 99 is secured to (and forms a part of) the movable telescopic tube 76. The distal abutment member 99 includes an annular groove 100 having a shape complementary to the shape of the ball 96. The radially resilient elongated finger 95, the ball 96 and the spring portion 98 of the socket member 97 function as a resilient positioning mechanism as follows.

Figure 63:
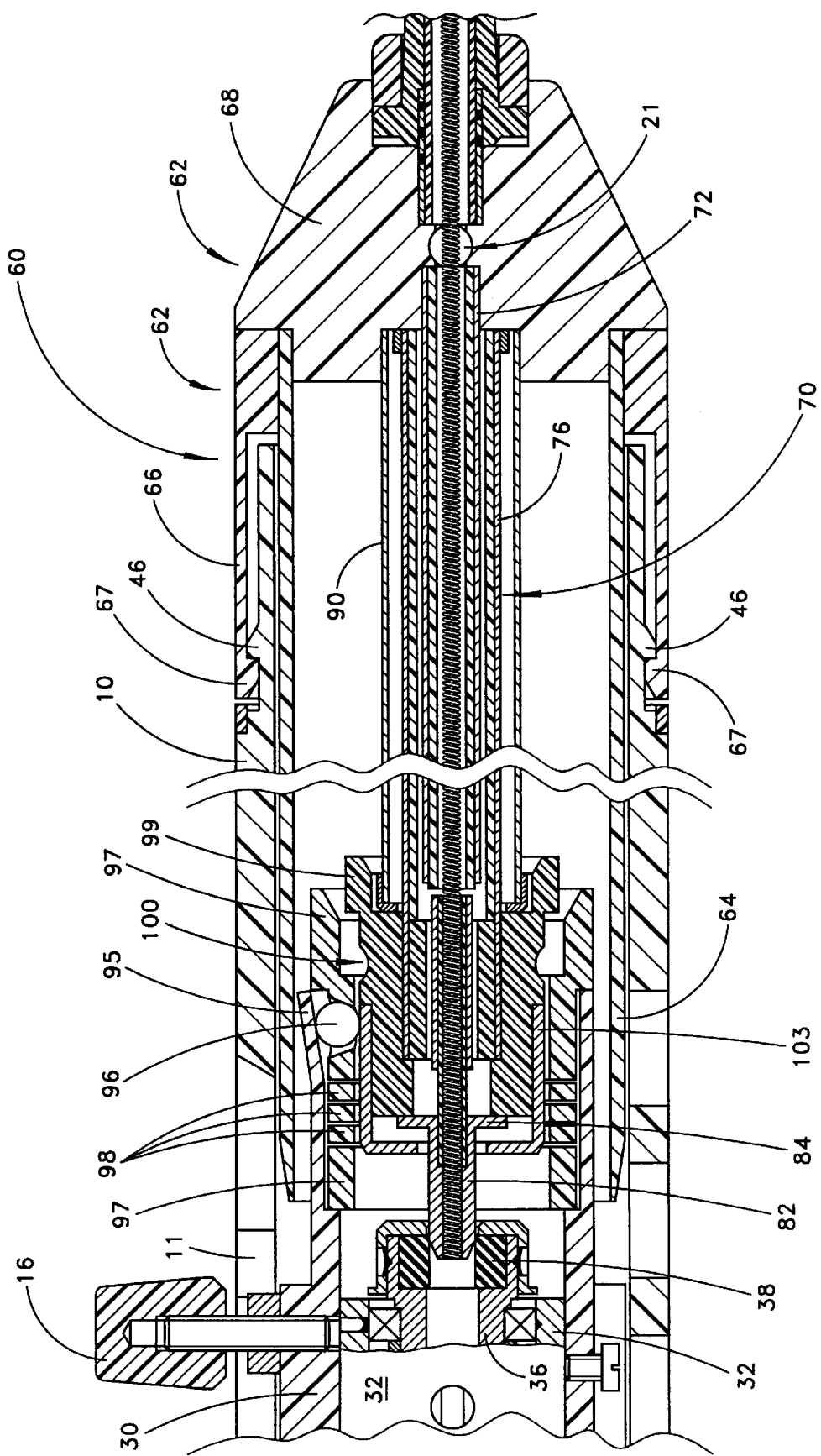
FIG. 63–66 illustrate the design and use of yet another tube attachment mechanism (each figure being in a slightly moved position)

In FIG. 63 the prime mover carriage 30 is being moved distally to insert the shank 82 into the prime mover socket 38 and to attach the prime mover carriage to the movable telescopic tube 76. As shown in FIG. 63, the flange 84 of the shank 82 abuts the distal abutment member 99, the spring portion 98 of the socket member 97 is compressed, and the ball 96 is riding on the outer surface of the proximal abutment member 103. The proximal abutment member 103 is carried by (and forms a part of) the moveable telescopic tube 76.

Figure 64:
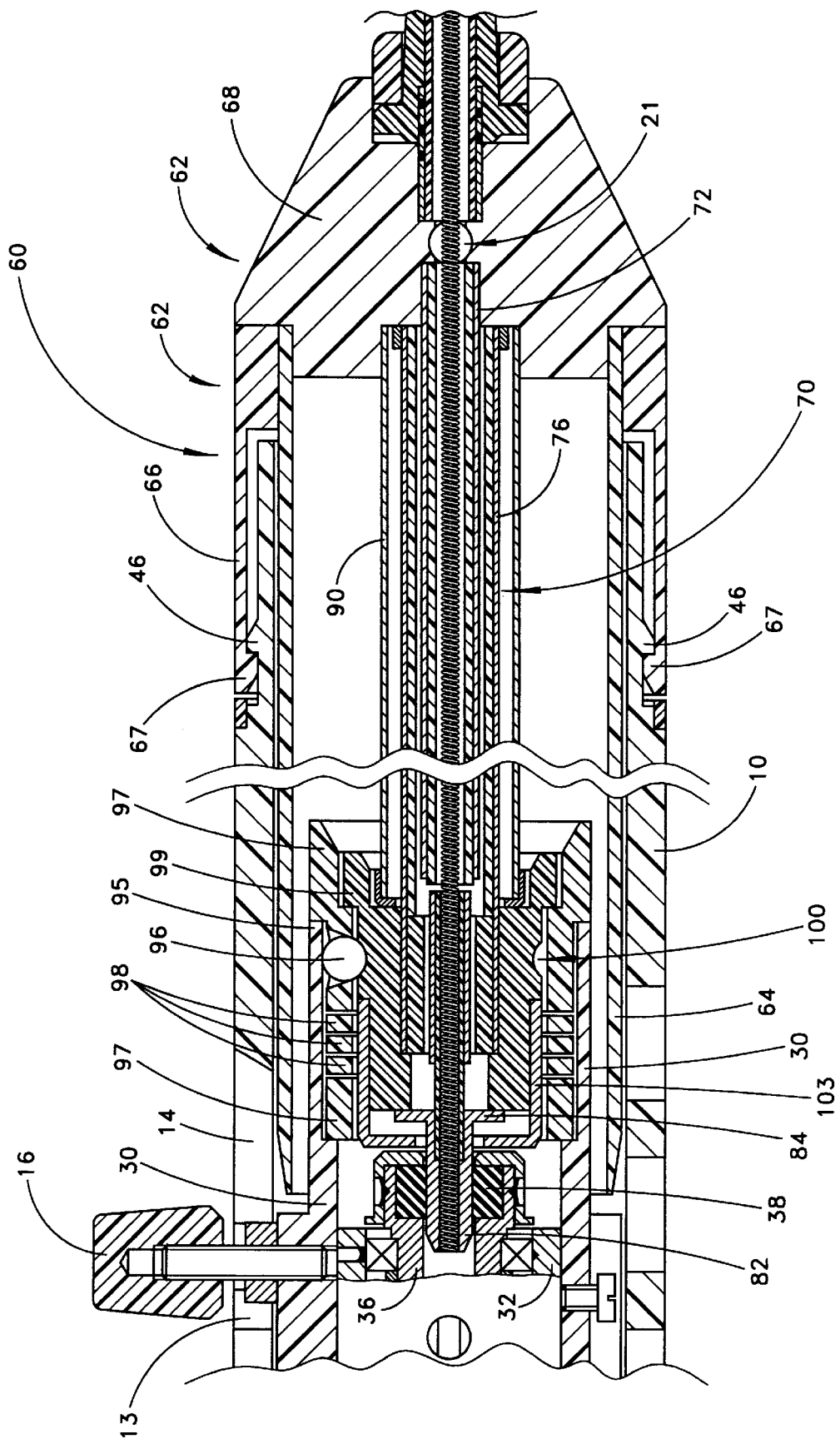
Figure 65:
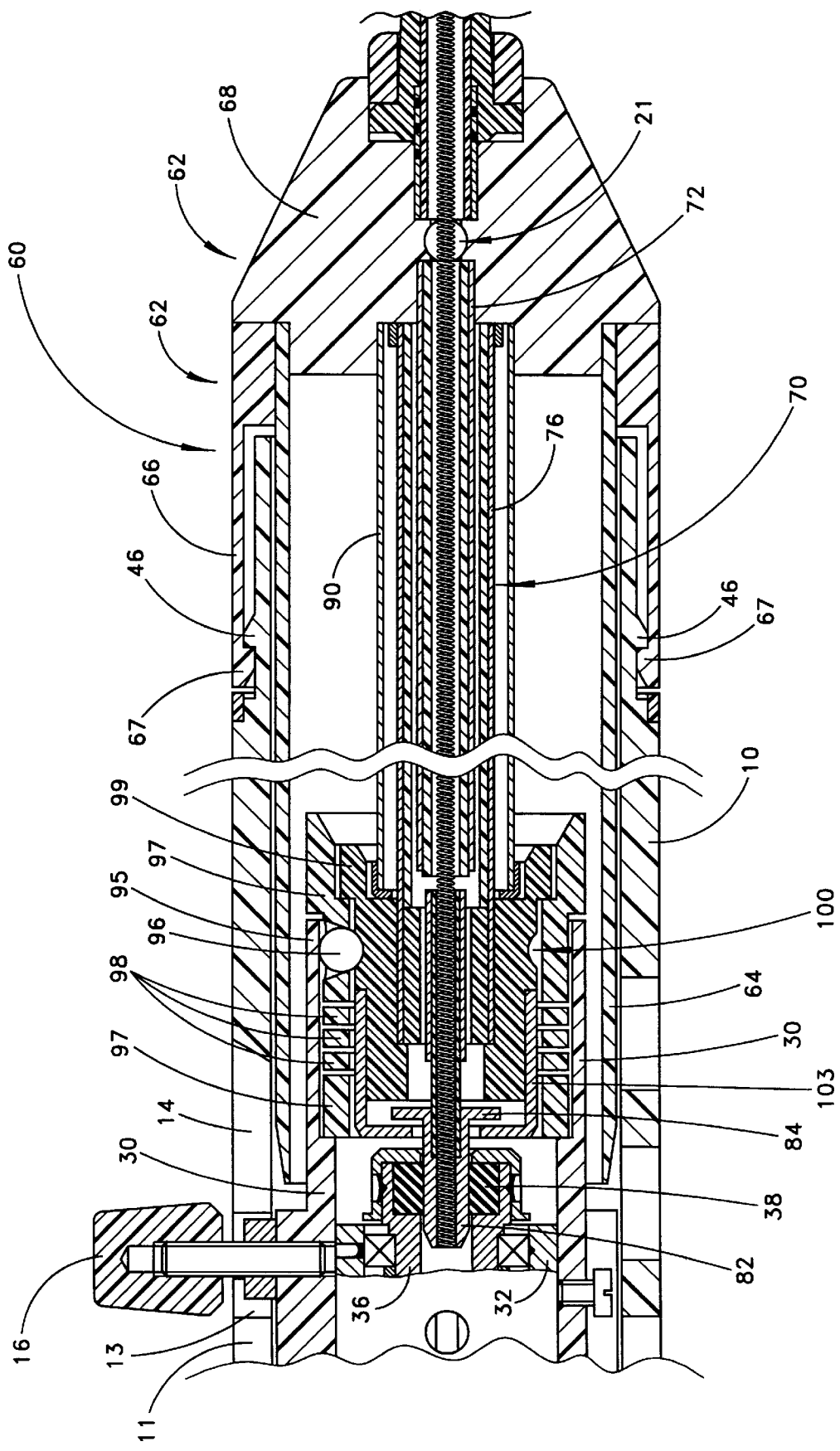
Figure 66:
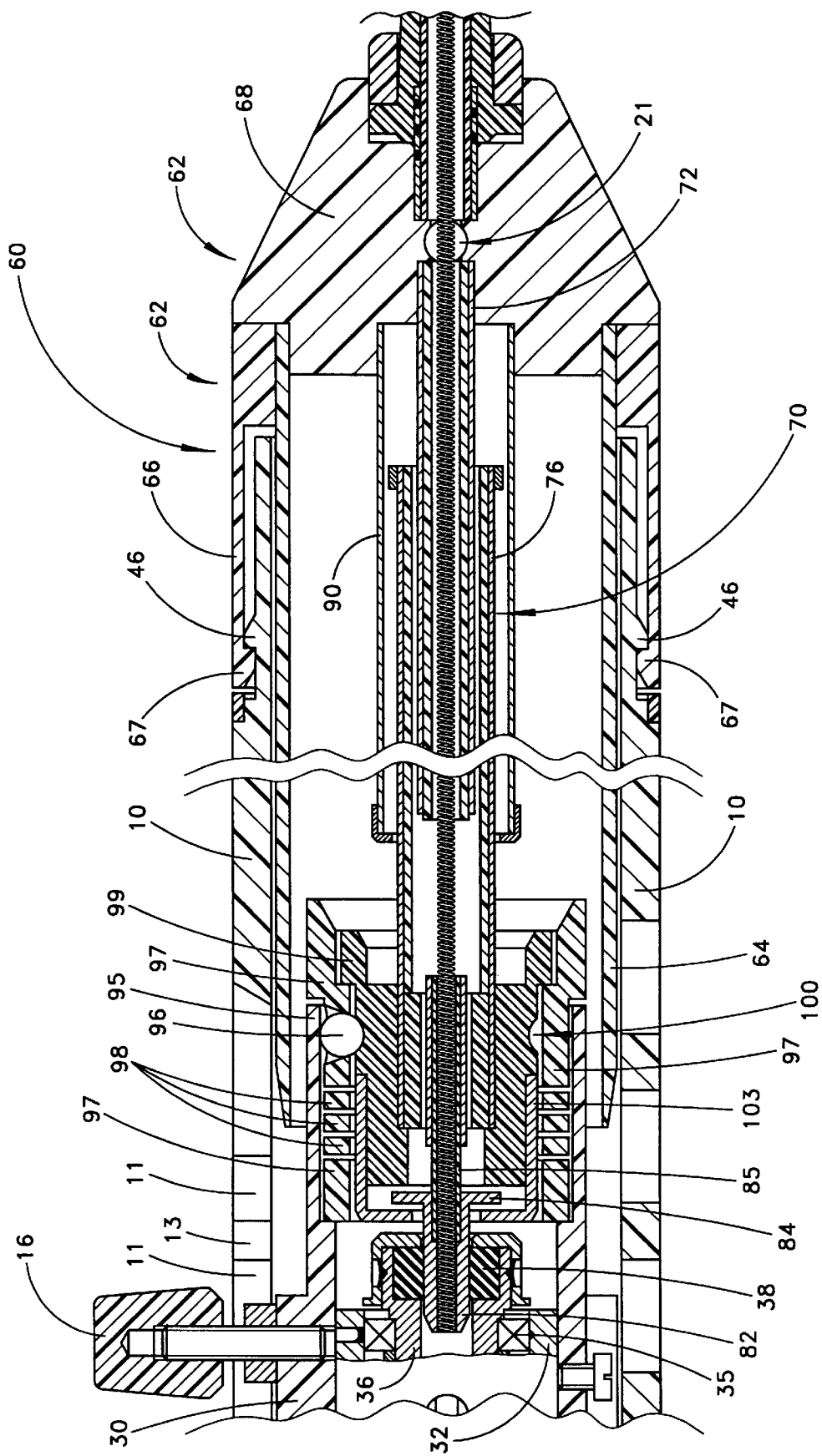

In FIG. 64 the prime mover carriage 30 has been advanced distally sufficiently so that the elongated finger 95 has urged the ball 96 into the annular groove 100 in the distal abutment member 99. In this position the drive shaft shank 82 is adequately inserted into the prime mover socket 38. In FIG. 65 pressure urging the prime mover carriage 30 distally has been removed, and the spring portion 98 of the socket member 97 has regained its original shape and has pushed the prime mover carriage 30, along with the shank 82, proximally with respect to the groove 100 of the distal abutment member 99. This proximal movement of the prime mover carriage 30 and the drive shaft shank 82 has spaced the shank's flange 84 away from the distal abutment member 99 (i.e. from the distal abutment surface associated with the moveable telescopic tube 76). In FIG. 66 the control knob 16 has been withdrawn proximally to the range of working positions and the flange 84 of the drive shaft shank 82 has been spaced from both the distal abutment member 99 and the proximal abutment member 103, thereby permitting the flange 84 of the drive shaft shank 82 to rotate freely with respect to the movable telescopic tube 76.

Figure 67:
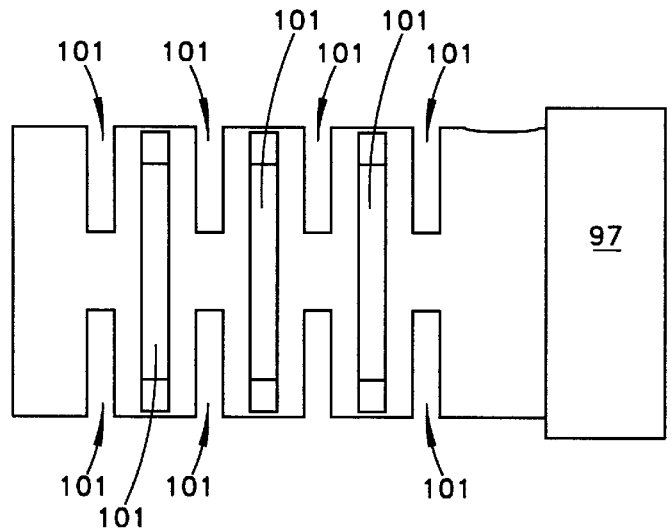
FIGS. 67–69 illustrate the design and function of one of the key components of the tube attachment mechanism shown in FIGS. 63–66 (FIG. 68 showing the component in a moved position, and FIG. 69 being a top view of FIG. 67)
Figure 68:
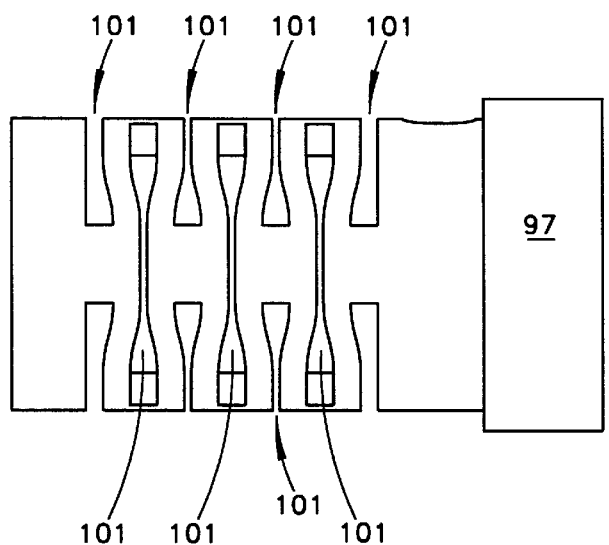
Figure 69:
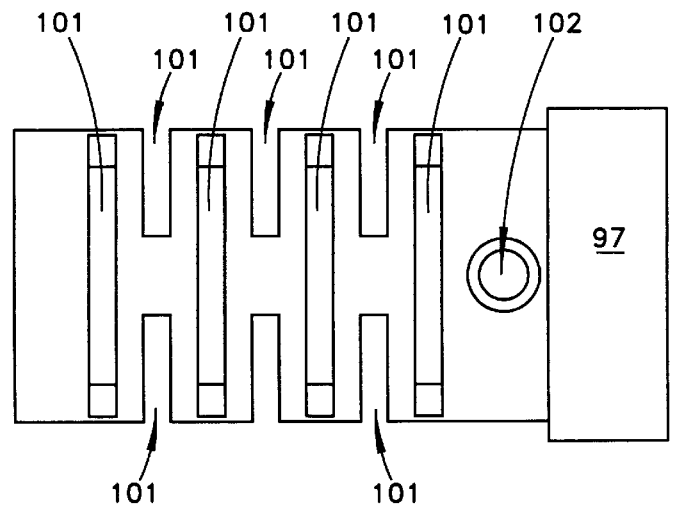

FIGS. 67–69 depict one embodiment of a socket member 97 usable with this embodiment. The socket member 97 is made to be longitudinally resilient by providing a series of transverse slots 101 in the body of the socket member 97. These slots are alternately oriented at 90° to one another, thus permitting the socket member 97 to be longitudinally compressed, as is shown in FIG. 68. Other suitable configurations may also be employed.

Figure 70:
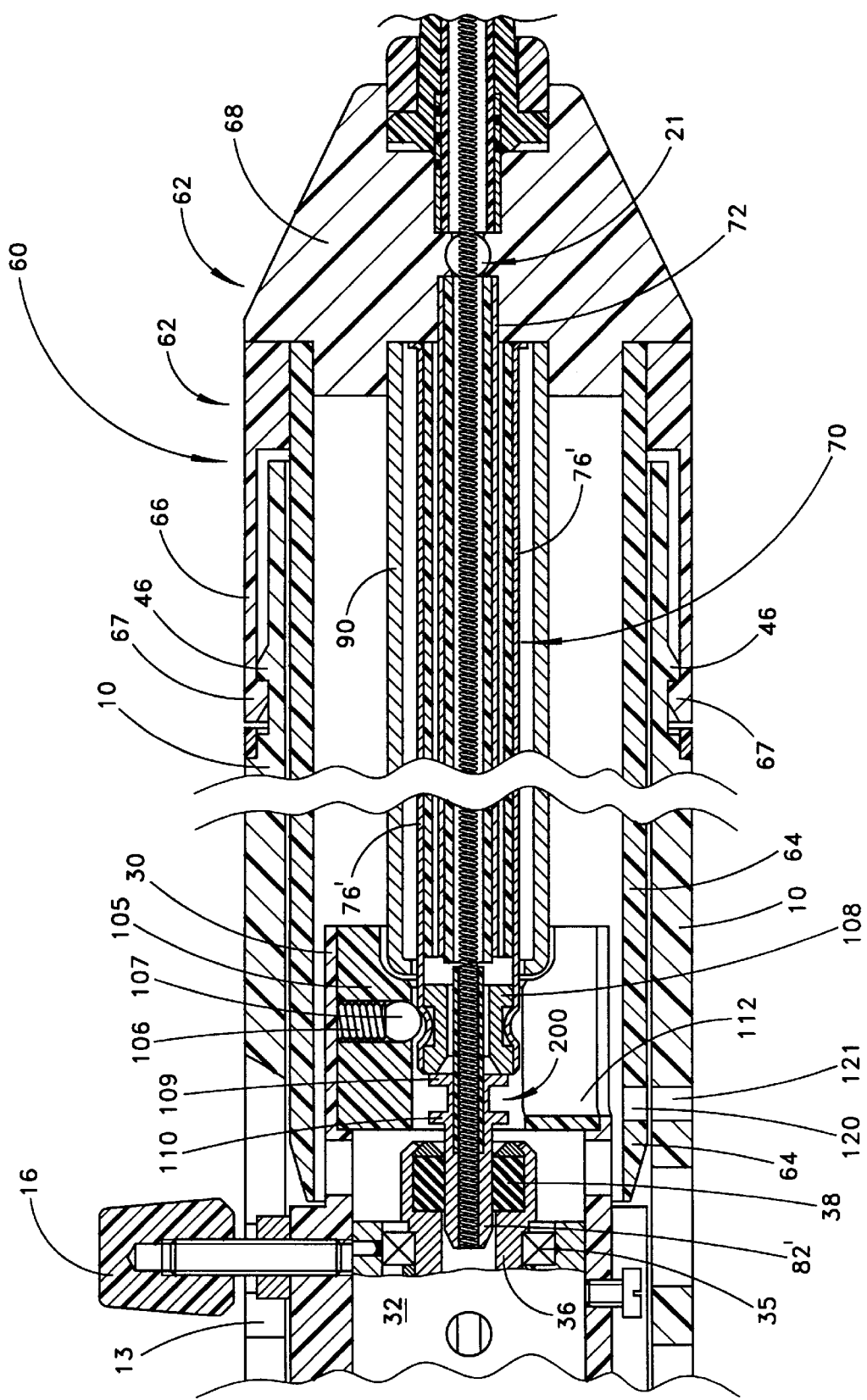
FIGS. 70–73 illustrate the design and function of another tube attachment mechanism as well as an alternative design for detachment of the shank from the prime mover socket and the longitudinally extendable tube from the prime mover carriage (FIGS. 70–73 being longitudinal cross-sectional views, and FIG. 73 being a transverse cross-sectional view taken along lines 73—73 of FIG. 72)
Figure 71:
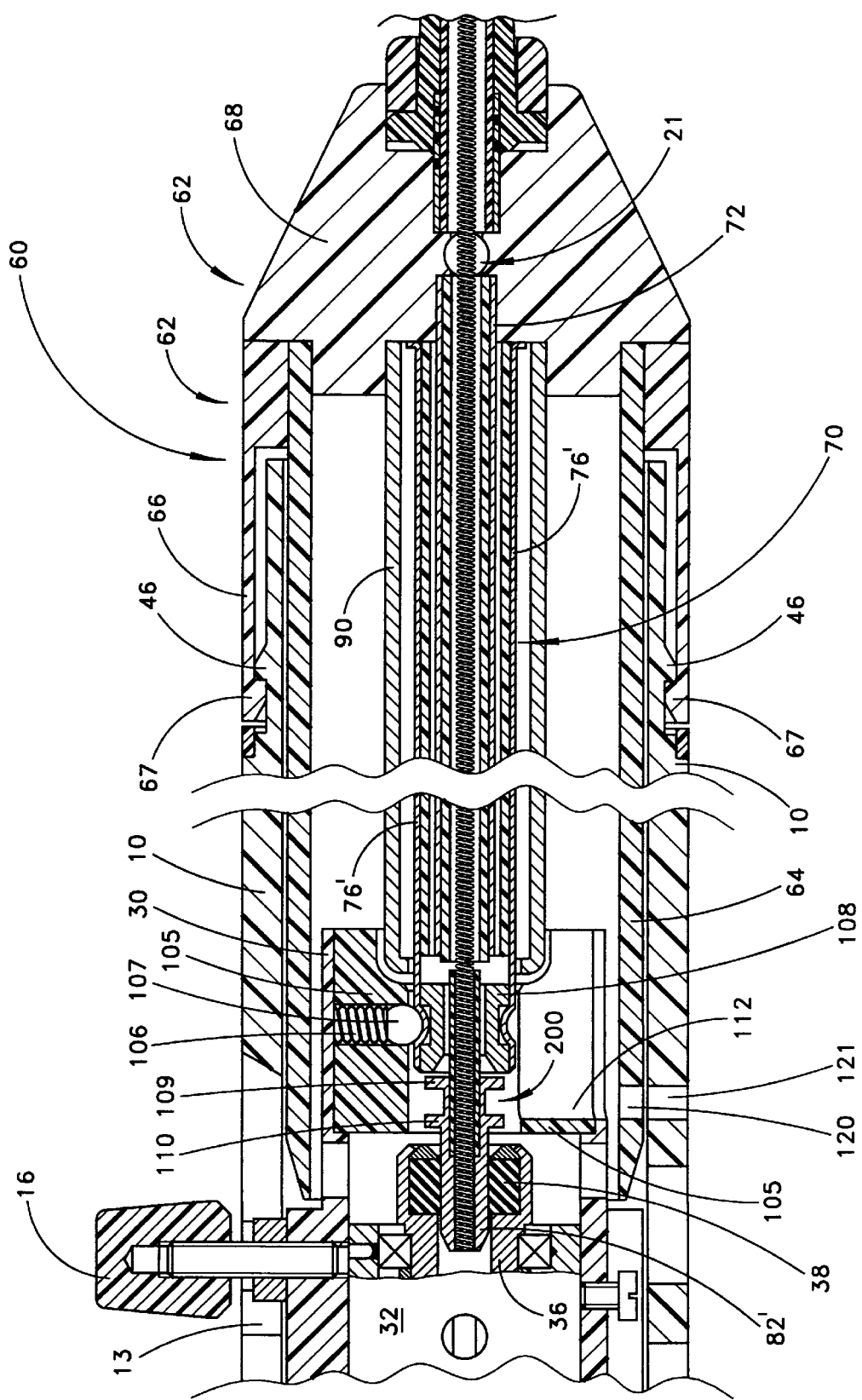

FIGS. 70–71 show another embodiment of a tube attachment mechanism. In this embodiment the prime mover carriage 30 includes a socket member 105 carrying a coil spring 106 pushing a ball 107 radially inwardly. A bushing 108 is secured within the proximal end portion of the movable tube 76' by crimping the tube 76' around a complementary annular groove in the outer surface of the bushing 108. The complementary annular groove in the outer surface of the bushing is sized so that the crimp in the movable telescopic tube 76' may be shaped in the form of an annular groove complementary to the shape of the ball 107. The coil spring 106 and the ball 107 function as a resilient positioning mechanism as follows.

In FIG. 70 the prime mover carriage 30 has been moved distally to insert a modified drive shaft shank 82' into the prime mover socket 38. The drive shaft shank 82' is modified in that it includes not one but two flanges—a distal flange 109 and a proximal flange 110, the flanges defining an annular groove 200 between them. The distal flange 109 of the modified shank 82' abuts the proximal end surface of the bushing 108. In FIG. 70 the prime mover carriage 30 has been advanced distally sufficiently that ball 96 is riding up on the distal slope of the annular groove formed in the movable telescopic tube 76'. In this position the drive shaft shank 82 is adequately inserted into the prime mover socket 38. In FIG. 71 pressure urging the prime mover carriage 30 distally has been removed, and the coil spring 106 has pushed the ball 107 radially inwardly into the groove in the movable telescopic tube 76', thereby moving the socket member 105 together with prime mover carriage 30 and the modified shank 82' proximally with respect to the movable telescopic tube 76'. This proximal movement of the prime mover carriage 30 and the modified drive shaft shank 82' spaces the shank's distal flange 109 away from the bushing 108, thereby permitting the drive shaft shank 82' to rotate freely with respect to the movable telescopic tube 76'.

FIGS. 70–71 also show that the socket member 105 includes a longitudinal slot 112 which has been aligned with a hole 120 in the inner tube 64 of the cartridge housing 62 and a hole 121 in the handle housing 10.

Figure 72:
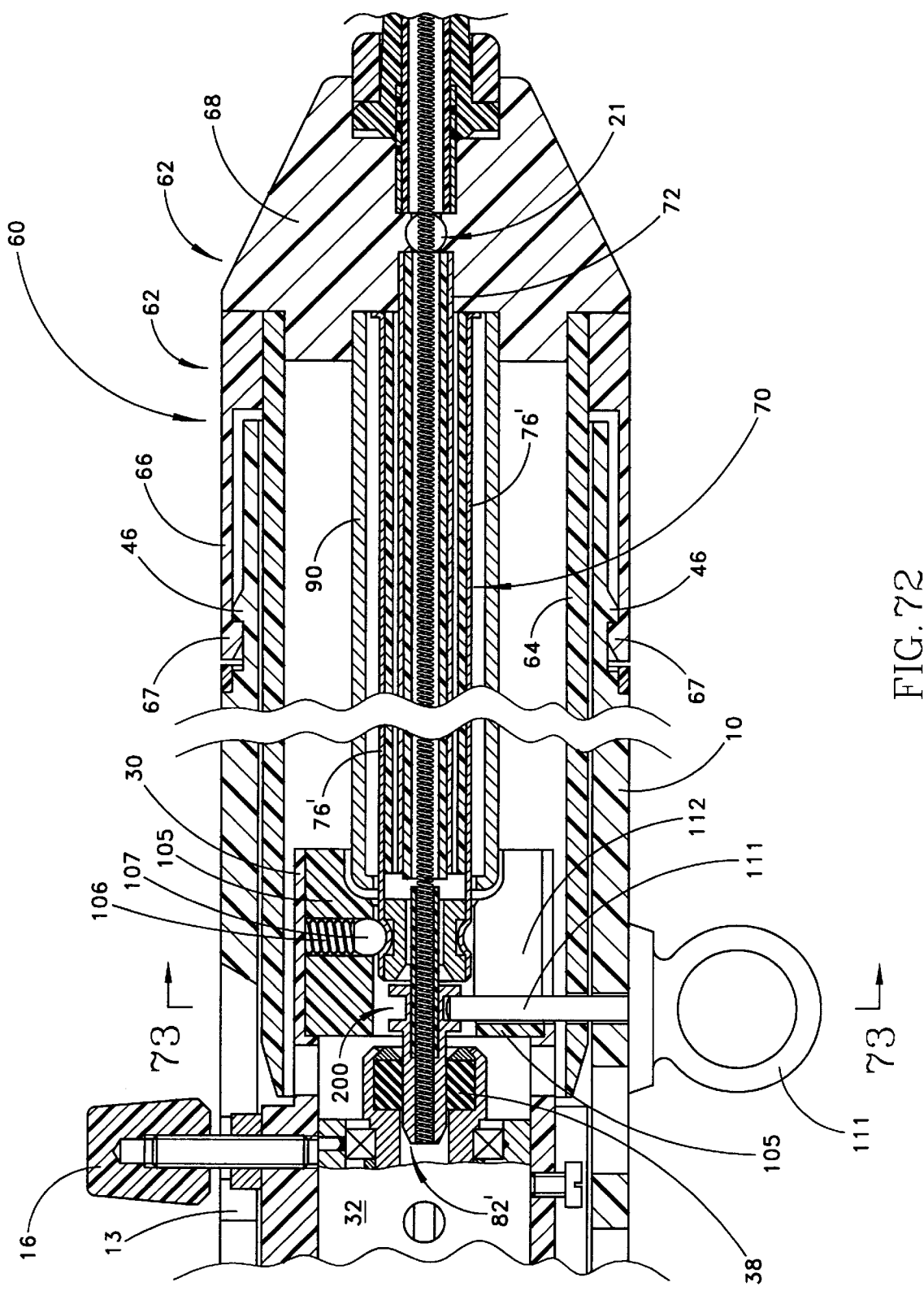
Figure 73:
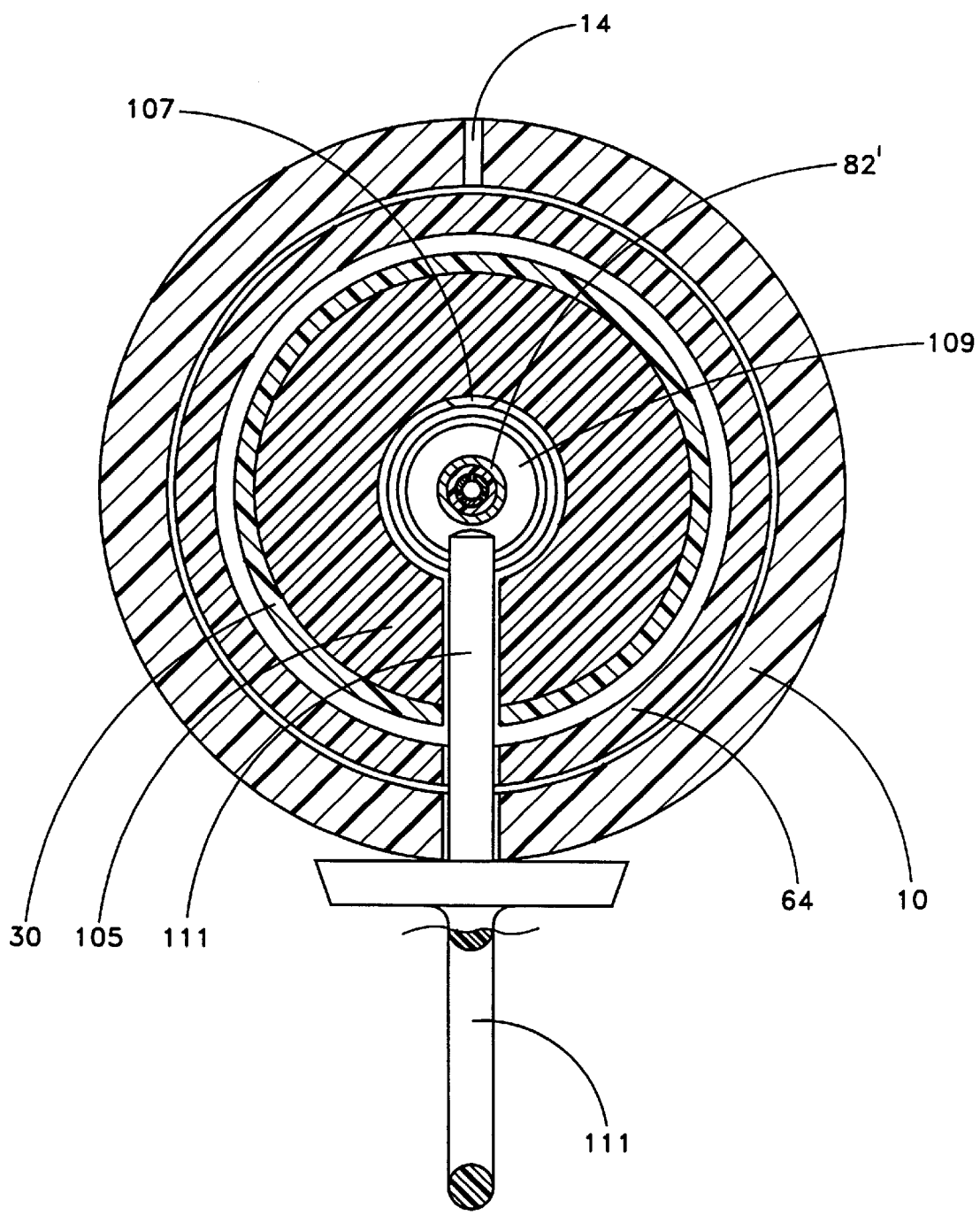

In FIGS. 72–73 a disengagement key 111 has been inserted through the holes 121 and 120 in the housings and the longitudinal slot 112 in the socket member 105. The end of the disengagement key 111 is received within the annular groove 200 formed between the distal and proximal flanges 109 and 100 of the modified shank 82', thus securing the shank 82' against longitudinal movement with respect to the cartridge housing 62. The control knob 16 may then be withdrawn proximally to disengage the prime mover socket 38 from the shank 82' and to disengage the socket member 105 (along with the ball 107) from the movable telescopic tube 76', the disengagement key 111 preventing proximal movement of the modified drive shaft shank 82' and the movable telescopic tube 76'.

FIGS. 74–95 illustrate the structures and functions of additional embodiments of two stage interlock mechanisms usable with the atherectomy device of the invention. The proximal complementary interlocking member used in embodiments illustrated in FIGS. 74–95 (i.e., the tabs 46) does not differ from the proximal complementary interlocking member shown in FIG. 9. The annular shoulder 67 of the cartridge housing 62 is interlockable with such proximal complementary interlocking member in the same way as in the device described above (see, e.g., FIGS. 5–7).

Figure 9:
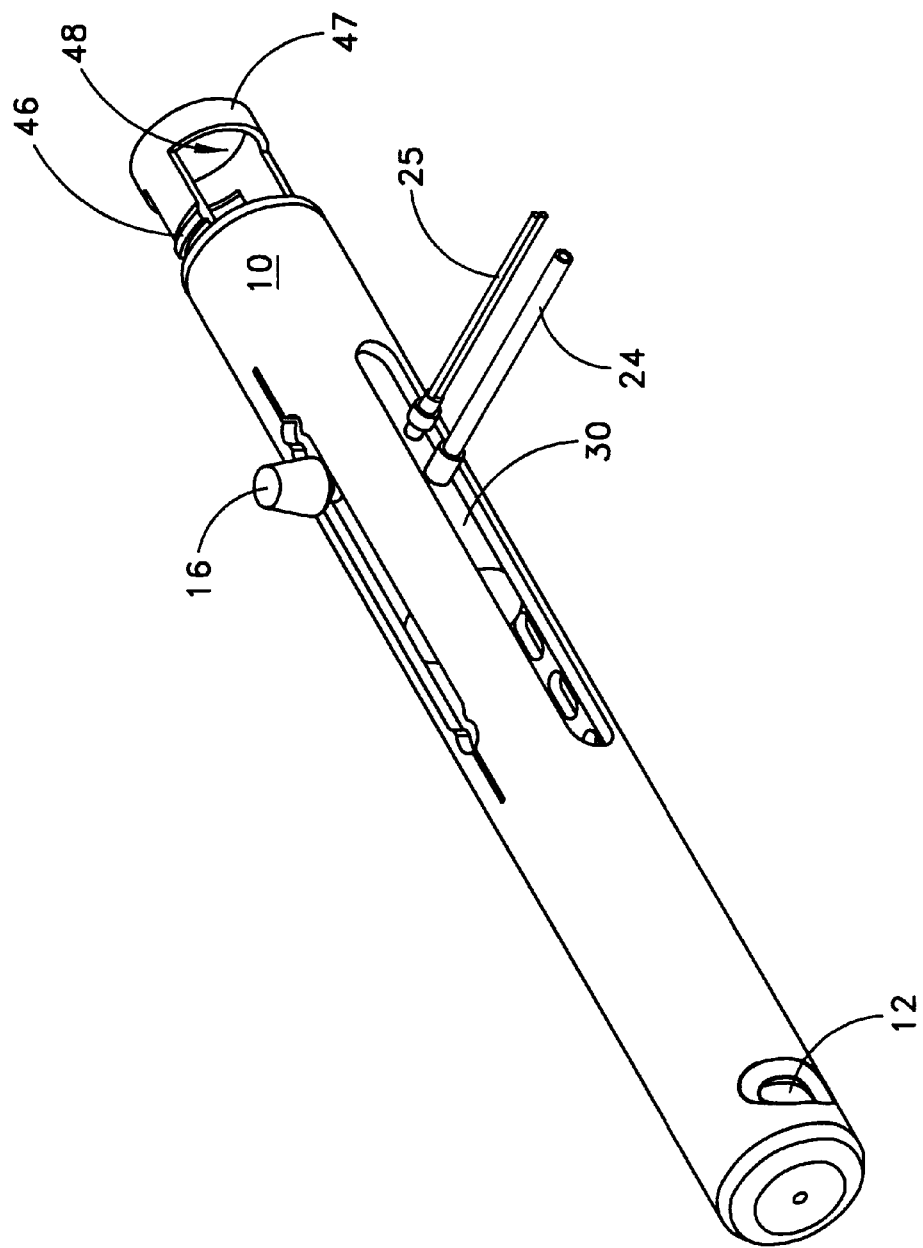
FIGS. 9–11 illustrate details of the handle housing and some of its internal elements, the exchangeable drive shaft cartridge having been entirely removed.
Figure 10:
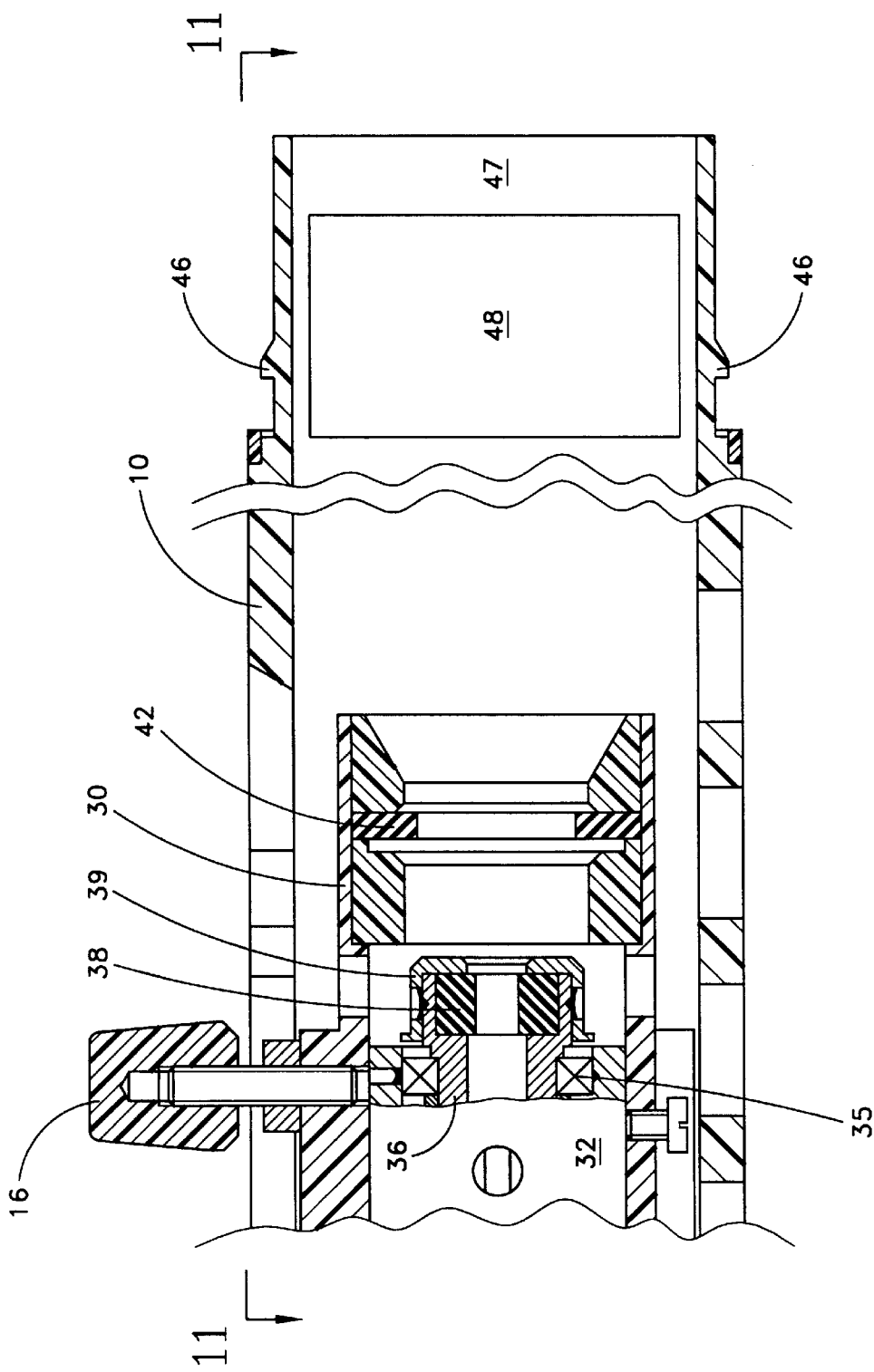
Figure 11:
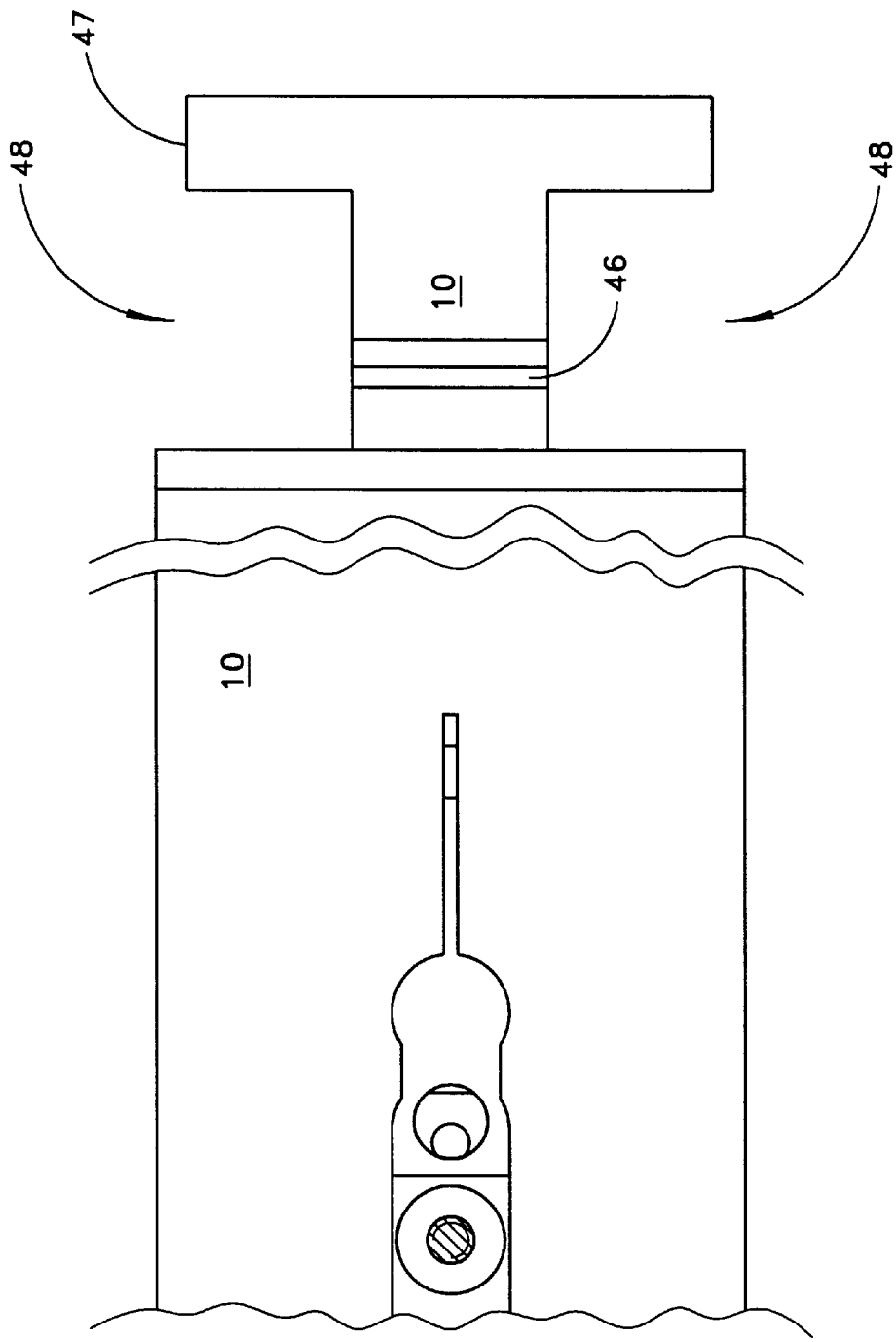
Figure 74:
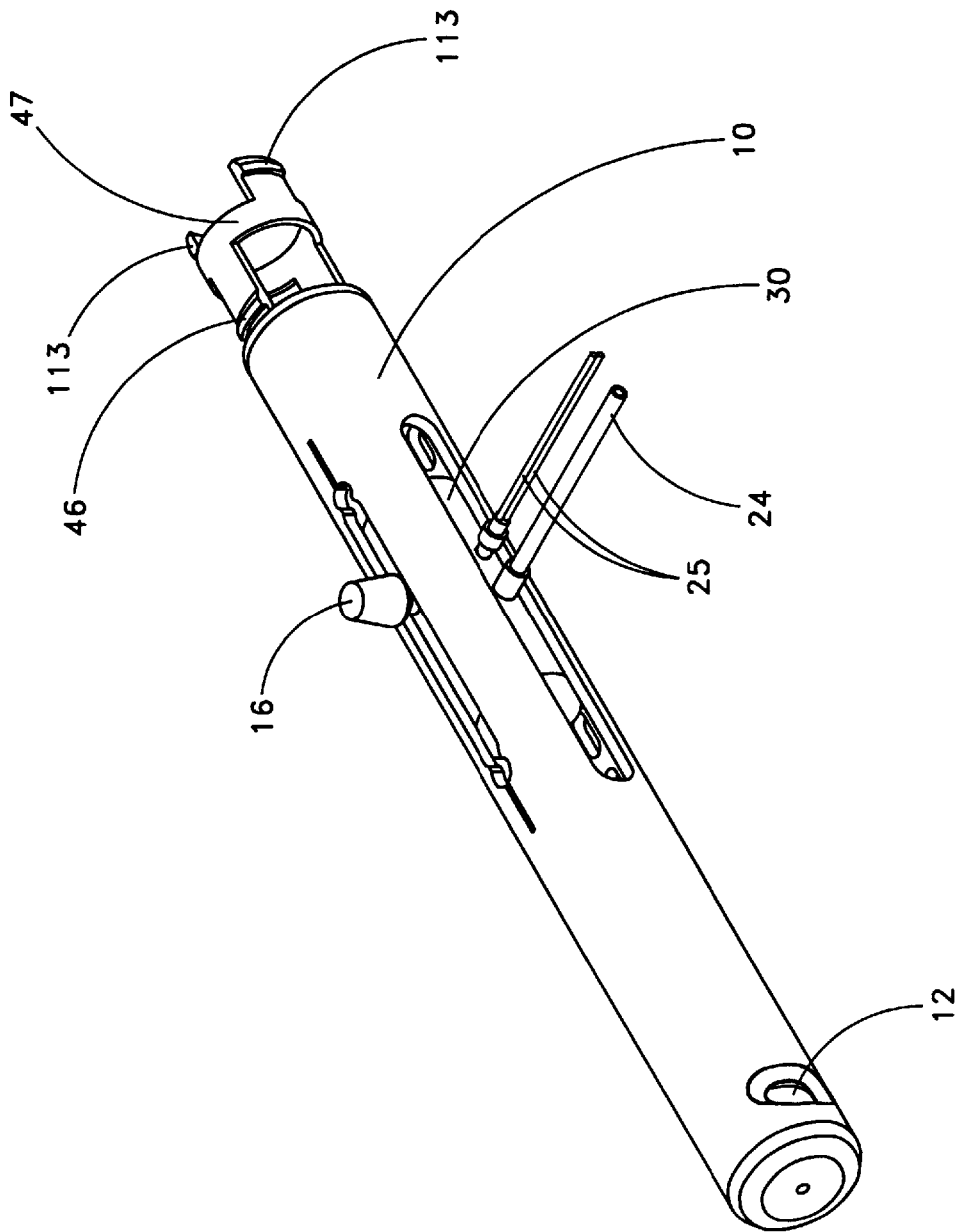
FIG. 74 is a perspective view of the handle housing showing a modified embodiment of the complementary interlocking members used in the two stage interlock mechanism for detaching the cartridge housing from the handle housing.

The two stage interlock mechanism shown in FIG. 74 is conceptually similar to the two stage interlock mechanism depicted in FIG. 9, but it prevents the user from inadvertently moving the primary interlocking member over the distal complementary interlocking member if, after moving compressed annular shoulder 67 distally over the tabs 46, the user stops compressing the annular shoulder 67 to an oval shape before the annular shoulder 67 reaches the proximal edge of the ring 47. The two stage interlock mechanism of FIG. 74 includes longitudinally spaced proximal and distal stages, and is designed to function with an exchangeable drive shaft cartridge 60 of the type shown in FIGS. 1–39—i.e., one having a cartridge housing 62 with a primary interlocking member carried by the outer tube 66 of the cartridge housing 62. Typically the primary interlocking member comprises an annular radially inwardly extending shoulder 67 carried by the outer tube 66 of the cartridge housing 62.

The embodiment shown in FIG. 74 differs from the embodiment shown in FIG. 9 in that an additional pair of distal radially outwardly extending tabs 113 is provided to function as the distal complementary interlocking member. During distal movement of the cartridge housing 62 these distal radially outwardly extending tabs 113 will stop distal movement of the annular shoulder 67 even if the user allows the annular shoulder 67 to return to its original shape before the annular shoulder 67 reaches the proximal edge of the ring 47. As will be described in greater detail below in connection with the embodiment depicted in FIGS. 75–94, the distal tabs 113 will stop the circularly shaped annular shoulder 67 from further distal movement, thereby requiring the user to again compress the annular shoulder 67 to an oval shape in order to move it distally over the tabs 113, thus disengaging the second stage of the two stage interlock mechanism. Preferably the tabs 46 of the proximal complementary interlocking member and the tabs 113 of the distal complementary interlocking member not only are spaced longitudinally from each other but are also circumferentially positioned at about a 90 degree angle with respect to each other so that, in the process of detaching the cartridge housing 60 from the handle housing 10, the annular shoulder 67 of the cartridge housing 62 must be compressed to an oval shape at least two times—the first time to be moved distally over the tabs 46 of the proximal complementary interlocking member, and the second time to be moved distally over the tabs 113 of the distal complementary interlocking member.

The embodiment of FIG. 74 assures that the primary interlocking member (i.e., the annular shoulder 67) will be stopped from inadvertent distal movement over the distal complementary interlocking member (i.e., the distal tabs 113). Nevertheless, the distal complementary interlocking member shown in FIG. 74 still requires the user to actively use both hands in order to withdraw the drive shaft shank 82 from the prime mover socket 38 and to detach the longitudinally extendable tube 70 from the prime mover carriage 30. As shown in FIG. 14, the user must use one hand to secure the relative positions of the cartridge housing 62 and the handle housing 10 while using the other hand to move the control knob 16 proximally to withdraw the shank 82 from the prime mover socket 38 and to detach the longitudinally extendable tube 70 from the prime mover carriage 30. FIGS. 75–94 depict another embodiment of the two stage interlock mechanism wherein the distal complementary interlocking member of the two stage interlock mechanism will capture the annular shoulder 67 and thereby eliminate the need to manually secure the relative positions of the cartridge housing 62 and the handle housing 10 during the process of pulling the shank 82 out of the prime socket 38 and detaching the longitudinally extendable tube 70 from the prime mover carriage 30.

Figure 75:
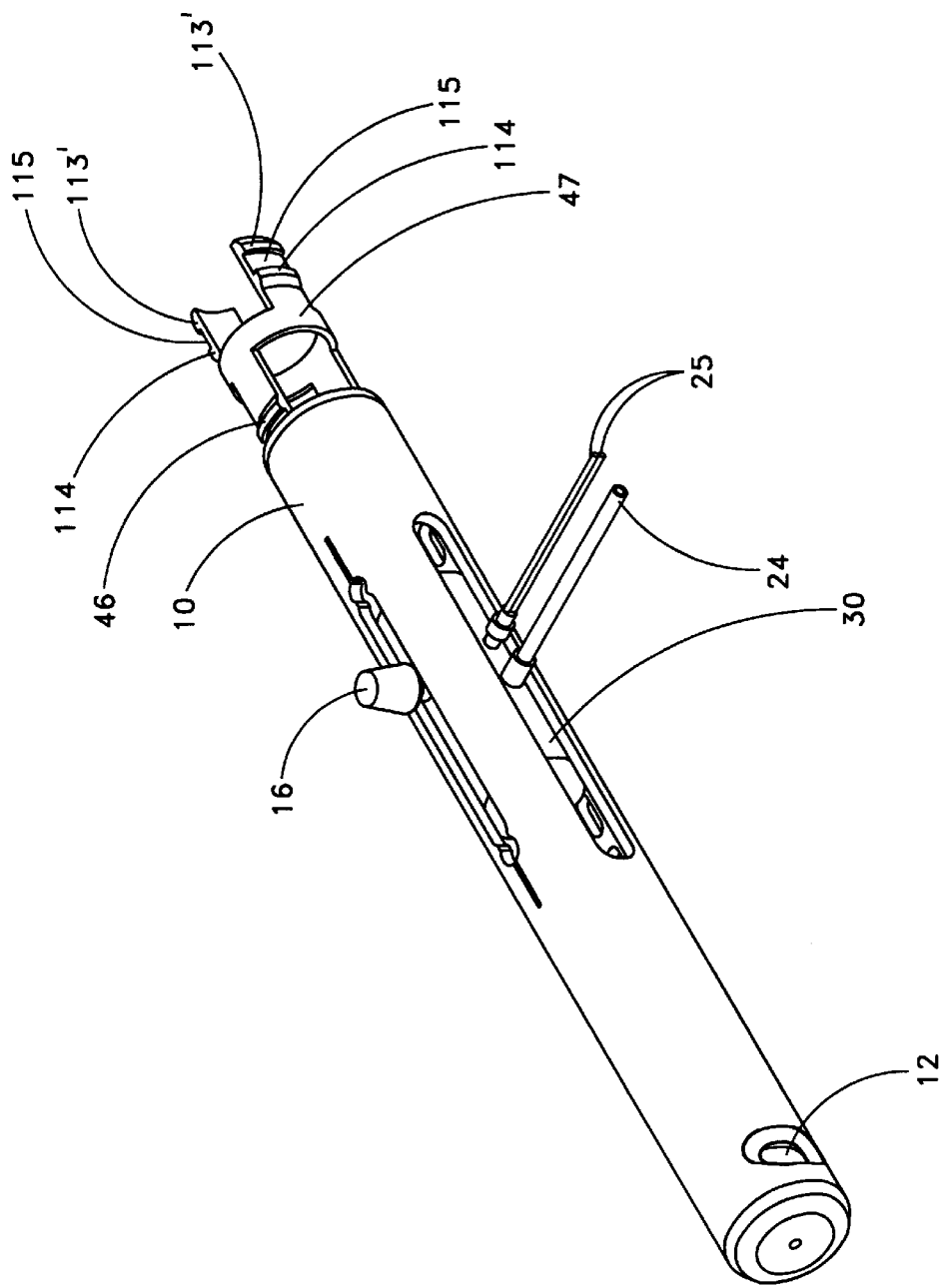
FIG. 75 is a perspective view of the handle housing showing another modified embodiment of the complementary interlocking members used in the two stage interlock mechanism for detaching the cartridge housing from the handle housing.
Figure 76:
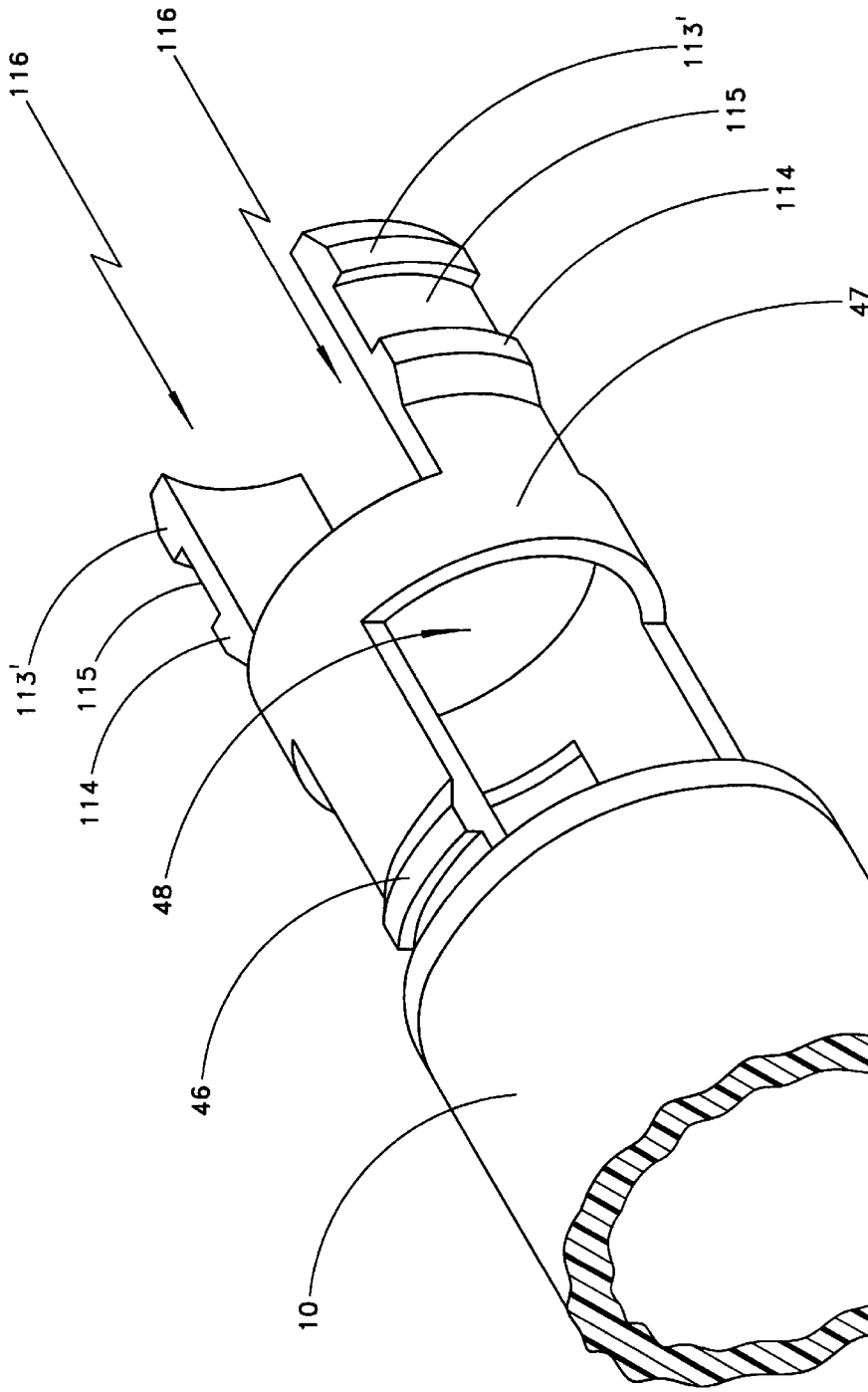
FIG. 76 is an enlarged view of the distal portion of the handle housing shown in FIG. 75.

As is shown in FIGS. 75–76, the distal complementary interlocking member of this embodiment is comprised of a distal pair of radially outwardly extending tabs 113' and an additional proximal pair of radially outwardly extending tabs 114. The tabs 113' and 114 are carried by the handle housing 10 and are longitudinally spaced away from each other to define a groove 115 having a longitudinal width which is sufficient to receive the annular shoulder 67 of the cartridge housing 62 so that when, in the process of detaching the cartridge housing 62 from the handle housing 10, the annular shoulder 67 of the cartridge housing 62 is received in the groove 115, it becomes captured between the distal and proximal tabs 113' and 114 defining the groove 115. As is shown in FIGS. 75–76, preferably the distal complementary interlocking member is comprised of two pairs of radially outwardly extending tabs 113' and 114 carried by the handle housing 10, each pair of tabs 113' and 114 defining a groove 115 having a longitudinal width which is sufficient to receive the annular shoulder 67 of the cartridge housing 62. Preferably the two grooves 115 defined by the tabs 113' and 114 are longitudinally aligned with each other and circumferentially opposed to each other so that when, in the process of detaching the cartridge housing 62 from the handle housing 10, the annular shoulder 67 of the cartridge housing 62 is received in the grooves 115, it becomes captured between the distal and proximal tabs 113' and 114 which define the grooves 115. To permit the annular shoulder 67 of the cartridge housing 62 to be compressed to an oval shape, the portion of the handle housing wall between the pairs of tabs 113' and 114 includes distally open recesses 116.

Figure 77:
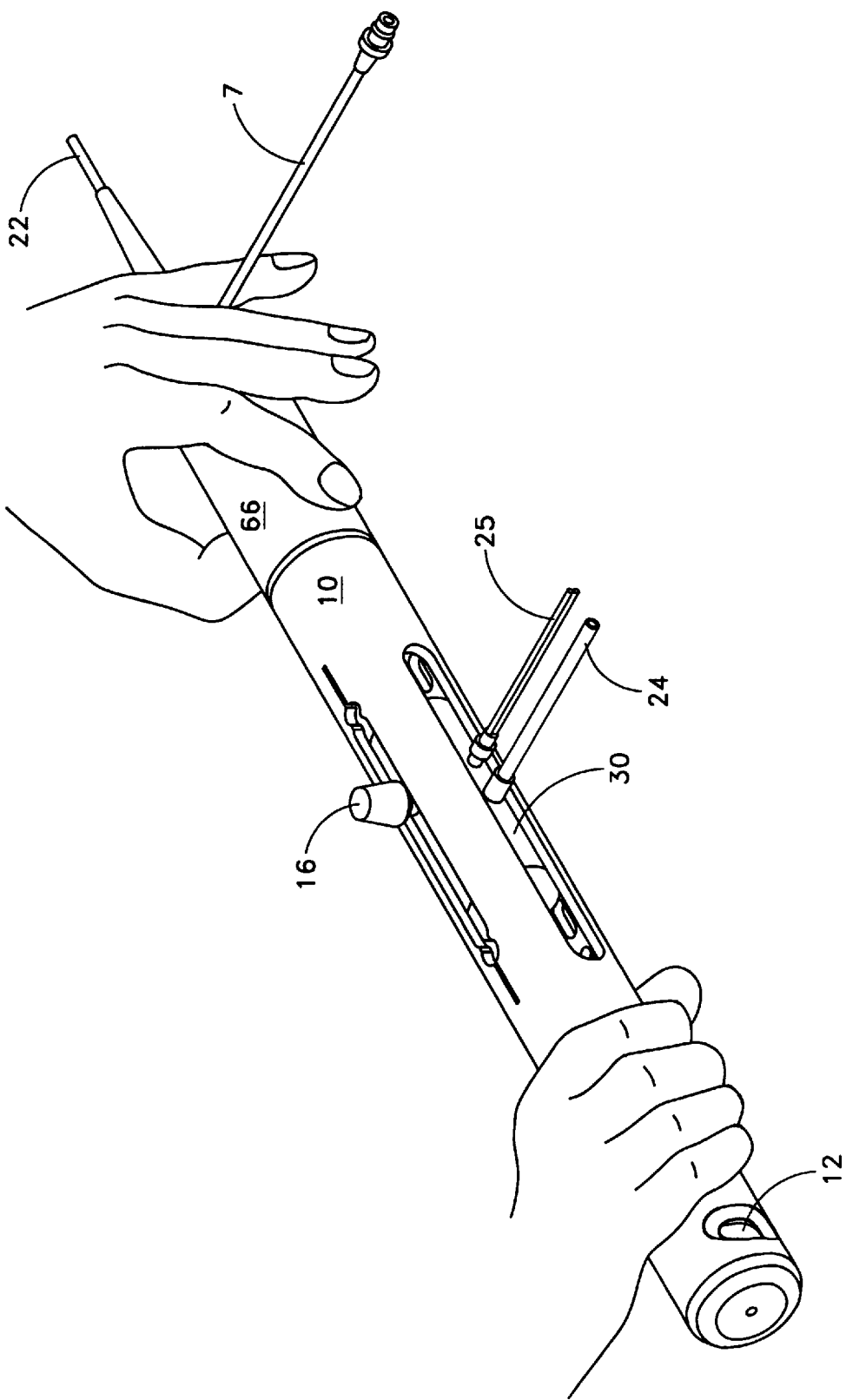
FIG. 77 is a perspective view illustrating the first step in the process of detaching the cartridge housing from a handle housing which has the complementary interlocking members shown in FIGS. 75–76.

FIGS. 77–85 illustrate the process of detaching an exchangeable drive shaft cartridge 60 from the handle housing 10 which has the distal complementary interlocking member shown in FIGS. 75–76. In FIG. 77 the user is compressing the outer tube 66 of the cartridge housing 62 between two points located circumferentially between the tabs 46. As a result, the annular shoulder 67 becomes deformed to an oval shape and becomes disengaged from the tabs 46.

Figure 78:
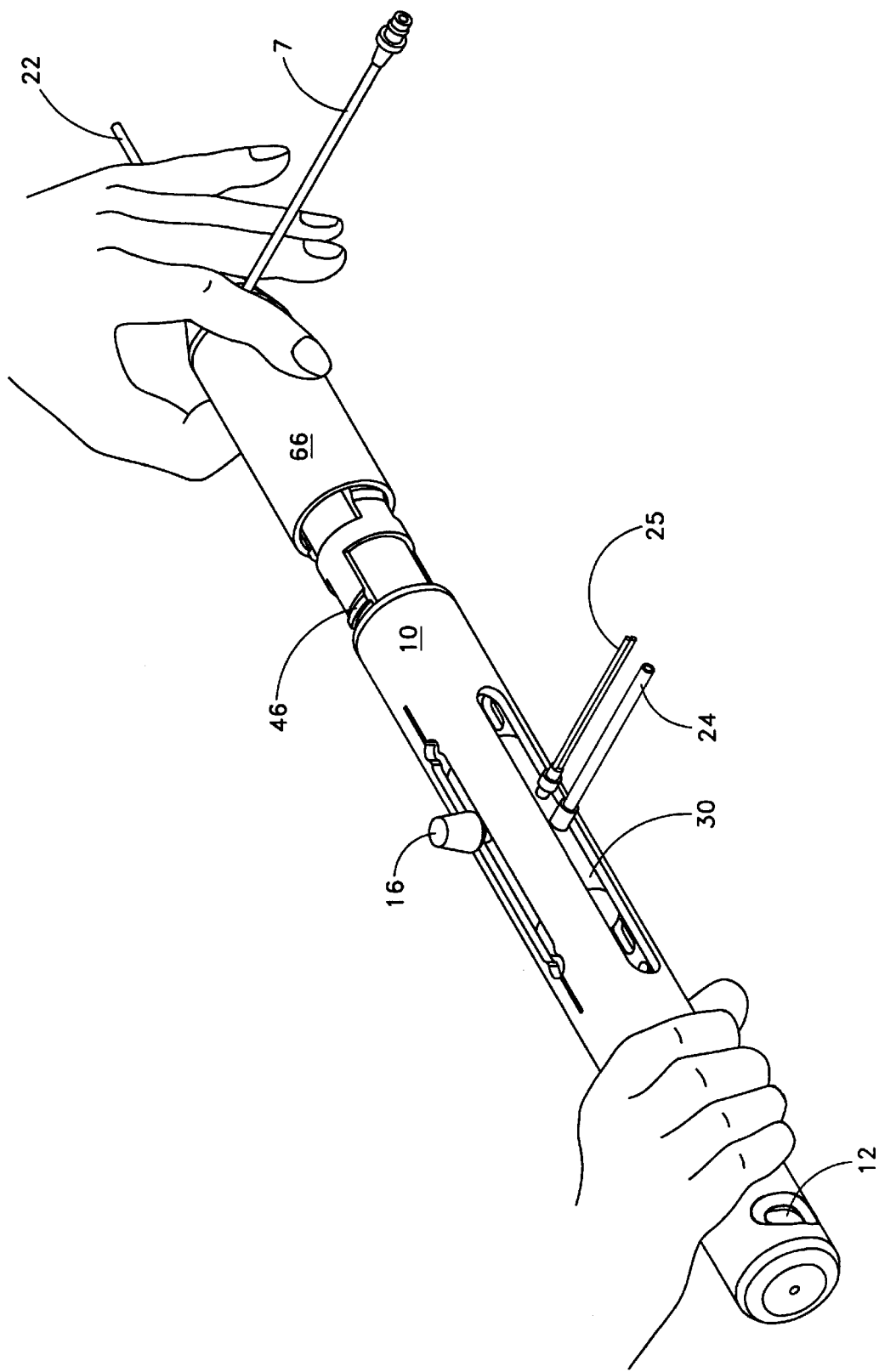
FIG. 78 is a perspective view illustrating the second step in the process of detaching the cartridge housing from the handle housing which has the complementary interlocking members shown in FIGS. 75–76.
Figure 79:
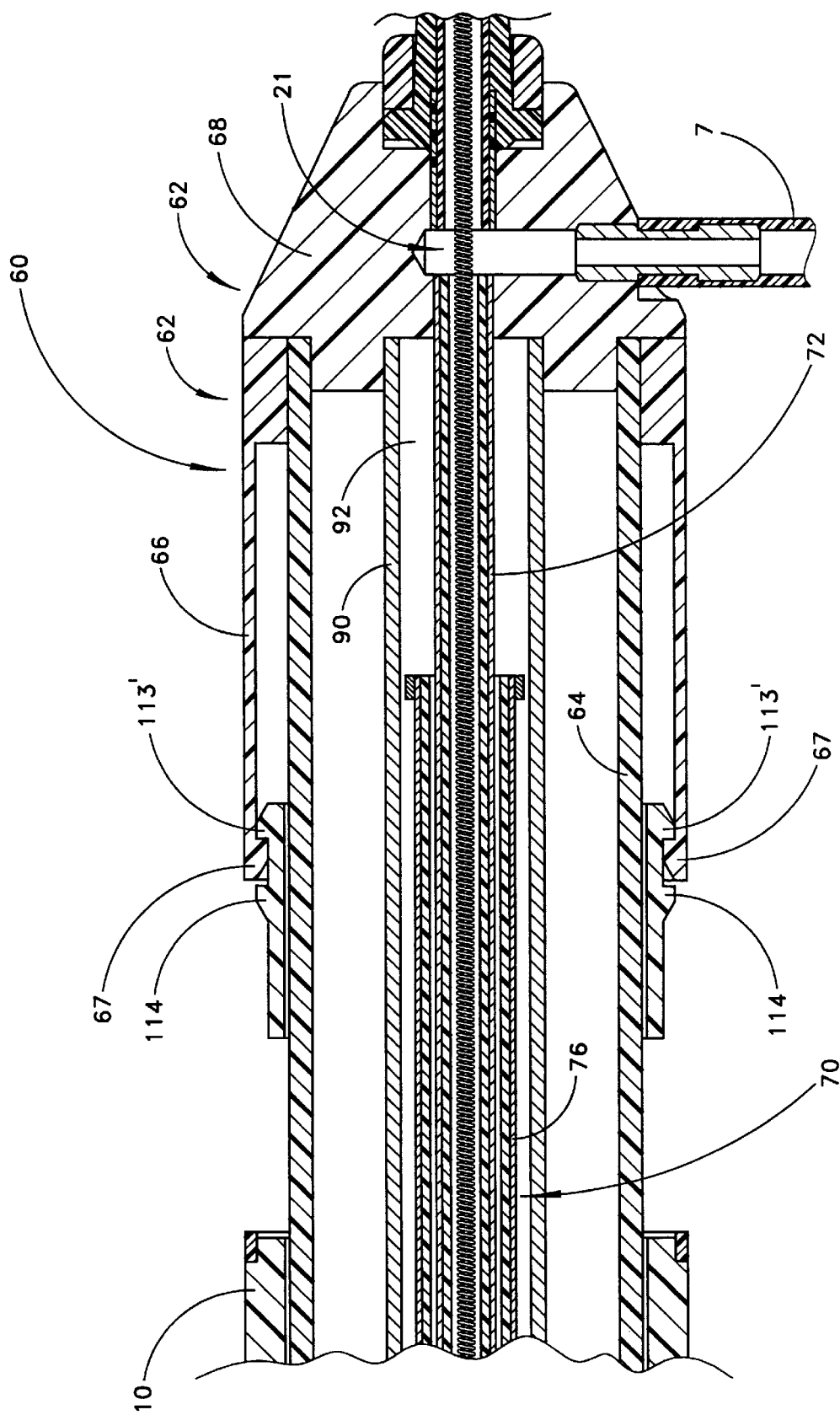
FIG. 79 is a broken away, longitudinal cross-sectional view of FIG. 78 showing the primary interlocking member of the cartridge housing interlocked with the distal complementary interlocking member of the handle housing.
Figure 80:
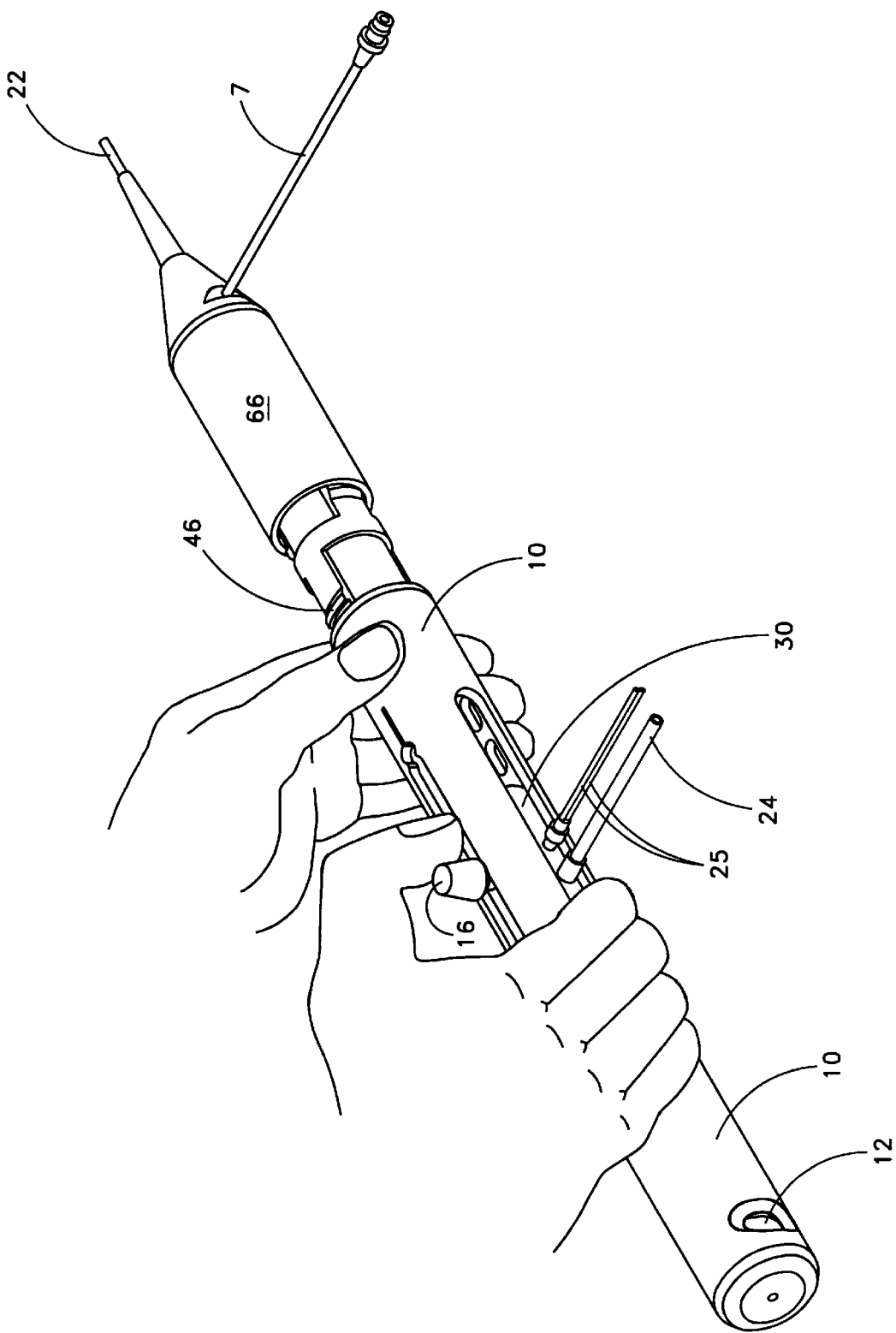
FIG. 80 is a perspective view illustrating the proximal movement of the prime mover carriage to disconnect the flexible drive shaft from the prime mover.

In FIGS. 78–79 the user has not only released the proximal stage of the two stage interlock mechanism (i.e., by compressing the annular shoulder 67 to an oval shape and moving it distally over the tabs 46), but also permitted the annular shoulder 67 to return to its original shape and has moved the cartridge housing 62 distally sufficiently far so that the annular shoulder 67 has become captured between the distal 113' and proximal 114 tabs, which define the groove 115. As is shown in FIG. 80, the cartridge housing 62 is reliably held in place with respect to the handle housing 10 by the distal complementary interlocking member of the two stage interlock mechanism. As is also shown in FIG. 80, the user does not have to hold the cartridge housing 62 when pulling proximally on the control knob 16 to move the prime mover carriage 30 proximally in order to withdraw the drive shaft shank 82 from the prime mover socket 38 and to detach the longitudinally extendable tube 70 from the prime mover carriage 30. Throughout this process the distal complementary interlocking member prevents proximal movement of the cartridge housing 62 with respect to the handle housing 10. Preferably the distal complementary interlocking member (particularly its proximal tabs 114) is positioned sufficiently distally with respect to the proximal complementary interlocking member (i.e., the tabs 46), so that when, in the process of detaching the cartridge housing 62 from the handle housing 10, the primary interlocking member (i.e., the annular shoulder 67 of the outer tube 66 of the cartridge housing 62) interlocks with the distal complementary interlocking member, movement of the prime mover carriage 30 to its proximal limit of movement assures that the drive shaft shank 82 will be withdrawn from the prime mover socket 38 and the longitudinally extendable tube 70 will be detached from the prime mover carriage 30.

Figure 81:
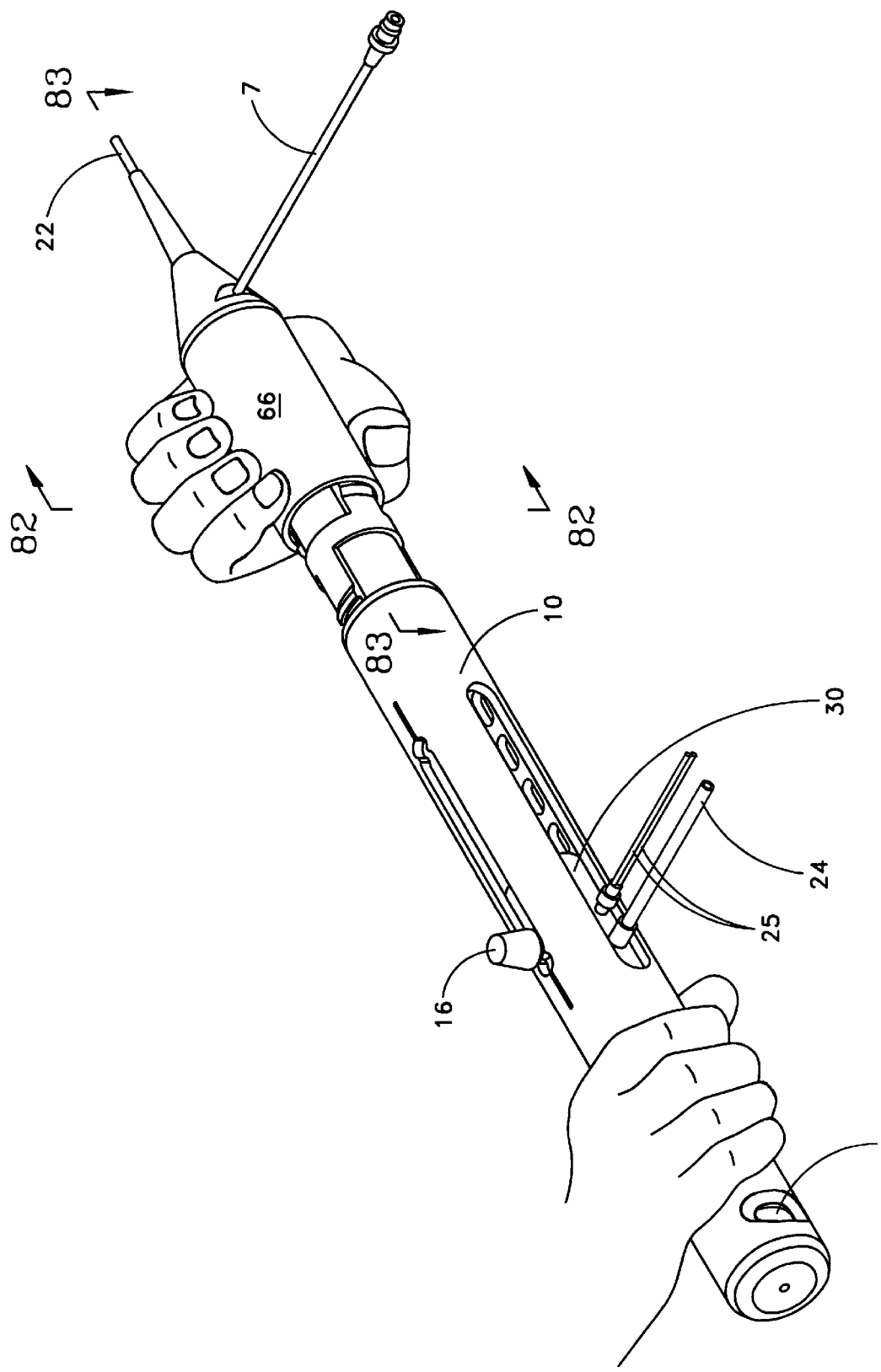
FIG. 81 is a perspective view illustrating a third step in the process of detaching the cartridge housing from the handle housing which has the complementary interlocking members shown in FIGS. 75–76.
Figure 82:
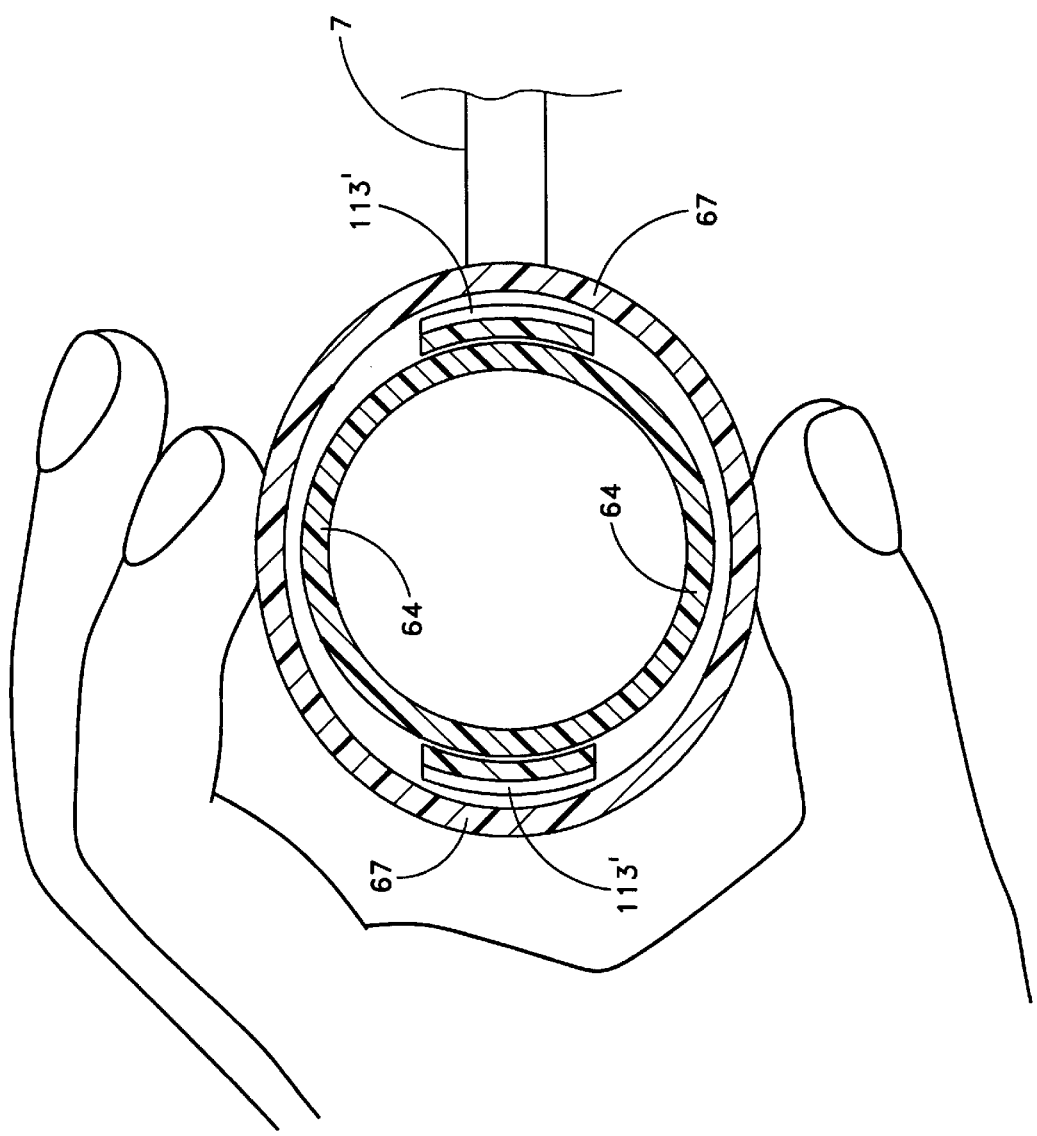
FIGS. 82–83 are cross-sectional views of FIG. 81 taken along lines 82—82 and 83—83, respectively, and illustrating that the distal stage of the two stage interlock mechanism is releasable by compressing the annular shoulder of the cartridge housing to an oval shape.
Figure 83:
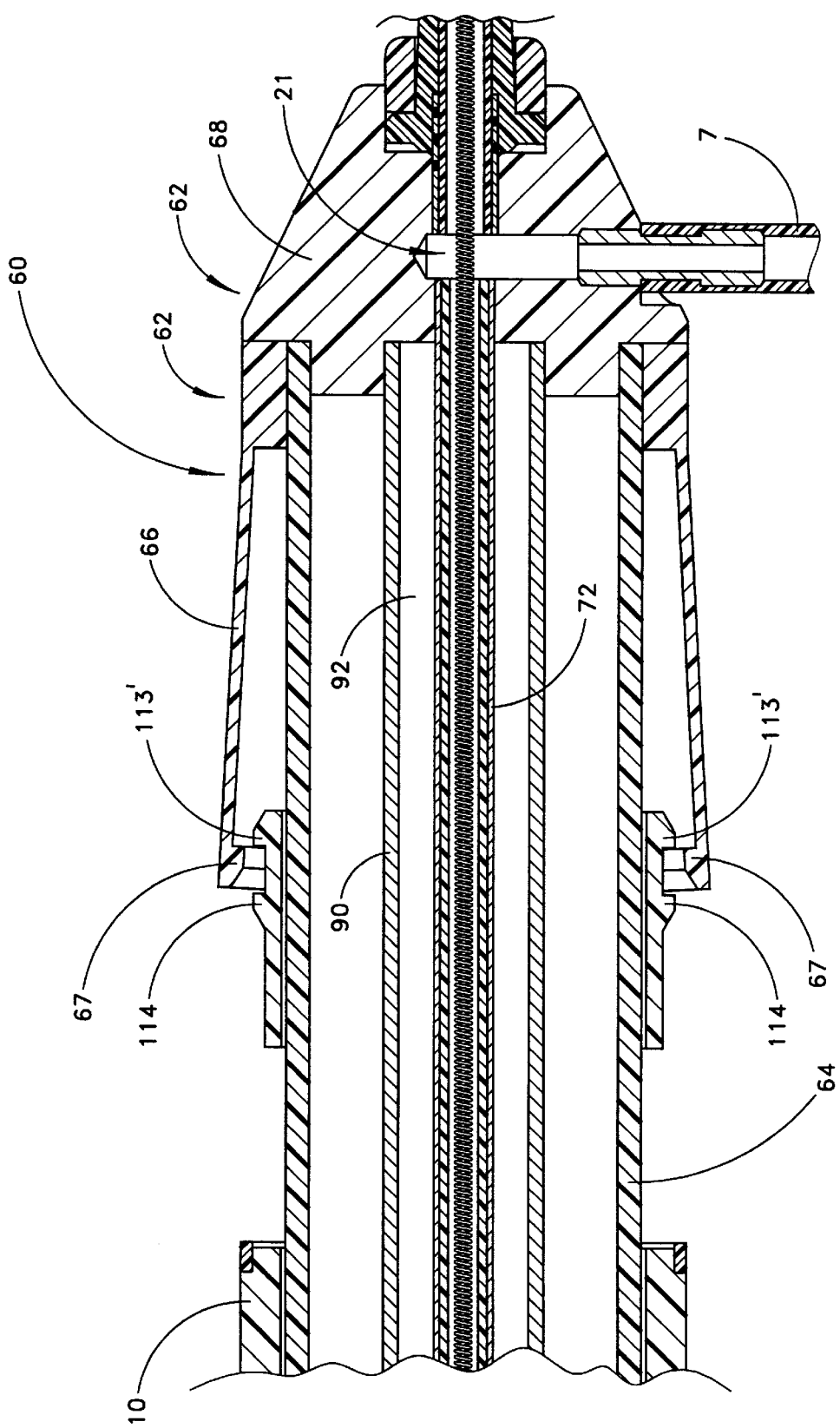

In FIGS. 81–83 the user is compressing the outer tube 66 of the cartridge housing 62 between two points located circumferentially between the tabs 113' and 114. As a result, the annular shoulder 67 becomes deformed to an oval shape and disengaged from the tabs 113' and 114.

Figure 84:
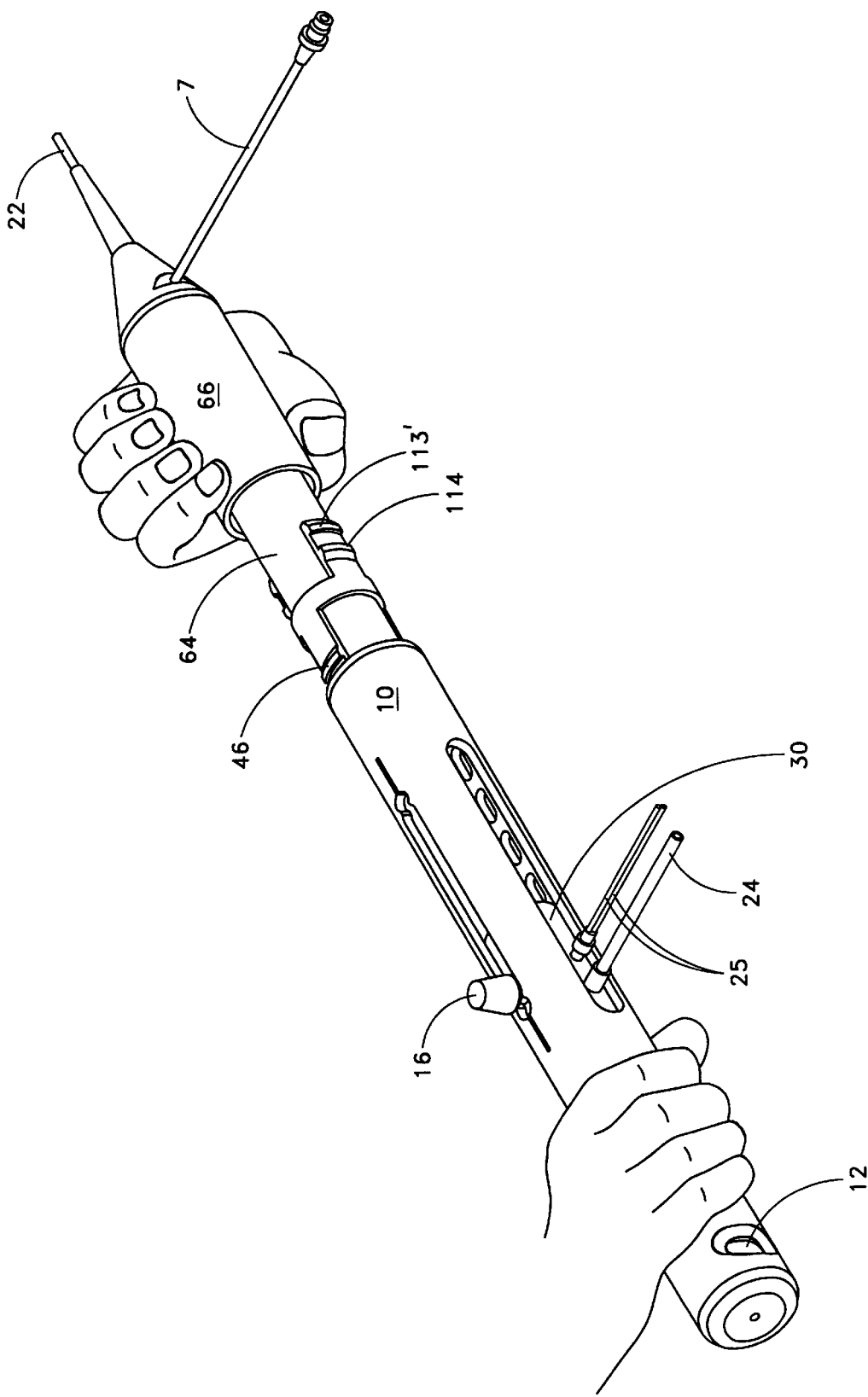
FIGS. 84–85 are perspective views showing the final step in detaching the exchangeable drive shaft cartridge from the handle housing, the cartridge being withdrawn distally from the handle housing.
Figure 85:
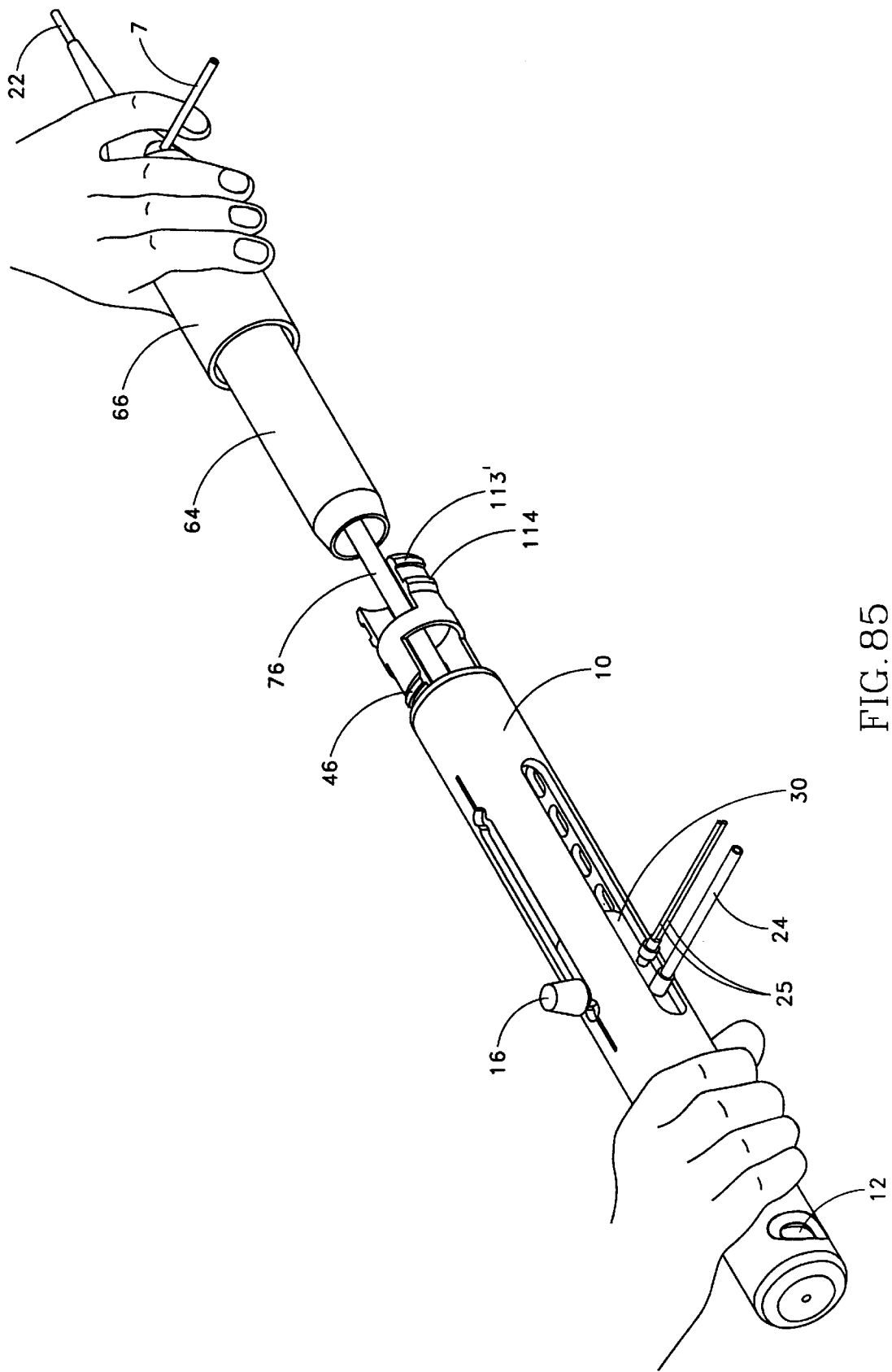
Figure 86:
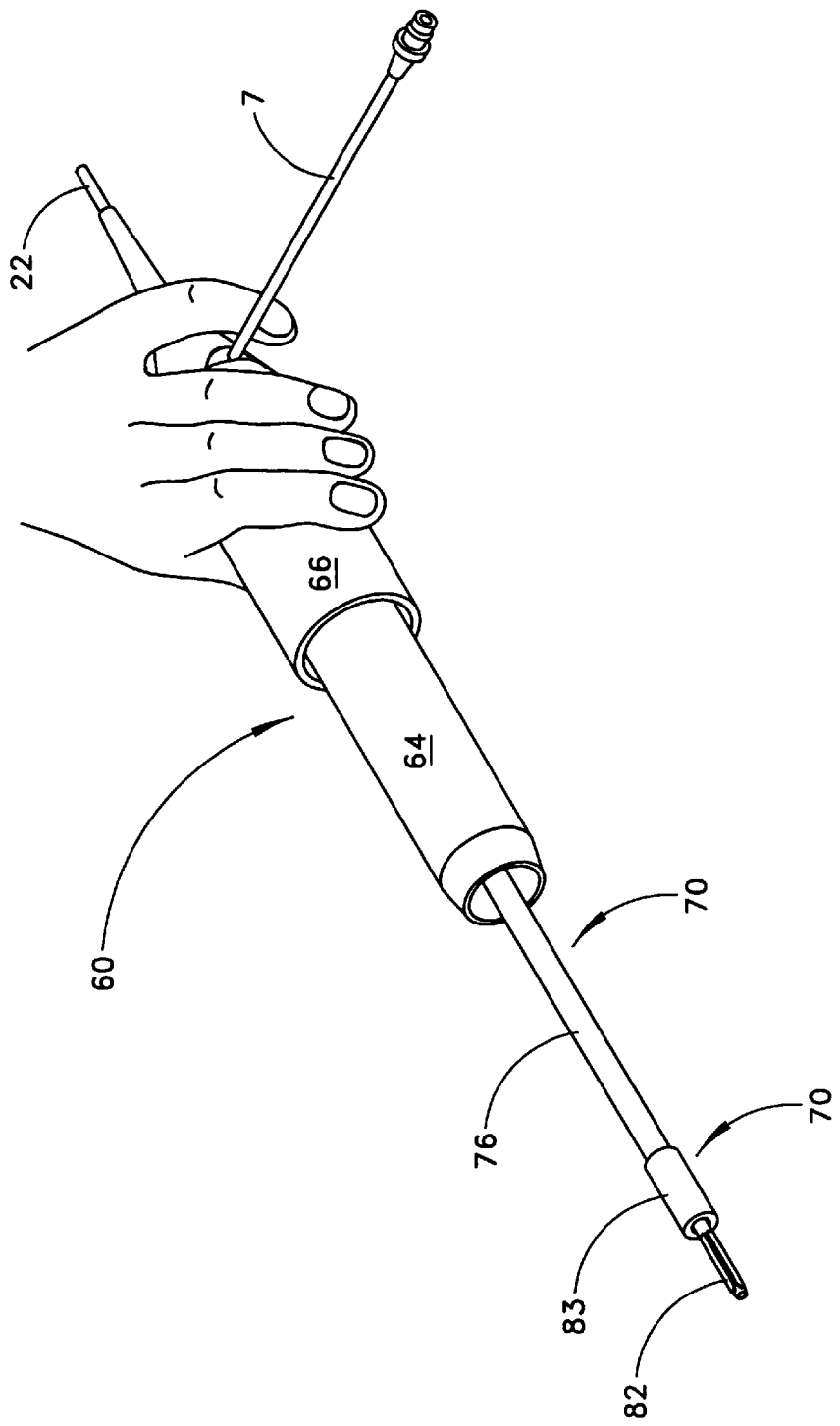
FIG. 86 illustrates the exchangeable drive shaft cartridge immediately after it has been detached from the handle housing.
Figure 87:
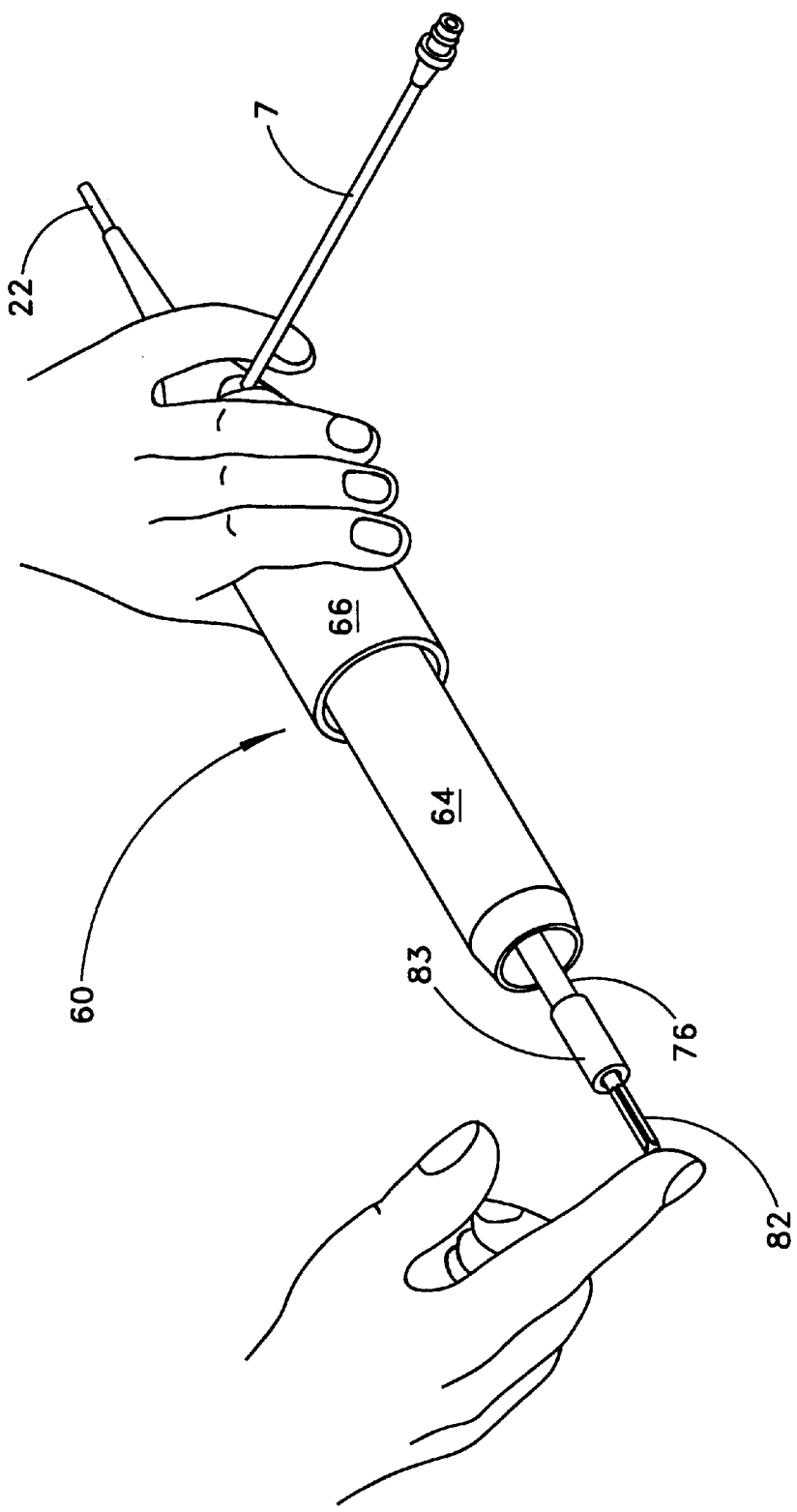
FIG. 87 illustrates how, by pushing distally on the drive shaft shank, one can push the movable telescopic tube inside the cartridge housing.

FIGS. 84–85 show the final step in detaching the exchangeable drive shaft cartridge 60 from the handle housing 10, the cartridge 60 being withdrawn distally from the handle housing 10. FIG. 86 illustrates the exchangeable drive shaft cartridge 60 immediately after it has been detached from the handle housing 10. Note that the longitudinally extendable tube 70 is in its extended position, extending proximally from the inner tube 64 of the drive shaft cartridge 60. FIG. 87 shows that the user, by pushing distally on the drive shaft shank 82, may push the moveable telescopic tube 76 distally so that the longitudinally extendable tube 70 shortens and is substantially confined within the cartridge housing 62.

FIGS. 88–94 illustrate the process of attaching an exchangeable drive shaft cartridge 60 to the handle housing 10 which has the distal complementary interlocking member shown in FIGS. 75–76. This process of attaching the exchangeable drive shaft cartridge 60 to the handle housing 10 is the same, regardless of whether it is the first or a subsequent exchangeable drive shaft cartridge used in the atherectomy procedure.

Figure 88:
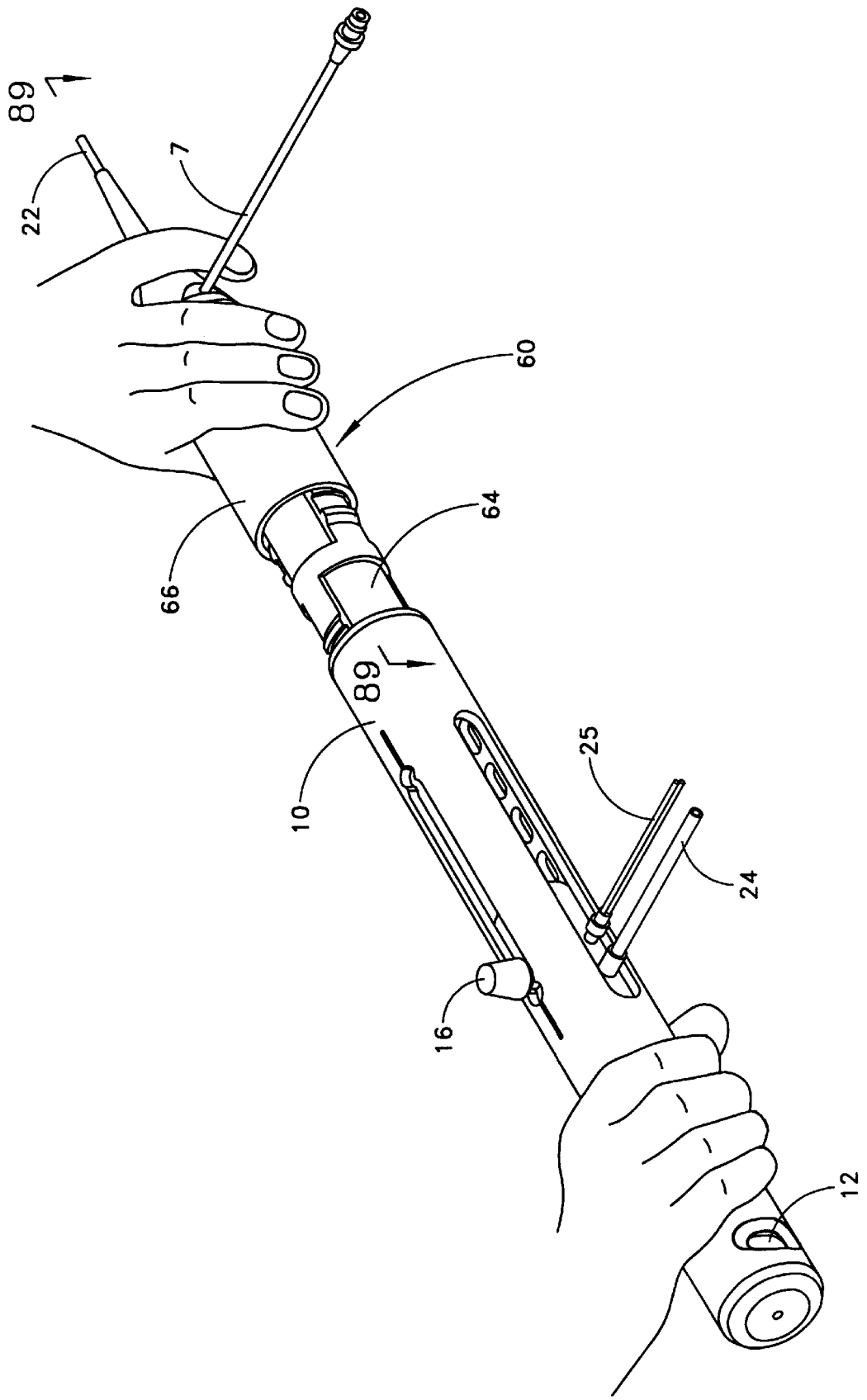
FIGS. 88–89 illustrate the first step in the process of attaching the cartridge housing to the handle housing which has the complementary interlocking members shown in FIGS. 75–76, FIG. 88 being a perspective view and FIG. 89 being a longitudinal cross-sectional view taken along lines 89—89 of FIG. 88.
Figure 89:
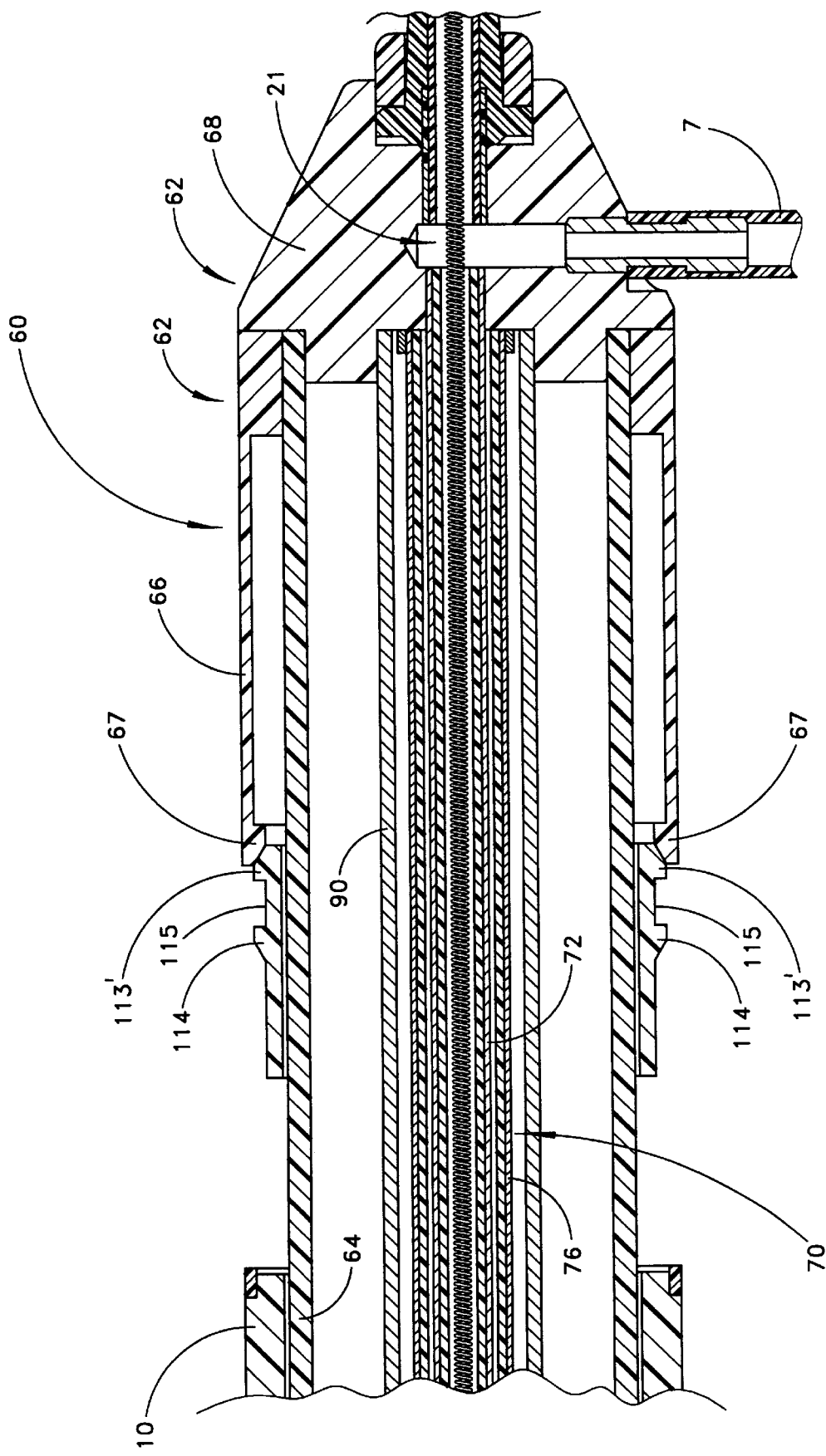
Figure 90:
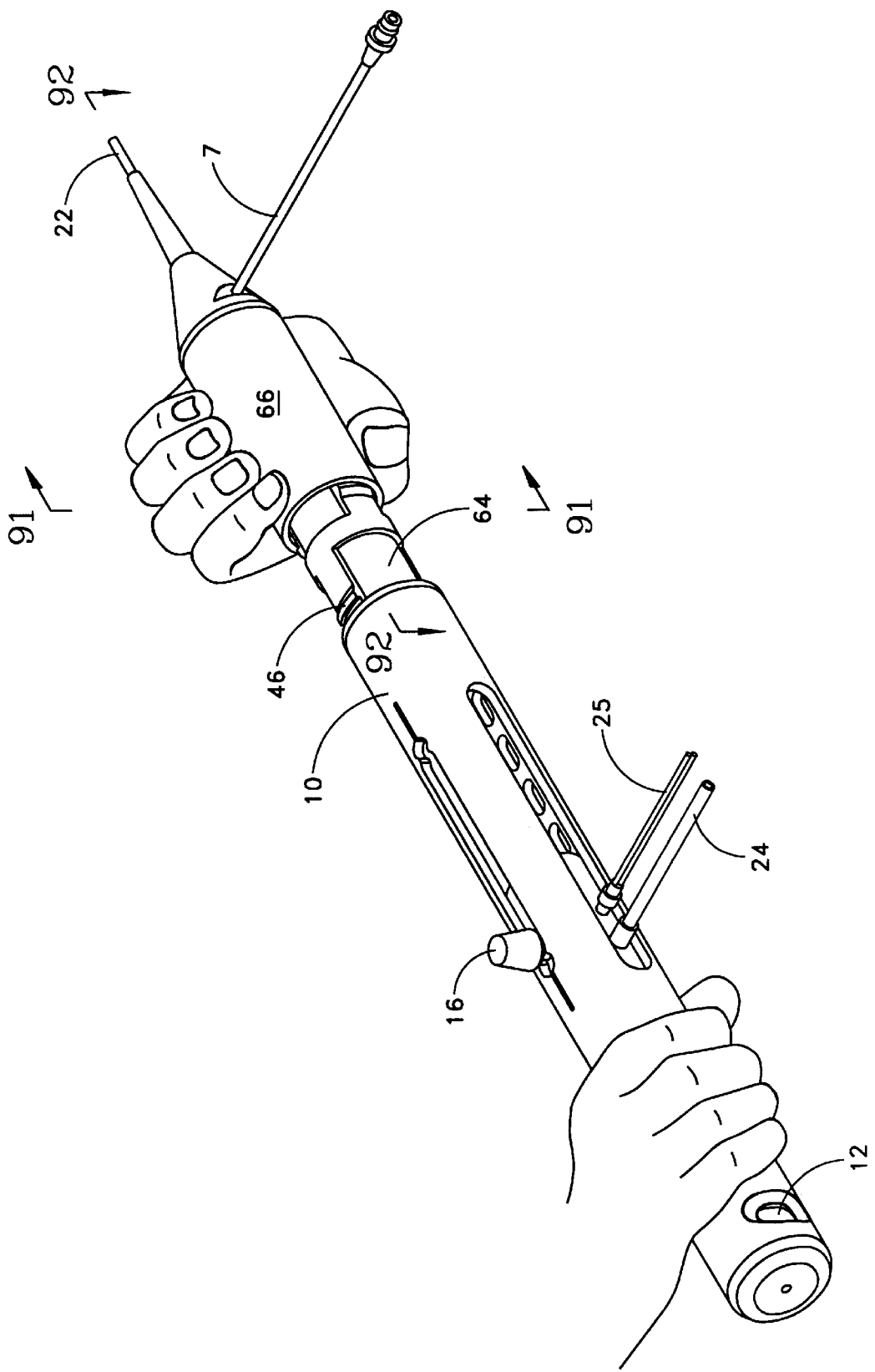
FIG. 90 is a perspective view illustrating the second step in the process of attaching the cartridge housing to the handle housing which has the complementary interlocking members shown in FIGS. 75–76.
Figure 91:
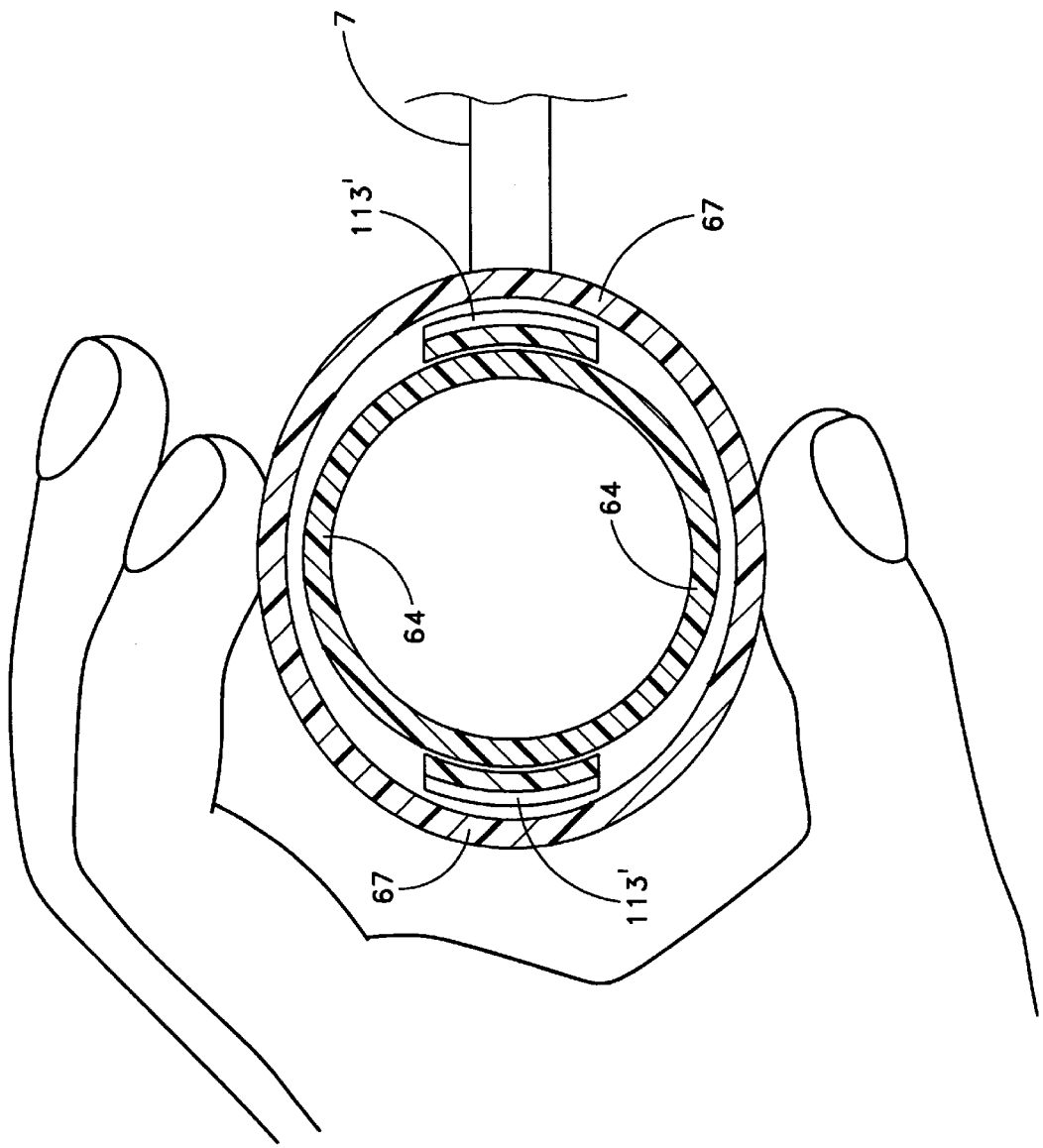
FIGS. 91–92 are cross-sectional views of FIG. 90 taken along lines 91—91 and 92—92, respectively, and illustrating that the distal stage of the two stage interlock mechanism is releasable by compressing the annular shoulder of the cartridge housing to an oval shape.
Figure 92:
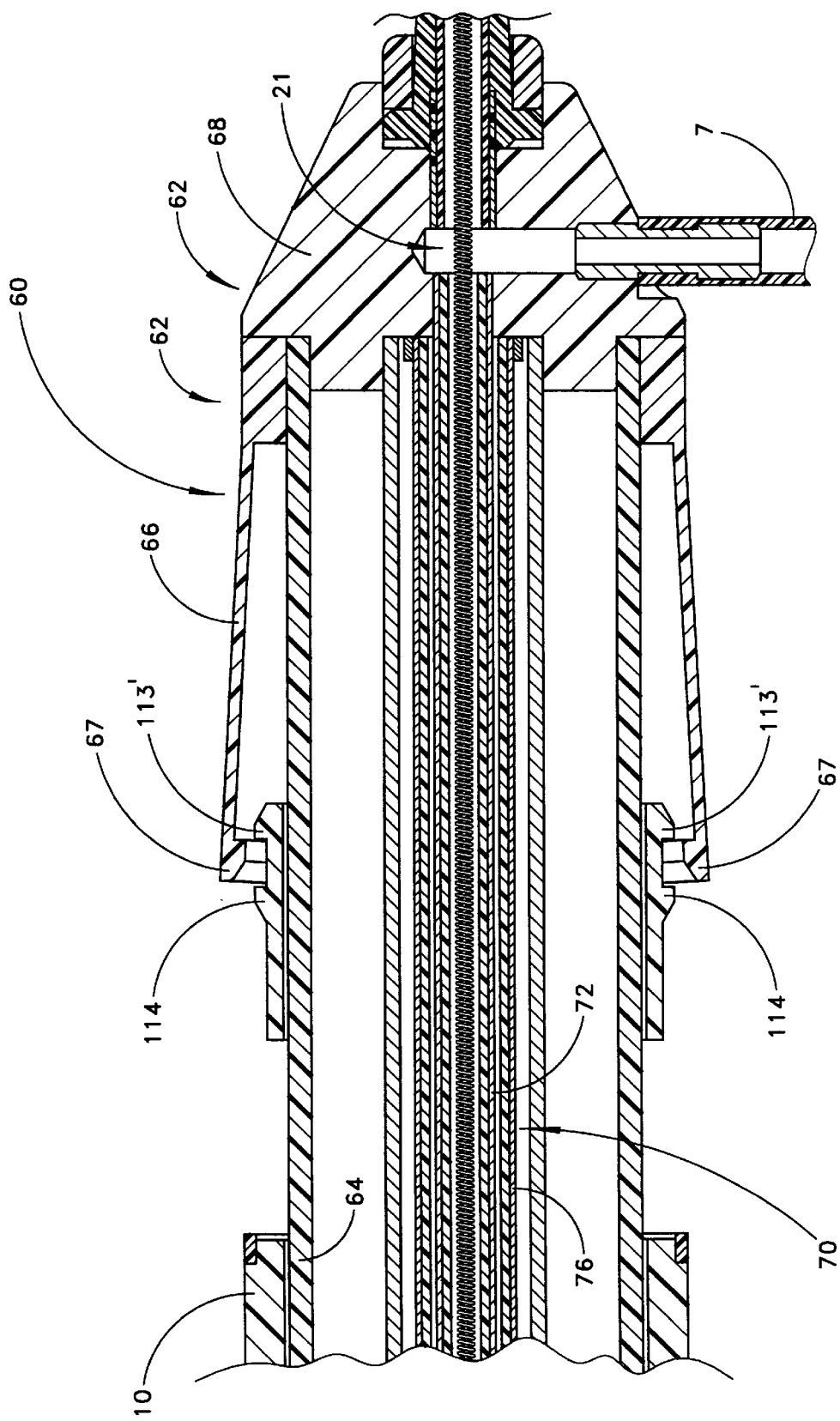

In FIGS. 88–89 the inner tube 64 of the cartridge housing 62 has been telescopically inserted into the handle housing 10 to a point where the annular shoulder 67 of the outer tube 66 of the cartridge housing 62 abuts the distal tabs 113'. As can be seen in FIG. 89, the proximal wall of the annular shoulder 67 and the distal walls of the distal tabs 113' are provided with complementary tapered surfaces. At this point further proximal movement of the cartridge housing 62 will cause the annular shoulder 67 to ride up and over the distal tabs 113'. While riding up and over the distal tabs 113', the annular shoulder 67 becomes deformed to an oval shape. After the annular shoulder 67 has been moved proximally over the distal tabs 113', it regains its original circular shape and becomes captured between the distal 113' and proximal 114 tabs of the distal complementary interlocking member of the two stage interlock mechanism. As is shown in FIGS. 90–92, the user then releases the annular shoulder 67 by compressing the outer tube 66 of the cartridge housing 62 between two points located circumferentially between the tabs 113' and 114. As a result, the annular shoulder 67 becomes deformed to an oval shape and disengaged from the tabs 113' and 114. The user then moves the compressed shoulder 67 proximally over the tabs 114.

As can be seen better in FIG. 76, the distal walls of the tabs 46 are provided with tapered surfaces which are complementary to the tapered surface of the proximal wall of the annular shoulder 67.

Figure 93:
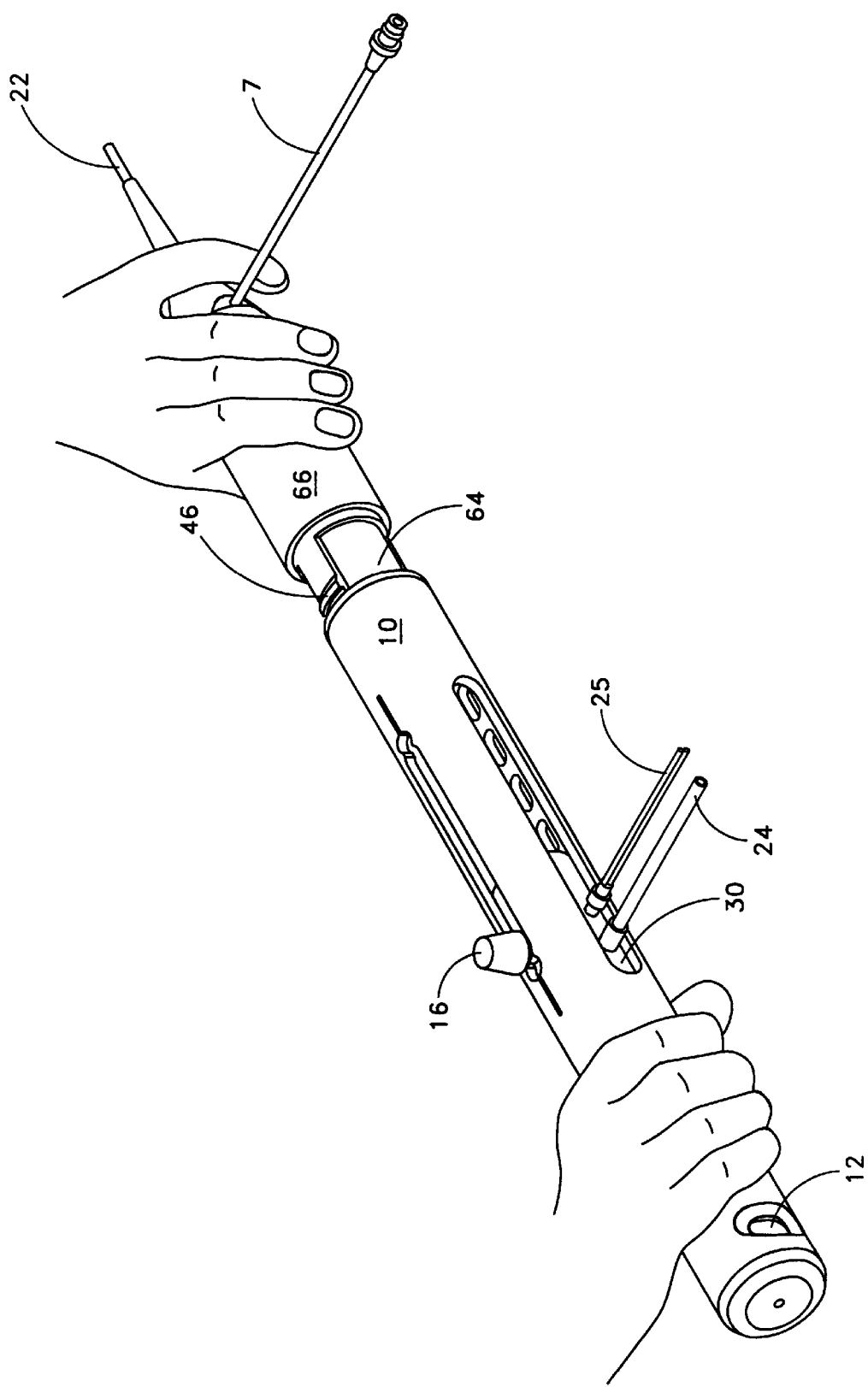
FIG. 93 is a perspective view illustrating the final step in attaching the cartridge housing to the handle housing.

FIG. 93 illustrates the final step in the process of attaching the cartridge housing 62 to the handle housing 10. This final step includes continuous proximal movement of the cartridge housing 62 until the annular shoulder 67 rides up and over the tabs 46. While riding up and over the tabs 46, the annular shoulder 67 becomes deformed to an oval shape. After the annular shoulder 67 has been moved proximally over the tabs 46, it regains its original circular shape, thereby interlocking the cartridge housing 62 with the handle housing 10.

Figure 94:
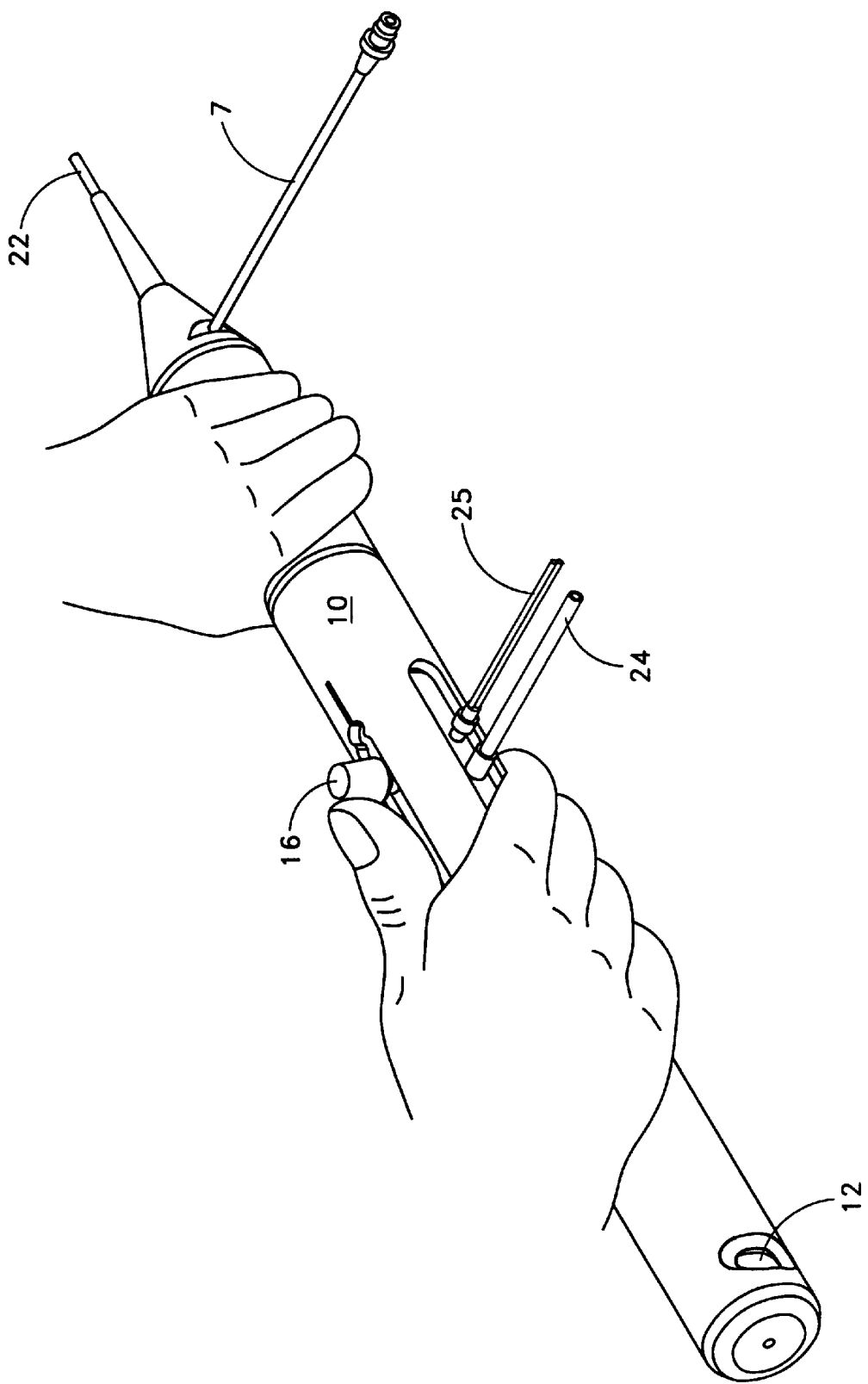
FIG. 94 is a perspective view similar to FIG. 26 illustrating the first step in the process of attaching the drive shaft shank to the prime mover socket and the longitudinally extendable tube to the prime mover carriage.

In FIG. 94 the exchangeable drive shaft cartridge 60 has been fully advanced proximally with respect to the handle housing 10 so that the primary interlocking member of the cartridge housing (i.e., the annular shoulder 67 of the outer tube 66 of the cartridge housing 62) has interlocked with the proximal complementary interlocking member of the handle housing 10 (i.e., the radially extending tabs 46). In this position the user may then advance the control knob 16 distally to attach the drive shaft shank 82 to the prime mover socket 38 and the longitudinally extendable tube 70 to the prime mover carriage 30, as is shown in detail in FIGS. 25–35.

Figure 95:
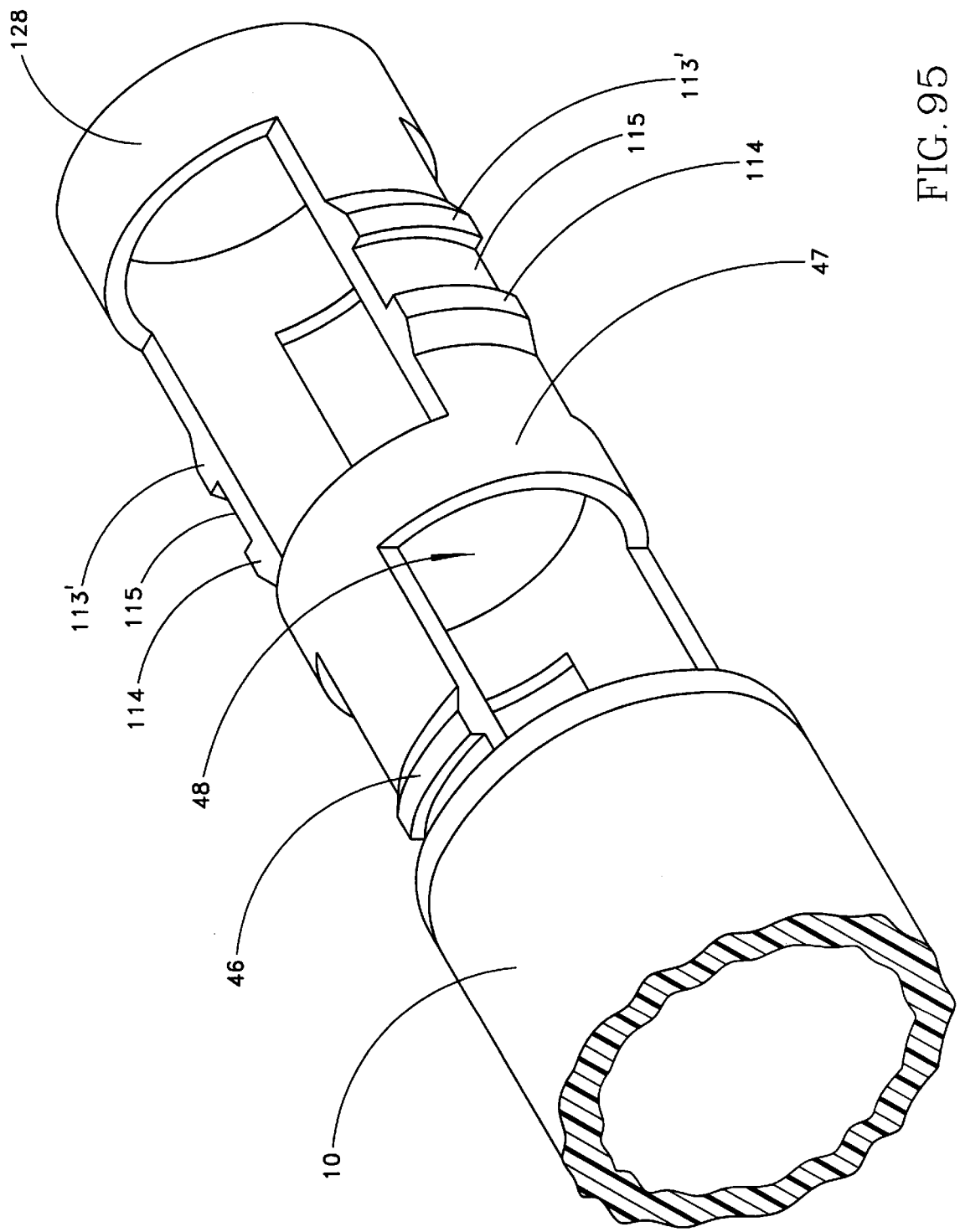
FIG. 95 illustrates another modified embodiment of the distal portion of the handle housing, differing from the embodiment shown in FIG. 76 by having a pair of distal windows instead of the pair of distally open recesses shown in FIG. 76.

FIG. 95 illustrates a modification of the distal portion of the handle housing containing the two stage interlock mechanism illustrated in FIG. 76. The embodiment illustrated in FIG. 95 differs from the embodiment shown in FIGS. 76 by having a distal ring 128 which converts the pair of distally open recesses shown in FIG. 76 into a pair of distal windows 117. The distal windows 117, like the proximal windows 48, are provided in the wall of the handle housing 10 circumferentially opposite each other and between the tabs 113' and 114 to permit compression of the annular shoulder 67 of the cartridge housing 62 to an oval shape to release the second stage of the two stage interlock mechanism.

Figure 96:
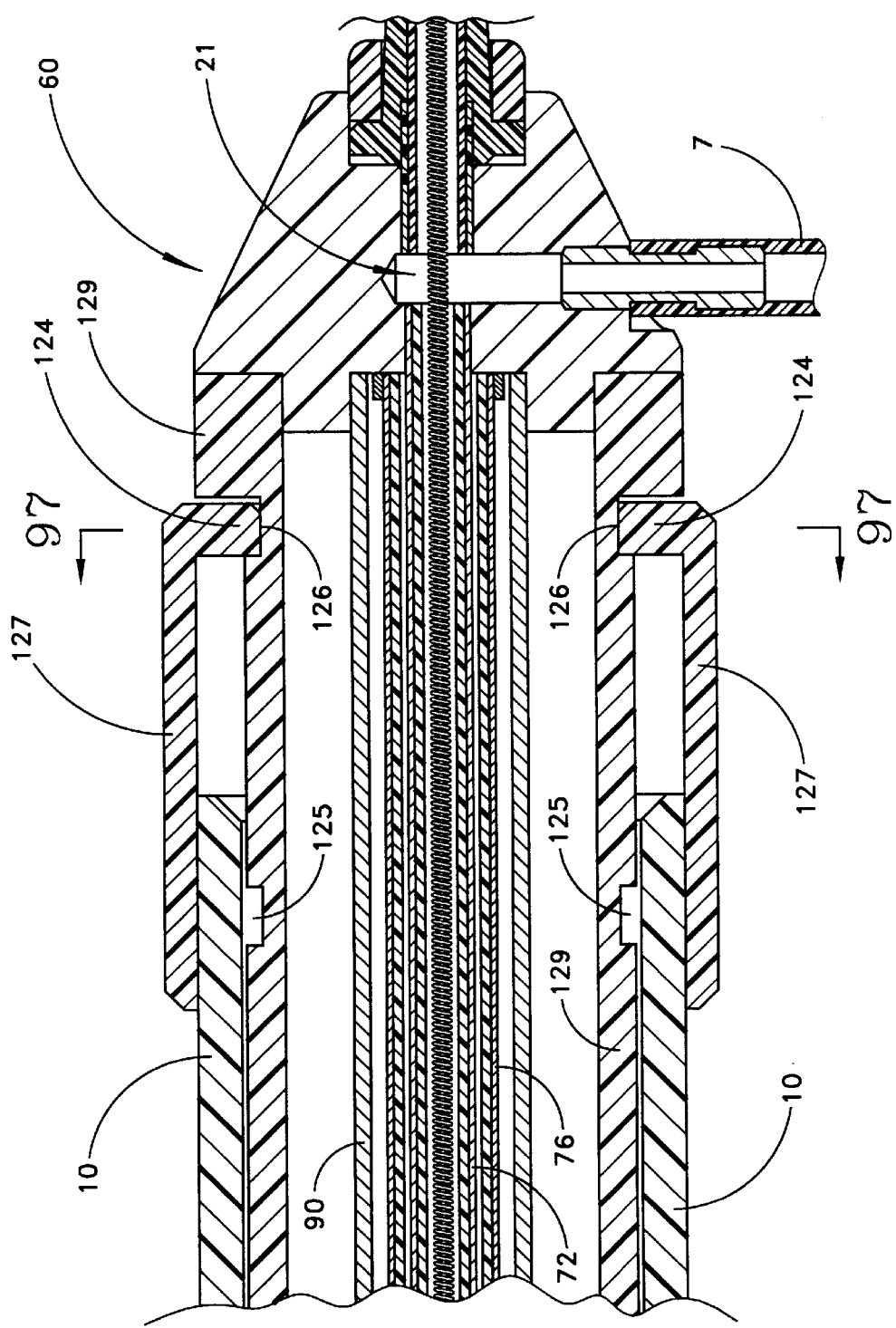
FIGS. 96–97 illustrate another embodiment of a two stage interlock mechanism having a primary interlocking member associated with the handle housing and two complementary interlocking members comprised of annular grooves in a wall of the cartridge housing, FIG. 96 being a broken away longitudinal cross-section, and FIG. 97 being a transverse cross-section of FIG. 96 taken along lines 97—97 thereof.
Figure 97:
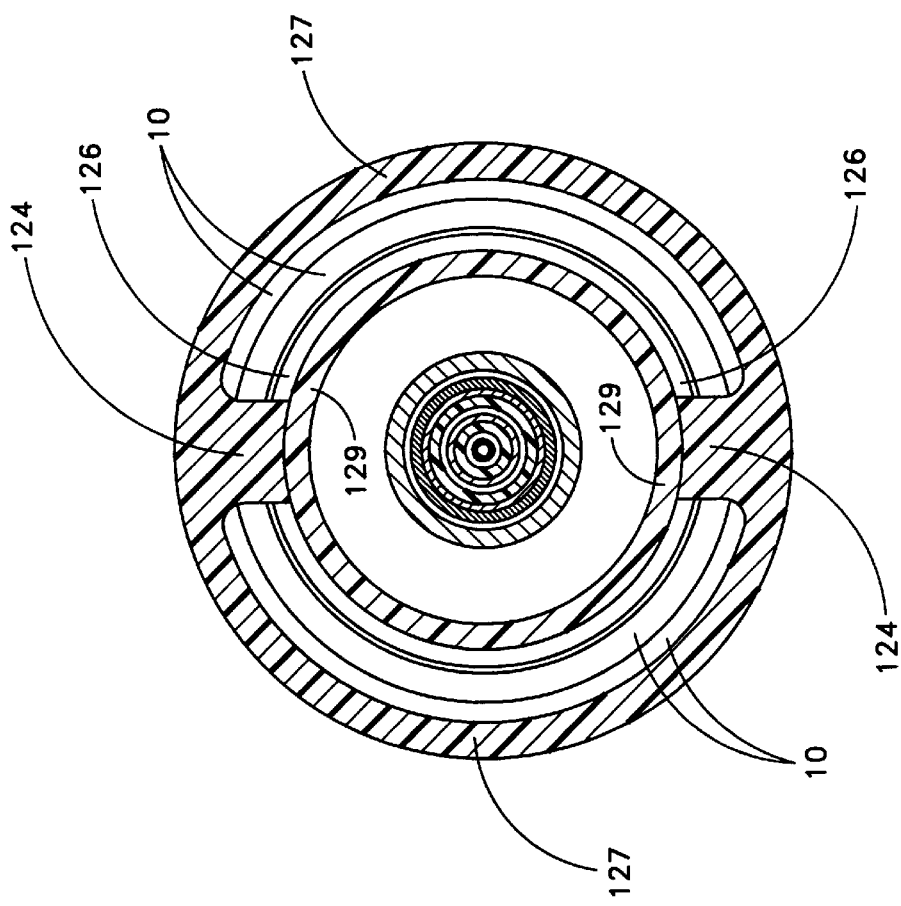

FIGS. 96–97 illustrate another embodiment of a two stage interlock mechanism. In this embodiment the primary interlocking member is carried by the handle housing 10 and the complementary interlocking members are carried by the tubular portion of the cartridge housing 129. The primary interlocking member is comprised of a pair of radially inwardly extending tabs 124 associated with the handle housing 10, and the two complementary interlocking members are comprised of proximal and distal annular grooves 125 and 126 formed in the outer surface of the cartridge housing 129. At least part of the generally tubular cartridge housing 129 is telescopically receivable within the generally tubular handle housing 10. Each of the grooves 125 and 126 has a longitudinal width sufficient to interlock with the radially inwardly extending tabs 124.

Preferably the longitudinal distance between the proximal and distal grooves 125 and 126 is sufficiently long so that when, in the process of detaching the exchangeable drive shaft cartridge 60 from the handle housing 10, the tabs 124 interlock with the proximal groove 125, movement of the prime mover carriage 30 to its proximal limit of movement assures that the drive shaft shank 82 will be withdrawn from the prime mover socket 38 and the longitudinally extendable tube 70 will be detached from the prime mover carriage 30.

In FIGS. 96–97 the radially inwardly extending tabs 124 are depicted as being carried by an annular collar 127 secured to the handle housing 10, a portion of the collar 127 extending distally from the handle housing 10. Alternately annular collar 127 and the tabs 124 may be formed integrally with the handle housing 10. The annular collar 127 has an inner diameter which is sufficiently larger than the outer diameter of the tubular portion of the cartridge housing 129 to permit the annular collar 127 to be compressed to an oval shape to disengage the tabs 124 from the grooves 125 and 126.

Figure 98:
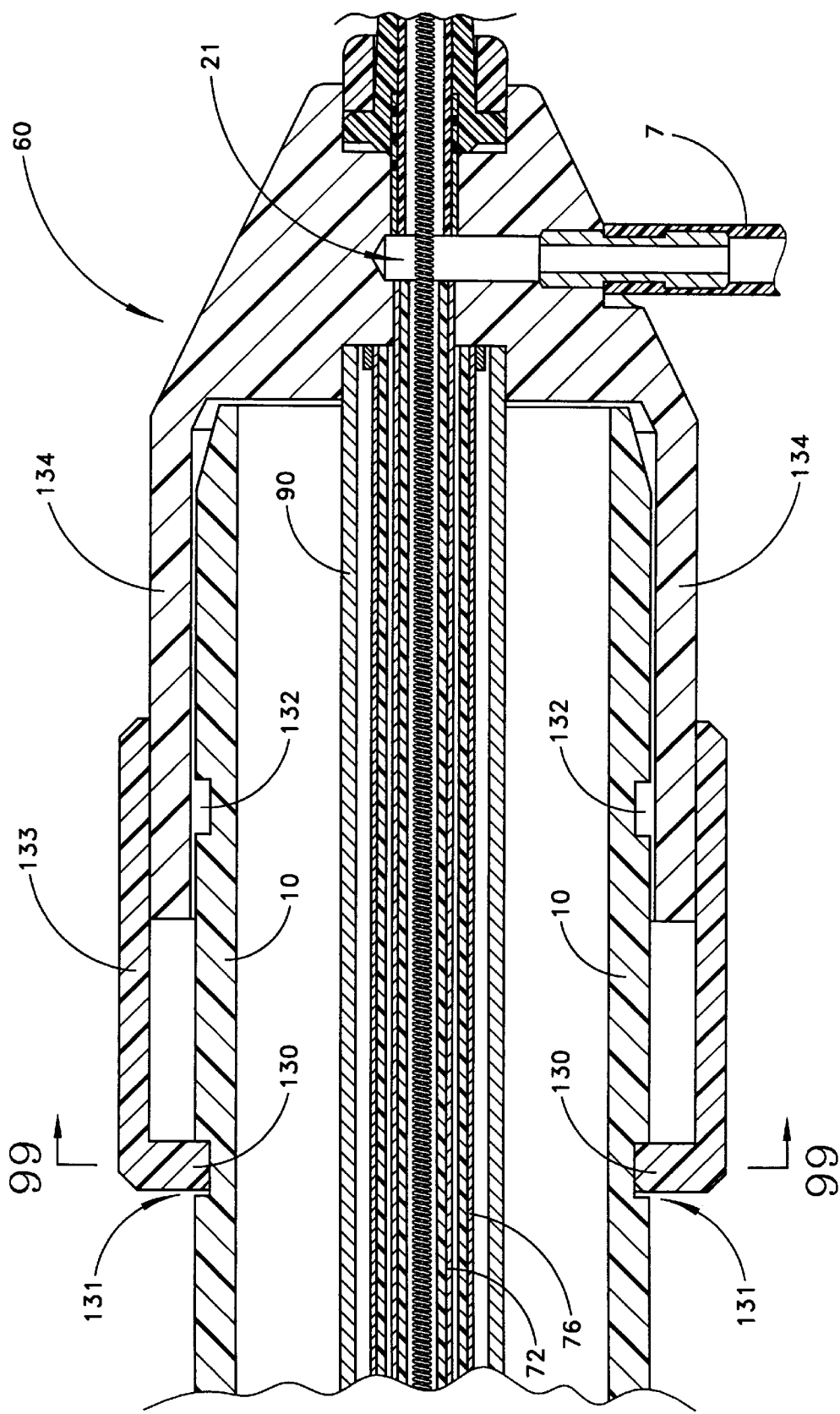
FIGS. 98–99 illustrate yet another embodiment of a two stage interlock mechanism wherein the primary interlocking member is associated with the cartridge housing and two complementary interlocking members are comprised of annular grooves in a wall of the handle housing.
Figure 99:
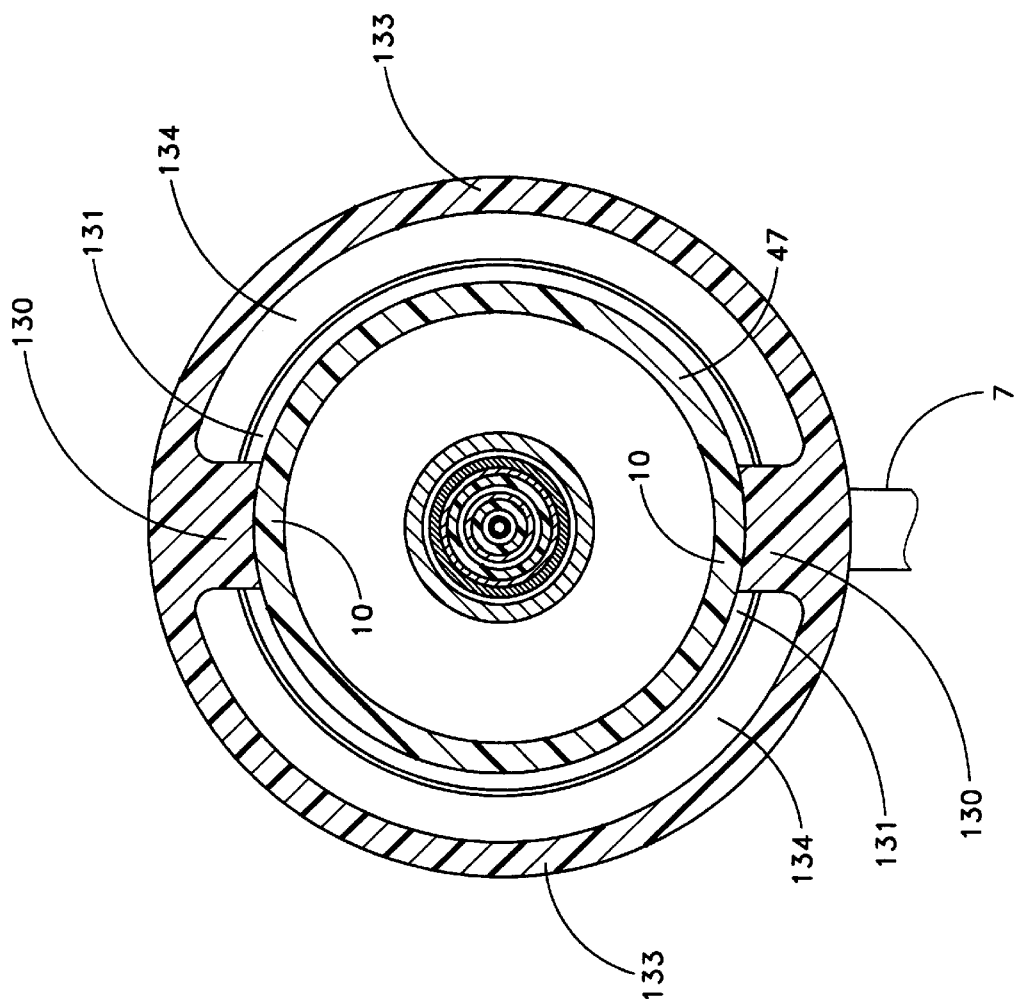

FIGS. 98–99 illustrate yet another embodiment of a two stage interlock mechanism. In this embodiment the primary interlocking member is comprised of a pair of radially inwardly extending tabs 130 associated with the cartridge housing 134, and the two complementary interlocking members are comprised of proximal and distal annular grooves 131 and 132 in the outer surface of the handle housing 10.

At least part of the generally tubular handle housing 10 is telescopically receivable within the generally tubular cartridge housing 134. Each of the grooves 131 and 132 has a longitudinal width sufficient to interlock with the radially inwardly extending tabs 130.

Preferably the longitudinal distance between the proximal and distal grooves 131 and 132 is sufficiently long so that when, in the process of detaching the exchangeable drive shaft cartridge 60 from the handle housing 10, the tabs 130 interlock with the distal groove 132, movement of the prime mover carriage 30 to its proximal limit of movement assures that the drive shaft shank 82 will be withdrawn from the prime mover socket 38 and the longitudinally extendable tube 70 will be detached from the prime mover carriage 30.

In FIGS. 98–99 the radially inwardly extending tabs 131 are depicted as being arried by an annular collar 133 secured to the cartridge housing 134, a portion of the collar 133 extending proximally from the cartridge housing 134. Alternately the annular collar 113 and the tabs 130 may be formed integrally with the cartridge housing 134. The annular collar 133 has an inner diameter which is sufficiently larger than the outer diameter of the handle housing 10 to permit the annular collar 133 to be compressed to an oval shape to disengage the tabs 130 from the grooves 131 and 132.

Figure 100:
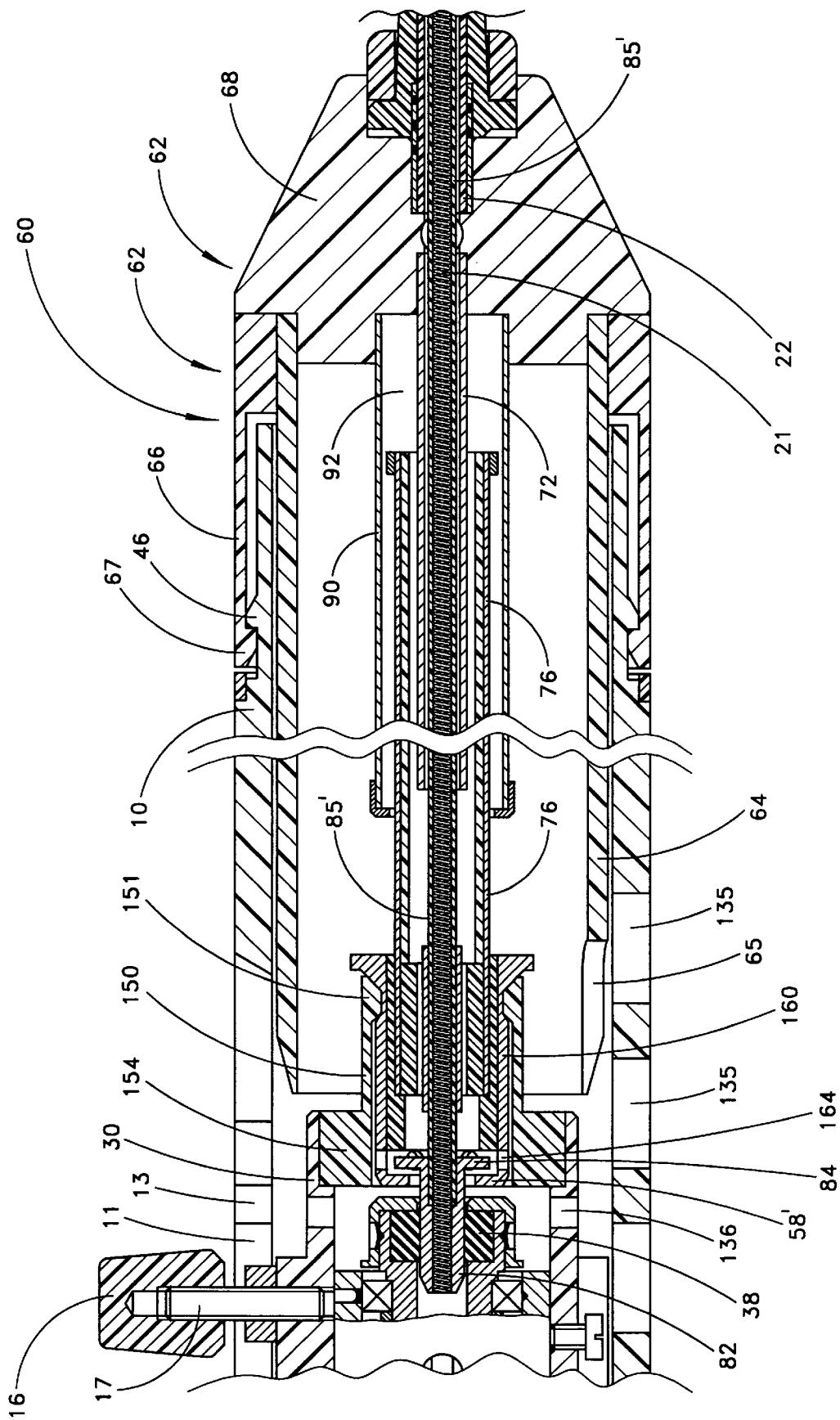
FIG. 100 is a broken away longitudinal cross-sectional view similar to FIG. 55, illustrating a flexible thin-walled tube heat shrunk onto a longer length of the proximal end portion of the flexible drive shaft.
Figure 101:
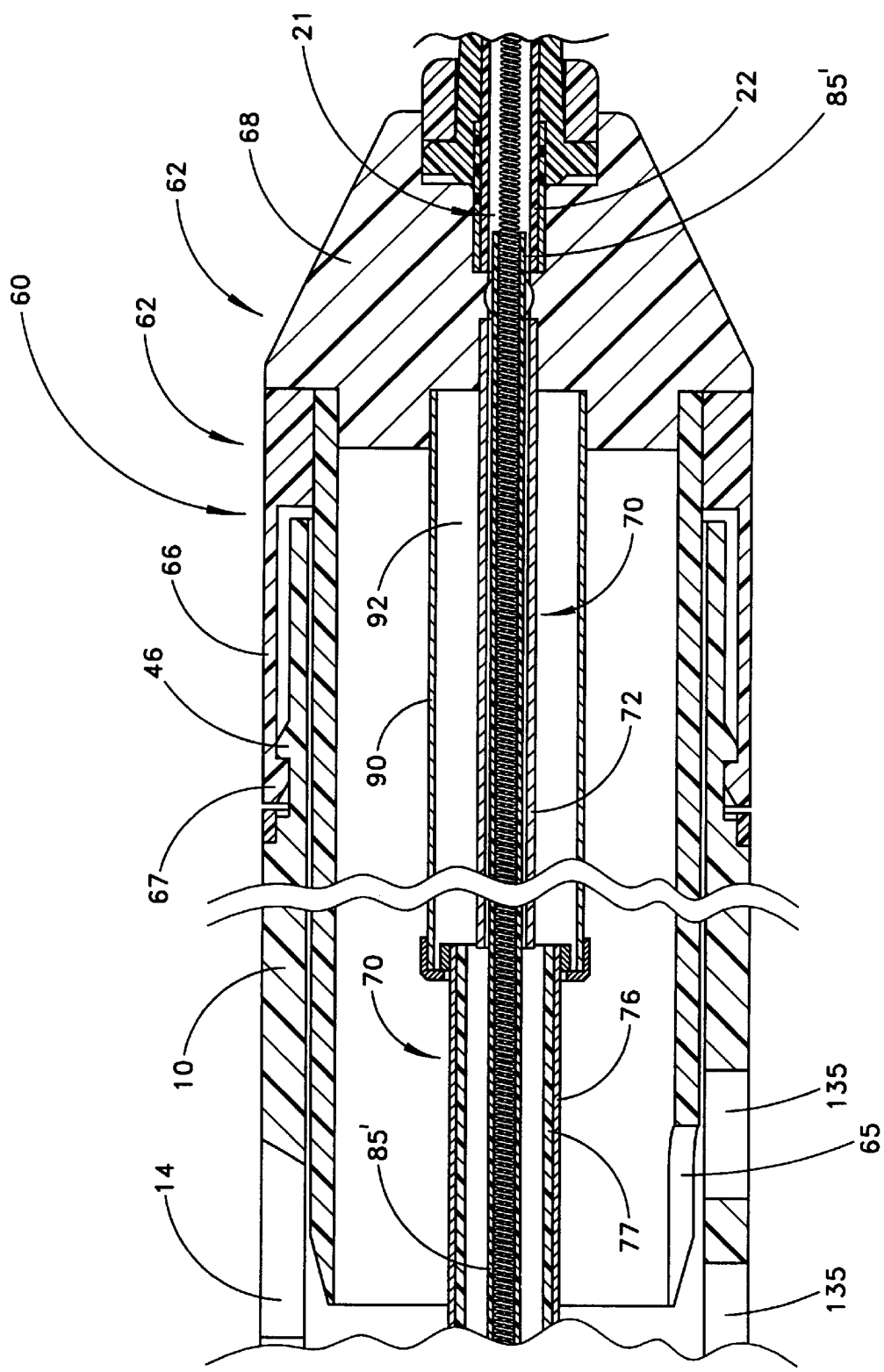
FIG. 101 is a broken away longitudinal cross-sectional view of the atherectomy device of FIG. 100, shown in a moved position, and illustrating that the heat shrunk thin-walled tube extends distally into the catheter even when the longitudinally extendable tube is in its maximum length position.

FIGS. 100–101 show an embodiment similar to FIG. 55. In this embodiment a flexible thin-walled tube 85' (preferably made from polyester) is heat shrunk onto a longer length of the proximal end portion of the flexible drive shaft 21. The thin-walled tube extends along a length of the proximal portion of the drive shaft from the distal end of the shank 82 to a point located distally of the distal end of the longitudinally extendable tube 70. In this embodiment the distal end of the thin-walled tube 85' extends distally beyond the location where the fluid supply tube 7 delivers fluid to the drive shaft lumen, the drive shaft lumen being defined by the lumens of the stationary 64 and movable 66 telescopic tubes and the lumen of the catheter 22. Desirably, as shown in FIG. 101, the thin-walled tube 85' extends into the proximal end portion of the catheter 22 even when the prime mover carriage 30 is moved to its most proximal position. Drainage outlets 136 are provided in the prime mover carriage 30, drainage slots 65 are provided in the inner tube 64 of the cartridge housing, and drainage outlets 135 are provided in the handle housing 10. Such drainage outlets and slots are omitted in some of the drawings for the sake of clarity. Additional drainage outlets may also be used if necessary.

While a preferred embodiment of the present invention has been described, it should be understood that various changes, adaptations and modifications may be made therein without departing from the spirit of the invention and the scope of the appended claims.

What is claimed is:

1. A rotational atherectomy device comprising:
   a handle housing and an exchangeable drive shaft cartridge having a housing which is removably attachable to the handle housing;
   a rotatable prime mover carried by a prime mover carriage which is disposed within the handle housing, the prime mover carriage being longitudinally movable with respect to the handle housing;
   the exchangeable drive shaft cartridge including
      a longitudinally extendable tube having a distal end portion carried by the cartridge housing and a proximal end portion which is removably attachable to the prime mover carriage for longitudinal movement therewith;

an elongated catheter having a proximal end portion which is carried by the cartridge housing; and a rotatable flexible drive shaft having proximal, intermediate and distal portions, the proximal portion being attached to an elongated shank, the intermediate portion being disposed primarily within the tube and the catheter, and the distal portion extending distally from the catheter and having a tissue removal implement; and a drive shaft attachment mechanism removably attaching the drive shaft to the prime mover, the drive shaft attachment mechanism comprising a prime mover socket carried by the prime mover and the elongated shank carried by the proximal end portion of the drive shaft, the shank being removably insertable into the socket, at least one of the shank and the socket being radially resilient;

whereby the cartridge housing may be attached to and detached from the handle housing, the longitudinally extendable tube may be attached to and detached from the prime mover carriage, and the drive shaft may be attached to and detached from the prime mover, thereby permitting the exchangeable drive shaft cartridge to be selectively attached to and detached from the handle housing.

2. The rotational atherectomy device of claim 1 wherein the prime mover includes a hollow prime mover shaft.

3. The rotational atherectomy device of claim 2 wherein the hollow shaft of the prime mover includes a recess for receiving the prime mover socket therein.

4. The rotational atherectomy device of claim 1 wherein the prime mover socket is radially resilient.

5. The rotational atherectomy device of claim 1 wherein the inner diameter of the socket is selected to provide a sufficiently tight interference fit with the shank so that, when the drive shaft is attached to the prime mover, the shank and the drive shaft both move longitudinally together with the socket and the prime mover when the prime mover is moved longitudinally with respect to the handle housing.

6. The rotational atherectomy device of claim 1 wherein the inner diameter of the socket is selected to provide a sufficiently tight interference fit with the shank so that, when the drive shaft is attached to the prime mover, the shank and the drive shaft both rotate together with the socket and the prime mover when the prime mover is rotated.

7. The rotational atherectomy device of claim 1 wherein the longitudinally extendable tube is comprised of two elongated telescopic tubes, one of them being a stationary telescopic tube carried by the cartridge housing, and the other being a movable telescopic tube which is carried by and is longitudinally movable with respect to the stationary telescopic tube, the movable telescopic tube being removably attachable to the prime mover carriage for longitudinal movement therewith.

8. The rotational atherectomy device of claim 7 further comprising a distal abutment surface defined by an element of a proximal end portion of the movable telescopic tube, the distal abutment surface being located distally of the shank and being positioned so that the shank abuts the distal abutment surface when the prime mover carriage is moved distally to insert the shank into the socket.

9. The rotational atherectomy device of claim 8 wherein the distal abutment surface defined by said element of the proximal end portion of the movable telescopic tube is a proximal surface of a bushing having a longitudinal lumen within which the drive shaft is disposed and may freely rotate, the bushing being secured to the movable telescopic tube distally of the shank.

10. The rotational atherectomy device of claim 7 wherein the elongated shank includes proximal and distal portions, the distal portion having a radially outwardly extending flange.

11. The rotational atherectomy device of claim 10 wherein the shank's flange is generally annular.

12. The rotational atherectomy device of claim 10 further comprising a proximal abutment surface defined by an element of a proximal end portion of the movable telescopic tube, the proximal abutment surface being located proximally of the shank's flange, the shank's flange abutting the proximal abutment surface when the shank is being removed from the prime mover socket.

13. The rotational atherectomy device of claim 12 further comprising an abutment member secured to the proximal end portion of the movable telescopic tube, the abutment member including a flange, the proximal abutment surface defined by said element of the movable telescopic tube being a surface of such flange.

14. The rotational atherectomy device of claim 1 further comprising a tube attachment mechanism positioned to removably attach the longitudinally extendable tube to the prime mover carriage, the tube attachment mechanism including a resilient positioning mechanism for moving the prime mover carriage and the shank proximally with respect to the longitudinally extendable tube after the prime mover carriage has been advanced distally and attached to the longitudinally extendable tube and after pressure moving the prime mover carriage distally with respect to the longitudinally extendable tube has been released, the resilient positioning mechanism thereby spacing the shank away from an abutment surface defined by an element of the longitudinally extendable tube to permit free rotation of the shank with respect to the longitudinally extendable tube.

15. The rotational atherectomy device of claim 14 wherein the longitudinally extendable tube is comprised of two elongated telescopic tubes, one of them being a stationary telescopic tube carried by the cartridge housing, and the other being a movable telescopic tube which is carried by and is longitudinally movable with respect to the stationary telescopic tube, the movable telescopic tube being removably attachable to the prime mover carriage for longitudinal movement therewith.

16. The rotational atherectomy device of claim 15 further comprising distal and proximal abutment surfaces defined by elements of a proximal end portion of the movable telescopic tube, the distal abutment surface being positioned to abut the shank when the shank is being inserted into the prime mover socket and the proximal abutment surface being positioned to abut a flange carried by the shank when the shank is being removed from the prime mover socket, the distal abutment surface being spaced away from the shank by the resilient positioning mechanism after the prime mover carriage has been advanced distally and attached to the movable telescopic tube and after pressure moving the prime mover carriage distally with respect to the movable telescopic tube has been released.

17. The rotational atherectomy device of claim 15 wherein the resilient positioning mechanism comprises a resilient positioning ring having a radially inner portion and a radially outer portion.

18. The rotational atherectomy device of claim 17 wherein the resilient positioning ring is carried by the prime mover carriage, the radially outer portion of the positioning ring being secured against longitudinal movement with respect to the prime mover carriage, and the radially inner portion of the resilient ring being configured with respect to the prime mover carriage so that such inner portion of the ring resiliently deflects proximally when the prime mover carriage and resilient positioning ring are moved distally over the movable telescopic tube, the radially inner portion of the resilient ring at least partially returning to its non-deflected configuration and moving the prime mover carriage and the shank proximally with respect to the movable telescopic tube after pressure urging the prime mover carriage and the resilient positioning ring over the movable telescopic tube has been removed, thus spacing the shank away from the distal abutment surface defined by said element of the movable telescopic tube and permitting the shank to rotate freely with respect to the movable telescopic tube.

19. The rotational atherectomy device of claim 17 wherein the resilient positioning ring is carried by the movable telescopic tube, the radially inner portion of the positioning ring being secured against longitudinal movement with respect to the movable telescopic tube, and the radially outer portion of the resilient ring being configured so that such outer portion of the ring resiliently deflects distally when the prime mover carriage is moved distally over the resilient positioning ring secured to the movable telescopic tube, the radially outer portion of the resilient ring at least partially returning to its non-deflected configuration and moving the prime mover carriage and the shank proximally with respect to the movable telescopic tube after pressure urging the prime mover carriage over the resilient positioning ring has been removed, thus spacing the shank away from the distal abutment surface defined by said element of the movable telescopic tube and permitting the shank to rotate freely with respect to the movable telescopic tube.

20. The rotational atherectomy device of claim 15 wherein the resilient positioning mechanism includes a detent carried by the prime mover carriage and a spring positioned to urge the detent radially into a complementary groove formed in an element of the movable telescopic tube.

21. The rotational atherectomy device of claim 20 wherein the detent comprises a ball.

22. The rotational atherectomy device of claim 20 wherein the spring is a coil spring.

23. The rotational atherectomy device of claim 20 wherein the spring is a leaf spring.

24. The rotational atherectomy device of claim 23 wherein the leaf spring is formed integrally as a portion of the prime mover carriage.

25. The rotational atherectomy device of claim 20 further including a longitudinal spring positioned longitudinally between the detent and the prime mover carriage for moving the prime mover carriage and the shank proximally with respect to the movable telescopic tube after the detent has engaged the complementary groove and after the pressure moving the prime mover carriage distally with respect to the longitudinally extendable tube has been released.

26. The rotational atherectomy device of claim 1 further comprising a tube attachment mechanism positioned to removably attach the longitudinally extendable tube to the prime mover carriage, the tube attachment mechanism including complementary camming surfaces defined by elements of the prime mover carriage and the longitudinally extendable tube, at least one of the camming surfaces being carried by a radially resilient member, the camming surfaces being oriented so that, when distal pressure moves the prime mover carriage distally to its most distal position with respect to the longitudinally extendable tube the distal pressure causes the camming surfaces to slide with respect to each other, thereby forcing the radially resilient member to deflect radially outwardly.

27. The rotational atherectomy device of claim 26 wherein the radially resilient member is carried by the prime mover carriage.

28. The rotational atherectomy device of claim 27 wherein the radially resilient member is comprised of a distally extending resilient finger having a detent which defines the camming surface defined by said element of the prime mover carriage.

29. The rotational atherectomy device of claim 26 wherein the camming surface defined by said element of the prime mover carriage is beveled distally outwardly.

30. The rotational atherectomy device of claim 26 wherein the camming surface defined by said element of the longitudinally extendable tube is beveled distally outwardly.

31. The rotational atherectomy device of claim 30 wherein the camming surface defined by said element of the longitudinally extendable tube comprises a distal portion of a radially inwardly extending groove.

32. The rotational atherectomy device of claim 26 wherein the tube attachment mechanism comprises a plurality of radially resilient members carried by the prime mover carriage, each radially resilient member including a distally extending finger having a detent which defines the camming surface associated with the prime mover carriage.

33. The rotational atherectomy device of claim 26 or 32 wherein the tube attachment mechanism includes at least three such radially resilient members.

34. The rotational atherectomy device of claim 1 further comprising a tube attachment mechanism positioned to removably attach the longitudinally extendable tube to the prime mover carriage, the tube attachment mechanism including complementary camming surfaces defined by elements of the prime mover carriage and the longitudinally extendable tube, at least one of the camming surfaces being carried by a radially resilient member, the camming surfaces being oriented so that, after the prime mover carriage has been advanced to its most distal position with respect to the longitudinally extendable tube and pressure moving the prime mover carriage distally with respect to the tube has been released, the radially resilient member attempts to regain its non-deflected configuration, causing the camming surfaces to slide and longitudinally move with respect to each other, thereby moving the prime mover carriage and the drive shaft shank proximally with respect to the longitudinally extendable tube.

35. The rotational atherectomy device of claim 1 further comprising a tube attachment mechanism positioned to removably attach the longitudinally extendable tube to the prime mover carriage, the tube attachment mechanism including one or more radially resilient members carried by the prime mover carriage, the radially resilient member(s) being sized and positioned to removably attach the longitudinally extendable tube to the prime mover carriage.

36. The rotational atherectomy device of claim 35 wherein each radially resilient member comprises a distally extending finger having a detent receivable in a complementary groove formed in an element of the longitudinally extendable tube.

37. The rotational atherectomy device of claim 1 further comprising a tube attachment mechanism positioned to removably attach the longitudinally extendable tube to the prime mover carriage, the tube attachment mechanism including complementary proximal camming surfaces defined by elements of the prime mover carriage and the longitudinally extendable tube, at least one of the proximal camming surfaces being carried by a radially resilient member, the proximal camming surfaces being oriented with respect to each other so that, when the prime mover carriage is attached to the longitudinally extendable tube, relative movement of the cartridge housing and the prime mover carriage away from each other will cause the proximal camming surfaces to slide and move longitudinally with respect to each other so that the proximal camming surfaces become disengaged from each other, thereby permitting the prime mover carriage to be detached from the longitudinally extendable tube.

38. The rotational atherectomy device of claim 1 wherein the elongated shank has a longitudinal axis and includes distal and proximal portions, the proximal portion of the elongated shank having at least one flat surface which is substantially parallel to the longitudinal axis of the shank.

39. The rotational atherectomy device of claim 38 wherein the proximal portion of the shank has two or more flat surfaces which are substantially parallel to the longitudinal axis of the shank.

40. The rotational atherectomy device of claim 38 wherein the outer periphery of the proximal portion of the elongated shank is comprised of two or more flat surfaces and two or more generally cylindrical surfaces.

41. The rotational atherectomy device of claim 38 wherein the proximal portion of the shank has four or more flat surfaces which are substantially parallel to the longitudinal axis of the shank.

42. The rotational atherectomy device of claim 38 wherein the outer periphery of the proximal portion of the elongated shank is comprised of four or more flat surfaces and four or more generally cylindrical surfaces.

43. The rotational atherectomy device of claim 38 wherein the proximal portion of the elongated shank has a generally frusto-conical proximal end.

44. The rotational atherectomy device of claim 38 wherein the distal portion of the elongated shank includes a radially outwardly extending flange.

45. The rotational atherectomy device of claim 1 wherein at least a portion of the shank's outer periphery is non-circular in transverse cross-section.

46. The rotational atherectomy device of claim 1 wherein the shank has a central lumen in which the drive shaft may be secured.

47. The rotational atherectomy device of claim 46 further comprising a length of flexible tubing disposed about at least a part of the proximal portion of the drive shaft.

48. The rotational atherectomy device of claim 47 wherein the central lumen of the shank has distal and proximal portions, the diameter of the distal portion of the shank being larger than the diameter of the proximal portion of the shank, a part of the length of the flexible tubing being disposed within the distal portion of the shank's lumen.

49. The rotational atherectomy device of claim 1 wherein the prime mover carriage is movable distally from a range of working positions to a carriage-restrained position, the carriage-restrained position of the prime mover carriage being positioned within the handle housing so that, when the cartridge housing is attached to the handle housing, advancement of the prime mover carriage to its carriage-restrained position assures sufficient distal movement of the prime mover carriage with respect to the shank and the longitudinally extendable tube so that the shank of the drive shaft is inserted into the prime mover socket and the movable telescopic tube is attached to the prime mover carriage.

50. The rotational atherectomy device of claim 49 further comprising a carriage restraining mechanism carried by the handle housing for inhibiting advancement of the prime mover carriage from the range of working positions to the carriage-restrained position.

51. The rotational atherectomy device of claim 50 wherein the carriage restraining mechanism comprises a disengageable mechanical linkage between the prime mover carriage and the handle housing.

52. The rotational atherectomy device of claim 51 wherein the disengageable mechanical linkage comprises a detent and a complementary member engageable with the detent.

53. The rotational atherectomy device of claim 52 wherein the handle housing includes an elongated slot defined by opposing walls of the handle housing and the carriage includes a shaft extending radially outwardly between the opposing walls of the elongated slot in the handle housing.

54. The rotational atherectomy device of claim 53 wherein the detent is comprised of a narrowed portion in the elongated slot of the handle housing.

55. The rotational atherectomy device of claim 54 wherein the shaft extending outwardly from the carriage has a diameter larger than the width of the narrowed portion in the elongated slot of the handle housing.

56. The rotational atherectomy device of claim 54 wherein the shaft extending outwardly from the carriage includes a collar disposed about the shaft, the collar having a diameter that is larger than the width of the narrowed portion in the elongated slot of the handle housing.

57. The rotational atherectomy device of claim 55 or 56 wherein the narrowed portion of the elongated slot is constructed so that when the shaft is urged into the narrowed portion of the elongated slot the narrowed portion resiliently widens to permit the shaft to pass therethrough.

58. The rotational atherectomy device of claim 53 wherein the handle housing includes a relief slot extending distally from a distal end of the elongated slot.

59. The rotational atherectomy device of claim 1 further comprising a one stage interlock mechanism for removably attaching the cartridge housing to the handle housing.

60. The rotational atherectomy device of claim 59 wherein both the cartridge housing and the handle housing are comprised of generally cylindrical tubes, at least part of one of the cylindrical tubes being telescopically receivable within the other cylindrical tube.

61. The rotational atherectomy device of claim 59 wherein the interlock mechanism comprises an annular radially inwardly extending shoulder carried by the cartridge housing, the shoulder being interlockable with a complementary interlocking member comprised of a radially outwardly extending tab carried by the handle housing.

62. The rotational atherectomy device of claim 61 wherein the complementary interlocking member carried by the handle housing is comprised of a pair of circumferentially opposed, radially outwardly extending tabs.

63. The rotational atherectomy device of claim 62 wherein the interlock mechanism is releasable by compressing the annular shoulder of the cartridge housing to an oval shape and moving the shoulder distally over the tabs of the handle housing.

64. The rotational atherectomy device of claim 1 further comprising a two stage interlock mechanism for removably attaching the cartridge housing to the handle housing.

65. The rotational atherectomy device of claim 64 wherein the two stage interlock mechanism includes proximal and distal stages.

66. The rotational atherectomy device of claim 65 wherein the two stage interlock mechanism comprises a primary interlocking member carried by one of the cartridge housing and the handle housing and two complementary interlocking members carried by the other of the cartridge housing and the handle housing, the two complementary interlocking members being longitudinally spaced away from each other so that the primary interlocking member may be selectively interlocked with either one of the complementary interlocking members.

67. The rotational atherectomy device of claim 66 wherein the primary interlocking member is carried by the cartridge housing and the two complementary interlocking members are carried by the handle housing.

68. The rotational atherectomy device of claim 67 wherein the two complementary interlocking members are comprised of proximal and distal complementary interlocking members, the proximal complementary interlocking member forming a part of the proximal stage of the two stage interlock mechanism and a distal complementary interlocking member forming a part of the distal stage of the two stage interlock mechanism.

69. The rotational atherectomy device of claim 68 wherein the longitudinal distance between the proximal and distal complementary interlocking members is sufficiently long so that when, in the process of detaching the cartridge housing from the handle housing, the primary interlocking member interlocks with the distal complementary interlocking member, movement of the prime mover carriage to its proximal limit of movement assures that the drive shaft shank will be withdrawn from the prime mover socket and the longitudinally extendable tube will be detached from the prime mover carriage.

70. The rotational atherectomy device of claim 69 wherein the cartridge housing includes inner and outer tubes, the inner tube being generally coaxial with the outer tube and being telescopically receivable within the handle housing.

71. The rotational atherectomy device of claim 70 wherein the outer tube of the cartridge housing carries the primary interlocking member.

72. The rotational atherectomy device of claim 70 wherein the outer tube of the cartridge housing is shorter than the inner tube.

73. The rotational atherectomy device of claim 71 wherein the primary interlocking member is comprised of an annular radially inwardly extending shoulder.

74. The rotational atherectomy device of claim 73 wherein the annular shoulder has an inner diameter which is sufficiently larger than an outer diameter of the inner tube so that the annular shoulder may be compressed to an oval shape.

75. The rotational atherectomy device of claim 74 wherein the proximal complementary interlocking member is comprised of a radially outwardly extending tab carried by the handle housing so that the proximal stage of the two stage interlock mechanism is releasable by compressing the annular shoulder of the cartridge housing to an oval shape and moving the shoulder distally over the tab.

76. The rotational atherectomy device of claim 75 wherein the distal complementary interlocking member is comprised of a radially outwardly extending tab carried by the handle housing so that each stage of the two stage interlock mechanism is releasable by compressing the annular shoulder of the cartridge housing to the oval shape and moving the shoulder distally over the tab.

77. The rotational atherectomy device of claim 75 wherein the distal interlocking member is comprised of a pair of radially outwardly extending tabs carried by the handle housing, the tabs being longitudinally spaced away from each other to define a groove having a longitudinal width which is sufficient to receive the annular shoulder of the cartridge housing so that when, in the process of detaching the cartridge housing from the handle housing, the annular shoulder of the cartridge housing is received in the groove, it becomes captured between the proximal and distal tabs defining the groove.

78. The rotational atherectomy device of claim 74 wherein the proximal complementary interlocking member is comprised of a pair of circumferentially opposed, radially outwardly extending tabs carried by the handle housing so that the proximal stage of the two stage interlock mechanism is releasable by compressing the annular shoulder of the cartridge housing to an oval shape and moving the shoulder distally over the tabs.

79. The rotational atherectomy device of claim 78 wherein a wall of the handle housing includes a pair of proximal windows located circumferentially opposite each other and between the tabs comprising the proximal interlocking member, the windows permitting the annular shoulder of the cartridge housing to be compressed to an oval shape.

80. The rotational atherectomy device of claim 78 wherein the distal complementary interlocking member is comprised of a pair of circumferentially opposed, radially outwardly extending tabs carried by the handle housing so that each stage of the two stage interlock mechanism is releasable by compressing the annular shoulder of the cartridge housing to the oval shape and moving the shoulder distally over the tabs.

81. The rotational atherectomy device of claim 80 wherein the distal interlocking member is comprised of a pair of radially outwardly extending tabs carried by the handle housing, the tabs being longitudinally spaced away from each other to define a groove having a longitudinal width which is sufficient to receive the annular shoulder of the cartridge housing therein so that when, in the process of detaching the cartridge housing from the handle housing, the annular shoulder of the cartridge housing is received in the groove, it becomes captured between the proximal and distal tabs defining the groove.

82. The rotational atherectomy device of claim 81 wherein the distal complementary interlocking member is comprised of two pairs of radially outwardly extending tabs carried by the handle housing, each pair of tabs defining a groove having a longitudinal width which is sufficient to receive the annular shoulder of the cartridge housing.

83. The rotational atherectomy device of claim 82 wherein the two grooves defined by the tabs are longitudinally aligned with each other and circumferentially opposed to each other so that when, in the process of detaching the cartridge housing from the handle housing, the annular shoulder of the cartridge housing is received in the grooves, it becomes captured between the proximal and distal tabs defining the grooves.

84. The rotational atherectomy device of claim 80 or 82 wherein a wall of the handle housing includes a pair of distal windows located circumferentially opposite each other and between the tabs comprising the distal interlocking member, the windows permitting the annular shoulder of the cartridge housing to be compressed to an oval shape.

85. The rotational atherectomy device of claim 80 or 82 wherein the wall of the handle housing includes a pair of distally open recesses located circumferentially opposite each other and between the tabs comprising the distal interlocking member, the recesses permitting the annular shoulder of the cartridge housing to be compressed to an oval shape.

86. The rotational atherectomy device of claim 80 or 82 wherein the tabs of the proximal complementary interlocking member and the tabs of the distal complementary interlocking member not only are spaced longitudinally from each other but are also circumferentially positioned at about a 90 degree angle with respect to each other so that, in the process of detaching the cartridge housing from the handle housing, the annular shoulder of the cartridge housing has to be compressed to the oval shape at least two times, the first time to be moved distally over the tabs comprising the proximal complementary interlocking member, and the second time to be moved distally over the tabs comprising the distal complementary interlocking member.

87. The rotational atherectomy device of claim 66 wherein the primary interlocking member is comprised of a radially inwardly extending tab carried by the handle housing, and each of the two complementary interlocking members is comprised of an annular radially inwardly extending groove formed in an outer surface of the cartridge housing, each of the grooves having a longitudinal width sufficient to interlock with the radially inwardly extending tab.

88. The rotational atherectomy device of claim 87 wherein the two complementary interlocking members are comprised of proximal and distal complementary interlocking members, the proximal complementary interlocking member forming a part of the proximal stage of the two stage interlock mechanism and the distal complementary interlocking member forming a part of the distal stage of the two stage interlock mechanism.

89. The rotational atherectomy device of claim 88 wherein the longitudinal distance between the proximal and distal complementary interlocking members is sufficiently long so that when, in the process of detaching the exchangeable cartridge from the handle housing, the primary interlocking member interlocks with the proximal complementary interlocking member, movement of the prime mover carriage to its proximal limit of movement assures that the drive shaft shank will be withdrawn from the prime mover socket and the longitudinally extendable tube will be detached from the prime mover carriage.

90. The rotational atherectomy device of claim 89 wherein both the cartridge housing and the handle housing are comprised of generally cylindrical tubes, at least part of the cartridge housing being telescopically receivable within the handle housing.

91. The rotational atherectomy device of claim 90 wherein the radially inwardly extending tab is carried by an annular collar secured to the handle housing, at least a portion of the collar extending distally from the handle housing.

92. The rotational atherectomy device of claim 91 wherein the annular collar carrying the tab has an inner diameter which is sufficiently larger than an outer diameter of the cartridge housing to permit the annular collar to be compressed to an oval shape to disengage the tab from the groove.

93. The rotational atherectomy device of claim 92 wherein the primary interlocking member is comprised of a pair of circumferentially opposed, radially inwardly extending tabs, each stage of the two stage interlock mechanism being releasable by compressing the annular collar to an oval shape so that the tabs become disengaged from the groove in the cartridge housing and the cartridge housing can be moved distally with respect to the handle housing.

94. The rotational atherectomy device of claim 66 wherein the primary interlocking member is comprised of a radially inwardly extending tab carried by the cartridge housing, and each of the two complementary interlocking members is comprised of an annular radially inwardly extending groove in a wall of the handle housing, each of the grooves having a longitudinal width sufficient to interlock with the radially inwardly extending tab.

95. The rotational atherectomy device of claim 94 wherein the two complementary interlocking members are comprised of proximal and distal complementary interlocking members, the proximal complementary interlocking member forming a part of the proximal stage of the two stage interlock mechanism and the distal complementary interlocking member forming a part of the distal stage of the two stage interlock mechanism.

96. The rotational atherectomy device of claim 95 wherein the longitudinal distance between the proximal and distal complementary interlocking members is sufficiently long so that when, in the process of detaching the exchangeable cartridge from the handle housing, the primary interlocking member interlocks with the distal complementary interlocking member, movement of the prime mover carriage to its proximal limit of movement assures that the drive shaft shank will be withdrawn from the prime mover socket and the longitudinally extendable tube will be detached from the prime mover carriage.

97. The rotational atherectomy device of claim 96 wherein both the handle housing and the cartridge housing are comprised of generally cylindrical tubes, at least part of the handle housing being telescopically receivable within the cartridge housing.

98. The rotational atherectomy device of claim 97 wherein the radially inwardly extending tab is carried by an annular collar secured to the cartridge housing, at least a portion of the collar extending proximally from the cartridge housing.

99. The rotational atherectomy device of claim 98 wherein the annular collar carrying the tab has an inner diameter which is sufficiently larger than an outer diameter of the handle housing to permit the annular collar to be compressed to an oval shape to disengage the tab from the groove.

100. The rotational atherectomy device of claim 99 wherein the primary interlocking member is comprised of a pair of circumferentially opposed, radially inwardly extending tabs, each stage of the two stage interlock mechanism being releasable by compressing the annular collar to an oval shape so that the tabs become disengaged from the groove and the cartridge housing can be moved distally with respect to the handle housing.

101. The rotational atherectomy device of claim 1 further comprising a flexible fluid supply tube attached to the exchangeable drive shaft cartridge and in fluid communication with a drive shaft lumen of the drive shaft cartridge, the drive shaft lumen being defined by a lumen of the catheter and a lumen of the longitudinally extendable tube.

102. The rotational atherectomy device of claim 101 wherein the drive shaft lumen receives a majority of the length of the drive shaft.

103. The rotational atherectomy device of claim 101 wherein a flexible thin-walled tube extends along a length of the drive shaft from a distal end of the drive shaft shank to a point located distally of a distal end of the longitudinally extendable tube.

104. The rotational atherectomy device of claim 103 wherein the flexible thin-walled tube extends distally beyond the location where the fluid supply tube delivers fluid to the drive shaft lumen.

105. The rotational atherectomy device of claim 103 wherein the flexible thin-walled tube extends distally into the proximal end portion of the catheter.

106. The rotational atherectomy device of claim 103 wherein the flexible thin-walled tube is a heat-shrinkable tube.

107. The rotational atherectomy device of claim 103 wherein the flexible thin-walled tube is a heat-shrinkable polyester tube.

108. The rotational atherectomy device of claim 101 wherein the fluid supply tube delivers fluid from a fluid supply external to the exchangeable drive shaft cartridge.

109. The rotational atherectomy device of claim 101 wherein the fluid supply tube is attached to the exchangeable drive shaft cartridge distally of the drive shaft shank.

110. The rotational atherectomy device of claim 101 wherein the fluid supply tube is attached to the exchangeable drive shaft cartridge distally of the drive shaft shank and proximally of the catheter.

111. The rotational atherectomy device of claim 101 wherein the fluid supply tube is attached to the exchangeable drive shaft cartridge distally of the prime mover carriage.

112. The rotational atherectomy device of claim 101 wherein the fluid supply tube is attached to the exchangeable drive shaft cartridge distally of the prime mover carriage and proximally of the catheter.

113. The rotational atherectomy device of claim 101 wherein the fluid supply tube is attached to the exchangeable drive shaft cartridge distally of the longitudinally extendable tube and proximally of the catheter.

114. The rotational atherectomy device of claim 101 wherein the fluid supply tube is attached to the exchangeable drive shaft cartridge adjacent a distal end of the longitudinally extendable tube.

115. The rotational atherectomy device of claim 101 wherein the fluid supply tube is attached to the cartridge housing adjacent to a distal end of the cartridge housing.

116. The rotational atherectomy device of claim 101 wherein the fluid supply tube is attached to a distal end piece of the cartridge housing.

117. The rotational atherectomy device of claim 101 wherein the longitudinally extendable tube includes at least two telescopic tubes.

118. The rotational atherectomy device of claim 117 wherein the fluid supply tube is attached to the exchangeable drive shaft cartridge distally of at least one of the telescopic tubes.

119. The rotational atherectomy device of claim 117 wherein the fluid supply tube is attached to the exchangeable drive shaft cartridge distally of all of the telescopic tubes.

120. The rotational atherectomy device of claim 117 wherein the fluid supply tube is attached to the exchangeable drive shaft cartridge distally of at least one of the telescopic tubes and proximally of the catheter.

121. The rotational atherectomy device of claim 117 wherein the fluid supply tube is attached to the cartridge housing proximally of the catheter.

122. The rotational atherectomy device of claim 1 wherein the prime mover carriage includes a tapered inlet for guiding the longitudinally extendable tube inside the prime mover carriage when the prime mover carriage is moved distally to be attached to the longitudinally extendable tube.

123. A rotational atherectomy device comprising:
a handle housing;
an exchangeable drive shaft cartridge including
a cartridge housing which is removably attachable to the handle housing;
an elongated catheter having a proximal end portion which is carried by the cartridge housing; and
a rotatable flexible drive shaft substantially disposed within the catheter,
the drive shaft having a tissue removal implement disposed near its distal end;
a two stage interlock mechanism removably attaching the cartridge housing to the handle housing;
a rotatable prime mover carried by a prime mover carriage which is disposed within the handle housing, the prime mover carriage being longitudinally movable with respect to the handle housing; and
a drive shaft attachment mechanism removably attaching the drive shaft to the prime mover;
whereby the cartridge housing may be attached to and detached from the handle housing and the drive shaft may be attached to and detached from the prime mover, thereby permitting the exchangeable drive shaft cartridge to be selectively attached to and detached from the handle housing.

124. A rotational atherectomy device comprising:
a handle housing;
a rotatable prime mover carried by a prime mover carriage which is disposed within the handle housing, the prime mover carriage being longitudinally movable with respect to the handle housing;
an exchangeable drive shaft cartridge having
a cartridge housing which is removably attachable to the handle housing;
a longitudinally extendable tube having a distal end portion carried by the cartridge housing and a proximal end portion which is removably attachable to the prime mover carriage for longitudinal movement therewith;
an elongated catheter having a proximal end portion which is carried by the cartridge housing; and
a rotatable flexible drive shaft having proximal, intermediate and distal portions, the intermediate portion being disposed primarily within the longitudinally extendable tube and the catheter, and the distal portion extending distally from the catheter and having a tissue removal implement; and
a drive shaft attachment mechanism removably attaching the proximal portion of the drive shaft to the prime mover.

125. A method of attaching an exchangeable drive shaft cartridge, having a tissue removal implement, to a handle housing portion of a rotational atherectomy device, comprising the steps of:
providing a handle housing having a rotatable prime mover carried by a prime mover carriage, the prime mover carriage being longitudinally movable with respect to the handle housing and having a distally facing prime mover socket;
providing an exchangeable drive shaft cartridge including
a cartridge housing which is removably attachable to the handle housing;
a longitudinally extendable tube having a distal end portion carried by the cartridge housing and a proximal end portion which is removably attachable to the prime mover carriage for longitudinal movement therewith; and
a rotatable flexible drive shaft having proximal and distal portions, the proximal portion being attached to an elongated shank removably attachable to the prime mover socket, the distal portion of the flexible drive shaft having a tissue removal implement;

attaching the cartridge housing to the handle housing by moving the cartridge housing proximally with respect to the handle housing; and connecting the longitudinally extendable tube to the prime mover carriage and inserting the shank into the prime mover socket by moving the prime mover carriage distally with respect to the longitudinally extendable tube and the shank.

126. A method of detaching an exchangeable drive shaft cartridge, having a tissue removal implement, from a rotational atherectomy device, comprising the steps of:

providing a handle housing having a rotatable prime mover carried by a prime mover carriage, the prime mover carriage being longitudinally movable with respect to the handle housing and having a distally facing prime mover socket;

providing an exchangeable drive shaft cartridge including
a cartridge housing which is removably attachable to the handle housing;
a longitudinally extendable tube having a distal end portion carried by the cartridge housing and a proximal end portion which is removably attachable to the prime mover carriage for longitudinal movement therewith; and
a rotatable flexible drive shaft having proximal and distal portions, the proximal portion being attached to an elongated shank removably attachable to the prime mover socket, the distal portion of the flexible drive shaft having a tissue removal implement;

at least partially detaching the cartridge housing from the handle housing by moving the cartridge housing distally with respect to the handle housing; and disconnecting the longitudinally extendable tube from the prime mover carriage and detaching the shank from the prime mover socket by moving the prime mover carriage proximally with respect to the longitudinally extendable tube and the shank.

127. A method of detaching one exchangeable drive shaft cartridge, having a tissue removal implement, from a rotational atherectomy device and replacing it with another exchangeable drive shaft cartridge, having another tissue removal implement, comprising the steps of:

providing a handle housing having a rotatable prime mover carried by a prime mover carriage, the prime mover carriage being longitudinally movable with respect to the handle housing and having a distally facing prime mover socket;

providing a first exchangeable drive shaft cartridge including
a cartridge housing which is removably attachable to the handle housing;
a longitudinally extendable tube having a distal end portion carried by the cartridge housing and a proximal end portion which is removably attachable to the prime mover carriage for longitudinal movement therewith; and
a rotatable flexible drive shaft having proximal and distal portions, the proximal portion being attached to an elongated shank removably attachable to the prime mover socket, the distal portion of the flexible drive shaft having a tissue removal implement;

at least partially detaching the cartridge housing from the handle housing by moving the cartridge housing distally with respect to the handle housing; and disconnecting the longitudinally extendable tube from the prime mover carriage and detaching the shank from the prime mover socket by moving the prime mover carriage proximally with respect to the longitudinally extendable tube and the shank;

providing a second exchangeable drive shaft cartridge including
a second cartridge housing which is removably attachable to the handle housing;
a second longitudinally extendable tube having a distal end portion carried by the second cartridge housing and a proximal end portion which is removably attachable to the prime mover carriage for longitudinal movement therewith; and
a second rotatable flexible drive shaft having proximal and distal portions, the proximal portion being attached to a second elongated shank removably attachable to the prime mover socket, the distal portion of the second flexible drive shaft having a second tissue removal implement;

attaching the second cartridge housing to the handle housing by moving the cartridge housing proximally with respect to the handle housing; and connecting the second longitudinally extendable tube to the prime mover carriage and inserting the second shank into the prime mover socket by moving the prime mover carriage distally with respect to the second longitudinally extendable tube and the second shank.

* * * * *